(12) United States Patent  
Dewdney et al.

(10) Patent No.: US 8,426,441 B2
(45) Date of Patent: Apr. 23, 2013

(54) INHIBITORS OF BRUTON'S TYROSINE KINASE

(75) Inventors: Nolan James Dewdney, Saratoga, CA (US); Yan Lou, San Jose, CA (US); Michael Soth, Milpitas, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 564 days.

(21) Appl. No.: 12/316,343

(22) Filed: Dec. 11, 2008

(65) Prior Publication Data

US 2009/0186898 A1 Jul. 23, 2009

Related U.S. Application Data

(60) Provisional application No. 61/080,865, filed on Jul. 15, 2008, provisional application No. 61/013,762, filed on Dec. 14, 2007.

(51) Int. Cl.
C07D 471/04 (2006.01)
A61K 31/437 (2006.01)
A61P 19/02 (2006.01)

(52) U.S. Cl.
USPC .......................... 514/300; 546/121

(58) Field of Classification Search .................. 546/121; 514/300
See application file for complete search history.

(56) References Cited

U.S. PATENT DOCUMENTS

2007/0083044 A1 4/2007 Paruch et al.
2011/0046127 A1* 2/2011 Pevarello et al. .......... 514/230.8
2011/0065745 A1* 3/2011 De Peretti et al. ............ 514/300

FOREIGN PATENT DOCUMENTS

WO 2004026867 1/2004
WO WO 2004026867 * 4/2004
WO WO 2006100119 * 3/2006
WO 2006/053121 5/2006

OTHER PUBLICATIONS

Dwyer, et al., Bioorg. & Med. Chem. Letrs. (2007), 17(22), 6216-6219.*
Yamamoto et al., JPET 306(3):1174-1181 ( 2003).
(Translation of Jap Off Act in Corres Jap App 2010537386 Dec. 11, 2012).

* cited by examiner

*Primary Examiner* — Susanna Moore
*Assistant Examiner* — Cecilia M Jaisle
(74) *Attorney, Agent, or Firm* — George W. Johnston; Dennis P. Tramaloni; Jennifer L. Kisko

(57) ABSTRACT

This application discloses novel imidazo[1,2-a]pyridine and imidazo[1,2-b]pyridazine derivatives according to Formulae I-VI:

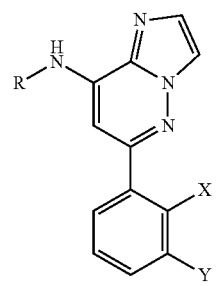

I

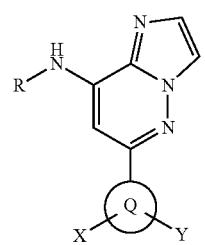

II

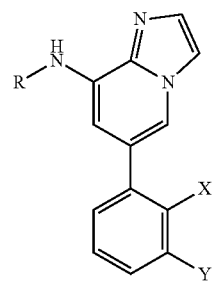

III

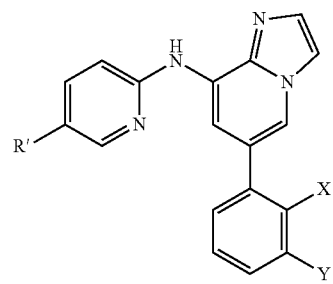

IV

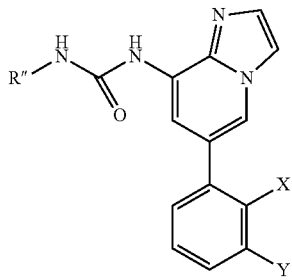

V

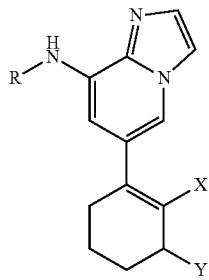

VI wherein R, R', R", Q, X, and Y are defined as described herein, which inhibit Btk. The compounds disclosed herein are useful to modulate the activity of Btk and treat diseases associated with excessive Btk activity. The compounds are further useful to treat inflammatory and auto immune diseases associated with aberrant B-cell proliferation such as rheumatoid arthritis. Also disclosed are compositions containing compounds of Formulae I-VI and at least one carrier, diluent or excipient.

21 Claims, No Drawings

INHIBITORS OF BRUTON'S TYROSINE KINASE

CROSS-REFERENCE TO RELATED APPLICATIONS

This application is entitled to the benefit of provisional patent application Ser. No. 61/013,762 filed on Dec. 14, 2007 and provisional patent application Ser. No. 61/080,865 filed on Jul. 15, 2008, the disclosures of which are incorporated herein by reference.

FIELD OF THE INVENTION

The present invention relates to the use of novel imidazo[1,2-a]pyridine and imidazo[1,2-b]pyridazine derivatives which inhibit Btk and are useful for the treatment of autoimmune and inflammatory diseases caused by aberrant B-cell activation. The novel imidazo[1,2-a]pyridine and imidazo[1,2-b]pyridazine derivatives described herein are useful for the treatment of arthritis.

BACKGROUND OF THE INVENTION

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. Annu Rev Med 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (Btk) is a non-BCR associated kinase that is membrane proximal and immediately downstream from BCR. Lack of Btk has been shown to block BCR signaling and therefore inhibition of Btk could be a useful therapeutic approach to block B-cell mediated disease processes.

Btk is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of Btk in humans leads to the condition X-linked agammaglobulinemia (XLA) (reviewed in Rosen et al. New Eng. J. Med. 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl Clin. Exp. Immunol. 1993 94:459). A selective Btk inhibitor has been demonstrated dose-dependent efficacy in a mouse arthritis model (Z. Pan et al., Chem. Med. Chem. 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. J. Biol. Chem. 2005 280:40261). This shows Btk could be useful to treat pathological mast cells responses such as allergy and asthma. Also monocytes from XLA patients, in which Btk activity is absent, show decreased TNF alpha production following stimulation (Horwood et al. J Exp Med 197:1603, 2003). Therefore TNF alpha mediated inflammation could be modulated by small molecular Btk inhibitors. Also, Btk has been reported to play a role in apoptosis (Islam and Smith Immunol. Rev. 2000 178:49) and thus Btk inhibitors would be useful for the treatment of certain B-cell lymphomas and leukemias (Feldhahn et al. J. Exp. Med. 2005 201:1837).

SUMMARY OF THE INVENTION

The present application provides a Btk inhibitor compound of formula I:

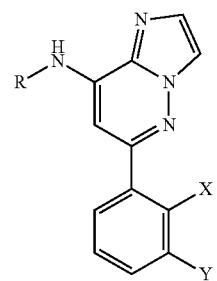

wherein:
R is H, —R$^1$, —R$^1$—R$^2$—R$^3$, or —R$^2$—R$^3$;
R$^1$ is aryl, heteroaryl, cycloalkyl, or heterocycloalkyl, and is optionally substituted with lower alkyl, hydroxy, lower alkoxy, halo, nitro, amino, cyano, or halo-lower alkyl;
R$^2$ is —C(=O), —C(=O)O, —C(=O)NH, or —S(=O)$_2$;
R$^3$ is H or R$^4$;
R$^4$ is lower alkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, or halo-lower alkyl;

X is H, halo, lower alkyl, hydroxy, hydroxy lower alkyl, or lower alkoxy;

Y is H, —R$^5$—R$^6$, —R$^6$ or —R$^5$—R$^6$—R$^7$;
  R$^5$ is —NHC(=O) or —(CH$_2$)$_n$C(=O);
  n is 0, 1, or 2;
  R$^6$ is lower alkyl, lower alkenyl, lower alkynyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl and is optionally substituted with one or more substituents selected from the group consisting of lower alkyl, hydroxy, halo-lower alkyl, lower alkoxy, halo-lower alkoxy, halo, nitro, amino, cyano, or trialkylsilanyl; and
  R$^7$ is aryl, heteroaryl, cycloalkyl, or heterocycloalkyl, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl, or is optionally connected to an aryl, heteroaryl, cycloalkyl, or heterocycloalkyl ring, such that the two rings form a bicyclic fused or spirocyclic ring system, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl; or a pharmaceutically acceptable salt thereof.

The present application provides a Btk inhibitor compound of formula II

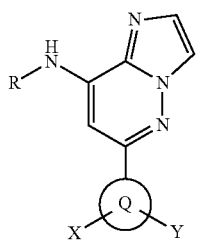

II wherein:
R is H, —R$^1$, —R$^1$—R$^2$—R$^3$, or —R$^2$—R$^3$;
  R$^1$ is aryl, heteroaryl, cycloalkyl, or heterocycloalkyl, and is optionally substituted with lower alkyl, hydroxy, lower alkoxy, halo, nitro, amino, cyano, or halo-lower alkyl;
  R$^2$ is C(=O), —C(=O)O, —C(=O)NH, or —S(=O)$_2$;
  R$^3$ is H or R$^4$;
  R$^4$ is lower alkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, or halo-lower alkyl;
X is H, halo, lower alkyl, hydroxy, hydroxy lower alkyl, or lower alkoxy;
Y is H, —R$^5$—R$^6$, —R$^6$ or —R$^5$—R$^6$—R$^7$;
  R$^5$ is —NHC(=O) or —(CH$_2$)$_n$C(=O);
  n is 0, 1, or 2;
  R$^6$ is lower alkyl, lower alkenyl, lower alkynyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl and is optionally substituted with one or more substituents selected from the group consisting of lower alkyl, hydroxy, halo-lower alkyl, lower alkoxy, halo-lower alkoxy, halo, nitro, amino, cyano, or trialkylsilanyl;

R$^7$ is aryl, heteroaryl, cycloalkyl, or heterocycloalkyl, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl, or is optionally connected to an aryl, heteroaryl, cycloalkyl, or heterocycloalkyl ring, such that the two rings form a bicyclic fused or spirocyclic ring system, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl; and Q is pyrrolyl, cycloalkyl or cycloalkenyl;
or a pharmaceutically acceptable salt thereof.

In certain embodiments of formula II, Q is pyrrolyl.
In certain embodiments of formula II, Q is cyclohexyl.
In certain embodiments of formula II, Q is cyclohexenyl.
In certain embodiments of formula II, Q is phenyl and X is o-hydroxymethyl The present application provides a Btk inhibitor compound of formula III:

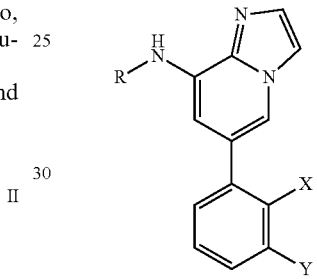

III wherein:
R is H, —R$^1$, —R$^1$—R$^2$—R$^3$, —R$^1$—R$^3$, or —R$^2$—R$^3$;
  R$^1$ is aryl, heteroaryl, cycloalkyl, or heterocycloalkyl, and is optionally substituted with lower alkyl, hydroxy, lower alkoxy, halo, nitro, amino, cyano, or halo-lower alkyl;
  R$^2$ is C(=O) or —C(=O)NH;
  R$^3$ is H or R$^4$;
  R$^4$ is lower alkyl, lower alkoxy, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, lower alkyl sulfonyl, heterocycloalkyl, or halo-lower alkyl;
X is H, lower alkyl, hydroxy, hydroxy lower alkyl, or lower alkoxy;
Y is H, —R$^5$—R$^6$, —R$^6$ or —R$^5$—R$^6$— R$^7$;
  R$^5$ is —NHC(=O), —NHC(=O)NR$^{5'}$, —CH$_2$)$_n$C(=O) NR$^{5'}$, —NH, or —(CH$_2$)$_n$C(=O);
  n is 0, 1, or 2; and
  R$^{5'}$ is H, lower alkyl, lower alkoxy, or hydroxy lower alkyl;
  R$^6$ is lower alkyl, lower alkenyl, lower alkynyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl and is optionally substituted with one or more substituents selected from the group consisting of lower alkyl, hydroxy, halo-lower alkyl, lower alkoxy, halo-lower alkoxy, halo, nitro, amino, cyano, or trialkylsilanyl; and
  R$^7$ is aryl, heteroaryl, cycloalkyl, or heterocycloalkyl, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl, or is optionally connected to an aryl, heteroaryl, cycloalkyl, or heterocycloalkyl ring, such that the two rings form a bicyclic fused or spirocyclic ring system, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl; with the proviso that if R is C(=O)CH$_3$ and X is H, then Y is not CF$_3$ or H; or a pharmaceutically acceptable salt thereof.

The present application provides a Btk inhibitor compound of formula IV

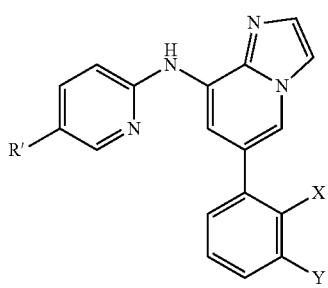

wherein:
R' is —R$^2$—R$^3$ or —R$^3$;
R$^2$ is —C(=O), —C(=O)O, —C(=O)NH, —S(=O)$_2$, O, NR$^3$, or lower alkyl;
R$^3$ is H or R$^4$;
R$^4$ is lower alkyl, lower alkoxy, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, lower alkyl sulfonyl, heterocycloalkyl, or halo-lower alkyl;
X is H, halo, lower alkyl, hydroxy, hydroxy lower alkyl, or lower alkoxy;
Y is H, —R$^5$—R$^6$, —R$^6$ or —R$^5$—R$^6$—R$^7$;
R$^5$ is —NHC(=O), —NHC(=O)NR$^{5'}$, —CH$_2$)$_n$C(=O)NR$^{5'}$, —NH, or —(CH$_2$)$_n$C(=O);
n is 0, 1, or 2;
R$^{5'}$ is H, lower alkyl, lower alkoxy, or hydroxy lower alkyl;
R$^6$ is lower alkyl, lower alkenyl, lower alkynyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl and is optionally substituted with one or more substituents selected from the group consisting of lower alkyl, hydroxy, halo-lower alkyl, lower alkoxy, halo-lower alkoxy, halo, nitro, amino, amido, amido lower alkyl, cyano, lower alkyl sulfonyl, or trialkylsilanyl; and
R$^7$ is aryl, heteroaryl, cycloalkyl, or heterocycloalkyl, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl, or is optionally connected to an aryl, heteroaryl, cycloalkyl, or heterocycloalkyl ring, such that the two rings form a bicyclic fused or spirocyclic ring system, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl;
or a pharmaceutically acceptable salt thereof.

The present application provides a Btk inhibitor compound of formula V

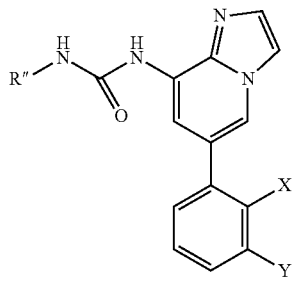

wherein:
R" is H or R$^4$;
R$^4$ is lower alkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, lower alkyl sulfonyl, cyano, heterocycloalkyl, or halo-lower alkyl;
X is H, halo, lower alkyl, hydroxy, hydroxy lower alkyl, or lower alkoxy;
Y is H, —R$^5$—R$^6$, —R$^6$ or —R$^5$—R$^6$—R$^7$;
R$^5$ is —NHC(=O), —NHC(=O)NH, —CH$_2$)$_n$C(=O)NH, or —(CH$_2$)$_n$C(=O);
n is 0, 1, or 2; and
R$^6$ is lower alkyl, lower alkenyl, lower alkynyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl and is optionally substituted with one or more substituents selected from the group consisting of lower alkyl, hydroxy, halo-lower alkyl, lower alkoxy, halo-lower alkoxy, halo, nitro, amino, cyano, or trialkylsilanyl; and
R$^7$ is aryl, heteroaryl, cycloalkyl, or heterocycloalkyl, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl, or is optionally connected to an aryl, heteroaryl, cycloalkyl, or heterocycloalkyl ring, such that the two rings form a bicyclic fused or spirocyclic ring system, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl;
or a pharmaceutically acceptable salt thereof.

In certain embodiments of the Btk inhibitor compound of formula III, R is —R$^1$—R$^2$—R$^3$ and R$^1$ is heteroaryl.

In one variation of the above embodiment, the heteroaryl is pyridine.

In certain embodiments of the Btk inhibitor compound of formula III, R$^2$ is —C(=O).

In certain embodiments of the Btk inhibitor compound of formula III, R$^3$ is R$^4$ and R$^4$ is heterocycloalkyl.

In one variation of the above embodiment, the heterocycloalkyl is morpholine.

In certain embodiments of the Btk inhibitor compound of formula III, R$^2$ is —C(=O), R$^3$ is R$^4$ and R$^4$ is heterocycloalkyl.

In one variation of the above embodiment, the heterocycloalkyl is morpholine.

In certain embodiments of the Btk inhibitor compound of formula IV, R' is —$R^2$—$R^3$ and $R^2$ is —C(=O).

In one variation of the above embodiment, $R^3$ is $R^4$ and $R^4$ is heterocycloalkyl.

In certain embodiments of the Btk inhibitor compound of formula III, X is hydroxymethyl.

In certain embodiments of the Btk inhibitor compound of formula III, X is methyl.

In certain embodiments of the Btk inhibitor compound of formula IV, X is hydroxymethyl.

In certain embodiments of the Btk inhibitor compound of formula I, R' is N, Y is —$R^5$—$R^6$ and $R^5$ is C(=O)NH.

In one variation of the above embodiment, $R^6$ is phenyl.

In one variation of the above embodiment, the phenyl is substituted with p-$^t$Bu.

In one variation of the above embodiment, X is methyl.

In another variation of the above embodiment, X is hydroxymethyl.

In certain embodiments of the Btk inhibitor compound of formula III, Y is —$R^5$—$R^6$ and $R^5$ is —C(=O)NH.

In one variation of the above embodiment, $R^6$ is phenyl.

In one variation of the above embodiment, the phenyl is substituted with p-$^t$Bu.

In certain embodiments of the Btk inhibitor compound of formula IV, wherein Y is —$R^5$—$R^6$ and $R^5$ is —C(=O)NH.

In one variation of the above embodiment, $R^6$ is phenyl.

In one variation of the above embodiment, the phenyl is substituted with p-$^t$Bu.

In certain embodiments of the Btk inhibitor compound of formula IV, X is methyl.

In certain embodiments of the Btk inhibitor compound of formula IV, X is hydroxymethyl.

In certain embodiments of the Btk inhibitor compound of formula IV, Y is —$R^5$—$R^6$ and $R^5$ is —C(=O)NH and X is hydroxymethyl.

In certain embodiments of the Btk inhibitor compound of formula V, Y is —$R^5$—$R^6$ and $R^5$ is —C(=O)NH.

In one variation of the above embodiment, $R^6$ is phenyl.

In one variation of the above embodiment, the phenyl is substituted with p-$^t$Bu.

In certain embodiments of the Btk inhibitor compound of formula V, X is methyl.

In certain embodiments of the Btk inhibitor compound of formula V, X is hydroxymethyl.

The present application provides a Btk inhibitor compound of formula VI:

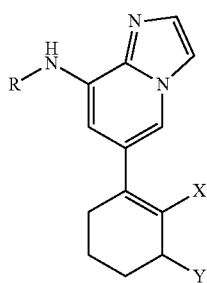

VI wherein:

R is H, —$R^1$, —$R^1$—$R^2$—$R^3$, —$R^1$—$R^3$, or —$R^2$—$R^3$;

$R^1$ is aryl, heteroaryl, cycloalkyl, or heterocycloalkyl, and is optionally substituted with lower alkyl, hydroxy, lower alkoxy, halo, nitro, amino, cyano, or halo-lower alkyl;

$R^2$ is —C(=O) or —C(=O)NH;

$R^3$ is H or $R^4$;

$R^4$ is lower alkyl, lower alkoxy, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, lower alkyl sulfonyl, heterocycloalkyl, or halo-lower alkyl;

X is H, lower alkyl, hydroxy, hydroxy lower alkyl, or lower alkoxy;

Y is H, —$R^5$—$R^6$, —$R^6$ or —$R^5$—$R^6$—$R^7$;

$R^5$ is —NHC(=O), —NHC(=O)$NR^{5'}$, —$CH_2)_nC$(=O)$NR^{5'}$, —NH, or —$(CH_2)_nC$(=O);

n is 0, 1, or 2; and $R^{5'}$ is H, lower alkyl, lower alkoxy, or hydroxy lower alkyl;

$R^6$ is lower alkyl, lower alkenyl, lower alkynyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl and is optionally substituted with one or more substituents selected from the group consisting of lower alkyl, hydroxy, halo-lower alkyl, lower alkoxy, halo-lower alkoxy, halo, nitro, amino, cyano, or trialkylsilanyl; and $R^7$ is aryl, heteroaryl, cycloalkyl, or heterocycloalkyl, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl, or is optionally connected to an aryl, heteroaryl, cycloalkyl, or heterocycloalkyl ring, such that the two rings form a bicyclic fused or spirocyclic ring system, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl;

or a pharmaceutically acceptable salt thereof.

The application further provides the compound of formula I that is selected from the group consisting of:

(6-Phenyl-imidazo[1,2-b]pyridazin-8-yl)-pyridin-2-yl-amine;

4-tert-Butyl-N-(2-methyl-3-{8-[5-(morpholine-4-carbonyl)-pyridin-2-ylamino]-imidazo[1,2-b]pyridazin-6-yl}-phenyl)-benzamide;

4-tert-Butyl-N-{3-[8-(3-isopropyl-ureido)-imidazo[1,2-b]pyridazin-6-yl]-2-methyl-phenyl}-benzamide;

4-tert-Butyl-N-{3-[8-(3-ethyl-ureido)-imidazo[1,2-b]pyridazin-6-yl]-2-methyl-phenyl}-benzamide;

4-tert-Butyl-N-{2-methyl-3-[8-(3-methyl-ureido)-imidazo[1,2-b]pyridazin-6-yl]-phenyl}-benzamide;

N-[3-(8-Amino-imidazo[1,2-b]pyridazin-6-yl)-2-methyl-phenyl]-4-tert-butyl-benzamide;

4-tert-Butyl-N-{3-[8-(3-tert-butyl-ureido)-imidazo[1,2-b]pyridazin-6-yl]-2-methyl-phenyl}-benzamide;

4-tert-Butyl-N-(3-{8-[3-(2-hydroxy-ethyl)-ureido]-imidazo[1,2-b]pyridazin-6-yl}-2-methyl-phenyl)-benzamide;

4-tert-Butyl-N-{2-methyl-3-[8-(thiazol-2-ylamino)-imidazo[1,2-b]pyridazin-6-yl]-phenyl}-benzamide;

1-Methyl-3-(6-phenyl-imidazo[1,2-b]pyridazin-8-yl)-urea;

1-(6-{3-[2-(1,3-Dihydro-isoindol-2-yl)-2-oxo-ethyl]-phenyl}-imidazo[1,2-b]pyridazin-8-yl)-3-methyl-urea;

4-tert-Butyl-N-(3-{8-[3-(3-dimethylamino-propyl)-ureido]-imidazo[1,2-b]pyridazin-6-yl}-2-methyl-phenyl)-benzamide;

N-{3-[8-(3-Ethyl-ureido)-imidazo[1,2-b]pyridazin-6-yl]-2-methyl-phenyl}-4-(1-hydroxy-1-methyl-ethyl)-benzamide;

4-Dimethylamino-N-{3-[8-(3-ethyl-ureido)-imidazo[1,2-b]pyridazin-6-yl]-2-methyl-phenyl}-benzamide;

N-{3-[8-(3-Ethyl-ureido)-imidazo[1,2-b]pyridazin-6-yl]-2-methyl-phenyl}-4-(2,2,2-trifluoro-1-hydroxy-1-trifluoromethyl-ethyl)-benzamide;
4-(Cyano-dimethyl-methyl)-N-{2-methyl-3-[8-(3-methyl-ureido)-imidazo[1,2-b]pyridazin-6-yl]-phenyl}-benzamide;
N-{3-[8-(3-Ethyl-ureido)-imidazo[1,2-b]pyridazin-6-yl]-2-methyl-phenyl}-4-(2,2,2-trifluoro-1-hydroxy-1-methyl-ethyl)-benzamide;
N-{3-[8-(3-Ethyl-ureido)-imidazo[1,2-b]pyridazin-6-yl]-2-methyl-phenyl}-4-(2,2,2-trifluoro-1-hydroxy-1-methyl-ethyl)-benzamide;
N-{2-Methyl-3-[8-(3-methyl-ureido)-imidazo[1,2-b]pyridazin-6-yl]-phenyl}-4-propoxy-benzamide;
4-Dimethylamino-N-{2-methyl-3-[8-(3-methyl-ureido)-imidazo[1,2-b]pyridazin-6-yl]-phenyl}-benzamide;
4-(Cyano-dimethyl-methyl)-N-{3-[8-(3-ethyl-ureido)-imidazo[1,2-b]pyridazin-6-yl]-2-methyl-phenyl}-benzamide;
4-(1-Hydroxy-1-methyl-ethyl)-N-{2-methyl-3-[8-(3-methyl-ureido)-imidazo[1,2-b]pyridazin-6-yl]-phenyl}-benzamide;
N-{2-Methyl-3-[8-(3-methyl-ureido)-imidazo[1,2-b]pyridazin-6-yl]-phenyl}-4-(2,2,2-trifluoro-1-hydroxy-1-trifluoromethyl-ethyl)-benzamide;
3-tert-Butoxy-azetidine-1-carboxylic acid {2-methyl-3-[8-(3-methyl-ureido)-imidazo[1,2-b]pyridazin-6-yl]-phenyl}-amide;
N-{2-Methyl-3-[8-(3-methyl-ureido)-imidazo[1,2-b]pyridazin-6-yl]-phenyl}-4-phenoxy-benzamide;
4-Isobutoxy-N-{2-methyl-3-[8-(3-methyl-ureido)-imidazo[1,2-b]pyridazin-6-yl]-phenyl}-benzamide;
N-(3-{8-[3-(3-Dimethylamino-propyl)-ureido]-imidazo[1,2-b]pyridazin-6-yl}-2-methyl-phenyl)-4-(1-hydroxy-1-methyl-ethyl)-benzamide;
N-(3-{8-[3-(3-Dimethylamino-propyl)-ureido]-imidazo[1,2-b]pyridazin-6-yl}-2-methyl-phenyl)-4-(2,2,2-trifluoro-1-hydroxy-1-trifluoromethyl-ethyl)-benzamide;
3-tert-Butoxy-azetidine-1-carboxylic acid (3-{8-[3-(2-cyano-ethyl)-ureido]-imidazo[1,2-b]pyridazin-6-yl}-2-methyl-phenyl)-amide;
3-tert-Butoxy-azetidine-1-carboxylic acid {3-[8-(3-ethyl-ureido)-imidazo[1,2-b]pyridazin-6-yl]-2-methyl-phenyl}-amide;
N-(3-{8-[3-(3-Dimethylamino-propyl)-ureido]-imidazo[1,2-b]pyridazin-6-yl}-2-methyl-phenyl)-4-(2,2,2-trifluoro-1-hydroxy-1-methyl-ethyl)-benzamide;
4-Dimethylamino-N-(3-{8-[3-(3-dimethylamino-propyl)-ureido]-imidazo[1,2-b]pyridazin-6-yl}-2-methyl-phenyl)-benzamide;
3-Benzyloxy-azetidine-1-carboxylic acid {2-methyl-3-[8-(3-methyl-ureido)-imidazo[1,2-b]pyridazin-6-yl]-phenyl}-amide;
4-Cyclopropyl-N-{2-hydroxymethyl-3-[8-(3-methyl-ureido)-imidazo[1,2-b]pyridazin-6-yl]-phenyl}-benzamide;
4-Cyclopropyl-N-{3-[8-(3-ethyl-ureido)-imidazo[1,2-b]pyridazin-6-yl]-2-hydroxymethyl-phenyl}-benzamide;
4-Cyclopropyl-N-{2-hydroxymethyl-3-[8-(3-propyl-ureido)-imidazo[1,2-b]pyridazin-6-yl]-phenyl}-benzamide;
4-Cyclopropyl-N-{2-hydroxymethyl-3-[8-(3-isobutyl-ureido)-imidazo[1,2-b]pyridazin-6-yl]-phenyl}-benzamide;
4-Cyclopropyl-N-{2-hydroxymethyl-3-[8-(3-isopropyl-ureido)-imidazo[1,2-b]pyridazin-6-yl]-phenyl}-benzamide;
4-Cyclopropyl-N-(2-hydroxymethyl-3-{8-[5-(morpholine-4-carbonyl)-pyridin-2-ylamino]-imidazo[1,2-b]pyridazin-6-yl}-phenyl)-benzamide;
4-Cyclopropyl-N-{2-hydroxymethyl-3-[8-(isoxazol-3-ylamino)-imidazo[1,2-b]pyridazin-6-yl]-phenyl}-benzamide;
4-Cyclopropyl-N-{2-hydroxymethyl-3-[8-(1-methyl-1H-pyrazol-3-ylamino)-imidazo[1,2-b]pyridazin-6-yl]-phenyl}-benzamide; and
4-Cyclopropyl-N-{3-[8-(4,6-dimethyl-pyridin-2-ylamino)-imidazo[1,2-b]pyridazin-6-yl]-2-hydroxymethyl-phenyl}-benzamide.

The application further provides the compound of formula II selected from the group consisting of:
[6-(1-Methyl-1H-pyrrol-2-yl)-imidazo[1,2-b]pyridazin-8-yl]-pyridin-2-yl-amine; and
1-Methyl-3-[6-(1-methyl-1H-pyrrol-2-yl)-imidazo[1,2-b]pyridazin-8-yl]-urea.

The application further provides the compound of formula II that is (6-Cyclohexyl-imidazo[1,2-b]pyridazin-8-yl)-pyridin-2-yl-amine.

The application further provides the compound of formula II that is (6-Cyclohex-1-enyl-imidazo[1,2-b]pyridazin-8-yl)-pyridin-2-yl-amine.

The application further provides the compound of formula III that is selected from the group consisting of:
N-[3-(8-Amino-imidazo[1,2-a]pyridin-6-yl)-2-methyl-phenyl]-4-tert-butyl-benzamide;
4-tert-Butyl-N-[2-methyl-3-(8-propionylamino-imidazo[1,2-a]pyridin-6-yl)-phenyl]-benzamide;
4-tert-Butyl-N-(3-{8-[2-((R)-3-hydroxy-pyrrolidin-1-yl)-pyrimidin-4-ylamino]-imidazo[1,2-a]pyridin-6-yl}-2-methyl-phenyl)-benzamide;
N-(3-{8-[2-((R)-3-Amino-pyrrolidin-1-yl)-pyrimidin-4-ylamino]-imidazo[1,2-a]pyridin-6-yl}-2-methyl-phenyl)-4-tert-butyl-benzamide;
4-tert-Butyl-N-{3-[8-(6-fluoro-pyridin-2-ylamino)-imidazo[1,2-a]pyridin-6-yl]-2-methyl-phenyl}-benzamide; and
4-tert-Butyl-N-(3-{8-[(1S,4S)-2-(2,5-diaza-bicyclo[2.2.1]hept-2-yl)-pyrimidin-4-ylamino]-imidazo[1,2-a]pyridin-6-yl}-2-methyl-phenyl)-benzamide.

The application further provides the compound of formula IV selected from the group consisting of
6-(6-Phenyl-imidazo[1,2-a]pyridin-8-ylamino)-nicotinic acid ethyl ester;
(6-Phenyl-imidazo[1,2-a]pyridin-8-yl)-pyridin-2-yl-amine;
Morpholin-4-yl-[6-(6-phenyl-imidazo[1,2-a]pyridin-8-ylamino)-pyridin-3-yl]-methanone;
4-tert-Butyl-N-(2-methyl-3-{8-[5-(morpholine-4-carbonyl)-pyridin-2-ylamino]-imidazo[1,2-a]pyridin-6-yl}-phenyl)-benzamide;
4-tert-Butyl-N-(2-methyl-3-{8-[5-(4-methyl-piperazine-1-carbonyl)-pyridin-2-ylamino]-imidazo[1,2-a]pyridin-6-yl}-phenyl)-benzamide;
2-(3-{8-[5-(Morpholine-4-carbonyl)-pyridin-2-ylamino]-imidazo[1,2-a]pyridin-6-yl}-phenyl)-N-(5,5,5-trifluoro-4-hydroxy-4-methyl-pent-2-ynyl)-acetamide;
N,N-Diisopropyl-2-(3-{8-[5-(morpholine-4-carbonyl)-pyridin-2-ylamino]-imidazo[1,2-a]pyridin-6-yl}-phenyl)-acetamide;
1-(4-Methoxy-piperidin-1-yl)-2-(3-{8-[5-(morpholine-4-carbonyl)-pyridin-2-ylamino]-imidazo[1,2-a]pyridin-6-yl}-phenyl)-ethanone;
N-(4-Fluoro-phenyl)-2-(3-{8-[5-(morpholine-4-carbonyl)-pyridin-2-ylamino]-imidazo[1,2-a]pyridin-6-yl}-phenyl)-acetamide;
N-[2-(4-Methoxy-phenyl)-1-methyl-ethyl]-2-(3-{8-[5-(morpholine-4-carbonyl)-pyridin-2-ylamino]-imidazo[1,2-a]pyridin-6-yl}-phenyl)-acetamide;

1-(4-Fluoro-phenyl)-3-(2-methyl-3-{8-[5-(morpholine-4-carbonyl)-pyridin-2-ylamino]-imidazo[1,2-a]pyridin-6-yl}-phenyl)-urea;
2-(3-{8-[5-(Morpholine-4-carbonyl)-pyridin-2-ylamino]-imidazo[1,2-a]pyridin-6-yl}-phenyl)-1-[3-(2,2,2-trifluoro-1-trifluoromethyl-ethoxy)-azetidin-1-yl]-ethanone;
Pyrrolidine-1-carboxylic acid (2-methyl-3-{8-[5-(morpholine-4-carbonyl)-pyridin-2-ylamino]-imidazo[1,2-a]pyridin-6-yl}-phenyl)-amide;
4-Hydroxymethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide;
1-[2-(4-Methoxy-phenyl)-1-methyl-ethyl]-3-(2-methyl-3-{8-[5-(morpholine-4-carbonyl)-pyridin-2-ylamino]-imidazo[1,2-a]pyridin-6-yl}-phenyl)-urea;
Azetidine-1-carboxylic acid (2-methyl-3-{8-[5-(morpholine-4-carbonyl)-pyridin-2-ylamino]-imidazo[1,2-a]pyridin-6-yl}-phenyl)-amide;
1-Isopropyl-3-(2-methyl-3-{8-[5-(morpholine-4-carbonyl)-pyridin-2-ylamino]-imidazo[1,2-a]pyridin-6-yl}-phenyl)-urea;
1-Isobutyl-3-(2-methyl-3-{8-[5-(morpholine-4-carbonyl)-pyridin-2-ylamino]-imidazo[1,2-a]pyridin-6-yl}-phenyl)-urea;
1-sec-Butyl-3-(2-methyl-3-{8-[5-(morpholine-4-carbonyl)-pyridin-2-ylamino]-imidazo[1,2-a]pyridin-6-yl}-phenyl)-urea;
3,6-Dihydro-2H-pyridine-1-carboxylic acid (2-methyl-3-{8-[5-(morpholine-4-carbonyl)-pyridin-2-ylamino]-imidazo[1,2-a]pyridin-6-yl}-phenyl)-amide;
Morpholine-4-carboxylic acid (2-methyl-3-{8-[5-(morpholine-4-carbonyl)-pyridin-2-ylamino]-imidazo[1,2-a]pyridin-6-yl}-phenyl)-amide;
1-(1,1-Dimethyl-propyl)-3-(2-methyl-3-{8-[5-(morpholine-4-carbonyl)-pyridin-2-ylamino]-imidazo[1,2-a]pyridin-6-yl}-phenyl)-urea;
1-(1-Ethyl-propyl)-3-(2-methyl-3-{8-[5-(morpholine-4-carbonyl)-pyridin-2-ylamino]-imidazo[1,2-a]pyridin-6-yl}-phenyl)-urea;
1-(2-Methoxy-1-methyl-ethyl)-3-(2-methyl-3-{8-[5-(morpholine-4-carbonyl)-pyridin-2-ylamino]-imidazo[1,2-a]pyridin-6-yl}-phenyl)-urea;
N-Isobutyl-2-(3-{8-[5-(morpholine-4-carbonyl)-pyridin-2-ylamino]-imidazo[1,2-a]pyridin-6-yl}-phenyl)-acetamide;
1-Cyclopropyl-3-(2-methyl-3-{8-[5-(morpholine-4-carbonyl)-pyridin-2-ylamino]-imidazo[1,2-a]pyridin-6-yl}-phenyl)-urea;
1,1-Diethyl-3-(2-methyl-3-{8-[5-(morpholine-4-carbonyl)-pyridin-2-ylamino]-imidazo[1,2-a]pyridin-6-yl}-phenyl)-urea;
N-Furan-2-ylmethyl-2-(3-{8-[5-(morpholine-4-carbonyl)-pyridin-2-ylamino]-imidazo[1,2-a]pyridin-6-yl}-phenyl)-acetamide;
N-Cyclopropyl-2-(3-{8-[5-(morpholine-4-carbonyl)-pyridin-2-ylamino]-imidazo[1,2-a]pyridin-6-yl}-phenyl)-acetamide;
N-Isopropyl-2-(3-{8-[5-(morpholine-4-carbonyl)-pyridin-2-ylamino]-imidazo[1,2-a]pyridin-6-yl}-phenyl)-acetamide;
1-(4-Methyl-piperidin-1-yl)-2-(3-{8-[5-(morpholine-4-carbonyl)-pyridin-2-ylamino]-imidazo[1,2-a]pyridin-6-yl}-phenyl)-ethanone;
N,N-Diethyl-2-(4-{8-[5-(morpholine-4-carbonyl)-pyridin-2-ylamino]-imidazo[1,2-a]pyridin-6-yl}-phenyl)-acetamide;
N-sec-Butyl-2-(3-{8-[5-(morpholine-4-carbonyl)-pyridin-2-ylamino]-imidazo[1,2-a]pyridin-6-yl}-phenyl)-acetamide;
1-(3,6-Dihydro-2H-pyridin-1-yl)-2-(3-{8-[5-(morpholine-4-carbonyl)-pyridin-2-ylamino]-imidazo[1,2-a]pyridin-6-yl}-phenyl)-ethanone;
2-(3-{8-[5-(Morpholine-4-carbonyl)-pyridin-2-ylamino]-imidazo[1,2-a]pyridin-6-yl}-phenyl)-1-morpholin-4-yl-ethanone;
1-(2-Cyano-ethyl)-3-(2-methyl-3-{8-[5-(morpholine-4-carbonyl)-pyridin-2-ylamino]-imidazo[1,2-a]pyridin-6-yl}-phenyl)-urea;
1-(2-Cyano-ethyl)-1-ethyl-3-(2-methyl-3-{8-[5-(morpholine-4-carbonyl)-pyridin-2-ylamino]-imidazo[1,2-a]pyridin-6-yl}-phenyl)-urea;
1-Benzyl-1-(2-cyano-ethyl)-3-(2-methyl-3-{8-[5-(morpholine-4-carbonyl)-pyridin-2-ylamino]-imidazo[1,2-a]pyridin-6-yl}-phenyl)-urea;
2,5-Dimethyl-2,5-dihydro-pyrrole-1-carboxylic acid (2-methyl-3-{8-[5-(morpholine-4-carbonyl)-pyridin-2-ylamino]-imidazo[1,2-a]pyridin-6-yl}-phenyl)-amide;
1-Cyclohexyl-3-(2-methyl-3-{8-[5-(morpholine-4-carbonyl)-pyridin-2-ylamino]-imidazo[1,2-a]pyridin-6-yl}-phenyl)-urea;
4-Methyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide;
Azepane-1-carboxylic acid (2-methyl-3-{8-[5-(morpholine-4-carbonyl)-pyridin-2-ylamino]-imidazo[1,2-a]pyridin-6-yl}-phenyl)-amide;
1-(2-Methyl-3-{8-[5-(morpholine-4-carbonyl)-pyridin-2-ylamino]-imidazo[1,2-a]pyridin-6-yl}-phenyl)-3-(tetrahydro-pyran-4-yl)-urea;
2-Ethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide;
3,5-Dimethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide;
2,6-Dimethyl-morpholine-4-carboxylic acid (2-methyl-3-{8-[5-(morpholine-4-carbonyl)-pyridin-2-ylamino]-imidazo[1,2-a]pyridin-6-yl}-phenyl)-amide;
N-(2-Methyl-3-{8-[5-(morpholine-4-carbonyl)-pyridin-2-ylamino]-imidazo[1,2-a]pyridin-6-yl}-phenyl)-4-(3-methyl-oxetan-3-yl)-benzamide;
N-(2-Methyl-3-{8-[5-(morpholine-4-carbonyl)-pyridin-2-ylamino]-imidazo[1,2-a]pyridin-6-yl}-phenyl)-4-(3-methyl-oxetan-3-yl)-benzamide;
4-Methyl-piperazine-1-carboxylic acid (2-methyl-3-{8-[5-(morpholine-4-carbonyl)-pyridin-2-ylamino]-imidazo[1,2-a]pyridin-6-yl}-phenyl)-amide;
1-(2-Dimethylamino-ethyl)-1-methyl-3-(2-methyl-3-{8-[5-(morpholine-4-carbonyl)-pyridin-2-ylamino]-imidazo[1,2-a]pyridin-6-yl}-phenyl)-urea; compound with formic acid;
1-[2-(3H-Imidazol-4-yl)-ethyl]-3-(2-methyl-3-{8-[5-(morpholine-4-carbonyl)-pyridin-2-ylamino]-imidazo[1,2-a]pyridin-6-yl}-phenyl)-urea;
4-Methyl-[1,4]diazepane-1-carboxylic acid (2-methyl-3-{8-[5-(morpholine-4-carbonyl)-pyridin-2-ylamino]-imidazo[1,2-a]pyridin-6-yl}-phenyl)-amide;
4-Ethyl-piperazine-1-carboxylic acid (2-methyl-3-{8-[5-(morpholine-4-carbonyl)-pyridin-2-ylamino]-imidazo[1,2-a]pyridin-6-yl}-phenyl)-amide;
4-Pyrrolidin-1-yl-piperidine-1-carboxylic acid (2-methyl-3-{8-[5-(morpholine-4-carbonyl)-pyridin-2-ylamino]-imidazo[1,2-a]pyridin-6-yl}-phenyl)-amide;

4-Dimethylcarbamoylmethyl-piperazine-1-carboxylic acid (2-methyl-3-{8-[5-(morpholine-4-carbonyl)-pyridin-2-ylamino]-imidazo[1,2-a]pyridin-6-yl}-phenyl)-amide;

4-(4-Chloro-benzyl)-piperazine-1-carboxylic acid (2-methyl-3-{8-[5-(morpholine-4-carbonyl)-pyridin-2-ylamino]-imidazo[1,2-a]pyridin-6-yl}-phenyl)-amide;

1-(2-Methyl-3-{8-[5-(morpholine-4-carbonyl)-pyridin-2-ylamino]-imidazo[1,2-a]pyridin-6-yl}-phenyl)-3-(1H-pyrazol-3-yl)-urea;

4-(2-Trifluoromethyl-benzyl)-piperazine-1-carboxylic acid (2-methyl-3-{8-[5-(morpholine-4-carbonyl)-pyridin-2-ylamino]-imidazo[1,2-a]pyridin-6-yl}-phenyl)-amide;

N—((S)-1-Hydroxymethyl-2-methyl-propyl)-2-(3-{8-[5-(morpholine-4-carbonyl)-pyridin-2-ylamino]-imidazo[1,2-a]pyridin-6-yl}-phenyl)-acetamide;

N—((S)-2-Hydroxy-1-methyl-ethyl)-2-(3-{8-[5-(morpholine-4-carbonyl)-pyridin-2-ylamino]-imidazo[1,2-a]pyridin-6-yl}-phenyl)-acetamide;

1-(1,4-Dioxa-8-aza-spiro[4.5]dec-8-yl)-2-(3-{8-[5-(morpholine-4-carbonyl)-pyridin-2-ylamino]-imidazo[1,2-a]pyridin-6-yl}-phenyl)-ethanone;

N—((S)-2-Hydroxy-propyl)-2-(3-{8-[5-(morpholine-4-carbonyl)-pyridin-2-ylamino]-imidazo[1,2-a]pyridin-6-yl}-phenyl)-acetamide;

N-(2,3-Dihydroxy-propyl)-2-(3-{8-[5-(morpholine-4-carbonyl)-pyridin-2-ylamino]-imidazo[1,2-a]pyridin-6-yl}-phenyl)-acetamide;

N—((R)-2-Hydroxy-1-methyl-ethyl)-2-(3-{8-[5-(morpholine-4-carbonyl)-pyridin-2-ylamino]-imidazo[1,2-a]pyridin-6-yl}-phenyl)-acetamide;

1-(4-Hydroxy-piperidin-1-yl)-2-(3-{8-[5-(morpholine-4-carbonyl)-pyridin-2-ylamino]-imidazo[1,2-a]pyridin-6-yl}-phenyl)-ethanone;

N,N-Bis-(2-hydroxy-ethyl)-2-(3-{8-[5-(morpholine-4-carbonyl)-pyridin-2-ylamino]-imidazo[1,2-a]pyridin-6-yl}-phenyl)-acetamide;

1-(3-Hydroxy-piperidin-1-yl)-2-(3-{8-[5-(morpholine-4-carbonyl)-pyridin-2-ylamino]-imidazo[1,2-a]pyridin-6-yl}-phenyl)-ethanone;

N-(2-Hydroxy-1,1-dimethyl-ethyl)-2-(3-{8-[5-(morpholine-4-carbonyl)-pyridin-2-ylamino]-imidazo[1,2-a]pyridin-6-yl}-phenyl)-acetamide;

1-(3-Hydroxy-pyrrolidin-1-yl)-2-(3-{8-[5-(morpholine-4-carbonyl)-pyridin-2-ylamino]-imidazo[1,2-a]pyridin-6-yl}-phenyl)-ethanone;

N-(4,4-Dimethyl-pent-2-ynyl)-2-(3-{8-[5-(morpholine-4-carbonyl)-pyridin-2-ylamino]-imidazo[1,2-a]pyridin-6-yl}-phenyl)-acetamide;

1-((R)-2-Hydroxy-1-methyl-ethyl)-3-(2-methyl-3-{8-[5-(morpholine-4-carbonyl)-pyridin-2-ylamino]-imidazo[1,2-a]pyridin-6-yl}-phenyl)-urea;

1-((S)-2-Hydroxy-propyl)-3-(2-methyl-3-{8-[5-(morpholine-4-carbonyl)-pyridin-2-ylamino]-imidazo[1,2-a]pyridin-6-yl}-phenyl)-urea;

1-(2-Hydroxy-1,1-dimethyl-ethyl)-3-(2-methyl-3-{8-[5-(morpholine-4-carbonyl)-pyridin-2-ylamino]-imidazo[1,2-a]pyridin-6-yl}-phenyl)-urea;

1-((S)-1-Hydroxymethyl-2-methyl-propyl)-3-(2-methyl-3-{8-[5-(morpholine-4-carbonyl)-pyridin-2-ylamino]-imidazo[1,2-a]pyridin-6-yl}-phenyl)-urea;

1-(1-Hydroxymethyl-cyclopentyl)-3-(2-methyl-3-{8-[5-(morpholine-4-carbonyl)-pyridin-2-ylamino]-imidazo[1,2-a]pyridin-6-yl}-phenyl)-urea;

1-((1S,2S)-1-Hydroxymethyl-2-methyl-butyl)-3-(2-methyl-3-{8-[5-(morpholine-4-carbonyl)-pyridin-2-ylamino]-imidazo[1,2-a]pyridin-6-yl}-phenyl)-urea;

2,5-Dihydro-pyrrole-1-carboxylic acid (2-methyl-3-{8-[5-(morpholine-4-carbonyl)-pyridin-2-ylamino]-imidazo[1,2-a]pyridin-6-yl}-phenyl)-amide;

1-Cyclopropylmethyl-3-(2-methyl-3-{8-[5-(morpholine-4-carbonyl)-pyridin-2-ylamino]-imidazo[1,2-a]pyridin-6-yl}-phenyl)-1-propyl-urea;

1-(2-Methyl-3-{8-[5-(morpholine-4-carbonyl)-pyridin-2-ylamino]-imidazo[1,2-a]pyridin-6-yl}-phenyl)-3-(1-phenyl-propyl)-urea;

1-((S)-1-Hydroxymethyl-2,2-dimethyl-propyl)-3-(2-methyl-3-{8-[5-(morpholine-4-carbonyl)-pyridin-2-ylamino]-imidazo[1,2-a]pyridin-6-yl}-phenyl)-urea;

1-(2-Methyl-3-{8-[5-(morpholine-4-carbonyl)-pyridin-2-ylamino]-imidazo[1,2-a]pyridin-6-yl}-phenyl)-3-((S)-1-phenyl-ethyl)-urea;

1-((3S,4S)-4-Hydroxy-1,1-dioxo-tetrahydro-1$\lambda^6$-thiophen-3-yl)-3-(2-methyl-3-{8-[5-(morpholine-4-carbonyl)-pyridin-2-ylamino]-imidazo[1,2-a]pyridin-6-yl}-phenyl)-urea;

1-(2-Methyl-3-{8-[5-(morpholine-4-carbonyl)-pyridin-2-ylamino]-imidazo[1,2-a]pyridin-6-yl}-phenyl)-3-(2,2,2-trifluoro-ethyl)-urea;

1-((S)-2-Hydroxy-1-methyl-ethyl)-3-(2-methyl-3-{8-[5-(morpholine-4-carbonyl)-pyridin-2-ylamino]-imidazo[1,2-a]pyridin-6-yl}-phenyl)-urea;

3-Hydroxy-pyrrolidine-1-carboxylic acid (2-methyl-3-{8-[5-(morpholine-4-carbonyl)-pyridin-2-ylamino]-imidazo[1,2-a]pyridin-6-yl}-phenyl)-amide;

(S)-2-Hydroxymethyl-pyrrolidine-1-carboxylic acid (2-methyl-3-{8-[5-(morpholine-4-carbonyl)-pyridin-2-ylamino]-imidazo[1,2-a]pyridin-6-yl}-phenyl)-amide;

4-Hydroxy-piperidine-1-carboxylic acid (2-methyl-3-{8-[5-(morpholine-4-carbonyl)-pyridin-2-ylamino]-imidazo[1,2-a]pyridin-6-yl}-phenyl)-amide;

3-Hydroxy-piperidine-1-carboxylic acid (2-methyl-3-{8-[5-(morpholine-4-carbonyl)-pyridin-2-ylamino]-imidazo[1,2-a]pyridin-6-yl}-phenyl)-amide;

1,1-Bis-(2-hydroxy-ethyl)-3-(2-methyl-3-{8-[5-(morpholine-4-carbonyl)-pyridin-2-ylamino]-imidazo[1,2-a]pyridin-6-yl}-phenyl)-urea;

2-Hydroxymethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide;

3-Hydroxymethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide;

1-(4-Hydroxy-cyclohexyl)-3-(2-methyl-3-{8-[5-(morpholine-4-carbonyl)-pyridin-2-ylamino]-imidazo[1,2-a]pyridin-6-yl}-phenyl)-urea;

4-tert-Butyl-N-(3-{8-[6-(3-hydroxy-pyrrolidin-1-yl)-pyridin-2-ylamino]-imidazo[1,2-a]pyridin-6-yl}-2-methyl-phenyl)-benzamide;

N-(1,1-Dimethyl-propyl)-2-(3-{8-[5-(morpholine-4-carbonyl)-pyridin-2-ylamino]-imidazo[1,2-a]pyridin-6-yl}-phenyl)-acetamide;

N-(1-Ethyl-propyl)-2-(3-{8-[5-(morpholine-4-carbonyl)-pyridin-2-ylamino]-imidazo[1,2-a]pyridin-6-yl}-phenyl)-acetamide;

N-(1-Ethyl-propyl)-2-(3-{8-[5-(morpholine-4-carbonyl)-pyridin-2-ylamino]-imidazo[1,2-a]pyridin-6-yl}-phenyl)-acetamide;

N-(2-Methoxy-1-methyl-ethyl)-2-(3-{8-[5-(morpholine-4-carbonyl)-pyridin-2-ylamino]-imidazo[1,2-a]pyridin-6-yl}-phenyl)-acetamide;

N-(2-Methoxy-1-methyl-ethyl)-2-(3-{8-[5-(morpholine-4-carbonyl)-pyridin-2-ylamino]-imidazo[1,2-a]pyridin-6-yl}-phenyl)-acetamide;

1-(2,5-Dimethyl-2,5-dihydro-pyrrol-1-yl)-2-(3-{8-[5-(morpholine-4-carbonyl)-pyridin-2-ylamino]-imidazo[1,2-a]pyridin-6-yl}-phenyl)-ethanone;

1-(2-Methyl-piperidin-1-yl)-2-(3-{8-[5-(morpholine-4-carbonyl)-pyridin-2-ylamino]-imidazo[1,2-a]pyridin-6-yl}-phenyl)-ethanone;

1-Azepan-1-yl-2-(3-{8-[5-(morpholine-4-carbonyl)-pyridin-2-ylamino]-imidazo[1,2-a]pyridin-6-yl}-phenyl)-ethanone;

1-((2S,6R)-2,6-Dimethyl-piperidin-1-yl)-2-(3-{8-[5-(morpholine-4-carbonyl)-pyridin-2-ylamino]-imidazo[1,2-a]pyridin-6-yl}-phenyl)-ethanone;

N-(2-Dimethylamino-ethyl)-N-methyl-2-(3-{8-[5-(morpholine-4-carbonyl)-pyridin-2-ylamino]-imidazo[1,2-a]pyridin-6-yl}-phenyl)-acetamide;

1-(4-Methyl-piperazin-1-yl)-2-(3-{8-[5-(morpholine-4-carbonyl)-pyridin-2-ylamino]-imidazo[1,2-a]pyridin-6-yl}-phenyl)-ethanone;

1-(4-Ethyl-piperazin-1-yl)-2-(3-{8-[5-(morpholine-4-carbonyl)-pyridin-2-ylamino]-imidazo[1,2-a]pyridin-6-yl}-phenyl)-ethanone;

4-(3-Methyl-azetidin-3-yl)-N-(2-methyl-3-{8-[5-(morpholine-4-carbonyl)-pyridin-2-ylamino]-imidazo[1,2-a]pyridin-6-yl}-phenyl)-benzamide;

[6-(6-{3-[1-(4-tert-Butyl-phenyl)-2,2,2-trifluoro-ethylamino]-2-methyl-phenyl}-imidazo[1,2-a]pyridin-8-ylamino)-pyridin-3-yl]-morpholin-4-yl-methanone;

3-Aza-bicyclo[3.2.2]nonane-3-carboxylic acid (2-methyl-3-{8-[5-(morpholine-4-carbonyl)-pyridin-2-ylamino]-imidazo[1,2-a]pyridin-6-yl}-phenyl)-amide;

Piperidine-1,3-dicarboxylic acid 3-amide 1-[(2-methyl-3-{8-[5-(morpholine-4-carbonyl)-pyridin-2-ylamino]-imidazo[1,2-a]pyridin-6-yl}-phenyl)-amide];

1,1-Bis-(2-methoxy-ethyl)-3-(2-methyl-3-{8-[5-(morpholine-4-carbonyl)-pyridin-2-ylamino]-imidazo[1,2-a]pyridin-6-yl}-phenyl)-urea;

3,4-Dihydro-2H-quinoline-1-carboxylic acid (2-methyl-3-{8-[5-(morpholine-4-carbonyl)-pyridin-2-ylamino]-imidazo[1,2-a]pyridin-6-yl}-phenyl)-amide;

(4aR,8aS)-Octahydro-isoquinoline-2-carboxylic acid (2-methyl-3-{8-[5-(morpholine-4-carbonyl)-pyridin-2-ylamino]-imidazo[1,2-a]pyridin-6-yl}-phenyl)-amide;

{6-[6-(2-Hydroxymethyl-phenyl)-imidazo[1,2-a]pyridin-8-ylamino]-pyridin-3-yl}-morpholin-4-yl-methanone;

1-Methyl-3-(2-methyl-3-{8-[5-(morpholine-4-carbonyl)-pyridin-2-ylamino]-imidazo[1,2-a]pyridin-6-yl}-phenyl)-1-phenyl-urea;

1-Ethyl-3-(2-methyl-3-{8-[5-(morpholine-4-carbonyl)-pyridin-2-ylamino]-imidazo[1,2-a]pyridin-6-yl}-phenyl)-1-phenyl-urea;

1-(2-Methyl-3-{8-[5-(morpholine-4-carbonyl)-pyridin-2-ylamino]-imidazo[1,2-a]pyridin-6-yl}-phenyl)-3-phenyl-urea;

1-Indan-1-yl-3-(2-methyl-3-{8-[5-(morpholine-4-carbonyl)-pyridin-2-ylamino]-imidazo[1,2-a]pyridin-6-yl}-phenyl)-urea;

1-(2-Methyl-3-{8-[5-(morpholine-4-carbonyl)-pyridin-2-ylamino]-imidazo[1,2-a]pyridin-6-yl}-phenyl)-3-(4-methyl-oxazol-2-yl)-urea;

1-(3-Chloro-phenyl)-3-(2-methyl-3-{8-[5-(morpholine-4-carbonyl)-pyridin-2-ylamino]-imidazo[1,2-a]pyridin-6-yl}-phenyl)-urea;

1-(2-Methyl-3-{8-[5-(morpholine-4-carbonyl)-pyridin-2-ylamino]-imidazo[1,2-a]pyridin-6-yl}-phenyl)-3-(2-trifluoromethyl-phenyl)-urea;

1-(4-tert-Butyl-phenyl)-3-(2-methyl-3-{8-[5-(morpholine-4-carbonyl)-pyridin-2-ylamino]-imidazo[1,2-a]pyridin-6-yl}-phenyl)-urea; and 1-(4-Methanesulfonyl-cyclohexyl)-3-(2-methyl-3-{8-[5-(morpholine-4-carbonyl)-pyridin-2-ylamino]-imidazo[1,2-a]pyridin-6-yl}-phenyl)-urea.

The application further provides the compound of formula V that is selected from the group consisting of 4-tert-Butyl-N-{3-[8-(3-ethyl-ureido)-imidazo[1,2-a]pyridin-6-yl]-2-methyl-phenyl}-benzamide;

4-tert-Butyl-N-{2-methyl-3-[8-(3-propyl-ureido)-imidazo[1,2-a]pyridin-6-yl]-phenyl}-benzamide;

4-tert-Butyl-N-{2-methyl-3-[8-(3-methyl-ureido)-imidazo[1,2-a]pyridin-6-yl]-phenyl}-benzamide;

N-[3-(8-Acetylamino-imidazo[1,2-a]pyridin-6-yl)-2-methyl-phenyl]-4-tert-butyl-benzamide;

4-(1-Hydroxy-1-methyl-ethyl)-N-{2-methyl-3-[8-(3-methyl-ureido)-imidazo[1,2-a]pyridin-6-yl]-phenyl}-benzamide;

1-(6-{3-[2-(1,3-Dihydro-isoindol-2-yl)-2-oxo-ethyl]-phenyl}-imidazo[1,2-a]pyridin-8-yl)-3-methyl-urea;

1-(6-{3-[2-(3-tert-Butoxy-azetidin-1-yl)-2-oxo-ethyl]-phenyl}-imidazo[1,2-a]pyridin-8-yl)-3-methyl-urea;

1-Methyl-3-(6-phenyl-imidazo[1,2-a]pyridin-8-yl)-urea;

4-Dimethylamino-N-{2-methyl-3-[8-(3-methyl-ureido)-imidazo[1,2-a]pyridin-6-yl]-phenyl}-benzamide;

4-Dimethylamino-N-(3-{8-[3-(2-hydroxy-ethyl)-ureido]-imidazo[1,2-a]pyridin-6-yl}-2-methyl-phenyl)-benzamide;

N-{2-Methyl-3-[8-(3-methyl-ureido)-imidazo[1,2-a]pyridin-6-yl]-phenyl}-4-trimethylsilanyl-benzamide;

4-(Cyano-dimethyl-methyl)-N-{2-methyl-3-[8-(3-methyl-ureido)-imidazo[1,2-a]pyridin-6-yl]-phenyl}-benzamide;

4-tert-Butyl-N-[2-methyl-3-(8-ureido-imidazo[1,2-a]pyridin-6-yl)-phenyl]-benzamide;

4-Dimethylamino-N-(2-methyl-3-{8-[3-(3-morpholin-4-yl-propyl)-ureido]-imidazo[1,2-a]pyridin-6-yl}-phenyl)-benzamide;

4-Dimethylamino-N-(3-{8-[3-(3-hydroxy-propyl)-ureido]-imidazo[1,2-a]pyridin-6-yl}-2-methyl-phenyl)-benzamide;

3-tert-Butoxy-azetidine-1-carboxylic acid (3-{8-[3-(3-dimethylamino-propyl)-ureido]-imidazo[1,2-a]pyridin-6-yl}-2-methyl-phenyl)-amide;

4-tert-Butyl-N-(3-{8-[3-(2-hydroxy-ethyl)-ureido]-imidazo[1,2-a]pyridin-6-yl}-2-methyl-phenyl)-benzamide;

4-Dimethylamino-N-[2-methyl-3-(8-{3-[3-(4-methyl-piperazin-1-yl)-propyl]-ureido}-imidazo[1,2-a]pyridin-6-yl)-phenyl]-benzamide;

Pyrrolidine-1-carboxylic acid {2-methyl-3-[8-(3-methyl-ureido)-imidazo[1,2-a]pyridin-6-yl]-phenyl}-amide;

4-Dimethylamino-N-{3-[8-(3-ethyl-ureido)-imidazo[1,2-a]pyridin-6-yl]-2-methyl-phenyl}-benzamide;

3-tert-Butoxy-azetidine-1-carboxylic acid {2-methyl-3-[8-(3-methyl-ureido)-imidazo[1,2-a]pyridin-6-yl]-phenyl}-amide;

Pyrrolidine-1-carboxylic acid {3-[8-(3-ethyl-ureido)-imidazo[1,2-a]pyridin-6-yl]-2-methyl-phenyl}-amide;

4-tert-Butyl-N-(3-{8-[3-(3-dimethylamino-propyl)-ureido]-imidazo[1,2-a]pyridin-6-yl}-2-methyl-phenyl)-benzamide;

4-Methoxy-N-{2-methyl-3-[8-(3-methyl-ureido)-imidazo[1,2-a]pyridin-6-yl]-phenyl}-benzamide;

N-{2-Methyl-3-[8-(3-methyl-ureido)-imidazo[1,2-a]pyridin-6-yl]-phenyl}-4-trifluoromethoxy-benzamide;

4-Ethoxy-N-{2-methyl-3-[8-(3-methyl-ureido)-imidazo[1,2-a]pyridin-6-yl]-phenyl}-benzamide;

4-Isopropoxy-N-{2-methyl-3-[8-(3-methyl-ureido)-imidazo[1,2-a]pyridin-6-yl]-phenyl}-benzamide;
N-(3-{8-[3-(3-Dimethylamino-propyl)-ureido]-imidazo[1,2-a]pyridin-6-yl}-2-methyl-phenyl)-4-(2,2,2-trifluoro-1-hydroxy-1-methyl-ethyl)-benzamide;
1,3-Dihydro-isoindole-2-carboxylic acid {2-methyl-3-[8-(3-methyl-ureido)-imidazo[1,2-a]pyridin-6-yl]-phenyl}-amide;
4-tert-Butyl-N-[2-methyl-3-(8-{3-[3-(4-methyl-piperazin-1-yl)-propyl]-ureido}-imidazo[1,2-a]pyridin-6-yl)-phenyl]-benzamide;
3-(2,2,2-Trifluoro-1-trifluoromethyl-ethoxy)-azetidine-1-carboxylic acid {2-methyl-3-[8-(3-methyl-ureido)-imidazo[1,2-a]pyridin-6-yl]-phenyl}-amide;
{2-Methyl-3-[8-(3-methyl-ureido)-imidazo[1,2-a]pyridin-6-yl]-phenyl}-carbamic acid 4,4-dimethyl-pent-2-ynyl ester;
1-(6-{3-[3-(4,4-Dimethyl-pent-2-ynyl)-ureido]-2-methyl-phenyl}-imidazo[1,2-a]pyridin-8-yl)-3-methyl-urea;
N-(3-{8-[3-(3-Dimethylamino-propyl)-ureido]-imidazo[1,2-a]pyridin-6-yl}-2-methyl-phenyl)-4-(2,2,2-trifluoro-1-hydroxy-1-trifluoromethyl-ethyl)-benzamide;
N-(4,4-Dimethyl-pent-2-ynyl)-2-{3-[8-(3-methyl-ureido)-imidazo[1,2-a]pyridin-6-yl]-phenyl}-acetamide;
4-tert-Butyl-N-(3-{8-[3-(3-imidazol-1-yl-propyl)-ureido]-imidazo[1,2-a]pyridin-6-yl}-2-methyl-phenyl)-benzamide;
3-Isopropoxy-azetidine-1-carboxylic acid {2-methyl-3-[8-(3-methyl-ureido)-imidazo[1,2-a]pyridin-6-yl]-phenyl}-amide;
4-tert-Butyl-N-[3-(8-{3-[3-(4-methanesulfonyl-piperazin-1-yl)-propyl]-ureido}-imidazo[1,2-a]pyridin-6-yl)-2-methyl-phenyl]-benzamide;
4-tert-Butyl-N-[3-(8-{3-[3-(4-methanesulfonyl-piperazin-1-yl)-propyl]-ureido}-imidazo[1,2-a]pyridin-6-yl)-2-methyl-phenyl]-benzamide;
4-tert-Butyl-N-(2-methyl-3-{8-[3-(3-thiomorpholin-4-yl-propyl)-ureido]-imidazo[1,2-a]pyridin-6-yl}-phenyl)-benzamide;
4-Cyclopropyl-N-{3-[8-(3-ethyl-ureido)-imidazo[1,2-a]pyridin-6-yl]-2-hydroxymethyl-phenyl}-benzamide;
4-Cyclopropyl-N-(3-{8-[3-(3-dimethylamino-propyl)-ureido]-imidazo[1,2-a]pyridin-6-yl}-2-hydroxymethyl-phenyl)-benzamide; and
4-Cyclopropyl-N-{2-hydroxymethyl-3-[8-(3-methyl-ureido)-imidazo[1,2-a]pyridin-6-yl]-phenyl}-benzamide.

The application further provides the compound of formula VI that is 1-(6-Cyclohex-1-enyl-imidazo[1,2-a]pyridin-8-yl)-3-methyl-urea.

In one aspect, the present application provides a method for treating an inflammatory and/or autoimmune condition comprising administering to a patient in need thereof a therapeutically effective amount of any of the above Btk inhibitor compounds of formulae I-VI.

In one aspect, the present application provides a method for treating an arthritis comprising administering to a patient in need thereof a therapeutically effective amount of any of the above Btk inhibitor compounds of formulae I-VI.

In one aspect, the present application provides a method of inhibiting B-cell proliferation comprising administering to a patient in need thereof a therapeutically effective amount of any of the above Btk inhibitor compounds of formulae I-VI.

In one aspect, the present application provides a method for inhibiting Btk activity comprising administering any of the above Btk inhibitor compounds of formulae I-VI, wherein the Btk inhibitor compound exhibits an $IC_{50}$ of 50 micromolar or less in an in vitro biochemical assay of Btk activity.

In one aspect, the present application provides the above method, wherein the Btk inhibitor compound exhibits an $IC_{50}$ of 100 nanomolar or less in an in vitro biochemical assay of Btk activity.

In one aspect, the present application provides the above method, wherein the compound exhibits an $IC_{50}$ of 10 nanomolar or less in an in vitro biochemical assay of Btk activity.

In one aspect, the present application provides a method for treating an inflammatory condition comprising co-administering to a patient in need thereof a therapeutically effective amount of an anti-inflammatory compound in combination with any of the above Btk inhibitor compounds of formulae I-VI.

In one aspect, the present application provides a method for treating arthritis comprising co-administering to a patient in need thereof a therapeutically effective amount of an anti-inflammatory compound in combination with of any of the above Btk inhibitor compounds of formulae I-VI.

In one aspect, the present application provides a method for treating a lymphoma or a BCR-ABL1+ leukemia cells by administering to a patient in need thereof a therapeutically effective amount of any of the above Btk inhibitor compounds of formulae I-VI.

In one aspect, the present application provides a pharmaceutical composition comprising any of the above Btk inhibitor compounds of formulae I-VI, admixed with at least one pharmaceutically acceptable carrier, excipient or diluent.

The compounds of formulae I-VI inhibit Bruton's tyrosine kinase (Btk). Activation of Btk by upstream kinases results in activation of phospholipase-Cγ which, in turn, stimulates release of pro-inflammatory mediators. Compounds of formulae I-VI are useful in the treatment of arthritis and other anti-inflammatory and auto-immune diseases. Compounds according to formulae I-VI are, according, useful for the treatment of arthritis. Compounds of formulae I-VI are useful for inhibiting Btk in cells and for modulating B-cell development. The present invention further comprises pharmaceutical compositions containing compounds of formulae I-VI admixed with pharmaceutically acceptable carrier, excipients or diluents.

DETAILED DESCRIPTION OF THE INVENTION

This application discloses novel imidazo[1,2-a]pyridine and imidazo[1,2-b]pyridazine derivatives according to Formulae I-VI:

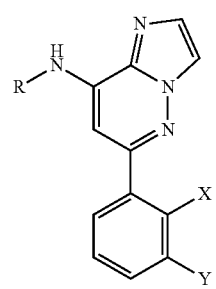

I

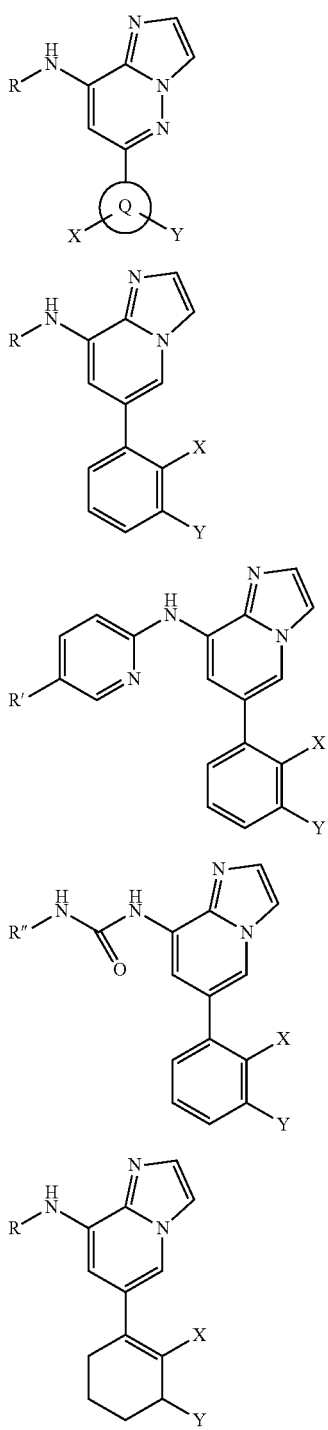

wherein R, R', R", Q, X, and Y are defined as described herein, which inhibit Btk. The compounds disclosed herein are useful to modulate the activity of Btk and treat diseases associated with excessive Btk activity. The compounds are further useful to treat inflammatory and auto immune diseases associated with aberrant B-cell proliferation such as rheumatoid arthritis. Also disclosed are compositions containing compounds of Formulae I-VI and at least one carrier, diluent or excipient.

The phrase "as defined herein above" refers to the broadest definition for each group as provided in the Summary of the Invention or the broadest claim. In all other aspects, variations and embodiments provided, substituents which can be present in each embodiment and which are not explicitly defined retain the broadest definition provided in the Summary of the Invention.

The compounds of Formulae I-VI inhibit Bruton's tyrosine kinase (Btk). Activation of Btk by upstream kinases results in activation of phospholipase-Cγ which, in turn, stimulates release of pro-inflammatory mediators. The compounds of Formulae I-VI incorporating 2-amino pyridine or urea sidechains at the 8-position on the imidazopyridine and imidazopyridazine ring systems in particular exhibit unexpectedly enhanced inhibitory activity compared to analogues with other side chains. The compounds of Formulae I-VI, wherein X is o-hydroxymethyl in particular exhibit unexpectedly enhanced inhibitory activity. Compounds of Formulae I-VI are useful in the treatment of arthritis and other anti-inflammatory and auto-immune diseases. Compounds according to Formulae I-VI are, according, useful for the treatment of arthritis. Compounds of Formulae I-VI are useful for inhibiting Btk in cells and for modulating B-cell development. The present invention further comprises pharmaceutical compositions containing compounds of Formulae I-VI admixed with pharmaceutically acceptable carrier, excipients or diluents.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R, $R^1$, $R^2$, $R^2$, $R^4$, $R^5$, $R^6$, $R^7$, Q, X, Y, or A) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-" drawn through a bond each refer to the point of attachment of a functional group or other chemical moiety to the rest of the molecule of which it is a part. Thus, for example:

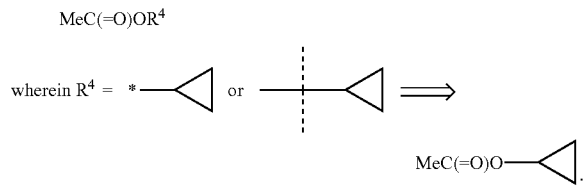

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of formulae I-VI may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. $C_{1-6}$ alkoxyalkyl denotes a group wherein the alkyl portion is comprised of 1-6 carbon atoms exclusive of carbon atoms in the alkoxy portion of the group. $C_{1-3}$ alkoxy-$C_{1-6}$ alkyl denotes a group wherein the alkyl portion is comprised of 1-6 carbon atoms and the alkoxy group is 1-3 carbons. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl including their isomers.

The term "hydroxyalkyl" as used herein denotes an alkyl radical as herein defined wherein one to three hydrogen atoms on different carbon atoms is/are replaced by hydroxyl groups.

The terms "alkylsulfonyl" or "lower alkyl sulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocycloalkyl" or "heterocycle" as used herein denotes a monovalent saturated cyclic radical, consisting of one or more rings, preferably one to two rings, of three to eight atoms per ring, incorporating one or more ring heteroatoms (chosen from N,O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), ethylene glycol dimethyl ether (DME), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

Compounds and Preparation

Examples of representative compounds encompassed by the present invention and within the scope of the invention are provided in the following Tables. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v. 4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE X

| Cmpd. No. | Structure | | MS | MP |
|---|---|---|---|---|
| I-1 | 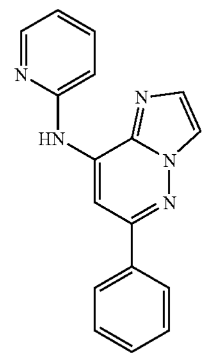 [SMILES: c1ccc(-c2cc(Nc3ccccn3)c3nccn3n2)cc1] | (6-Phenyl-imidazol[1,2-b]pyridazin-8-yl)-pyridin-2-yl-amine | 288 | |
| I-2 | 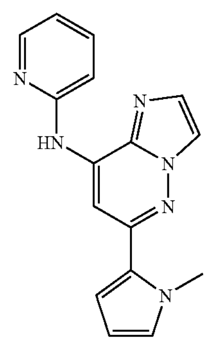 [SMILES: Cn1cccc1-c1cc(Nc2ccccn2)c2nccn2n1] | [6-(1-Methyl-1H-pyrrol-2-yl)-imidazo[1,2-b]pyridazin-8-yl]-pyridin-2-yl-amine | 291 | |
| I-3 | 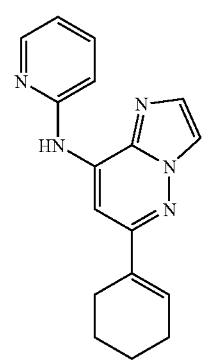 [SMILES: C1=C(c2cc(Nc3ccccn3)c3nccn3n2)CCCC1] | (6-Cyclohex-1-enyl-imidazo[1,2-b]pyridazin-8-yl)-pyridin-2-yl-amine | 292 | 160.7-161.5 |

TABLE X-continued

| Cmpd. No. | Structure | | MS | MP |
|---|---|---|---|---|
| I-4 | 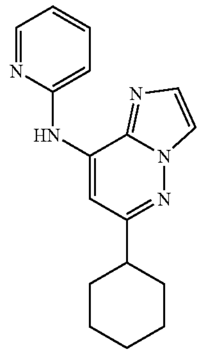 [SMILES: c1ccc(Nc2cc(C3CCCCC3)nn3ccnc23)nc1] | (6-Cyclohexyl-imidazo[1,2-b]pyridazin-8-yl)-pyridin-2-yl-amine | 294 | |
| I-5 | 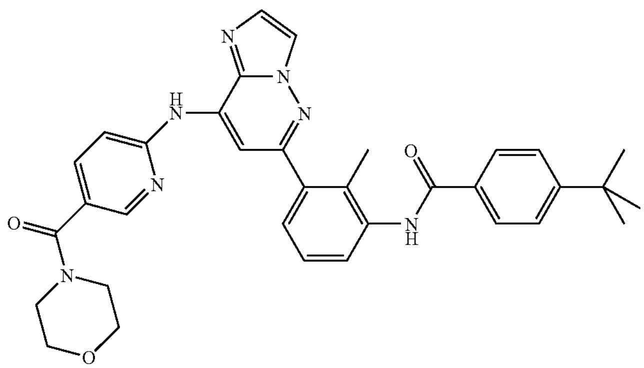 [SMILES: Cc1c(NC(=O)c2ccc(C(C)(C)C)cc2)cccc1-c1cc(Nc2ccc(C(=O)N3CCOCC3)cn2)c2nccn2n1] | 4-tert-Butyl-N-(2-methyl-3-{8-[5-(morpholine-4-carbonyl)-pyridin-2-ylamino]-imidazo[1,2-b]pyridazin-6-yl}-phenyl)-benzamide | 590 | |
| I-6 | 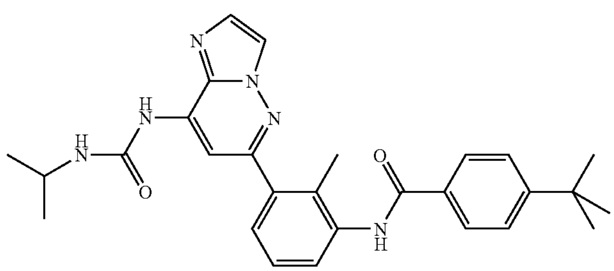 [SMILES: Cc1c(NC(=O)c2ccc(C(C)(C)C)cc2)cccc1-c1cc(NC(=O)NC(C)C)c2nccn2n1] | 4-tert-Butyl-N-{3-[8-(3-isopropyl-ureido)-imidazo[1,2-b]pyridazin-6-yl]-2-methyl-phenyl}-benzamide | 485 | 178.0-180.0 |
| I-7 | 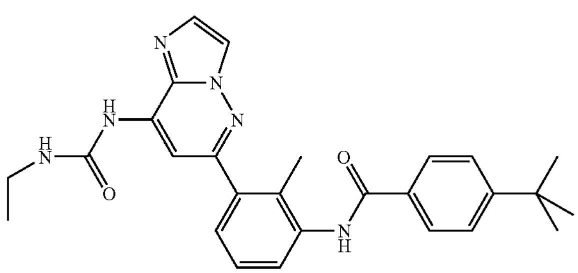 | 4-tert-Butyl-N-{3-[8-(3-ethyl-ureido)-imidazo[1,2-b]pyridazin-6-yl]-2-methyl-phenyl}-benzamide | 471 | 181.0-183.0 |
| I-8 | 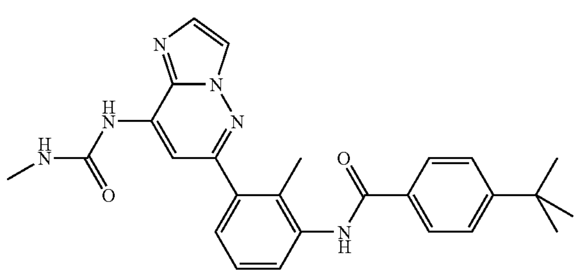 [SMILES: CNC(=O)Nc1cc(-c2cccc(NC(=O)c3ccc(C(C)(C)C)cc3)c2C)nn2ccnc12] | 4-tert-Butyl-N-{2-methyl-3-[8-(3-methyl-ureido)-imidazo[1,2-b]pyridazin-6-yl]-phenyl}-benzamide | 457 | 163.0-165.0 |

TABLE X-continued

| Cmpd. No. | Structure | | MS | MP |
|---|---|---|---|---|
| I-9 | 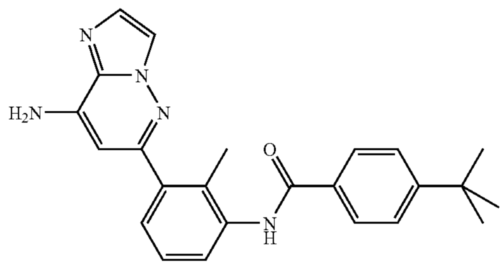 [SMILES: Cc1c(NC(=O)c2ccc(C(C)(C)C)cc2)cccc1-c1cc(N)c2nccn2n1] | N-[3-(8-Amino-imidazo[1,2-b]pyridazin-6-yl)-2-methyl-phenyl]-4-tert-butyl-benzamide | 400 | |
| I-10 | 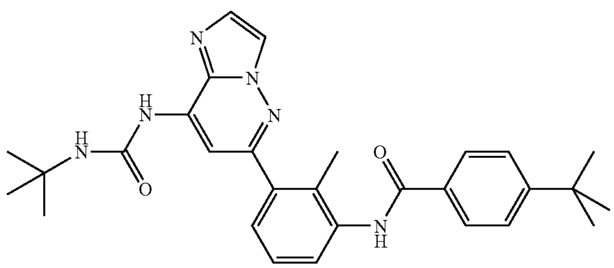 [SMILES: Cc1c(NC(=O)c2ccc(C(C)(C)C)cc2)cccc1-c1cc(NC(=O)NC(C)(C)C)c2nccn2n1] | 4-tert-Butyl-N-{3-[8-(3-tert-butyl-ureido)-imidazo[1,2-b]pyridazin-6-yl]-2-methyl-phenyl}-benzamide | 499 | 191.0-193.0 |
| I-11 | 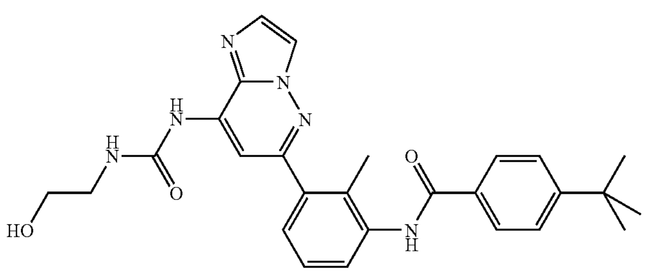 [SMILES: Cc1c(NC(=O)c2ccc(C(C)(C)C)cc2)cccc1-c1cc(NC(=O)NCCO)c2nccn2n1] | 4-tert-Butyl-N-(3-{8-[3-(2-hydroxy-ethyl)-ureido]-imidazo[1,2-b]pyridazin-6-yl}-2-methyl-phenyl)-benzamide | 487 | 183.0-184.0 |
| I-12 | 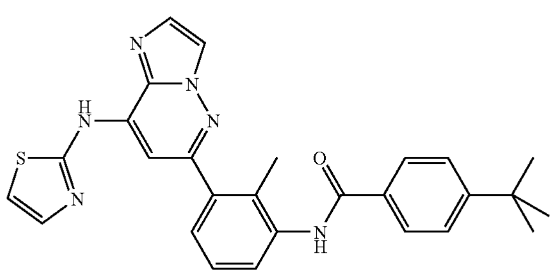 [SMILES: Cc1c(NC(=O)c2ccc(C(C)(C)C)cc2)cccc1-c1cc(Nc2nccs2)c2nccn2n1] | 4-tert-Butyl-N-{2-methyl-3-[8-(thiazol-2-ylamino)-imidazo[1,2-b]pyridazin-6-yl]-phenyl}-benzamide | 483 | 178.0-179.0 |
| I-13 | 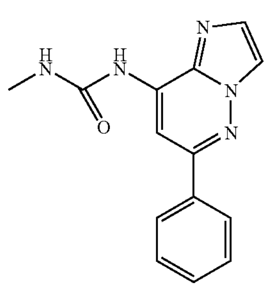 [SMILES: CNC(=O)Nc1cc(-c2ccccc2)nn2ccnc12] | 1-Methyl-3-(6-phenyl-imidazo[1,2-b]pyridazin-8-yl)-urea | 268 | 192.0-193.0 |

TABLE X-continued

| Cmpd. No. | Structure | | MS | MP |
|---|---|---|---|---|
| I-14 | 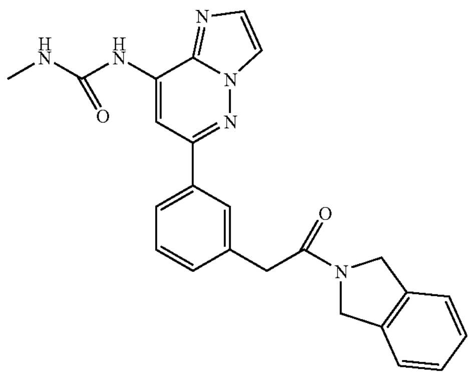 | 1-(6-{3-[2-(1,3-Dihydro-isoindol-2-yl)-2-oxo-ethyl]-phenyl}-imidazo[1,2-b]pyridazin-8-yl)-3-methyl-urea | 427 | 244.0–245.0 |
| I-15 | 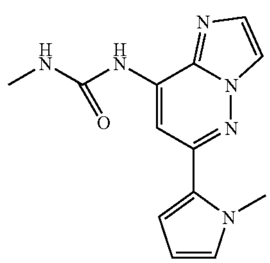 | 1-Methyl-3-[6-(1-methyl-1H-pyrrol-2-yl)-imidazo[1,2-b]pyridazin-8-yl]-urea | 271 | |
| I-16 | 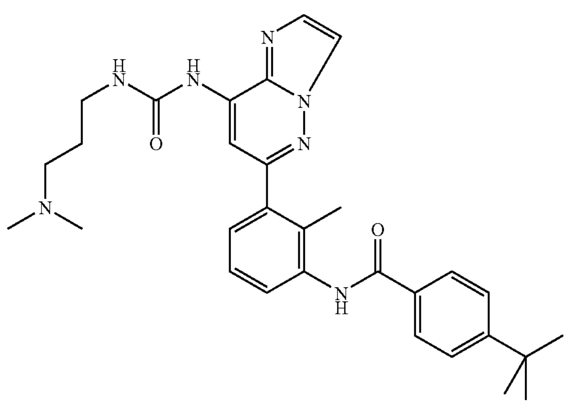 [SMILES: Cc1c(NC(=O)c2ccc(C(C)(C)C)cc2)cccc1-c1cc(NC(=O)NCCCN(C)C)c2nccn2n1] | 4-tert-Butyl-N-(3-{8-[3-(3-dimethylamino-propyl)-ureido]-imidazo[1,2-b]pyridazin-6-yl}-2-methyl-phenyl)-benzamide | | |
| I-17 | 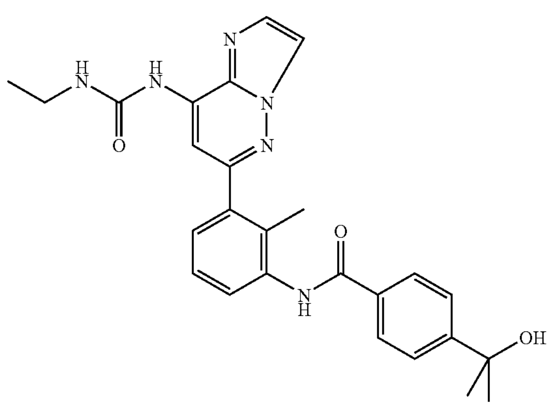 [SMILES: CCNC(=O)Nc1cc(-c2cccc(NC(=O)c3ccc(C(C)(C)O)cc3)c2C)nn2ccnc12] | N-{3-[8-(3-Ethyl-ureido)-imidazo[1,2-b]pyridazin-6-yl]-2-methyl-phenyl}-4-(1-hydroxy-1-methyl-ethyl)-benzamide | | |

TABLE X-continued
| Cmpd. No. | Structure | MS | MP |
|---|---|---|---|
| I-18 | 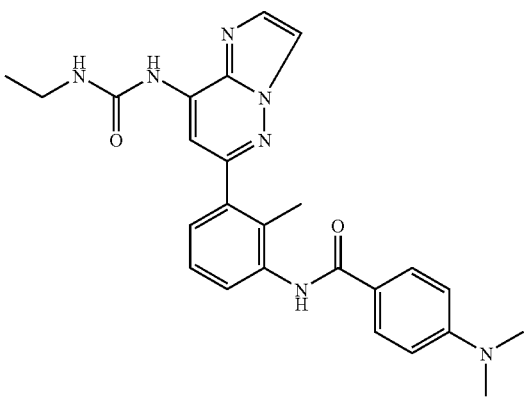 [SMILES: CCNC(=O)Nc1cc(-c2cccc(NC(=O)c3ccc(N(C)C)cc3)c2C)nn2ccnc12] | 4-Dimethylamino-N-{3-[8-(3-ethyl-ureido)-imidazo[1,2-b]pyridazin-6-yl]-2-methyl-phenyl}-benzamide | |
| I-19 | 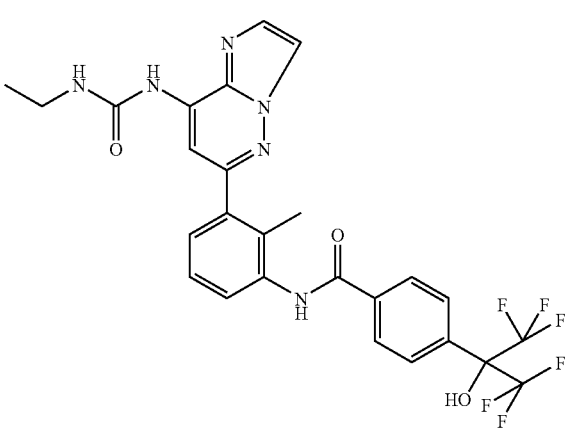 [SMILES: CCNC(=O)Nc1cc(-c2cccc(NC(=O)c3ccc(C(O)(C(F)(F)F)C(F)(F)F)cc3)c2C)nn2ccnc12] | N-{3-[8-(3-Ethyl-ureido)-imidazo[1,2-b]pyridazin-6-yl]-2-methyl-phenyl}-4-(2,2,2-trifluoro-1-hydroxy-1-trifluoromethyl-ethyl)-benzamide | |
| I-20 | 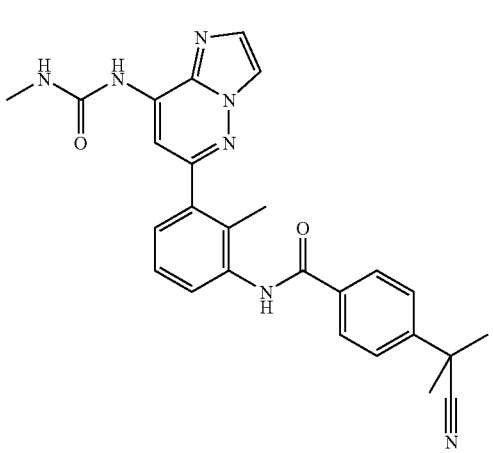 [SMILES: CNC(=O)Nc1cc(-c2cccc(NC(=O)c3ccc(C(C)(C)C#N)cc3)c2C)nn2ccnc12] | 4-(Cyano-dimethyl-methyl)-N-{2-methyl-3-[8-(3-methyl-ureido)-imidazo[1,2-b]pyridazin-6-yl]-phenyl}-benzamide | |

TABLE X-continued
| Cmpd. No. | Structure | MS | MP |
|---|---|---|---|
| I-21 | 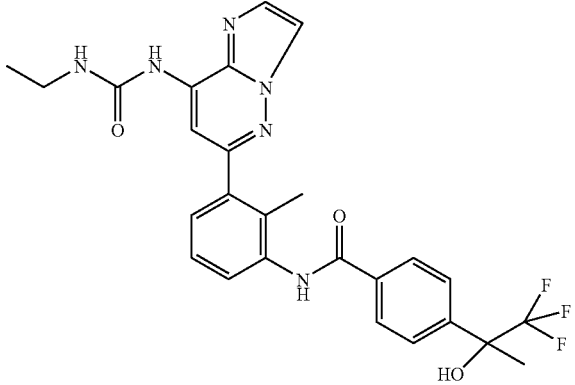 [SMILES: CCNC(=O)Nc1cc(-c2cccc(NC(=O)c3ccc(C(C)(O)C(F)(F)F)cc3)c2C)nn2ccnc12] N-{3-[8-(3-Ethyl-ureido)-imidazo[1,2-b]pyridazin-6-yl]-2-methyl-phenyl}-4-(2,2,2-trifluoro-1-hydroxy-1-methyl-ethyl)-benzamide | | |
| I-22 | 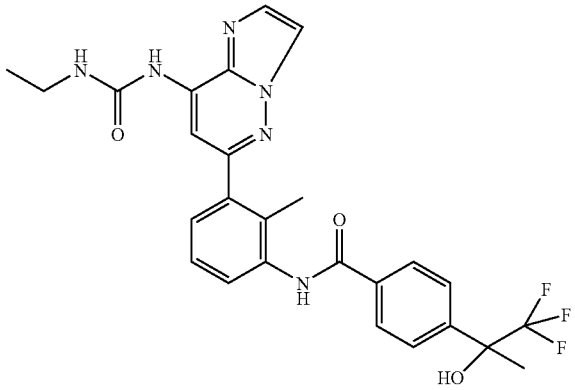 [SMILES: CCNC(=O)Nc1cc(-c2cccc(NC(=O)c3ccc(C(C)(O)C(F)(F)F)cc3)c2C)nn2ccnc12] N-{3-[8-(3-Ethyl-ureido)-imidazo[1,2-b]pyridazin-6-yl]-2-methyl-phenyl}-4-(2,2,2-trifluoro-1-hydroxy-1-methyl-ethyl)-benzamide | | |
| I-23 | 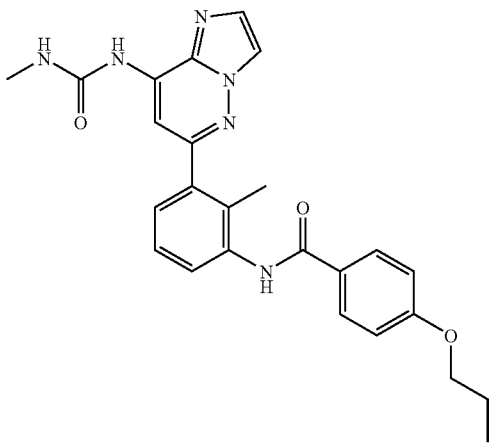 [SMILES: CCCOc1ccc(C(=O)Nc2cccc(-c3cc(NC(=O)NC)c4nccn4n3)c2C)cc1] N-{2-Methyl-3-[8-(3-methyl-ureido)-imidazo[1,2-b]pyridazin-6-yl]-phenyl}-4-propoxy-benzam | | |

TABLE X-continued

| Cmpd. No. | Structure | MS | MP |
|---|---|---|---|
| I-24 | 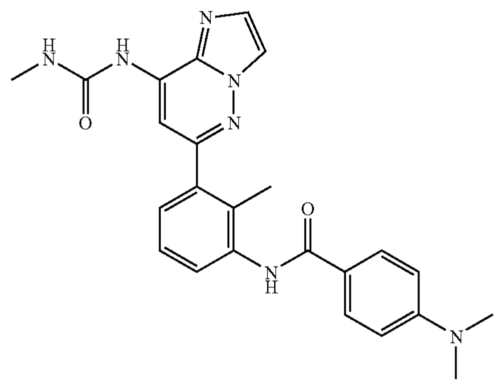 | 4-Dimethylamino-N-{2-methyl-3-[8-(3-methyl-ureido)-imidazo[1,2-b]pyridazin-6-yl]-phenyl}-benzamide | |
| I-25 | 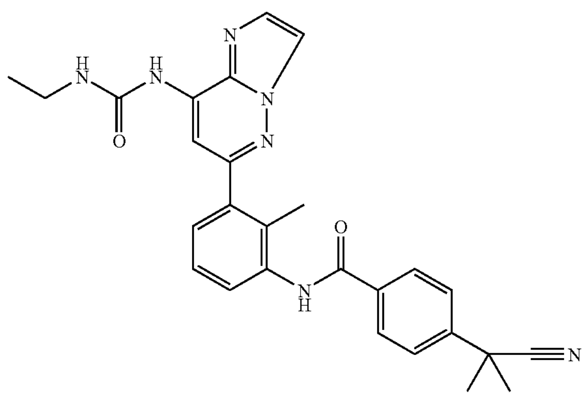 [SMILES: CCNC(=O)Nc1cc(-c2cccc(NC(=O)c3ccc(C(C)(C)C#N)cc3)c2C)nn2ccnc12] | 4-(Cyano-dimethyl-methyl)-N-{3-[8-(3-ethyl-ureido)-imidazo[1,2-b]pyridazin-6-yl]-2-methyl-phenyl}-benzamide | |
| I-26 | 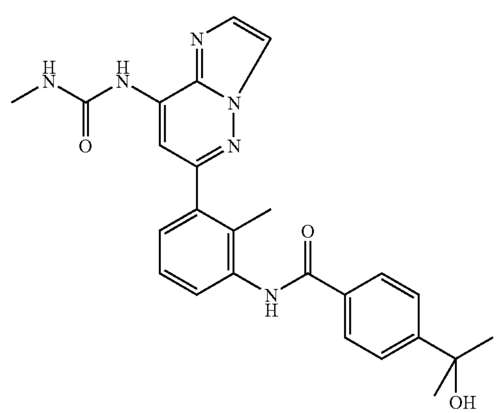 [SMILES: CNC(=O)Nc1cc(-c2cccc(NC(=O)c3ccc(C(C)(C)O)cc3)c2C)nn2ccnc12] | 4-(1-Hydroxy-1-methyl-ethyl)-N-{2-methyl-3-[8-(3-methyl-ureido)-imidazo[1,2-b]pyridazin-6-yl]-phenyl}-benzamide | |
| I-27 | 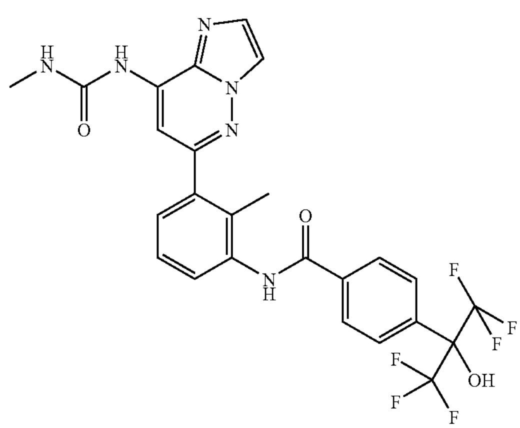 [SMILES: CNC(=O)Nc1cc(-c2cccc(NC(=O)c3ccc(C(O)(C(F)(F)F)C(F)(F)F)cc3)c2C)nn2ccnc12] | N-{2-Methyl-3-[8-(3-methyl-ureido)-imidazo[1,2-b]pyridazin-6-yl]-phenyl}-4-(2,2,2-trifluoro-1-hydroxy-1-trifluoromethyl-ethyl)-benzamide | |

TABLE X-continued

| Cmpd. No. | Structure | MS | MP |
|---|---|---|---|
| I-28 | 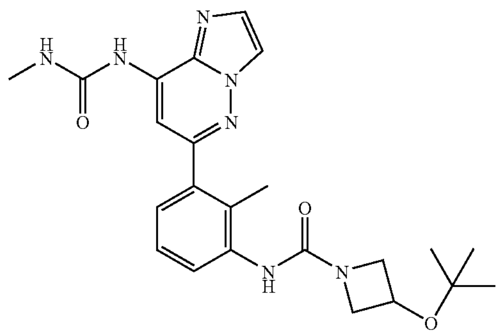 [SMILES: CNC(=O)Nc1cc(-c2cccc(NC(=O)N3CC(OC(C)(C)C)C3)c2C)nn2ccnc12] | 3-tert-Butoxy-azetidine-1-carboxylic acid {2-methyl-3-[8-(3-methyl-ureido)-imidazo[1,2-b]pyridazin-6-yl]-phenyl}-amide | |
| I-29 | 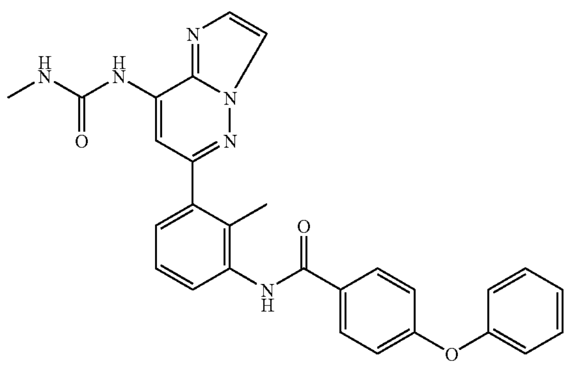 [SMILES: CNC(=O)Nc1cc(-c2cccc(NC(=O)c3ccc(Oc4ccccc4)cc3)c2C)nn2ccnc12] | N-{2-Methyl-3-[8-(3-methyl-ureido)-imidazo[1,2-b]pyridazin-6-yl]-phenyl}-4-phenoxy-benzamide | |
| I-30 | 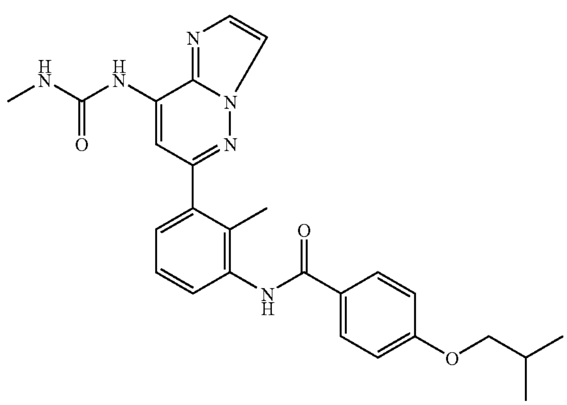 [SMILES: CNC(=O)Nc1cc(-c2cccc(NC(=O)c3ccc(OCC(C)C)cc3)c2C)nn2ccnc12] | 4-Isobutoxy-N-{2-methyl-3-[8-(3-methyl-ureido)-imidazo[1,2-b]pyridazin-6-yl]-phenyl}-benzamide | |
| I-31 | 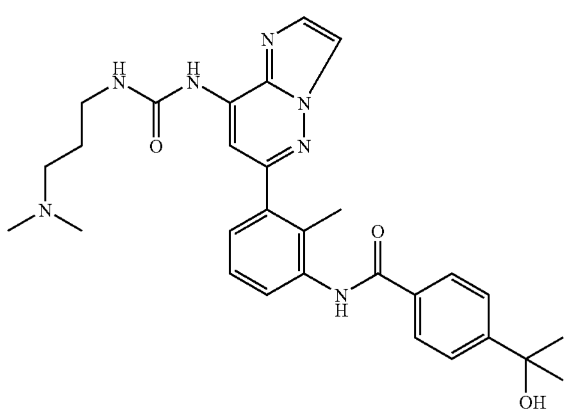 [SMILES: Cc1c(NC(=O)c2ccc(C(C)(C)O)cc2)cccc1-c1cc(NC(=O)NCCCN(C)C)c2nccn2n1] | N-(3-{8-[3-(3-Dimethylamino-propyl)-ureido]-imidazo[1,2-b]pyridazin-6-yl}-2-methyl-phenyl)-4-(1-hydroxy-1-methyl-ethyl)-benzamide | |

TABLE X-continued

| Cmpd. No. | Structure | MS | MP |
|---|---|---|---|
| I-32 | 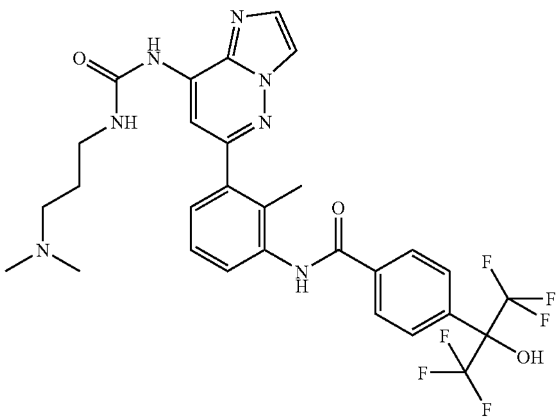 [SMILES: Cc1c(NC(=O)c2ccc(C(O)(C(F)(F)F)C(F)(F)F)cc2)cccc1-c1cc(NC(=O)NCCCN(C)C)c2nccn2n1] | N-(3-{8-[3-(3-Dimethylamino-propyl)-ureido]-imidazo[1,2-b]pyridazin-6-yl}-2-methyl-phenyl)-4-(2,2,2-trifluoro-1-hydroxy-1-trifluoromethyl-ethyl)-benzamide | |
| I-33 | 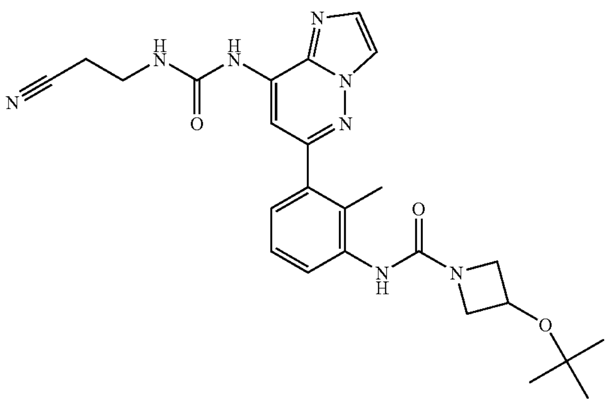 [SMILES: Cc1c(NC(=O)N2CC(OC(C)(C)C)C2)cccc1-c1cc(NC(=O)NCCC#N)c2nccn2n1] | 3-tert-Butoxy-azetidine-1-carboxylic acid (3-{8-[3-(2-cyano-ethyl)-ureido]-imidazo[1,2-b]pyridazin-6-yl}-2-methyl-phenyl)-amide | |
| I-34 | 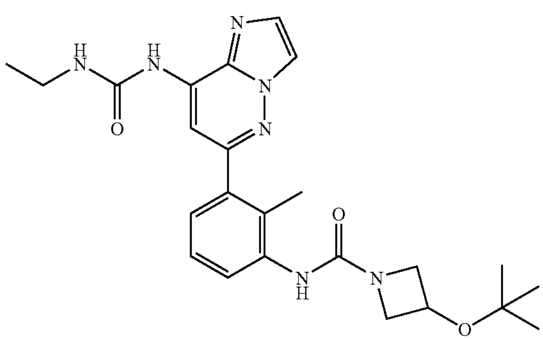 [SMILES: CCNC(=O)Nc1cc(-c2cccc(NC(=O)N3CC(OC(C)(C)C)C3)c2C)nn2ccnc12] | 3-tert-Butoxy-azetidine-1-carboxylic acid {3-[8-(3-ethyl-ureido)-imidazo[1,2-b]pyridazin-6-yl]-2-methyl-phenyl}-amide | |
| I-35 | 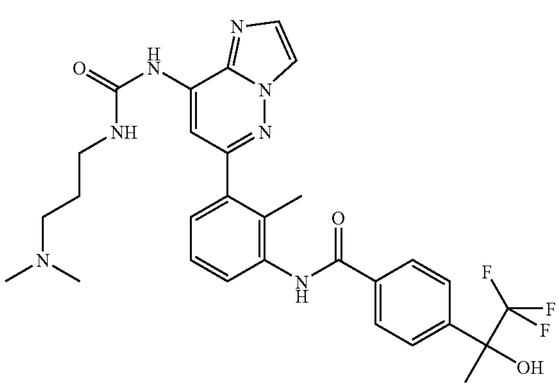 [SMILES: Cc1c(NC(=O)c2ccc(C(C)(O)C(F)(F)F)cc2)cccc1-c1cc(NC(=O)NCCCN(C)C)c2nccn2n1] | N-(3-{8-[3-(3-Dimethylamino-propyl)-ureido]-imidazo[1,2-b]pyridazin-6-yl}-2-methyl-phenyl)-4-(2,2,2-trifluoro-1-hydroxy-1-methyl-ethyl)-benzamide | |

TABLE X-continued

| Cmpd. No. | Structure | MS | MP |
|---|---|---|---|
| I-36 | 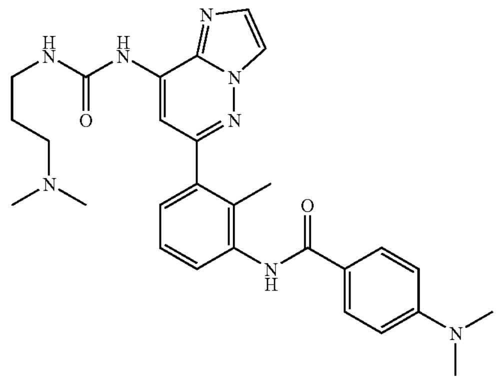 [SMILES: Cc1c(NC(=O)c2ccc(N(C)C)cc2)cccc1-c1cc(NC(=O)NCCCN(C)C)c2nccn2n1] | | 4-Dimethylamino-N-(3-{8-[3-(3-dimethylamino-propyl)-ureido]-imidazo[1,2-b]pyridazin-6-yl}-2-methyl-phenyl)-benzamide |
| I-37 | 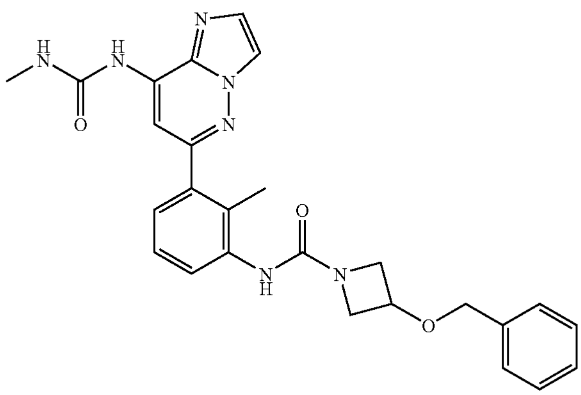 [SMILES: CNC(=O)Nc1cc(-c2cccc(NC(=O)N3CC(OCc4ccccc4)C3)c2C)nn2ccnc12] | | 3-Benzyloxy-azetidine-1-carboxylic acid {2-methyl-3-[8-(3-methyl-ureido)-imidazo[1,2-b]pyridazin-6-yl]-phenyl}-amide |
| I-38 | 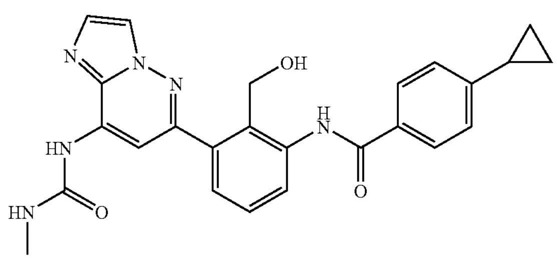 [SMILES: CNC(=O)Nc1cc(-c2cccc(NC(=O)c3ccc(C4CC4)cc3)c2CO)nn2ccnc12] | | 4-Cyclopropyl-N-{2-hydroxymethyl-3-[8-(3-methyl-ureido)-imidazo[1,2-b]pyridazin-6-yl]-phenyl}-benzamide |
| I-39 | 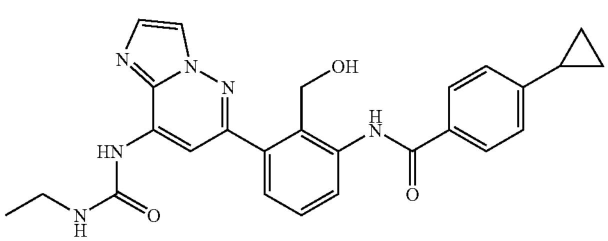 [SMILES: CCNC(=O)Nc1cc(-c2cccc(NC(=O)c3ccc(C4CC4)cc3)c2CO)nn2ccnc12] | | 4-Cyclopropyl-N-{3-[8-(3-ethyl-ureido)-imidazo[1,2-b]pyridazin-6-yl]-2-hydroxymethyl-phenyl}-benzamide |
| I-40 | 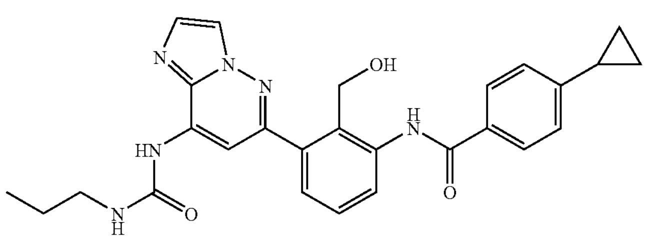 [SMILES: CCCNC(=O)Nc1cc(-c2cccc(NC(=O)c3ccc(C4CC4)cc3)c2CO)nn2ccnc12] | | 4-Cyclopropyl-N-{2-hydroxymethyl-3-[8-(3-propyl-ureido)-imidazo[1,2-b]pyridazin-6-yl]-phenyl}-benzamide |

TABLE X-continued

| Cmpd. No. | Structure | MS | MP |
|---|---|---|---|
| I-41 | 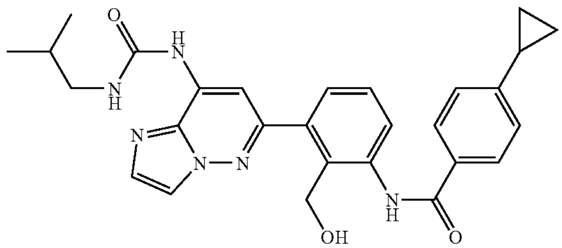 [SMILES: CC(C)CNC(=O)Nc1cc(-c2cccc(NC(=O)c3ccc(C4CC4)cc3)c2CO)nn2ccnc12] | | 4-Cyclopropyl-N-{2-hydroxymethyl-3-[8-(3-isobutyl-ureido)-imidazo[1,2-b]pyridazin-6-yl]-phenyl}-benzamide |
| I-42 | 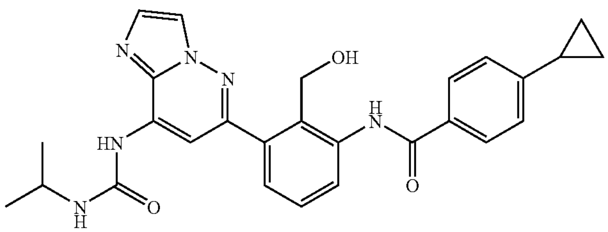 | | 4-Cyclopropyl-N-{2-hydroxymethyl-3-[8-(3-isopropyl-ureido)-imidazo[1,2-b]pyridazin-6-yl]-phenyl}-benzamide |
| I-43 | 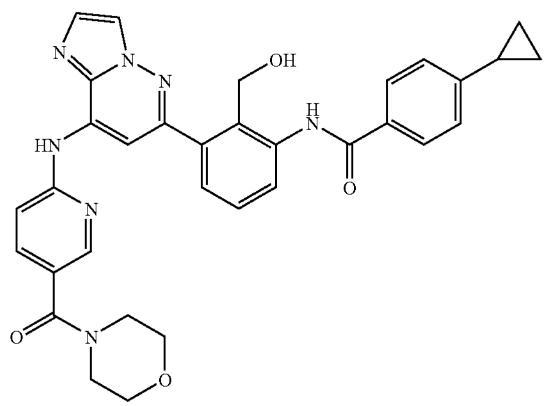 [SMILES: O=C(Nc1cccc(-c2cc(Nc3ccc(C(=O)N4CCOCC4)cn3)c3nccn3n2)c1CO)c1ccc(C2CC2)cc1] | | 4-Cyclopropyl-N-(2-hydroxymethyl-3-{8-[5-(morpholine-4-carbonyl)-pyridin-2-ylamino]-imidazo[1,2-b]pyridazin-6-yl}-phenyl)-benzamide |
| I-44 | 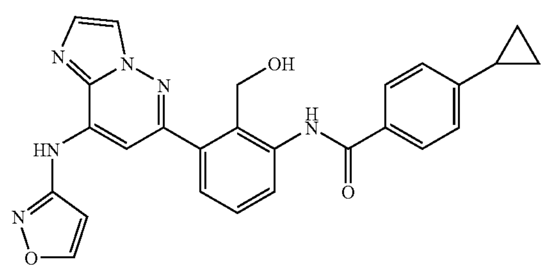 [SMILES: O=C(Nc1cccc(-c2cc(Nc3ccon3)c3nccn3n2)c1CO)c1ccc(C2CC2)cc1] | | 4-Cyclopropyl-N-{2-hydroxymethyl-3-[8-(isoxazol-3-ylamino)-imidazo[1,2-b]pyridazin-6-yl]-phenyl}-benzamide |
| I-45 | 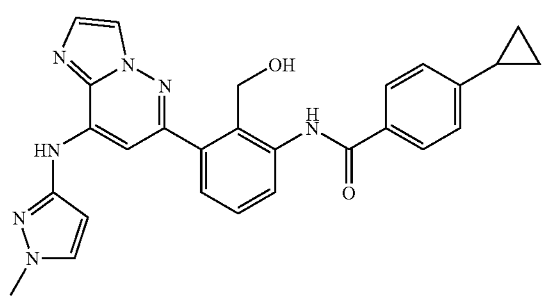 [SMILES: Cn1ccc(Nc2cc(-c3cccc(NC(=O)c4ccc(C5CC5)cc4)c3CO)nn3ccnc23)n1] | | 4-Cyclopropyl-N-{2-hydroxymethyl-3-[8-(1-methyl-1H-pyrazol-3-ylamino)-imidazo[1,2-b]pyridazin-6-yl]-phenyl}-benzamide |

TABLE X-continued

| Cmpd. No. | Structure | | MS | MP |
|---|---|---|---|---|
| I-46 | 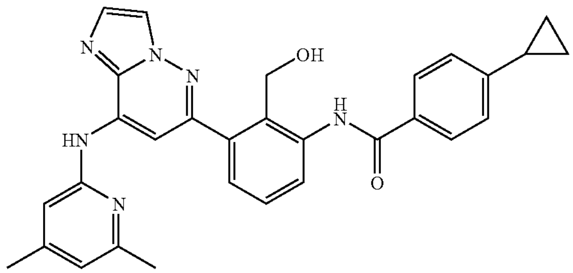 [SMILES: Cc1cc(C)nc(Nc2cc(-c3cccc(NC(=O)c4ccc(C5CC5)cc4)c3CO)nn3ccnc23)c1] | 4-Cyclopropyl-N-{3-[8-(4,6-dimethyl-pyridin-2-ylamino)-imidazo[1,2-b]pyridazin-6-yl]-2-hydroxymethyl-phenyl}-benzamide | | |

TABLE Y

| # | Structure | | MS | MP |
|---|---|---|---|---|
| I-47 | 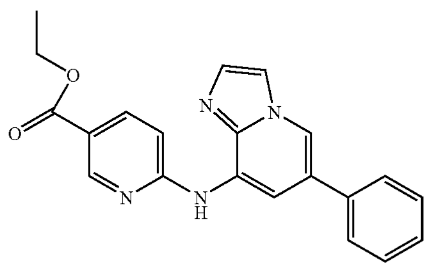 [SMILES: CCOC(=O)c1ccc(Nc2cc(-c3ccccc3)cn3ccnc23)nc1] | 6-(6-Phenyl-imidazo[1,2-a]pyridin-8-ylamino)-nicotinic acid ethyl ester | | 141.5-42.5 |
| I-48 | 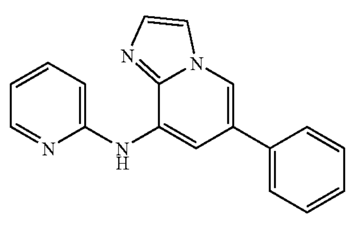 [SMILES: c1ccc(-c2cc(Nc3ccccn3)c3nccn3c2)cc1] | (6-Phenyl-imidazo[1,2-a]pyridin-8-yl)-pyridin-2-yl-amine | 287 | |
| I-49 | 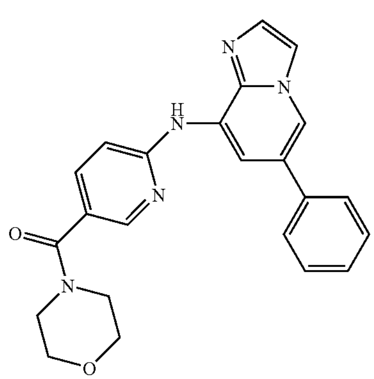 [SMILES: O=C(c1ccc(Nc2cc(-c3ccccc3)cn3ccnc23)nc1)N1CCOCC1] | Morpholin-4-yl-[6-(6-phenyl-imidazo[1,2-a]pyridin-8-ylamino)-pyridin-3-yl]-methanone | 400 | |

TABLE Y-continued

| # | Structure | | MS | MP |
|---|---|---|---|---|
| I-50 | 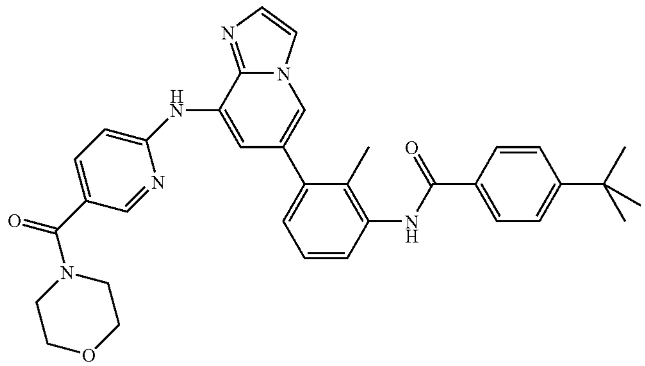 | 4-tert-Butyl-N-(2-methyl-3-{8-[5-(morpholine-4-carbonyl)-pyridin-2-ylamino]-imidazo[1,2-a]pyridin-6-yl}-phenyl)-benzamide | 589 | |
| I-51 | 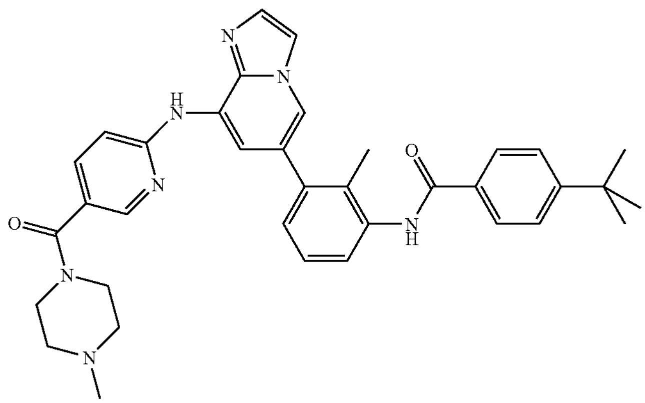 [SMILES: Cc1c(NC(=O)c2ccc(C(C)(C)C)cc2)cccc1-c1cc(Nc2ccc(C(=O)N3CCN(C)CC3)cn2)c2nccn2c1] | 4-tert-Butyl-N-(2-methyl-3-{8-[5-(4-methyl-piperazine-1-carbonyl)-pyridin-2-ylamino]-imidazo[1,2-a]pyridin-6-yl}-phenyl)-benzamide | 602 | |
| I-52 | 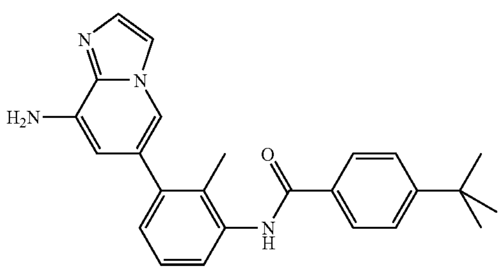 | N-[3-(8-Amino-imidazo[1,2-a]pyridin-6-yl)-2-methyl-phenyl]-4-tert-butyl-benzamide | 399 | |
| I-53 | 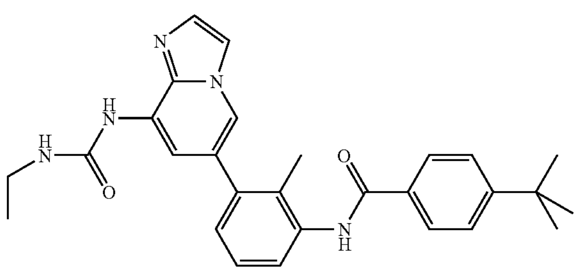 [SMILES: CCNC(=O)Nc1cc(-c2cccc(NC(=O)c3ccc(C(C)(C)C)cc3)c2C)cn2ccnc12] | 4-tert-Butyl-N-{3-[8-(3-ethyl-ureido)-imidazo[1,2-a]pyridin-6-yl]-2-methyl-phenyl}-benzamide | 470 | |
| I-54 | 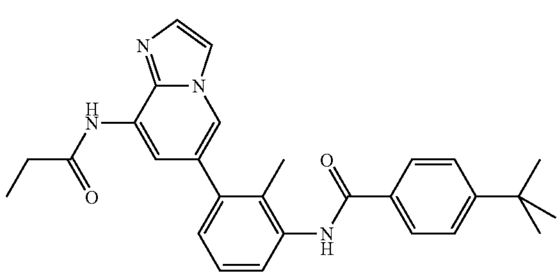 [SMILES: CCC(=O)Nc1cc(-c2cccc(NC(=O)c3ccc(C(C)(C)C)cc3)c2C)cn2ccnc12] | 4-tert-Butyl-N-[2-methyl-3-(8-propionylamino-imidazo[1,2-a]pyridin-6-yl)-phenyl]-benzamide | | 99.0-100.0 |

TABLE Y-continued

| # | Structure | | MS | MP |
|---|---|---|---|---|
| I-55 | 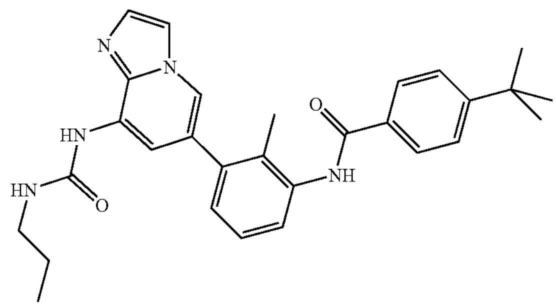 [SMILES: CCCNC(=O)Nc1cc(-c2cccc(NC(=O)c3ccc(C(C)(C)C)cc3)c2C)cn2ccnc12] | 4-tert-Butyl-N-{2-methyl-3-[8-(3-propyl-ureido)-imidazo[1,2-a]pyridin-6-yl]-phenyl}-benzamide | 484 | |
| I-56 | 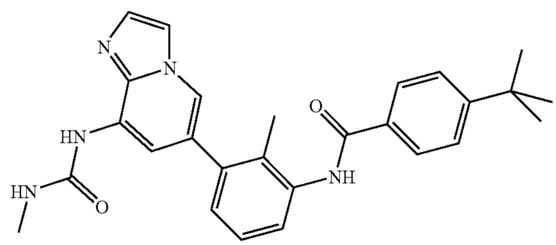 [SMILES: CNC(=O)Nc1cc(-c2cccc(NC(=O)c3ccc(C(C)(C)C)cc3)c2C)cn2ccnc12] | 4-tert-Butyl-N-{2-methyl-3-[8-(3-methyl-ureido)-imidazo[1,2-a]pyridin-6-yl]-phenyl}-benzamide | | 148.0-149.0 |
| I-57 | 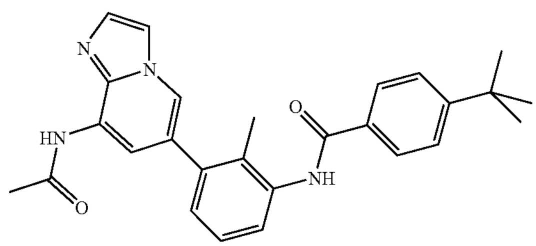 [SMILES: CC(=O)Nc1cc(-c2cccc(NC(=O)c3ccc(C(C)(C)C)cc3)c2C)cn2ccnc12] | N-[3-(8-Acetylamino-imidazo[1,2-a]pyridin-6-yl)-2-methyl-phenyl]-4-tert-butyl-benzamide | | 132.0-133.0 |
| I-58 | 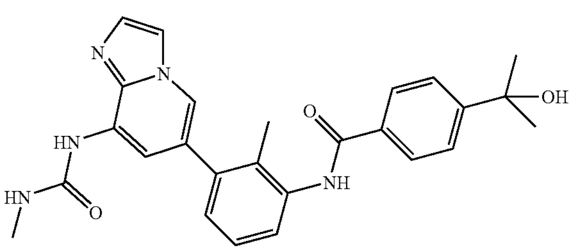 [SMILES: CNC(=O)Nc1cc(-c2cccc(NC(=O)c3ccc(C(C)(C)O)cc3)c2C)cn2ccnc12] | 4-(1-Hydroxy-1-methyl-ethyl)-N-{2-methyl-3-[8-(3-methyl-ureido)-imidazo[1,2-a]pyridin-6-yl]-phenyl}-benzamide | 458 | |
| I-59 | 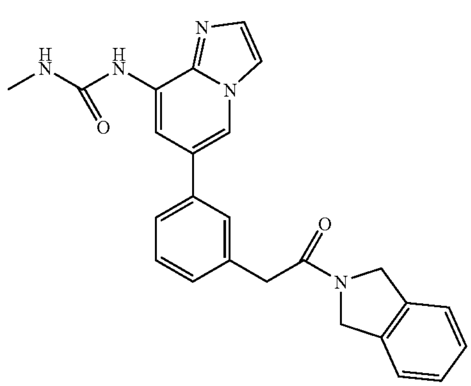 [SMILES: CNC(=O)Nc1cc(-c2cccc(CC(=O)N3Cc4ccccc4C3)c2)cn2ccnc12] | 1-(6-{3-[2-(1,3-Dihydro-isoindol-2-yl)-2-oxo-ethyl]-phenyl}-imidazo[1,2-a]pyridin-8-yl)-3-methyl-urea | 426 | |

TABLE Y-continued

| # | Structure | | MS | MP |
|---|---|---|---|---|
| I-60 | 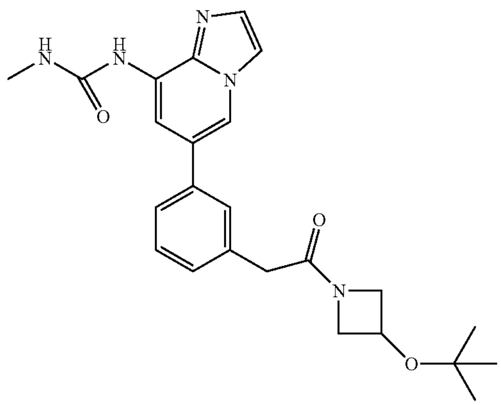 [SMILES: CNC(=O)Nc1cc(-c2cccc(CC(=O)N3CC(OC(C)(C)C)C3)c2)cn2ccnc12] | 1-(6-{3-[2-(3-tert-Butoxy-azetidin-1-yl)-2-oxo-ethyl]-phenyl}-imidazo[1,2-a]pyridin-8-yl)-3-methyl-urea | 436 | |
| I-61 | 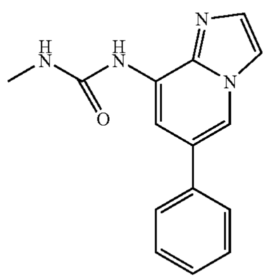 [SMILES: CNC(=O)Nc1cc(-c2ccccc2)cn2ccnc12] | 1-Methyl-3-(6-phenyl-imidazo[1,2-a]pyridin-8-yl)-urea | | 69.0-70.0 |
| I-62 | 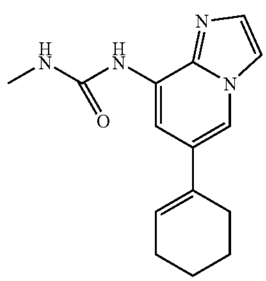 [SMILES: CNC(=O)Nc1cc(C2=CCCCC2)cn2ccnc12] | 1-(6-Cyclohex-1-enyl-imidazo[1,2-a]pyridin-8-yl)-3-methyl-urea | 271 | |
| I-63 | 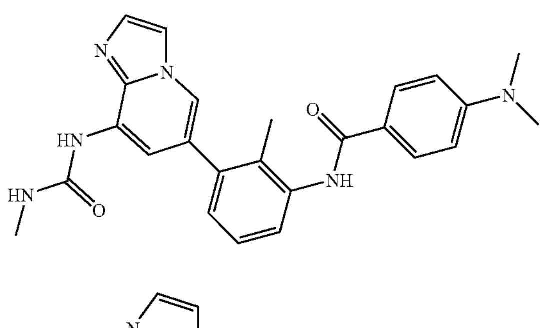 | 4-Dimethylamino-N-{2-methyl-3-[8-(3-methyl-ureido)-imidazo[1,2-a]pyridin-6-yl]-phenyl}-benzamide | 443 | |
| I-64 | 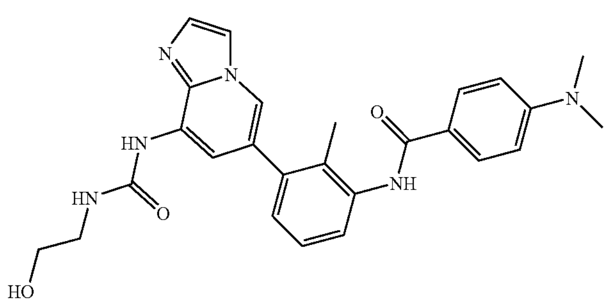 [SMILES: Cc1c(NC(=O)c2ccc(N(C)C)cc2)cccc1-c1cc(NC(=O)NCCO)c2nccn2c1] | 4-Dimethylamino-N-(3-{8-[3-(2-hydroxy-ethyl)-ureido]-imidazo[1,2-a]pyridin-6-yl}-2-methyl-phenyl)-benzamide | | 153.7-164.4 |

TABLE Y-continued

| # | Structure | | MS | MP |
|---|---|---|---|---|
| I-65 | 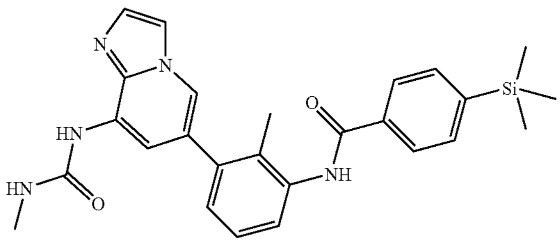 | N-{2-Methyl-3-[8-(3-methyl-ureido)-imidazo[1,2-a]pyridin-6-yl]-phenyl}-4-trimethylsilanyl-benzamide | | 143.5-154.4 |
| I-66 | 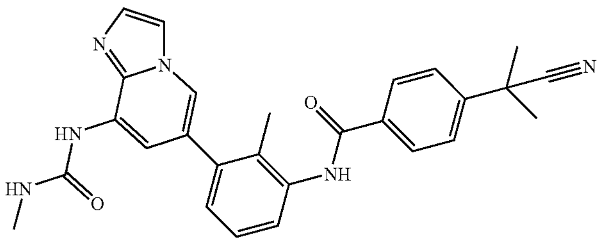 [SMILES: CNC(=O)Nc1cc(-c2cccc(NC(=O)c3ccc(C(C)(C)C#N)cc3)c2C)cn2ccnc12] | 4-(Cyano-dimethyl-methyl)-N-{2-methyl-3-(3-methyl-ureido)-imidazo[1,2-a]pyridin-6-yl]-phenyl}-benzamide | | 128.0-188.3 |
| I-67 | 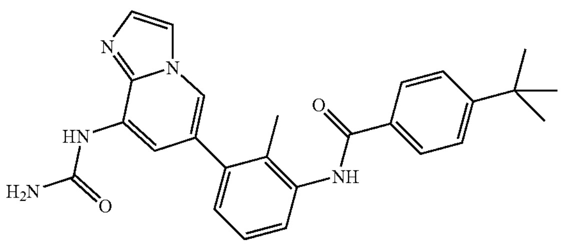 [SMILES: Cc1c(NC(=O)c2ccc(C(C)(C)C)cc2)cccc1-c1cc(NC(N)=O)c2nccn2c1] | 4-tert-Butyl-N-[2-methyl-3-(8-ureido-imidazo[1,2-a]pyridin-6-yl)-phenyl]-benzamide | | 185.4-215.0 |
| I-68 | 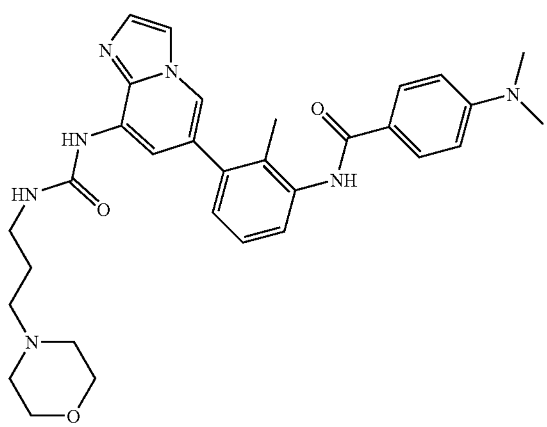 [SMILES: Cc1c(NC(=O)c2ccc(N(C)C)cc2)cccc1-c1cc(NC(=O)NCCCN2CCOCC2)c2nccn2c1] | 4-Dimethylamino-N-(2-methyl-3-{8-[3-(3-morpholin-4-yl-propyl)-ureido]-imidazo[1,2-a]pyridin-6-yl}-phenyl)-benzamide | | 190.2-209.7 |
| I-69 | 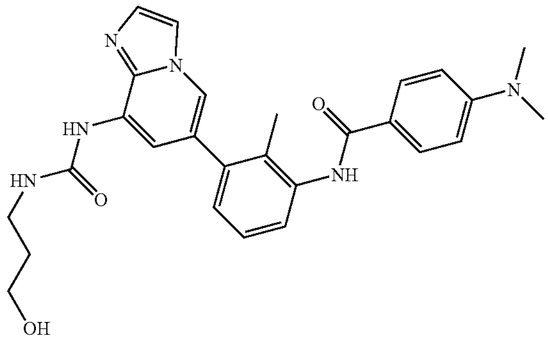 [SMILES: Cc1c(NC(=O)c2ccc(N(C)C)cc2)cccc1-c1cc(NC(=O)NCCCO)c2nccn2c1] | 4-Dimethylamino-N-(3-{8-[3-(3-hydroxy-propyl)-ureido]-imidazo[1,2-a]pyridin-6-yl}-2-methyl-phenyl)-benzamide | | 144.1-188.6 |

TABLE Y-continued

| # | Structure | | MS | MP |
|---|---|---|---|---|
| I-70 | 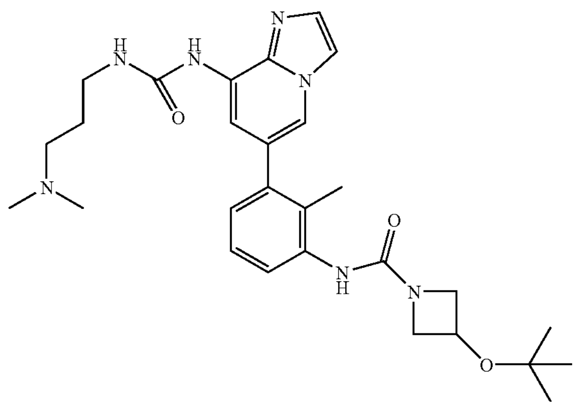 [SMILES: Cc1c(NC(=O)N2CC(OC(C)(C)C)C2)cccc1-c1cc(NC(=O)NCCCN(C)C)c2nccn2c1] | 3-tert-Butoxy-azetidine-1-carboxylic acid {3-{8-[3-(3-dimethylamino-propyl)-ureido]-imidazo[1,2-a]pyridin-6-yl}-2-methyl-phenyl)-amide | | 129.0-130.0 |
| I-71 | 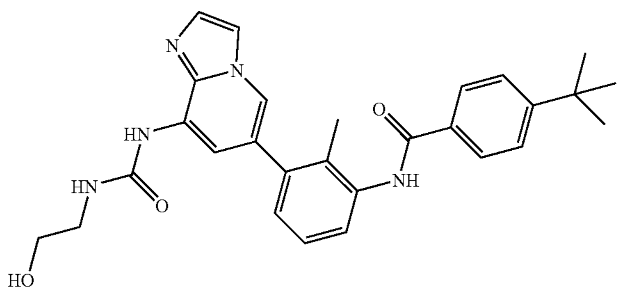 [SMILES: Cc1c(NC(=O)c2ccc(C(C)(C)C)cc2)cccc1-c1cc(NC(=O)NCCO)c2nccn2c1] | 4-tert-Butyl-N-(3-{8-[3-(2-hydroxy-ethyl)-ureido]-imidazo[1,2-a]pyridin-6-yl}-2-methyl-phenyl)-benzamide | | 176.0-177.0 |
| I-72 | 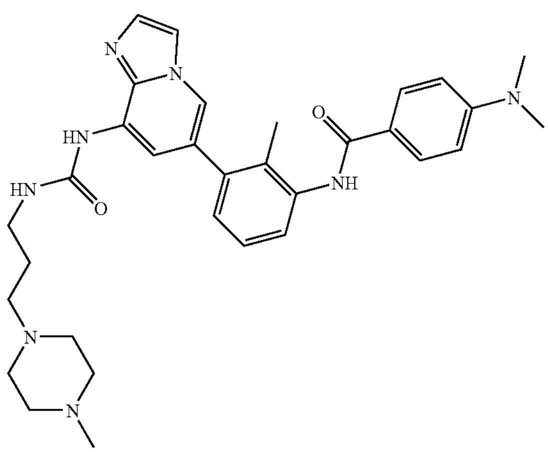 [SMILES: Cc1c(NC(=O)c2ccc(N(C)C)cc2)cccc1-c1cc(NC(=O)NCCCN2CCN(C)CC2)c2nccn2c1] | 4-Dimethylamino-N-[2-methyl-3-(8-{3-[3-(4-methyl-piperazin-1-yl)-propyl]-ureido}-imidazo[1,2-a]pyridin-6-yl)-phenyl]-benzamide | | 144.0-145. |
| I-73 | 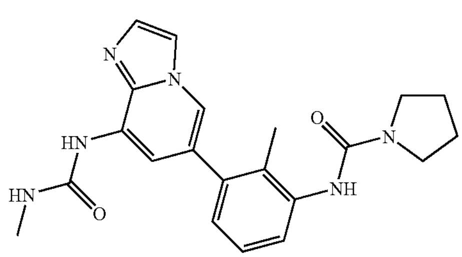 [SMILES: CNC(=O)Nc1cc(-c2cccc(NC(=O)N3CCCC3)c2C)cn2ccnc12] | Pyrrolidine-1-carboxylic acid {2-methyl-3-[8-(3-methyl-ureido)-imidazo[1,2-a]pyridin-6-yl]-phenyl}-amide | | 393 |

TABLE Y-continued

| # | Structure | | MS | MP |
|---|---|---|---|---|
| I-74 | 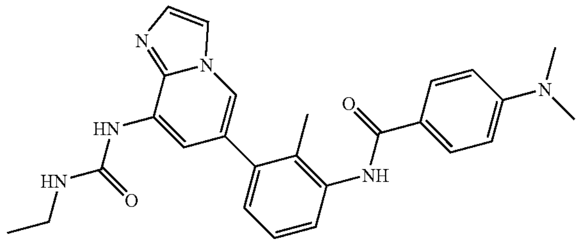 [SMILES: CCNC(=O)Nc1cc(-c2cccc(NC(=O)c3ccc(N(C)C)cc3)c2C)cn2ccnc12] | 4-Dimethylamino-N-{3-[8-(3-ethyl-ureido)-imidazo[1,2-a]pyridin-6-yl]-2-methyl-phenyl}-benzamide | 457 | |
| I-75 | 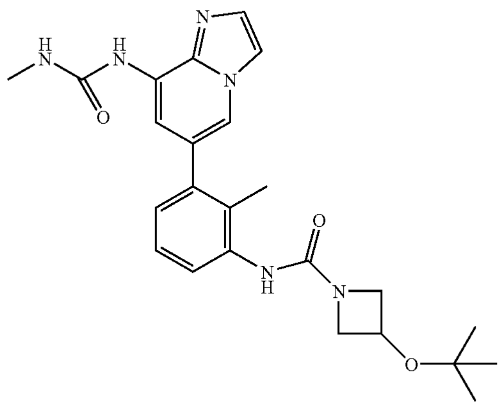 [SMILES: CNC(=O)Nc1cc(-c2cccc(NC(=O)N3CC(OC(C)(C)C)C3)c2C)cn2ccnc12] | 3-tert-Butoxy-azetidine-1-carboxylic acid {2-methyl-3-[8-(3-methyl-ureido)-imidazo[1,2-a]pyridin-6-yl]-phenyl}-amide | 451 | 158.0-161.0 |
| I-76 | 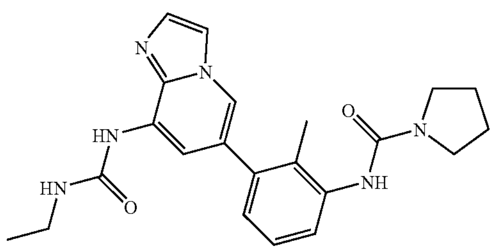 [SMILES: CCNC(=O)Nc1cc(-c2cccc(NC(=O)N3CCCC3)c2C)cn2ccnc12] | Pyrrolidine-1-carboxylic acid {3-[8-(3-ethyl-ureido)-imidazo[1,2-a]pyridin-6-yl]-2-methyl-phenyl}-amide | 407 | |
| I-77 | 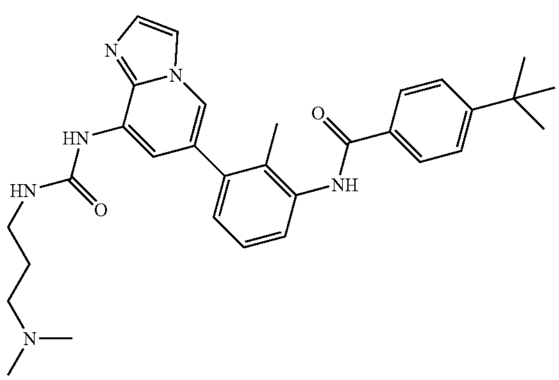 [SMILES: Cc1c(NC(=O)c2ccc(C(C)(C)C)cc2)cccc1-c1cc(NC(=O)NCCCN(C)C)c2nccn2c1] | 4-tert-Butyl-N-(3-{8-[3-(3-dimethylamino-propyl)-ureido]-imidazo[1,2-a]pyridin-6-yl}-2-methyl-phenyl)-benzamide | | 182.7-199.7 |
| I-78 | 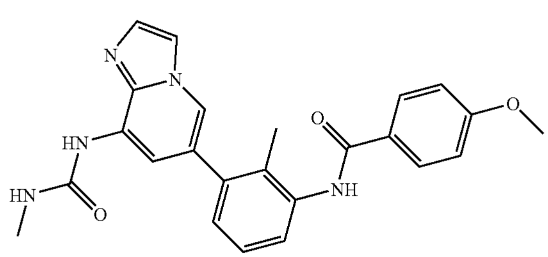 | 4-Methoxy-N-{2-methyl-3-[8-(3-methyl-ureido)-imidazo[1,2-a]pyridin-6-yl]-phenyl}-benzamide | | 147.6-152.9 |

TABLE Y-continued

| # | Structure | | MS | MP |
|---|-----------|---|----|----|
| I-79 | 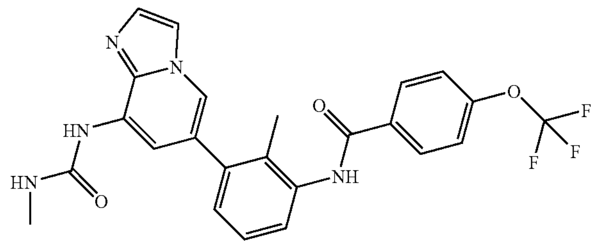 [SMILES: CNC(=O)Nc1cc(-c2cccc(NC(=O)c3ccc(OC(F)(F)F)cc3)c2C)cn2ccnc12] | N-{2-Methyl-3-[8-(3-methyl-ureido)-imidazo[1,2-a]pyridin-6-yl]-phenyl}-4-trifluoromethoxy-benzamide | | 148.4-153.2 |
| I-80 | 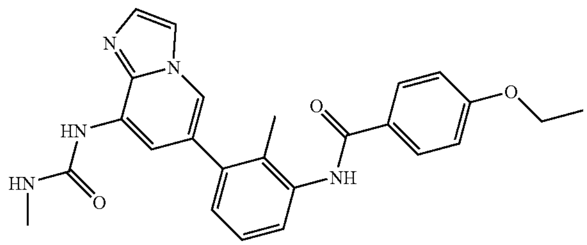 [SMILES: CCOc1ccc(C(=O)Nc2cccc(-c3cc(NC(=O)NC)c4nccn4c3)c2C)cc1] | 4-Ethoxy-N-{2-methyl-3-[8-(3-methyl-ureido)-imidazo[1,2-a]pyridin-6-yl]-phenyl}-benzamide | 444 | |
| I-81 | 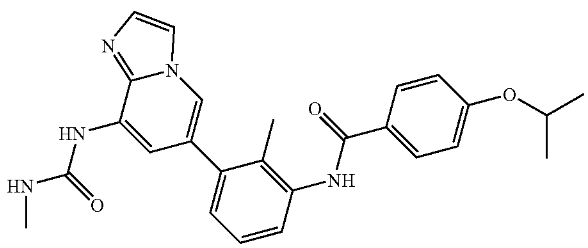 [SMILES: CNC(=O)Nc1cc(-c2cccc(NC(=O)c3ccc(OC(C)C)cc3)c2C)cn2ccnc12] | 4-Isopropoxy-N-[2-methyl-3-[8-(3-methyl-ureido)-imidazo[1,2-a]pyridin-6-yl]-phenyl}-benzamide | | 147.1-151.7 |
| I-82 | 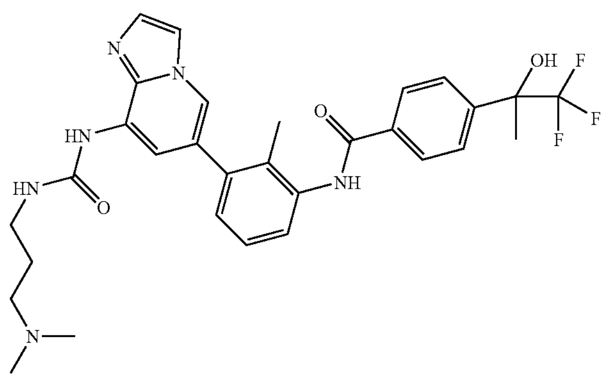 [SMILES: Cc1c(NC(=O)c2ccc(C(C)(O)C(F)(F)F)cc2)cccc1-c1cc(NC(=O)NCCCN(C)C)c2nccn2c1] | N-(3-{8-[3-(3-Dimethylamino-propyl)-ureido]-imidazo[1,2-a]pyridin-6-yl}-2-methyl-phenyl)-4-(2,2,2-trifluoro-1-hydroxy-1-methyl-ethyl)-benzamide | 583 | |
| I-83 | 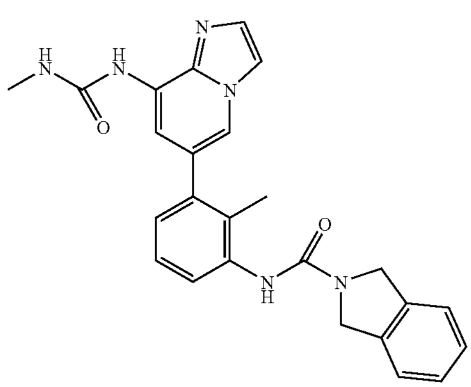 [SMILES: CNC(=O)Nc1cc(-c2cccc(NC(=O)N3Cc4ccccc4C3)c2C)cn2ccnc12] | 1,3-Dihydro-isoindole-2-carboxylic acid [2-methyl-3-[8-(3-methyl-ureido)-imidazo[1,2-a]pyridin-6-yl]-phenyl]-amide | 441 | |

TABLE Y-continued
| # | Structure | | MS | MP |
|---|---|---|---|---|
| I-84 | 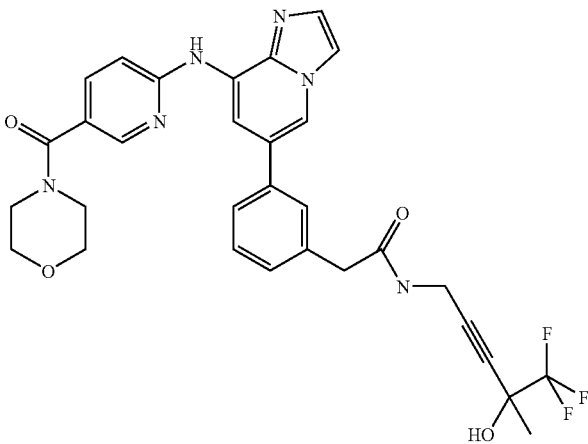 [SMILES: CC(O)(C#CCNC(=O)Cc1cccc(-c2cc(Nc3ccc(C(=O)N4CCOCC4)cn3)c3nccn3c2)c1)C(F)(F)F] | 2-(3-{8-[5-(Morpholine-4-carbonyl)-pyridin-2-ylamino]-imidazo[1,2-a]pyridin-6-yl}-phenyl)-N-(5,5,5-trifluoro-4-hydroxy-4-methyl-pent-2-ynyl)-acetamide | | 136.8-147. |
| I-85 | 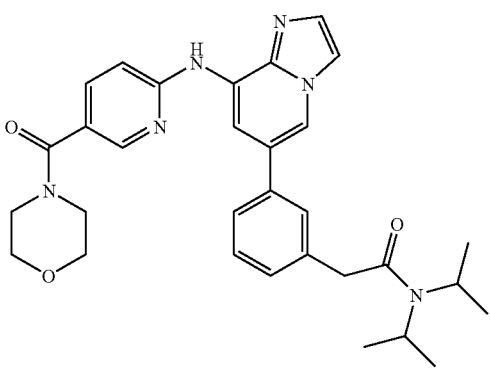 [SMILES: CC(C)N(C(=O)Cc1cccc(-c2cc(Nc3ccc(C(=O)N4CCOCC4)cn3)c3nccn3c2)c1)C(C)C] | N,N-Diisopropyl-2-(3-{8-[5-(morpholine-4-carbonyl)-pyridin-2-ylamino]-imidazo[1,2-a]pyridin-6-yl}-phenyl)-acetamide | 541 | |
| I-86 | 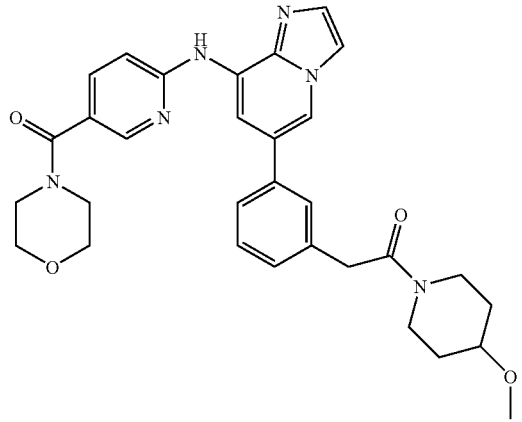 [SMILES: COC1CCN(C(=O)Cc2cccc(-c3cc(Nc4ccc(C(=O)N5CCOCC5)cn4)c4nccn4c3)c2)CC1] | 1-(4-Methoxy-piperidin-1-yl)-2-(3-{8-[5-(morpholine-4-carbonyl)-pyridin-2-ylamino]-imidazo[1,2-a]pyridin-6-yl}-phenyl)-ethanone | 555 | |

TABLE Y-continued

| # | Structure | | MS | MP |
|---|---|---|---|---|
| I-87 | 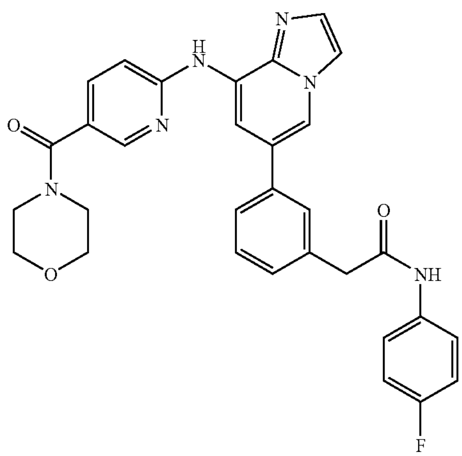 [SMILES: O=C(Cc1cccc(-c2cc(Nc3ccc(C(=O)N4CCOCC4)cn3)c3nccn3c2)c1)Nc1ccc(F)cc1] | N-(4-Fluoro-phenyl)-2-(3-{8-[5-(morpholine-4-carbonyl)-pyridin-2-ylamino]-imidazo[1,2-a]pyridin-6-yl}-phenyl)-acetamide | 551 | |
| I-88 | 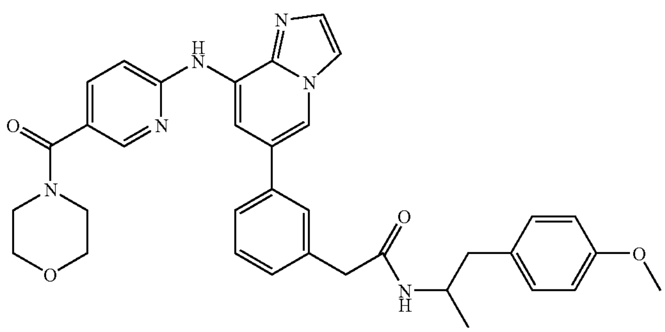 [SMILES: COc1ccc(CC(C)NC(=O)Cc2cccc(-c3cc(Nc4ccc(C(=O)N5CCOCC5)cn4)c4nccn4c3)c2)cc1] | N-[2-(4-Methoxy-phenyl)-1-methyl-ethyl]-2-(3-{8-[5-(morpholine-4-carbonyl)-pyridin-2-ylamino]-imidazo[1,2-a]pyridin-6-yl}-phenyl)-acetamide | 605 | |
| I-89 | 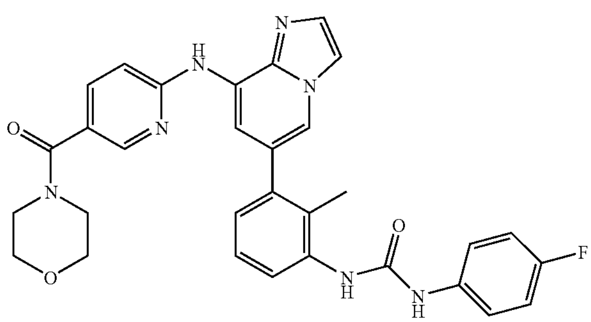 [SMILES: Cc1c(NC(=O)Nc2ccc(F)cc2)cccc1-c1cc(Nc2ccc(C(=O)N3CCOCC3)cn2)c2nccn2c1] | 1-(4-Fluoro-phenyl)-3-(2-methyl-3-{8-[5-(morpholine-4-carbonyl)-pyridin-2-ylamino]-imidazo[1,2-a]pyridin-6-yl}-phenyl)-urea | 566 | |
| I-90 | 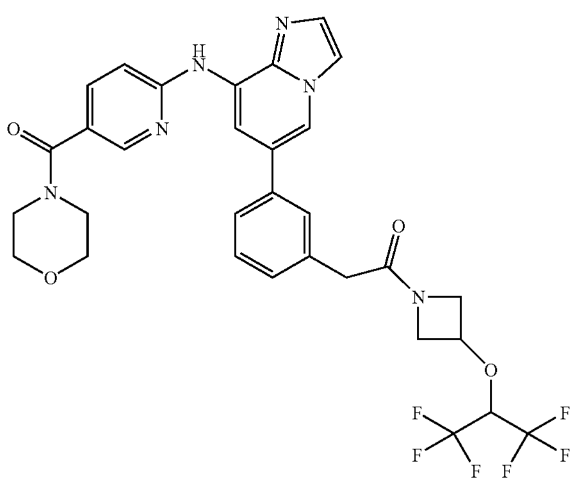 [SMILES: O=C(Cc1cccc(-c2cc(Nc3ccc(C(=O)N4CCOCC4)cn3)c3nccn3c2)c1)N1CC(OC(C(F)(F)F)C(F)(F)F)C1] | 2-(3-{8-[5-(Morpholine-4-carbonyl)-pyridin-2-ylamino]-imidazo[1,2-a]pyridin-6-yl}-phenyl)-1-[3-(2,2,2-trifluoro-1-trifluoromethyl-ethoxy)-azetidin-1-yl]-ethanone | | 137.0-138.0 |

TABLE Y-continued

| # | Structure | MS | MP |
|---|---|---|---|
| I-91 | | Pyrrolidine-1-carboxylic acid (2-methyl-3-{8-[5-(morpholine-4-carbonyl)-pyridin-2-ylamino]-imidazo[1,2-a]pyridin-6-yl}-phenyl)-amide | 526 | |
| I-92 | | 4-Hydroxymethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide | 570 | |
| I-93 | | 1-[2-(4-Methoxy-phenyl)-1-methyl-ethyl]-3-(2-methyl-3-{8-[5-(morpholine-4-carbonyl)-pyridin-2-ylamino]-imidazo[1,2-a]pyridin-6-yl}-phenyl)-urea | 620 | |
| I-94 | | 4-tert-Butyl-N-[2-methyl-3-(8-{3-[3-(4-methyl-piperazin-1-yl)-propyl]-ureido}-imidazo[1,2-a]pyridin-6-yl)-phenyl]-benzamide | | 167.0-168.0 |

| # | Structure | | MS | MP |
|---|---|---|---|---|
| I-95 | 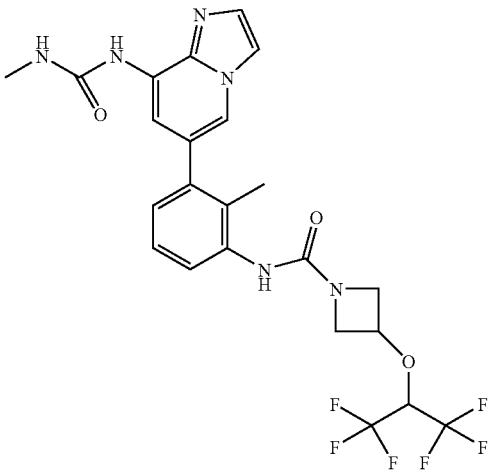 [SMILES: CNC(=O)Nc1cc(-c2cccc(NC(=O)N3CC(OC(C(F)(F)F)C(F)(F)F)C3)c2C)cn2ccnc12] | 3-(2,2,2-Trifluoro-1-trifluoromethyl-ethoxy)-azetidine-1-carboxylic acid {2-methyl-3-[8-(3-methyl-ureido)-imidazo[1,2-a]pyridin-6-yl]-phenyl}-amide | 545 | |
| I-96 | 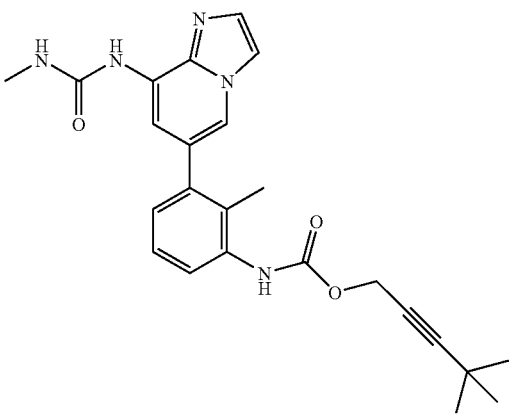 [SMILES: CNC(=O)Nc1cc(-c2cccc(NC(=O)OCC#CC(C)(C)C)c2C)cn2ccnc12] | {2-Methyl-3-[8-(3-methyl-ureido)-imidazo[1,2-a]pyridin-6-yl]-phenyl}-carbamic acid 4,4-dimethyl-pent-2-ynyl ester | 434 | |
| I-97 | 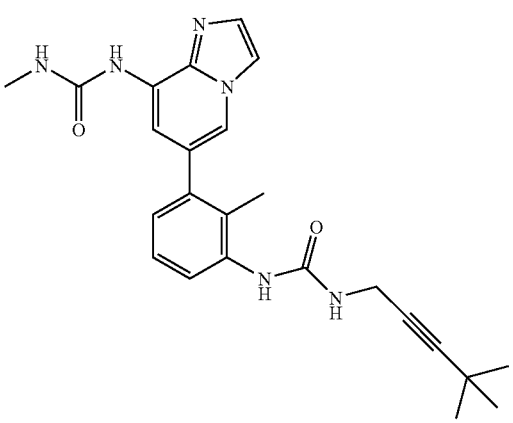 [SMILES: CNC(=O)Nc1cc(-c2cccc(NC(=O)NCC#CC(C)(C)C)c2C)cn2ccnc12] | 1-(6-{3-[3-(4,4-Dimethyl-pent-2-ynyl)-ureido]-2-methyl-phenyl}-imidazo[1,2-a]pyridin-8-yl)-3-methyl-urea | 433 | |

TABLE Y-continued
| # | Structure | | MS | MP |
|---|---|---|---|---|
| I-98 | 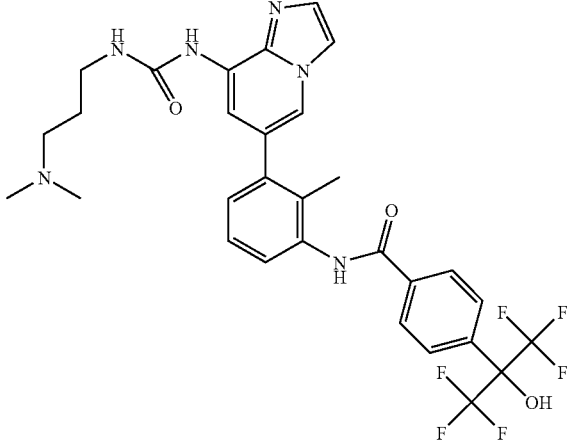 [SMILES: Cc1c(NC(=O)c2ccc(C(O)(C(F)(F)F)C(F)(F)F)cc2)cccc1-c1cc(NC(=O)NCCCN(C)C)c2nccn2c1] | N-(3-{8-[3-(3-Dimethylamino-propyl)-ureido]-imidazo[1,2-a]pyridin-6-yl}-2-methyl-phenyl)-4-(2,2,2-trifluoro-1-hydroxy-1-trifluoromethyl-ethyl)-benzamide | | 198.0-200.0 |
| I-99 | 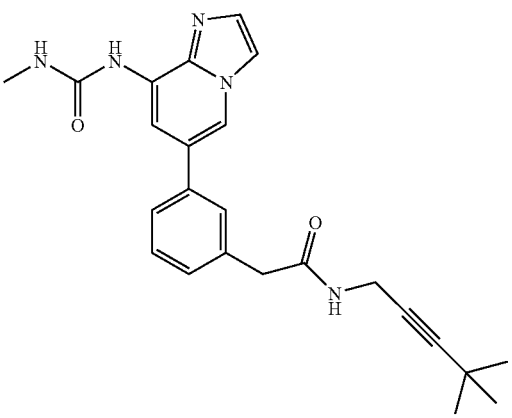 [SMILES: CNC(=O)Nc1cc(-c2cccc(CC(=O)NCC#CC(C)(C)C)c2)cn2ccnc12] | N-(4,4-Dimethyl-pent-2-ynyl)-2-{3-[8-(3-methyl-ureido)-imidazo[1,2-a]pyridin-6-yl]-phenyl}-acetamide | | 129.0-130.0 |
| I-100 | 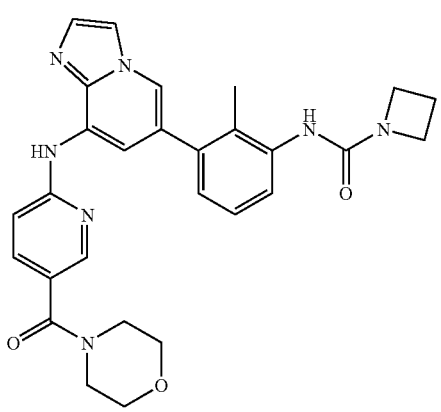 [SMILES: Cc1c(NC(=O)N2CCC2)cccc1-c1cc(Nc2ccc(C(=O)N3CCOCC3)cn2)c2nccn2c1] | Azetidine-1-carboxylic acid (2-methyl-3-{8-[5-(morpholine-4-carbonyl)-pyridin-2-ylamino]-imidazo[1,2-a]pyridin-6-yl}-phenyl)-amide | | |

TABLE Y-continued

| # | Structure | MS | MP |
|---|---|---|---|
| I-101 | 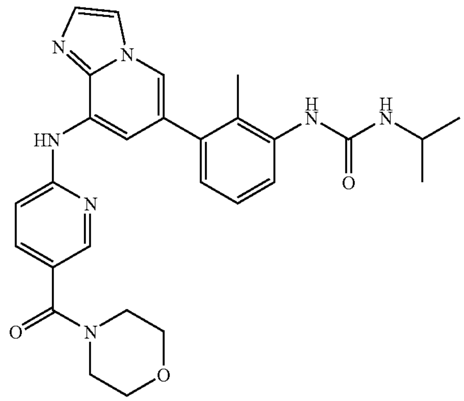 [SMILES: Cc1c(NC(=O)NC(C)C)cccc1-c1cc(Nc2ccc(C(=O)N3CCOCC3)cn2)c2nccn2c1] | | |

1-Isopropyl-3-(2-methyl-3-{8-[5-(morpholine-4-carbonyl)-pyridin-2-ylamino]-imidazo[1,2-a]pyridin-6-yl}-phenyl)-urea

| I-102 | | | |

1-Isobutyl-3-(2-methyl-3-{8-[5-(morpholine-4-carbonyl)-pyridin-2-ylamino]-imidazo[1,2-a]pyridin-6-yl}-phenyl)-urea

| I-103 | | | |

1-sec-Butyl-3-(2-methyl-3-{8-[5-(morpholine-4-carbonyl)-pyridin-2-ylamino]-imidazo[1,2-a]pyridin-6-yl}-phenyl)-urea

| I-104 | | | |

3,6-Dihydro-2H-pyridine-1-carboxylic acid (2-methyl-3-{8-[5-(morpholine-4-carbonyl)-pyridin-2-ylamino]-imidazo[1,2-a]pyridin-6-yl}-phenyl)-amide

TABLE Y-continued

| # | Structure | | MS | MP |
|---|---|---|---|---|

I-105 — Morpholine-4-carboxylic acid (2-methyl-3-{8-[5-(morpholine-4-carbonyl)-pyridin-2-ylamino]-imidazo[1,2-a]pyridin-6-yl}-phenyl)-amide I-106 — 1-(1,1-Dimethyl-propyl)-3-(2-methyl-3-{8-[5-(morpholine-4-carbonyl)-pyridin-2-ylamino]-imidazo[1,2-a]pyridin-6-yl}-phenyl)-urea I-107 — 1-(1-Ethyl-propyl)-3-(2-methyl-3-{8-[5-(morpholine-4-carbonyl)-pyridin-2-ylamino]-imidazo[1,2-a]pyridin-6-yl}-phenyl)-urea TABLE Y-continued

| # | Structure | | MS | MP |
|---|---|---|---|---|
| I-108 | 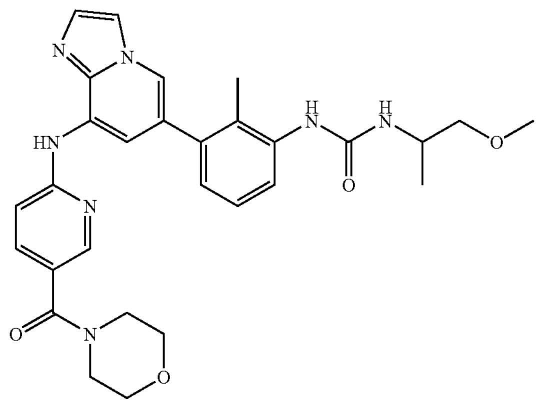 [SMILES: COCC(C)NC(=O)Nc1cccc(-c2cc(Nc3ccc(C(=O)N4CCOCC4)cn3)c3nccn3c2)c1C] | 1-(2-Methoxy-1-methyl-ethyl)-3-(2-methyl-3-{8-[5-(morpholine-4-carbonyl)-pyridin-2-ylamino]-imidazo[1,2-a]pyridin-6-yl}-phenyl)-urea | | |
| I-109 | 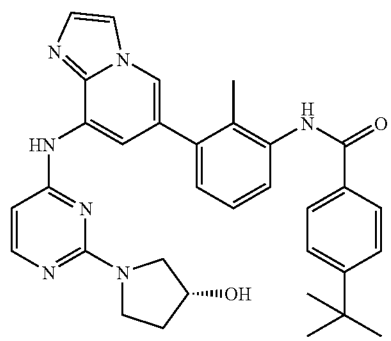 [SMILES: Cc1c(NC(=O)c2ccc(C(C)(C)C)cc2)cccc1-c1cc(Nc2ccnc(N3CC[C@@H](O)C3)n2)c2nccn2c1] | 4-tert-Butyl-N-(3-(8-[2-((R)-3-hydroxy-pyrrolidin-1-yl)-pyrimidin-4-ylamino]-imidazo[1,2-a]pyridin-6-yl}-2-methyl-phenyl)-benzamide | | |
| I-110 | 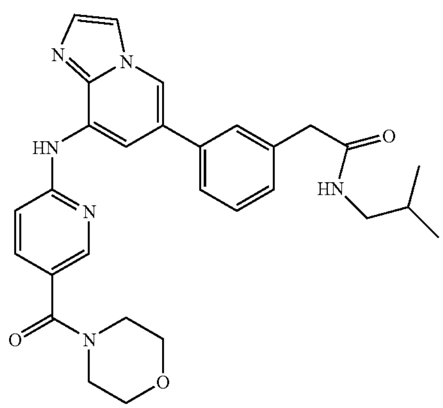 [SMILES: CC(C)CNC(=O)Cc1cccc(-c2cc(Nc3ccc(C(=O)N4CCOCC4)cn3)c3nccn3c2)c1] | N-isobutyl-2-(3-{8-[5-(morpholine-4-carbonyl)-pyridin-2-ylamino]-imidazo[1,2-a]pyridin-6-yl}-phenyl)-acetamide | | |
| I-111 | 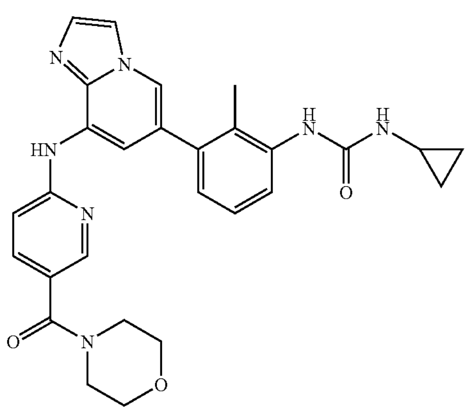 [SMILES: Cc1c(NC(=O)NC2CC2)cccc1-c1cc(Nc2ccc(C(=O)N3CCOCC3)cn2)c2nccn2c1] | 1-Cyclopropyl-3-(2-methyl-3-{8-[5-(morpholine-4-carbonyl)-pyridin-2-ylamino]-imidazo[1,2-a]pyridin-6-yl}-phenyl)-urea | | |

TABLE Y-continued

| # | Structure | | MS | MP |
|---|---|---|---|---|
| I-112 | 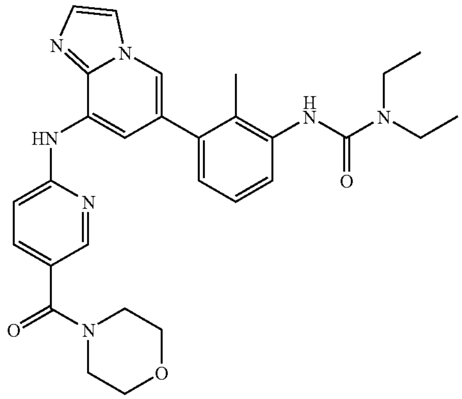 [SMILES: CCN(CC)C(=O)Nc1cccc(-c2cc(Nc3ccc(C(=O)N4CCOCC4)cn3)c3nccn3c2)c1C] | 1,1-Diethyl-3-(2-methyl-3-{8-[5-(morpholine-4-carbonyl)-pyridin-2-ylamino]-imidazo[1,2-a]pyridin-6-yl}-phenyl)-urea | | |
| I-113 | 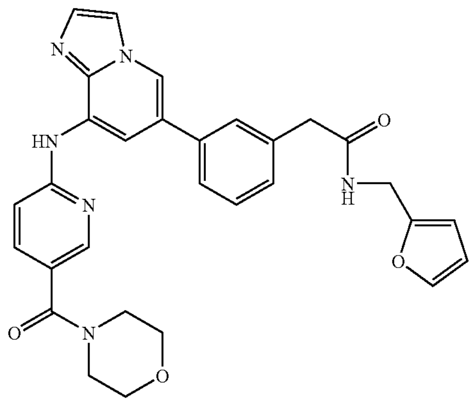 [SMILES: O=C(Cc1cccc(-c2cc(Nc3ccc(C(=O)N4CCOCC4)cn3)c3nccn3c2)c1)NCc1ccco1] | N-Furan-2-ylmethyl-2-(3-{8-[5-(morpholine-4-carbonyl)-pyridin-2-ylamino]-imidazo[1,2-a]pyridin-6-yl}-phenyl)-acetamide | | |
| I-114 | 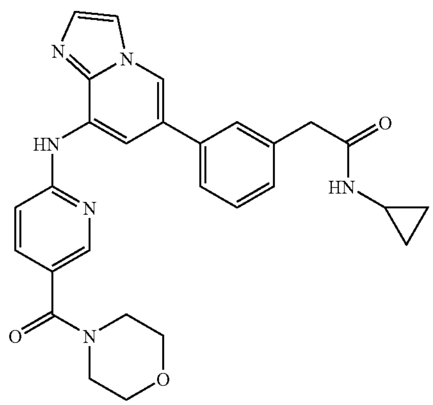 [SMILES: O=C(Cc1cccc(-c2cc(Nc3ccc(C(=O)N4CCOCC4)cn3)c3nccn3c2)c1)NC1CC1] | N-Cyclopropyl-2-(3-{8-[5-(morpholine-4-carbonyl)-pyridin-2-ylamino]-imidazo[1,2-a]pyridin-6-yl}-phenyl)-acetamide | | |
| I-115 | 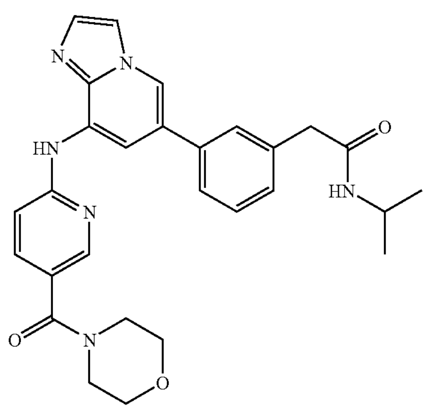 [SMILES: CC(C)NC(=O)Cc1cccc(-c2cc(Nc3ccc(C(=O)N4CCOCC4)cn3)c3nccn3c2)c1] | N-Isopropyl-2-(3-{8-[5-(morpholine-4-carbonyl)-pyridin-2-ylamino]-imidazo[1,2-a]pyridin-6-yl}-phenyl)-acetamide | | |

TABLE Y-continued
| # | Structure | | MS | MP |
|---|---|---|---|---|
| I-116 | 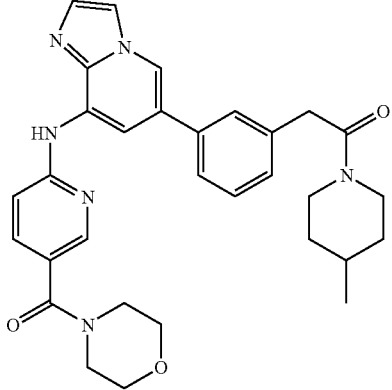 [SMILES: CC1CCN(C(=O)Cc2cccc(-c3cc(Nc4ccc(C(=O)N5CCOCC5)cn4)c4nccn4c3)c2)CC1] | 1-(4-Methyl-piperidin-1-yl)-2-(3-{8-[5-(morpholine-4-carbonyl)-pyridin-2-ylamino]-imidazo[1,2-a]pyridin-6-yl}-phenyl)-ethanone | | |
| I-117 | 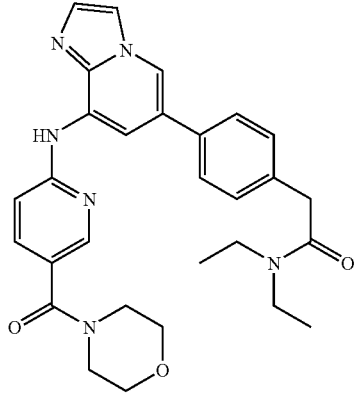 [SMILES: CCN(CC)C(=O)Cc1ccc(-c2cc(Nc3ccc(C(=O)N4CCOCC4)cn3)c3nccn3c2)cc1] | N,N-Diethyl-2-(4-{8-[5-(morpholine-4-carbonyl)-pyridin-2-ylamino]-imidazo[1,2-a]pyridin-6-yl}-phenyl)-acetamide | | |
| I-118 | 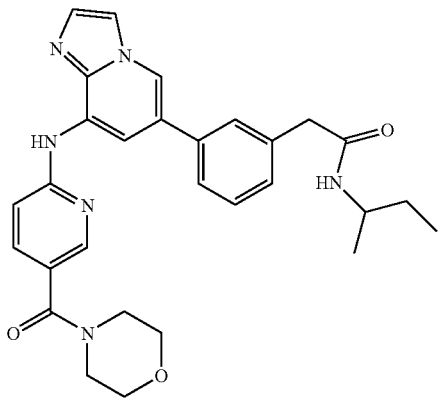 [SMILES: CCC(C)NC(=O)Cc1cccc(-c2cc(Nc3ccc(C(=O)N4CCOCC4)cn3)c3nccn3c2)c1] | N-sec-Butyl-2-(3-{8-[5-(morpholine-4-carbonyl)-pyridin-2-ylamino]-imidazo[1,2-a]pyridin-6-yl}-phenyl)-acetamide | | |

TABLE Y-continued

| # | Structure | | MS | MP |
|---|---|---|---|---|
| I-119 | 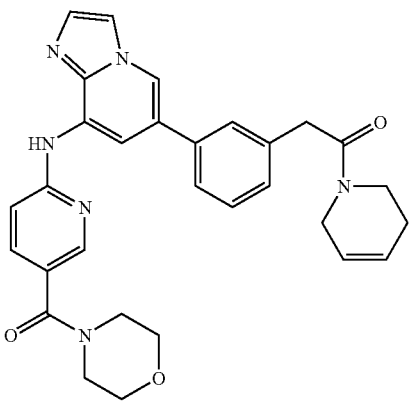 [SMILES: O=C(Cc1cccc(-c2cc(Nc3ccc(C(=O)N4CCOCC4)cn3)c3nccn3c2)c1)N1CC=CCC1] | 1-(3,6-Dihydro-2H-pyridin-1-yl)-2-(3-{8-[5-(morpholine-4-carbonyl)-pyridin-2-ylamino]-imidazo[1,2-a]pyridin-6-yl}-phenyl)-ethanone | | |
| I-120 | 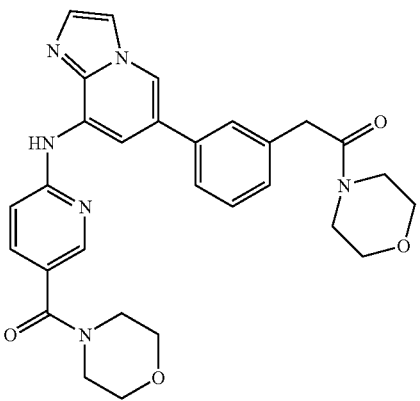 [SMILES: O=C(Cc1cccc(-c2cc(Nc3ccc(C(=O)N4CCOCC4)cn3)c3nccn3c2)c1)N1CCOCC1] | 2-(3-{8-[5-(Morpholine-4-carbonyl)-pyridin-2-ylamino]-imidazo[1,2-a]pyridin-6-yl}-phenyl)-1-morpholin-4-yl-ethanone | | |
| I-121 | 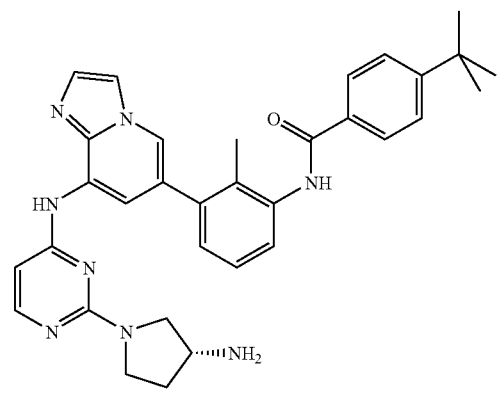 [SMILES: Cc1c(NC(=O)c2ccc(C(C)(C)C)cc2)cccc1-c1cc(Nc2ccnc(N3CC[C@@H](N)C3)n2)c2nccn2c1] | N-(3-{8-[2-((R)-3-Amino-pyrrolidin-1-yl)-pyrimidin-4-ylamino]-imidazo[1,2-a]pyridin-6-yl}-2-methyl-phenyl)-4-tert-butyl-benzamide | | |
| I-122 | 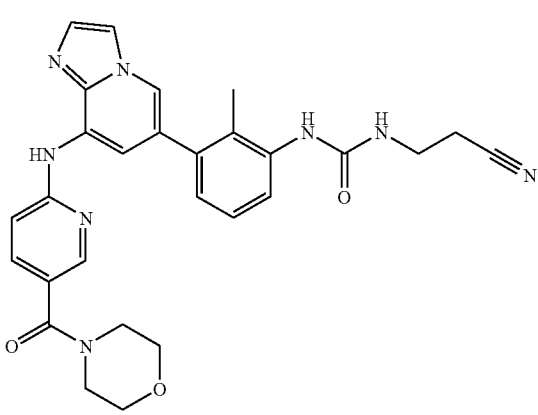 [SMILES: Cc1c(NC(=O)NCCC#N)cccc1-c1cc(Nc2ccc(C(=O)N3CCOCC3)cn2)c2nccn2c1] | 1-(2-Cyano-ethyl)-3-(2-methyl-3-{8-[5-(morpholine-4-carbonyl)-pyridin-2-ylamino]-imidazo[1,2-a]pyridin-6-yl}-phenyl)-urea | | |

US 8,426,441 B2
TABLE Y-continued
| # | Structure | | MS | MP |
|---|---|---|---|---|
| I-123 | 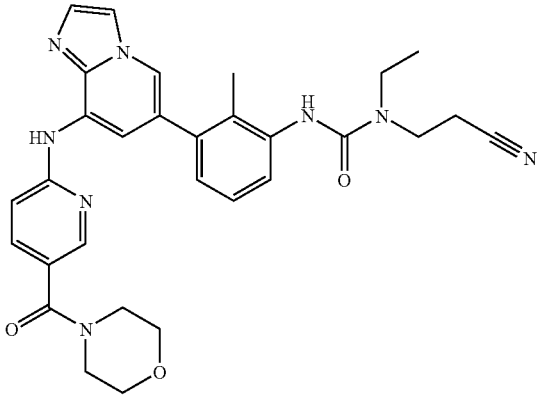 [SMILES: CCN(CCC#N)C(=O)Nc1cccc(-c2cc(Nc3ccc(C(=O)N4CCOCC4)cn3)c3nccn3c2)c1C] | 1-(2-Cyano-ethyl)-1-ethyl-3-(2-methyl-3-{8-[5-(morpholine-4-carbonyl)-pyridin-2-ylamino]-imidazo[1,2-a]pyridin-6-yl}-phenyl)-urea | | |
| I-124 | 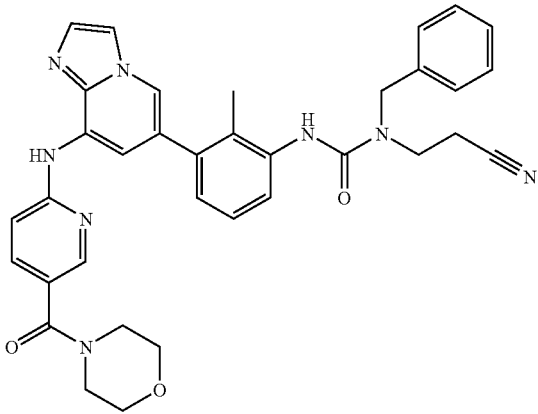 [SMILES: Cc1c(NC(=O)N(CCC#N)Cc2ccccc2)cccc1-c1cc(Nc2ccc(C(=O)N3CCOCC3)cn2)c2nccn2c1] | 1-Benzyl-1-(2-cyano-ethyl)-3-(2-methyl-3-{8-[5-(morpholine-4-carbonyl)-pyridin-2-ylamino]-imidazo[1,2-a]pyridin-6-yl}-phenyl)-urea | | |
| I-125 | 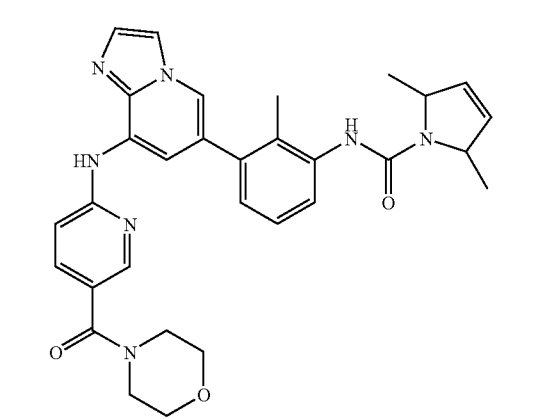 [SMILES: Cc1c(NC(=O)N2C(C)C=CC2C)cccc1-c1cc(Nc2ccc(C(=O)N3CCOCC3)cn2)c2nccn2c1] | 2,5-Dimethyl-2,5-dihydro-pyrrole-1-carboxylic acid (2-methyl-3-{8-[5-(morpholine-4-carbonyl)-pyridin-2-ylamino]-imidazo[1,2-a]pyridin-6-yl}-phenyl)-amide | | |

TABLE Y-continued

| # | Structure | MS | MP |
|---|---|---|---|
| I-126 | 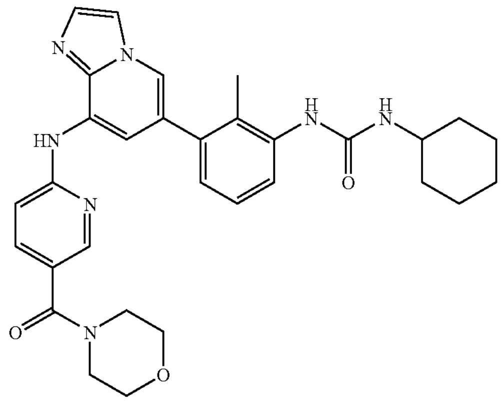 [SMILES: Cc1c(NC(=O)NC2CCCCC2)cccc1-c1cc(Nc2ccc(C(=O)N3CCOCC3)cn2)c2nccn2c1] | | |
| | 1-Cyclohexyl-3-(2-methyl-3-{8-[5-(morpholine-4-carbonyl)-pyridin-2-ylamino]-imidazo[1,2-a]pyridin-6-yl}-phenyl)-urea | | |
| I-127 | 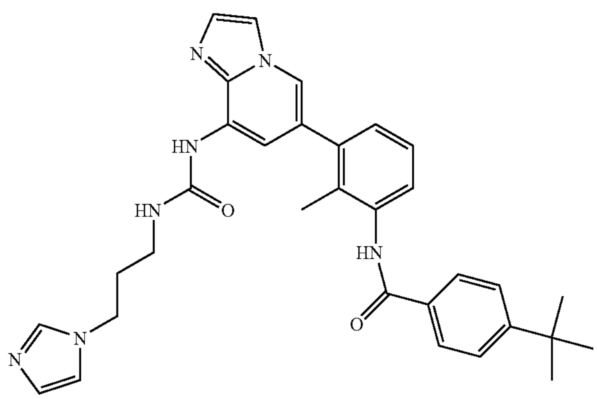 [SMILES: Cc1c(NC(=O)c2ccc(C(C)(C)C)cc2)cccc1-c1cc(NC(=O)NCCCn2ccnc2)c2nccn2c1] | | |
| | 4-tert-Butyl-N-(3-{8-[3-(3-imidazol-1-yl-propyl)-ureido]-imidazo[1,2-a]pyridin-6-yl}-2-methyl-phenyl)-benzamide | | |
| I-128 | 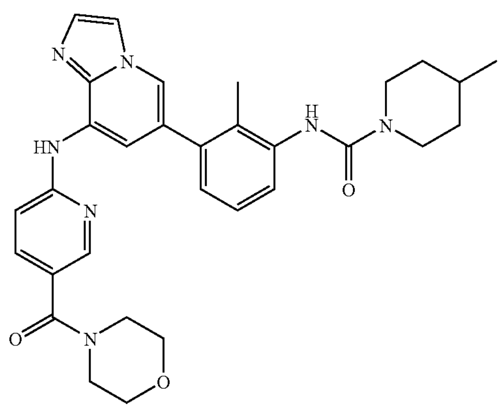 [SMILES: Cc1c(NC(=O)N2CCC(C)CC2)cccc1-c1cc(Nc2ccc(C(=O)N3CCOCC3)cn2)c2nccn2c1] | | |
| | 4-Methyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide | | |
| I-129 | 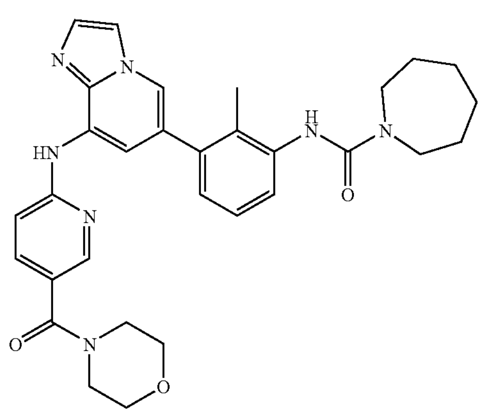 [SMILES: Cc1c(NC(=O)N2CCCCCC2)cccc1-c1cc(Nc2ccc(C(=O)N3CCOCC3)cn2)c2nccn2c1] | | |
| | Azepane-1-carboxylic acid (2-methyl-3-{8-[5-(morpholine-4-carbonyl)-pyridin-2-ylamino]-imidazo[1,2-a]pyridin-6-yl}-phenyl)-amide | | |

TABLE Y-continued

| # | Structure | MS | MP |
|---|-----------|----|----|
| I-130 | 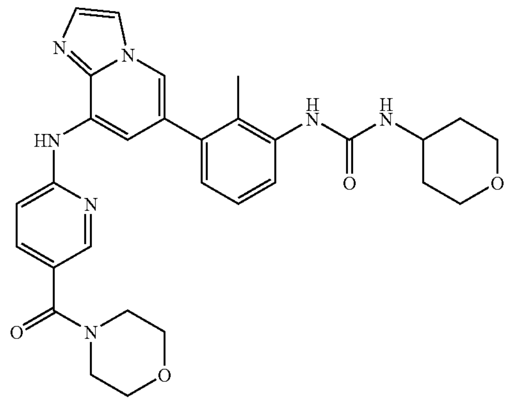 [SMILES: Cc1c(NC(=O)NC2CCOCC2)cccc1-c1cc(Nc2ccc(C(=O)N3CCOCC3)cn2)c2nccn2c1] | | 1-(2-Methyl-3-{8-[5-(morpholine-4-carbonyl)-pyridin-2-ylamino]-imidazo[1,2-a]pyridin-6-yl}-phenyl)-3-(tetrahydro-pyran-4-yl)-urea |
| I-131 | 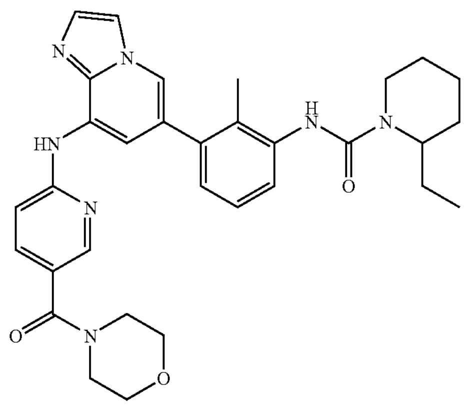 [SMILES: CCC1CCCCN1C(=O)Nc1cccc(-c2cc(Nc3ccc(C(=O)N4CCOCC4)cn3)c3nccn3c2)c1C] | | 2-Ethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide |
| I-132 | 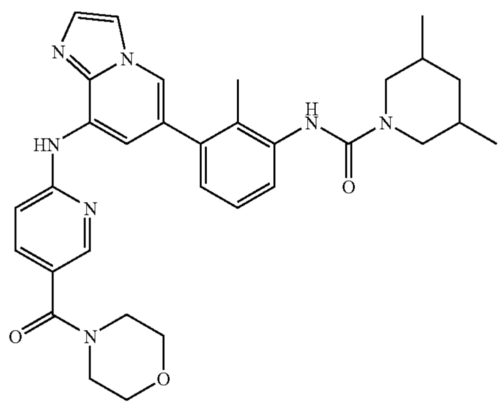 | | 3,5-Dimethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide |
| I-133 | 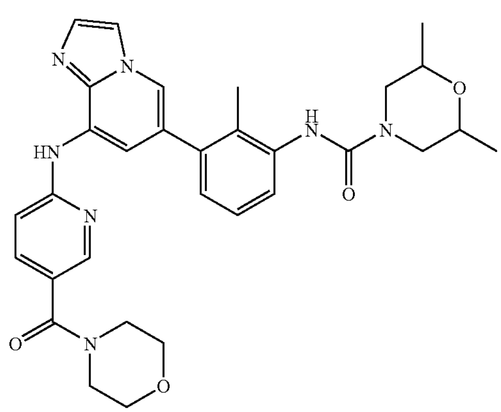 [SMILES: Cc1c(NC(=O)N2CC(C)OC(C)C2)cccc1-c1cc(Nc2ccc(C(=O)N3CCOCC3)cn2)c2nccn2c1] | | 2,6-Dimethyl-morpholine-4-carboxylic acid (2-methyl-3-{8-[5-(morpholine-4-carbonyl)-pyridin-2-ylamino]-imidazo[1,2-a]pyridin-6-yl}-phenyl)-amide |

TABLE Y-continued

| # | Structure | MS | MP |
|---|-----------|----|----|
| I-134 | 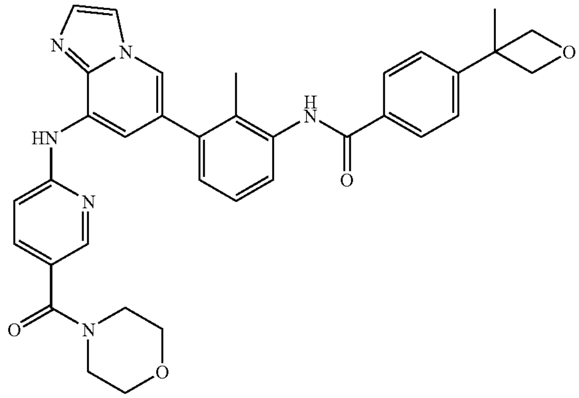 [SMILES: Cc1c(NC(=O)c2ccc(C3(C)COC3)cc2)cccc1-c1cc(Nc2ccc(C(=O)N3CCOCC3)cn2)c2nccn2c1] | N-(2-Methyl-3-{8-[5-(morpholine-4-carbonyl)-pyridin-2-ylamino]-imidazo[1,2-a]pyridin-6-yl}-phenyl)-4-(3-methyl-oxetan-3-yl)-benzamide | |
| I-135 | 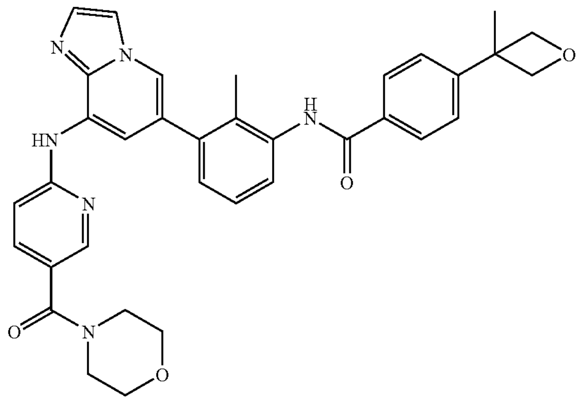 [SMILES: Cc1c(NC(=O)c2ccc(C3(C)COC3)cc2)cccc1-c1cc(Nc2ccc(C(=O)N3CCOCC3)cn2)c2nccn2c1] | N-(2-Methyl-3-{8-[5-(morpholine-4-carbonyl)-pyridin-2-ylamino]-imidazo[1,2-a]pyridin-6-yl}-phenyl)-4-(3-methyl-oxetan-3-yl)-benzamide | |
| I-136 | 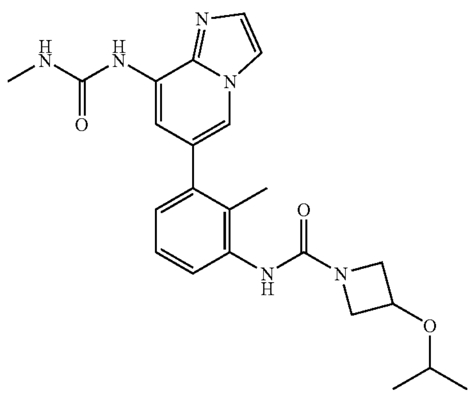 [SMILES: CNC(=O)Nc1cc(-c2cccc(NC(=O)N3CC(OC(C)C)C3)c2C)cn2ccnc12] | 3-Isopropoxy-azetidine-1-carboxylic acid {2-methyl-3-{8-(3-methyl-ureido)-imidazo[1,2-a]pyridin-6-yl]-phenyl}-amide | |
| I-137 | 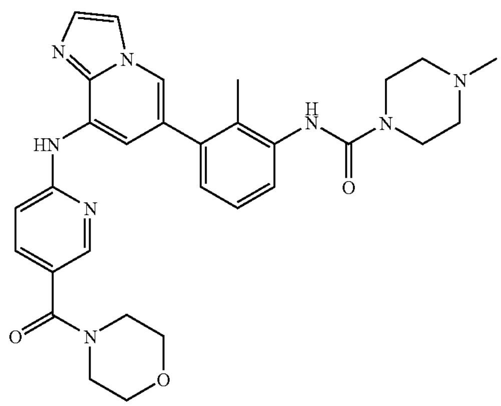 | 4-Methyl-piperazine-1-carboxylic acid (2-methyl-3-{8-[5-(morpholine-4-carbonyl)-pyridin-2-ylamino]-imidazo[1,2-a]pyridin-6-yl}-phenyl)-amide | |

TABLE Y-continued

| # | Structure | MS | MP |
|---|-----------|----|----|

I-138 — 1-(2-Dimethylamino-ethyl)-1-methyl-3-(2-methyl-3-{8-[5-(morpholine-4-carbonyl)-pyridin-2-ylamino]-imidazo[1,2-a]pyridin-6-yl}-phenyl)-urea I-139 — 1-[2-(3H-Imidazol-4-yl)-ethyl]-3-(2-methyl-3-{8-[5-(morpholine-4-carbonyl)-pyridin-2-ylamino]-imidazo[1,2-a]pyridin-6-yl}-phenyl)-urea I-140 — 4-Methyl-[1,4]diazepane-1-carboxylic acid (2-methyl-3-{8-[5-(morpholine-4-carbonyl)-pyridin-2-ylamino]-imidazo[1,2-a]pyridin-6-yl}-phenyl)-amide TABLE Y-continued

| # | Structure | | MS | MP |
|---|---|---|---|---|
| I-141 | 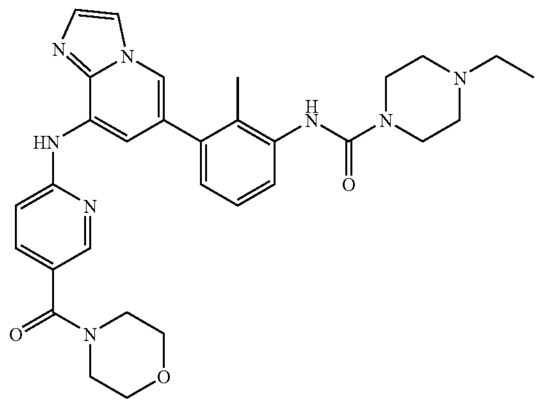 [SMILES: CCN1CCN(C(=O)Nc2cccc(-c3cc(Nc4ccc(C(=O)N5CCOCC5)cn4)c4nccn4c3)c2C)CC1] | 4-Ethyl-piperazine-1-carboxylic acid (2-methyl-3-{8-[5-(morpholine-4-carbonyl)-pyridin-2-ylamino]-imidazo[1,2-a]pyridin-6-yl}-phenyl)-amide | | |
| I-142 | 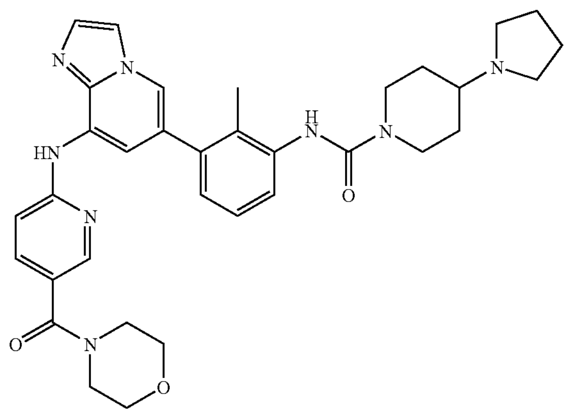 [SMILES: Cc1c(NC(=O)N2CCC(N3CCCC3)CC2)cccc1-c1cc(Nc2ccc(C(=O)N3CCOCC3)cn2)c2nccn2c1] | 4-Pyrrolidin-1-yl-piperidine-1-carboxylic acid (2-methyl-3-{8-[5-(morpholine-4-carbonyl)-pyridin-2-ylamino]-imidazo[1,2-a]pyridin-6-yl}-phenyl)-amide | | |
| I-143 | 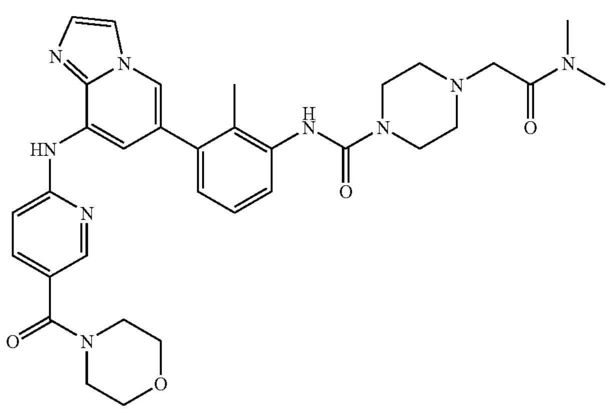 [SMILES: Cc1c(NC(=O)N2CCN(CC(=O)N(C)C)CC2)cccc1-c1cc(Nc2ccc(C(=O)N3CCOCC3)cn2)c2nccn2c1] | 4-Dimethylcarbamoylmethyl-piperazine-1-carboxylic acid (2-methyl-3-{8-[5-(morpholine-4-carbonyl)-pyridin-2-ylamino]-imidazo[1,2-a]pyridin-6-yl}-phenyl)-amide | | |
| I-144 | 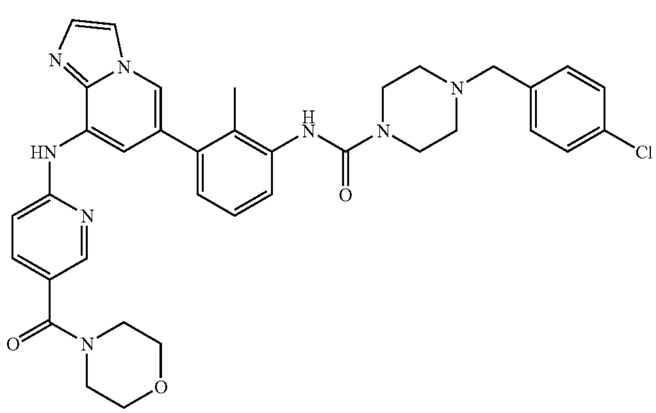 [SMILES: Cc1c(NC(=O)N2CCN(Cc3ccc(Cl)cc3)CC2)cccc1-c1cc(Nc2ccc(C(=O)N3CCOCC3)cn2)c2nccn2c1] | 4-(4-Chloro-benzyl)-piperazine-1-carboxylic acid (2-methyl-3-{8-[5-(morpholine-4-carbonyl)-pyridin-2-ylamino]-imidazo[1,2-a]pyridin-6-yl}-phenyl)-amide | | |

TABLE Y-continued

| # | Structure | | MS | MP |
|---|---|---|---|---|
| I-145 | 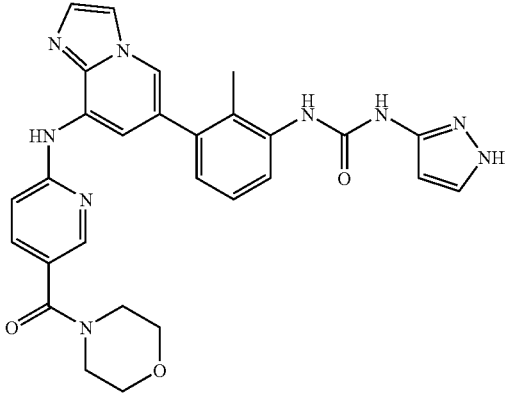 [SMILES: Cc1c(NC(=O)Nc2cc[nH]n2)cccc1-c1cc(Nc2ccc(C(=O)N3CCOCC3)cn2)c2nccn2c1] | 1-(2-Methyl-3-{8-[5-(morpholine-4-carbonyl)-pyridin-2-ylamino]-imidazo[1,2-a]pyridin-6-yl}-phenyl)-3-(1H-pyrazol-3-yl)-urea | | |
| I-146 | 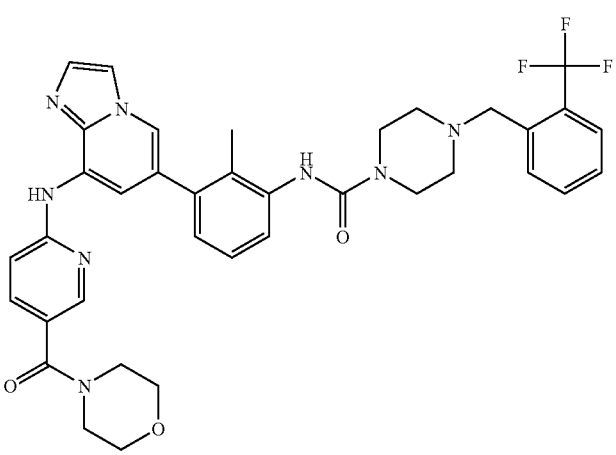 [SMILES: Cc1c(NC(=O)N2CCN(Cc3ccccc3C(F)(F)F)CC2)cccc1-c1cc(Nc2ccc(C(=O)N3CCOCC3)cn2)c2nccn2c1] | 4-(2-Trifluoromethyl-benzyl)-piperazine-1-carboxylic acid (2-methyl-3-{8-[5-(morpholine-4-carbonyl)-pyridin-2-ylamino]-imidazo[1,2-a]pyridin-6-yl}-phenyl)-amide | | |
| I-147 | 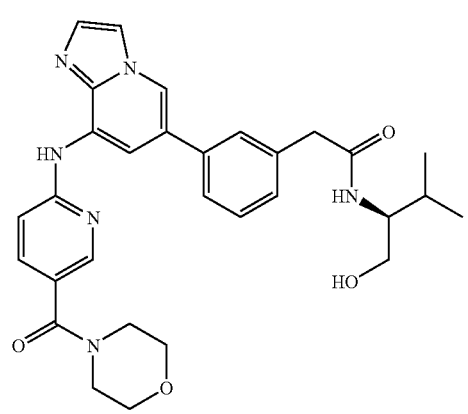 [SMILES: CC(C)[C@@H](CO)NC(=O)Cc1cccc(-c2cc(Nc3ccc(C(=O)N4CCOCC4)cn3)c3nccn3c2)c1] | N-((S)-1-Hydroxymethyl-2-methyl-propyl)-2-(3-{8-[5-(morpholine-4-carbonyl)-pyridin-2-ylamino]-imidazo[1,2-a]pyridin-6-yl}-phenyl)-acetamide | | |

TABLE Y-continued

| # | Structure | | MS | MP |
|---|---|---|---|---|
| I-148 | 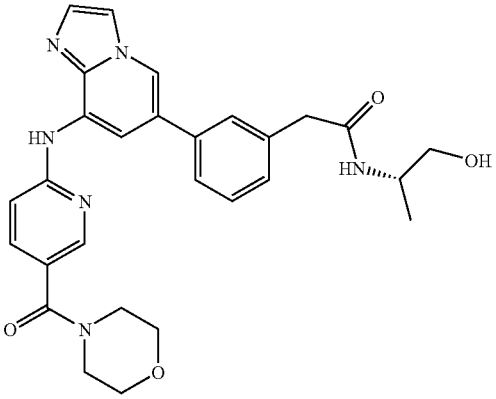 [SMILES: C[C@@H](CO)NC(=O)Cc1cccc(-c2cc(Nc3ccc(C(=O)N4CCOCC4)cn3)c3nccn3c2)c1] | N-((S)-2-Hydroxy-1-methyl-ethyl)-2-(3-{8-[5-(morpholine-4-carbonyl)-pyridin-2-ylamino]-imidazo[1,2-a]pyridin-6-yl}-phenyl)-acetamide | | |
| I-149 | 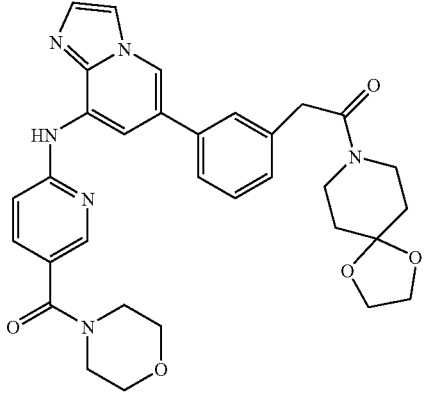 [SMILES: O=C(Cc1cccc(-c2cc(Nc3ccc(C(=O)N4CCOCC4)cn3)c3nccn3c2)c1)N1CCC2(CC1)OCCO2] | 1-(1,4-Dioxa-8-aza-spiro[4.5]dec-8-yl)-2-(3-{8-[5-(morpholine-4-carbonyl)-pyridin-2-ylamino]-imidazo[1,2-a]pyridin-6-yl}-phenyl)-ethanone | | |
| I-150 | 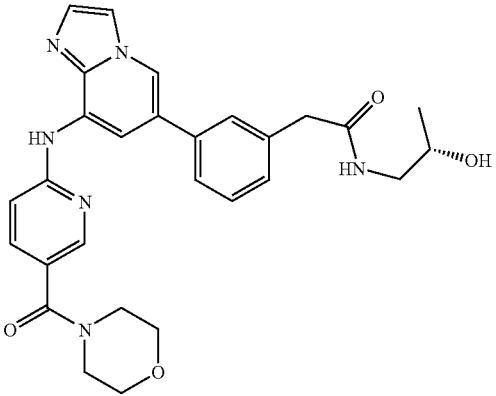 [SMILES: C[C@H](O)CNC(=O)Cc1cccc(-c2cc(Nc3ccc(C(=O)N4CCOCC4)cn3)c3nccn3c2)c1] | N-((S)-2-Hydroxy-propyl)-2-(3-{8-[5-(morpholine-4-carbonyl)-pyridin-2-ylamino]-imidazo[1,2-a]pyridin-6-yl}-phenyl)-acetamide | | |
| I-151 | 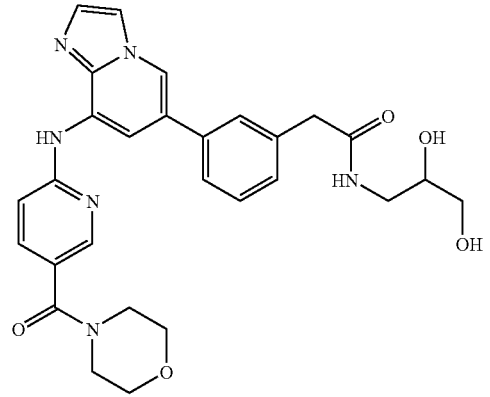 [SMILES: O=C(Cc1cccc(-c2cc(Nc3ccc(C(=O)N4CCOCC4)cn3)c3nccn3c2)c1)NCC(O)CO] | N-(2,3-Dihydroxy-propyl)-2-(3-{8-[5-(morpholine-4-carbonyl)-pyridin-2-ylamino]-imidazo[1,2-a]pyridin-6-yl}-phenyl)-acetamide | | |

TABLE Y-continued
| # | Structure | | MS | MP |
|---|---|---|---|---|
I-152 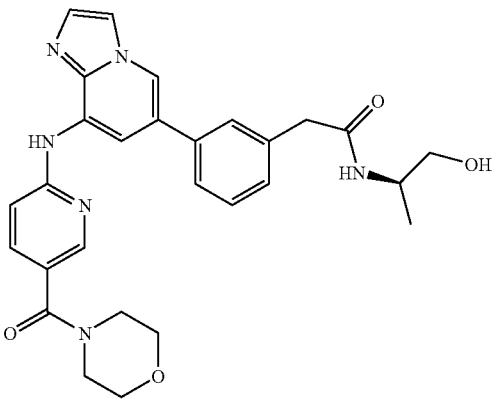 [SMILES: C[C@H](CO)NC(=O)Cc1cccc(-c2cc(Nc3ccc(C(=O)N4CCOCC4)cn3)c3nccn3c2)c1] N-((R)-2-Hydroxy-1-methyl-ethyl)-2-(3-{8-[5-(morpholine-4-carbonyl)-pyridin-2-ylamino]-imidazo[1,2-a]pyridin-6-yl}-phenyl)-acetamide
I-153 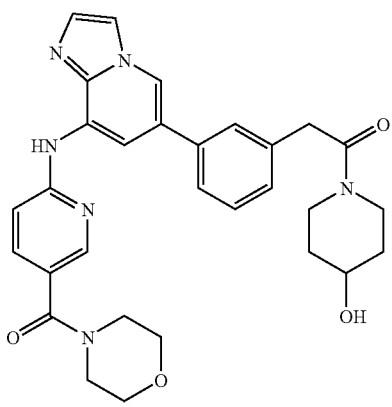 1-(4-Hydroxy-piperidin-1-yl)-2-(3-{8-[5-(morpholine-4-carbonyl)-pyridin-2-ylamino]-imidazo[1,2-a]pyridin-6-yl}-phenyl)-ethanone
I-154 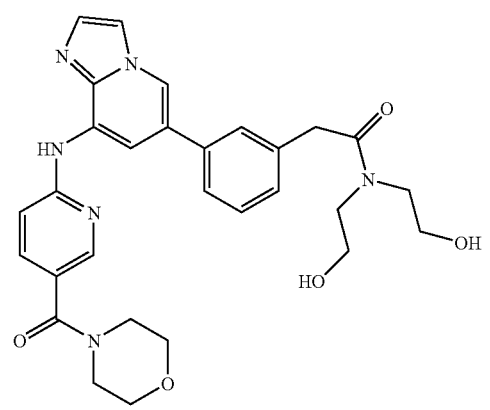 [SMILES: O=C(Cc1cccc(-c2cc(Nc3ccc(C(=O)N4CCOCC4)cn3)c3nccn3c2)c1)N(CCO)CCO] N,N-Bis-(2-hydroxy-ethyl)-2-(3-{8-[5-(morpholine-4-carbonyl)-pyridin-2-ylamino]-imidazo[1,2-a]pyridin-6-yl}-phenyl)-acetamide TABLE Y-continued

| # | Structure | | MS | MP |
|---|---|---|---|---|
| I-155 | 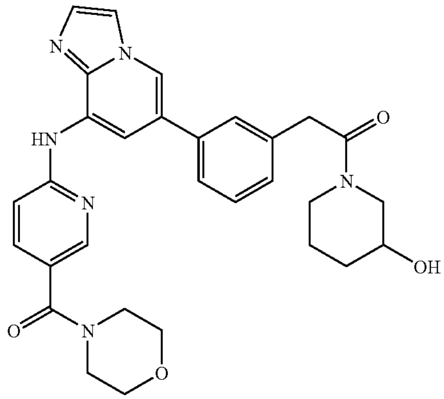 [SMILES: O=C(Cc1cccc(-c2cc(Nc3ccc(C(=O)N4CCOCC4)cn3)c3nccn3c2)c1)N1CCCC(O)C1] | 1-(3-Hydroxy-piperidin-1-yl)-2-(3-{8-[5-(morpholine-4-carbonyl)-pyridin-2-ylamino]-imidazo[1,2-a]pyridin-6-yl}-phenyl)-ethanone | | |
| I-156 | 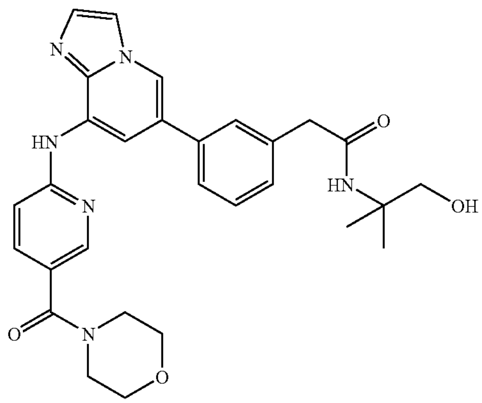 [SMILES: CC(C)(CO)NC(=O)Cc1cccc(-c2cc(Nc3ccc(C(=O)N4CCOCC4)cn3)c3nccn3c2)c1] | N-(2-Hydroxy-1,1-dimethyl-ethyl)-2-(3-{8-[5-(morpholine-4-carbonyl)-pyridin-2-ylamino]-imidazo[1,2-a]pyridin-6-yl}-phenyl)-acetamide | | |
| I-157 | 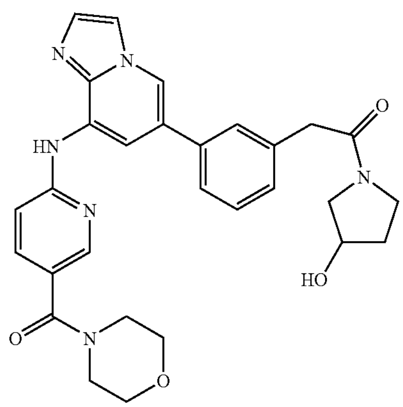 [SMILES: O=C(Cc1cccc(-c2cc(Nc3ccc(C(=O)N4CCOCC4)cn3)c3nccn3c2)c1)N1CCC(O)C1] | 1-(3-Hydroxy-pyrrolidin-1-yl)-2-(3-{8-[5-(morpholine-4-carbonyl)-pyridin-2-ylamino]-imidazo[1,2-a]pyridin-6-yl}-phenyl)-ethanone | | |
| I-158 | 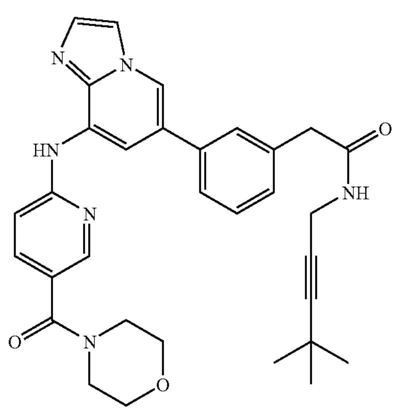 [SMILES: CC(C)(C)C#CCNC(=O)Cc1cccc(-c2cc(Nc3ccc(C(=O)N4CCOCC4)cn3)c3nccn3c2)c1] | N-(4,4-Dimethyl-pent-2-ynyl)-2-(3-{8-[5-(morpholine-4-carbonyl)-pyridin-2-ylamino]-imidazo[1,2-a]pyridin-6-yl}-phenyl)-acetamide | | |

| # | Structure | | MS | MP |
|---|---|---|---|---|
| I-159 | 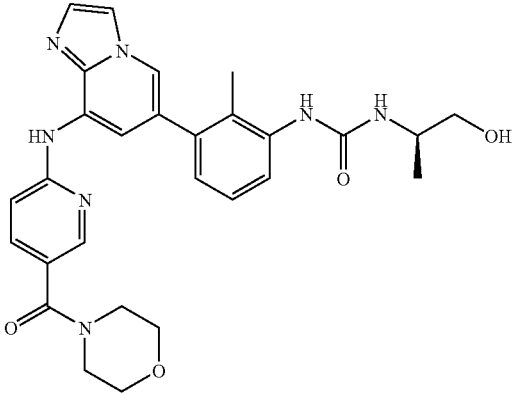 [SMILES: Cc1c(NC(=O)N[C@H](C)CO)cccc1-c1cc(Nc2ccc(C(=O)N3CCOCC3)cn2)c2nccn2c1] | 1-((R)-2-Hydroxy-1-methyl-ethyl)-3-(2-methyl-3-{8-[5-(morpholine-4-carbonyl)-pyridin-2-ylamino]-imidazo[1,2-a]pyridin-6-yl}-phenyl)-urea | | |
| I-160 | 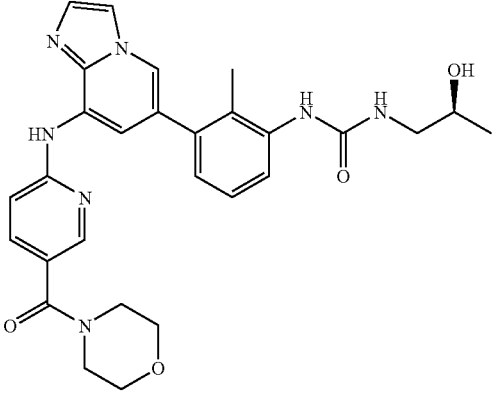 [SMILES: Cc1c(NC(=O)NC[C@H](C)O)cccc1-c1cc(Nc2ccc(C(=O)N3CCOCC3)cn2)c2nccn2c1] | 1-((S)-2-Hydroxy-propyl)-3-(2-methyl-3-{8-[5-(morpholine-4-carbonyl)-pyridin-2-ylamino]-imidazo[1,2-a]pyridin-6-yl}-phenyl)-urea | | |
| I-161 | 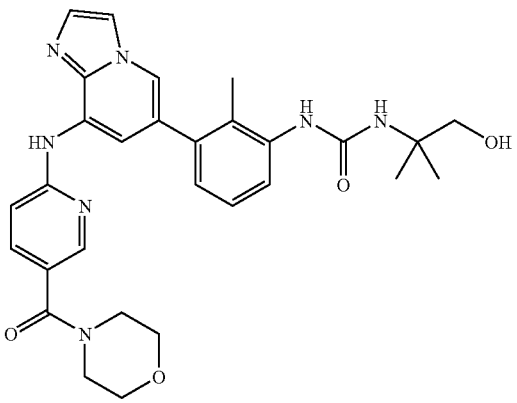 [SMILES: Cc1c(NC(=O)NC(C)(C)CO)cccc1-c1cc(Nc2ccc(C(=O)N3CCOCC3)cn2)c2nccn2c1] | 1-(2-Hydroxy-1,1-dimethyl-ethyl)-3-(2-methyl-3-{8-[5-(morpholine-4-carbonyl)-pyridin-2-ylamino]-imidazo[1,2-a]pyridin-6-yl}-phenyl)-urea | | |

TABLE Y-continued

| # | Structure | MS | MP |
|---|---|---|---|
| I-162 | 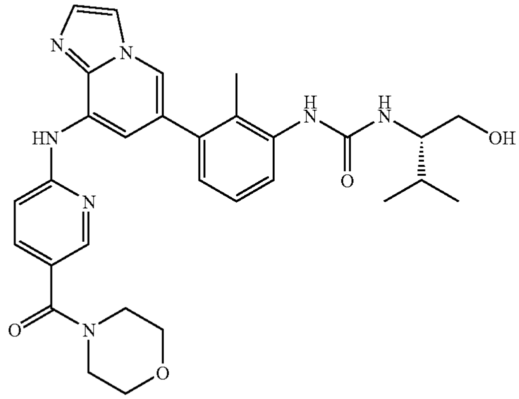 [SMILES: Cc1c(NC(=O)N[C@H](CO)C(C)C)cccc1-c1cc(Nc2ccc(C(=O)N3CCOCC3)cn2)c2nccn2c1] | 1-((S)-1-Hydroxymethyl-2-methyl-propyl)-3-(2-methyl-3-{8-[5-(morpholine-4-carbonyl)-pyridin-2-ylamino]-imidazo[1,2-a]pyridin-6-yl}-phenyl)-urea | |
| I-163 | 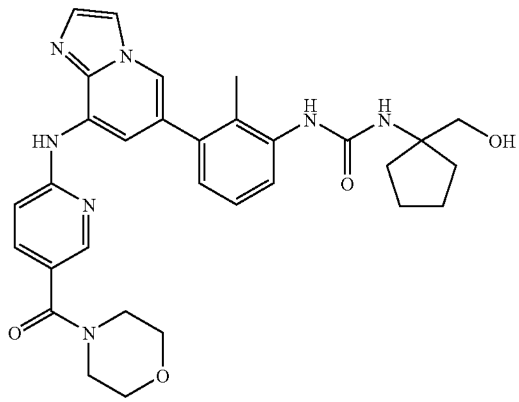 [SMILES: Cc1c(NC(=O)NC2(CO)CCCC2)cccc1-c1cc(Nc2ccc(C(=O)N3CCOCC3)cn2)c2nccn2c1] | 1-(1-Hydroxymethyl-cyclopentyl)-3-(2-methyl-3-{8-[5-(morpholine-4-carbonyl)-pyridin-2-ylamino]-imidazo[1,2-a]pyridin-6-yl}-phenyl)-urea | |
| I-164 | 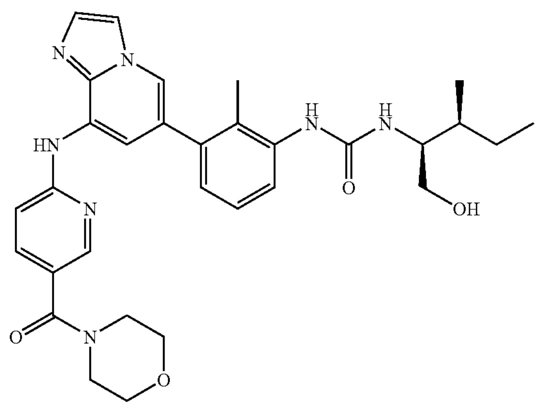 [SMILES: CC[C@H](C)[C@@H](CO)NC(=O)Nc1cccc(-c2cc(Nc3ccc(C(=O)N4CCOCC4)cn3)c3nccn3c2)c1C] | 1-((1S,2S)-1-Hydroxymethyl-2-methyl-butyl)-3-(2-methyl-3-{8-[5-(morpholine-4-carbonyl)-pyridin-2-ylamino]-imidazo[1,2-a]pyridin-6-yl}-phenyl)-urea | |
| I-165 | 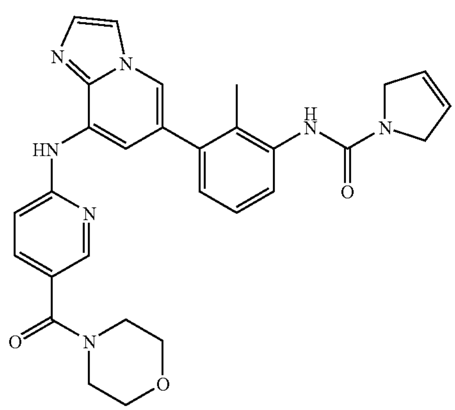 [SMILES: Cc1c(NC(=O)N2CC=CC2)cccc1-c1cc(Nc2ccc(C(=O)N3CCOCC3)cn2)c2nccn2c1] | 2,5-Dihydro-pyrrole-1-carboxylic acid (2-methyl-3-{8-[5-(morpholine-4-carbonyl)-pyridin-2-ylamino]-imidazo[1,2-a]pyridin-6-yl}-phenyl)-amide | |

TABLE Y-continued
| # | Structure | | MS | MP |
|---|---|---|---|---|
| I-166 | 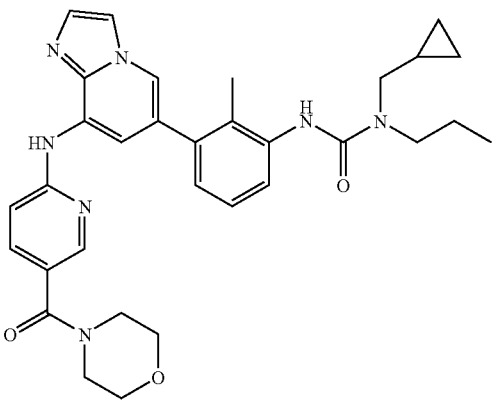 [SMILES: CCCN(CC1CC1)C(=O)Nc1cccc(-c2cc(Nc3ccc(C(=O)N4CCOCC4)cn3)c3nccn3c2)c1C] | 1-Cyclopropylmethyl-3-(2-methyl-3-{8-[5-(morpholine-4-carbonyl)-pyridin-2-ylamino]-imidazo[1,2-a]pyridin-6-yl}-phenyl)-1-propyl-urea | | |
| I-167 | 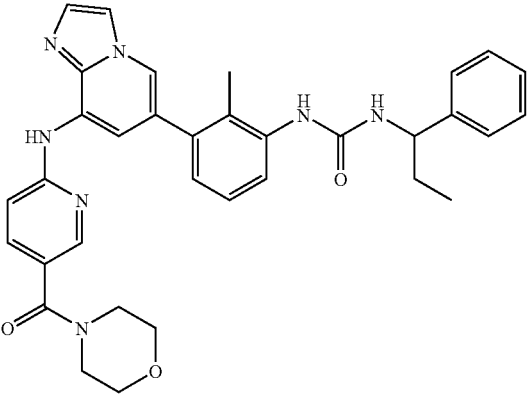 [SMILES: CCC(NC(=O)Nc1cccc(-c2cc(Nc3ccc(C(=O)N4CCOCC4)cn3)c3nccn3c2)c1C)c1ccccc1] | 1-(2-Methyl-3-{8-[5-(morpholine-4-carbonyl)-pyridin-2-ylamino]-imidazo[1,2-a]pyridin-6-yl}-phenyl)-3-(1-phenyl-propyl)-urea | | |
| I-168 | 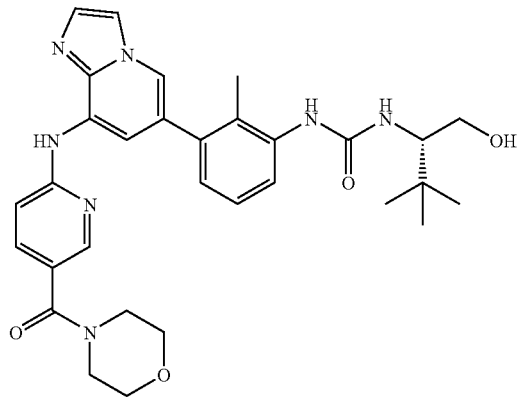 [SMILES: Cc1c(NC(=O)N[C@H](CO)C(C)(C)C)cccc1-c1cc(Nc2ccc(C(=O)N3CCOCC3)cn2)c2nccn2c1] | 1-((S)-1-Hydroxymethyl-2,2-dimethyl-propyl)-3-(2-methyl-3-{8-[5-(morpholine-4-carbonyl)-pyridin-2-ylamino]-imidazo[1,2-a]pyridin-6-yl}-phenyl)-urea | | |

TABLE Y-continued

| # | Structure | | MS | MP |
|---|---|---|---|---|
| I-169 | 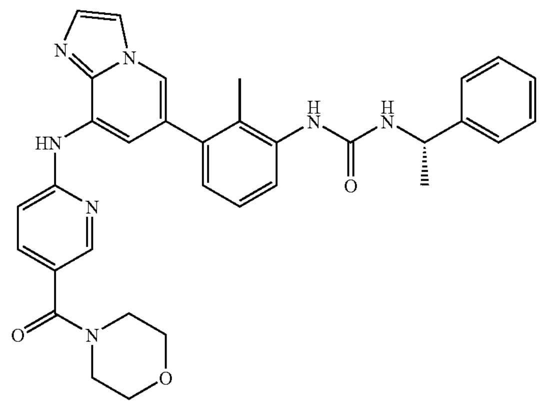 [SMILES: Cc1c(NC(=O)N[C@@H](C)c2ccccc2)cccc1-c1cc(Nc2ccc(C(=O)N3CCOCC3)cn2)c2nccn2c1] | 1-(2-Methyl-3-{8-[5-(morpholine-4-carbonyl)-pyridin-2-ylamino]-imidazo[1,2-a]pyridin-6-yl}-phenyl)-3-((S)-1-phenyl-ethyl)-urea | | |
| I-170 | 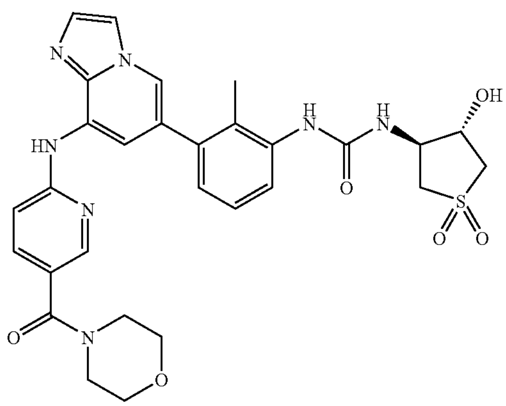 [SMILES: Cc1c(NC(=O)N[C@@H]2CS(=O)(=O)C[C@H]2O)cccc1-c1cc(Nc2ccc(C(=O)N3CCOCC3)cn2)c2nccn2c1] | 1-((3S,4S)-4-Hydroxy-1,1-dioxo-tetrahydro-1$\lambda^6$-thiophen-3-yl)-3-(2-methyl-3-{8-[5-(morpholine-4-carbonyl)-pyridin-2-ylamino]-imidazo[1,2-a]pyridin-6-yl}-phenyl)-urea | | |
| I-171 | 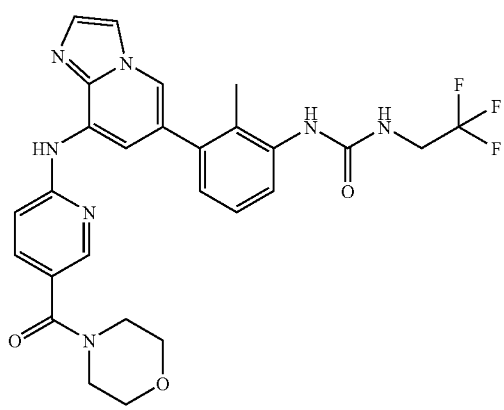 [SMILES: Cc1c(NC(=O)NCC(F)(F)F)cccc1-c1cc(Nc2ccc(C(=O)N3CCOCC3)cn2)c2nccn2c1] | 1-(2-Methyl-3-{8-[5-(morpholine-4-carbonyl)-pyridin-2-ylamino]-imidazo[1,2-a]pyridin-6-yl}-phenyl)-3-(2,2,2-trifluoro-ethyl)-urea | | |
| I-172 | 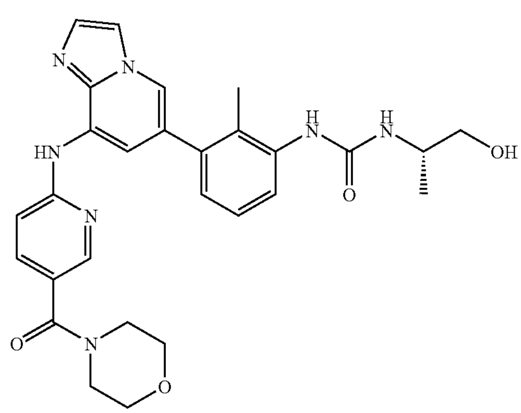 [SMILES: Cc1c(NC(=O)N[C@@H](C)CO)cccc1-c1cc(Nc2ccc(C(=O)N3CCOCC3)cn2)c2nccn2c1] | 1-((S)-2-Hydroxy-1-methyl-ethyl)-3-(2-methyl-3-{8-[5-(morpholine-4-carbonyl)-pyridin-2-ylamino]-imidazo[1,2-a]pyridin-6-yl}-phenyl)-urea | | |

TABLE Y-continued

| # | Structure | | MS | MP |
|---|---|---|---|---|
| I-173 | 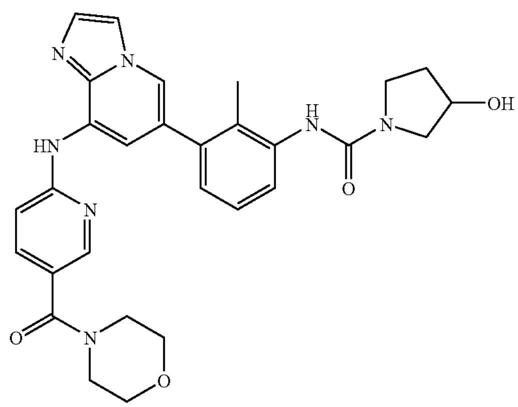 [SMILES: Cc1c(NC(=O)N2CCC(O)C2)cccc1-c1cc(Nc2ccc(C(=O)N3CCOCC3)cn2)c2nccn2c1] | 3-Hydroxy-pyrrolidine-1-carboxylic acid (2-methyl-3-{8-[5-(morpholine-4-carbonyl)-pyridin-2-ylamino]-imidazo[1,2-a]pyridin-6-yl}-phenyl)-amide | | |
| I-174 | 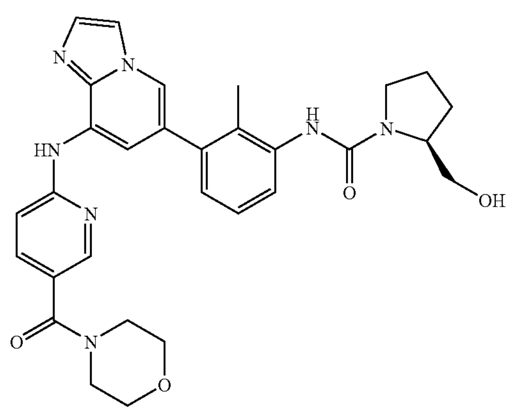 [SMILES: Cc1c(NC(=O)N2CCC[C@H]2CO)cccc1-c1cc(Nc2ccc(C(=O)N3CCOCC3)cn2)c2nccn2c1] | (S)-2-Hydroxymethyl-pyrrolidine-1-carboxylic acid (2-methyl-3-{8-[5-(morpholine-4-carbonyl)-pyridin-2-ylamino]-imidazo[1,2-a]pyridin-6-yl}-phenyl)-amide | | |
| I-175 | 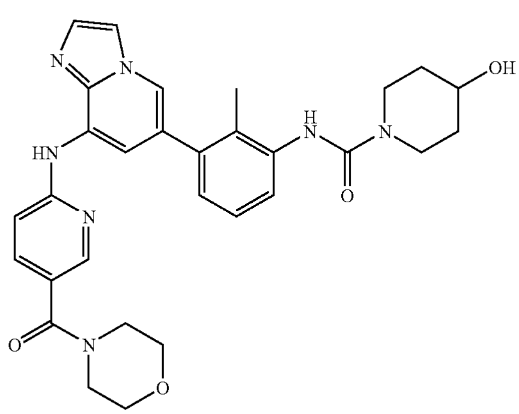 [SMILES: Cc1c(NC(=O)N2CCC(O)CC2)cccc1-c1cc(Nc2ccc(C(=O)N3CCOCC3)cn2)c2nccn2c1] | 4-Hydroxy-piperidine-1-carboxylic acid (2-methyl-3-{8-[5-(morpholine-4-carbonyl)-pyridin-2-ylamino]-imidazo[1,2-a]pyridin-6-yl}-phenyl)-amide | | |

TABLE Y-continued

| # | Structure | | MS | MP |
|---|---|---|---|---|
| I-176 | 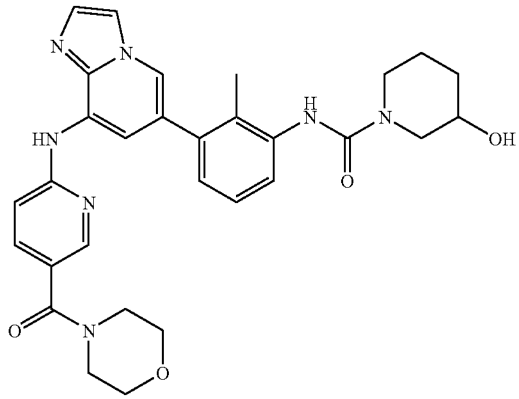 [SMILES: Cc1c(NC(=O)N2CCCC(O)C2)cccc1-c1cc(Nc2ccc(C(=O)N3CCOCC3)cn2)c2nccn2c1] | 3-Hydroxy-piperidine-1-carboxylic acid (2-methyl-3-{8-[5-(morpholine-4-carbonyl)-pyridin-2-ylamino]-imidazo[1,2-a]pyridin-6-yl}-phenyl)-amide | | |
| I-177 | 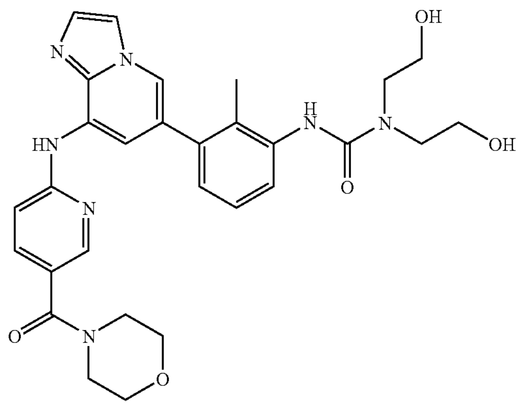 [SMILES: Cc1c(NC(=O)N(CCO)CCO)cccc1-c1cc(Nc2ccc(C(=O)N3CCOCC3)cn2)c2nccn2c1] | 1,1-Bis-(2-hydroxy-ethyl)-3-(2-methyl-3-{8-[5-(morpholine-4-carbonyl)-pyridin-2-ylamino]-imidazo[1,2-a]pyridin-6-yl}-phenyl)-urea | | |
| I-178 | 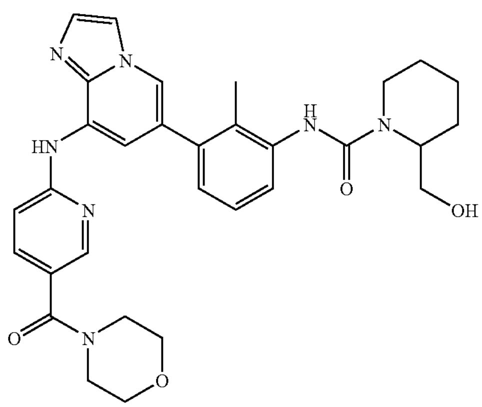 [SMILES: Cc1c(NC(=O)N2CCCCC2CO)cccc1-c1cc(Nc2ccc(C(=O)N3CCOCC3)cn2)c2nccn2c1] | 2-Hydroxymethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide | | |
| I-179 | 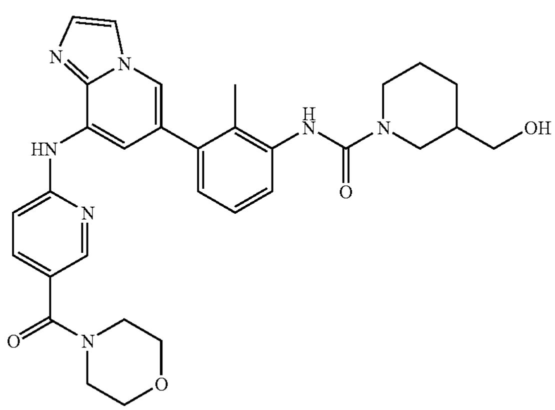 [SMILES: Cc1c(NC(=O)N2CCCC(CO)C2)cccc1-c1cc(Nc2ccc(C(=O)N3CCOCC3)cn2)c2nccn2c1] | 3-Hydroxymethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide | | |

| # | Structure | | MS | MP |
|---|---|---|---|---|
| I-180 | 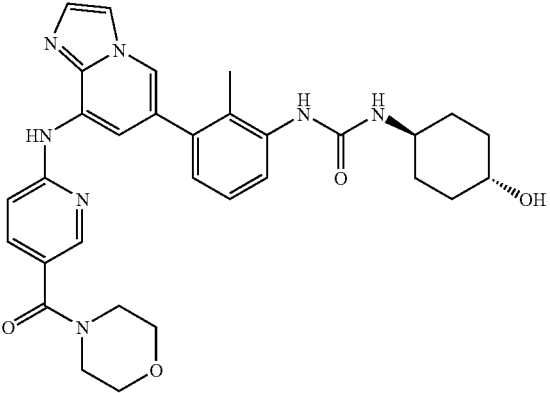 [SMILES: Cc1c(NC(=O)N[C@H]2CC[C@H](O)CC2)cccc1-c1cc(Nc2ccc(C(=O)N3CCOCC3)cn2)c2nccn2c1] | 1-(4-Hydroxy-cyclohexyl)-3-(2-methyl-3-{8-[5-(morpholine-4-carbonyl)-pyridin-2-ylamino]-imidazo[1,2-a]pyridin-6-yl}-phenyl)-urea | | |
| I-181 | 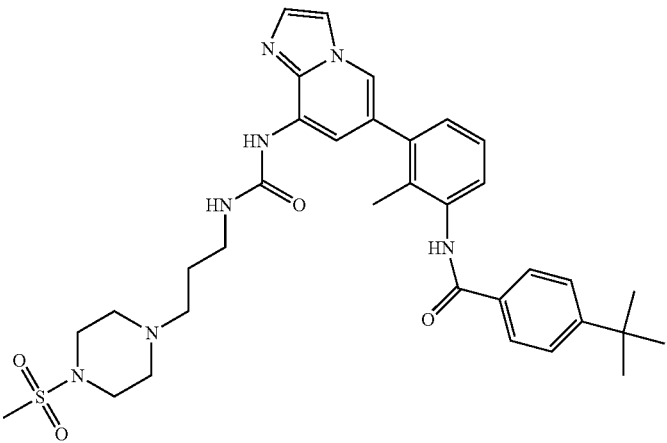 [SMILES: Cc1c(NC(=O)c2ccc(C(C)(C)C)cc2)cccc1-c1cc(NC(=O)NCCCN2CCN(S(C)(=O)=O)CC2)c2nccn2c1] | 4-tert-Butyl-N-[3-(8-{3-[3-(4-methanesulfonyl-piperazin-1-yl)-propyl]-ureido}-imidazo[1,2-a]pyridin-6-yl)-2-methyl-phenyl]-benzamide | | |
| I-182 | 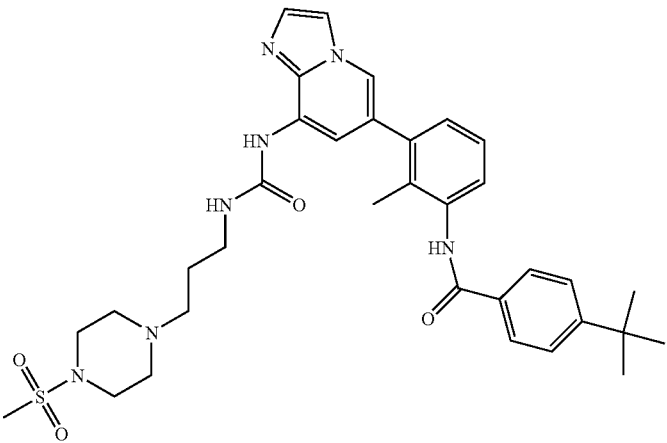 [SMILES: Cc1c(NC(=O)c2ccc(C(C)(C)C)cc2)cccc1-c1cc(NC(=O)NCCCN2CCN(S(C)(=O)=O)CC2)c2nccn2c1] | 4-tert-Butyl-N-[3-(8-{3-[3-(4-methanesulfonyl-piperazin-1-yl)-propyl]-ureido}-imidazo[1,2-a]pyridin-6-yl)-2-methyl-phenyl]-benzamide | | |

TABLE Y-continued

| # | Structure | | MS | MP |
|---|---|---|---|---|
| I-183 | 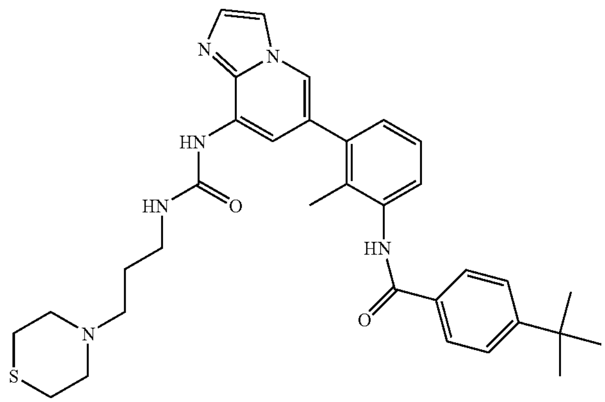 [SMILES: Cc1c(NC(=O)c2ccc(C(C)(C)C)cc2)cccc1-c1cc(NC(=O)NCCCN2CCSCC2)c2nccn2c1] | 4-tert-Butyl-N-(2-methyl-3-{8-[3-(3-thiomorpholin-4-yl-propyl)-ureido]-imidazo[1,2-a]pyridin-6-yl}-phenyl)-benzamide | | |
| I-184 | 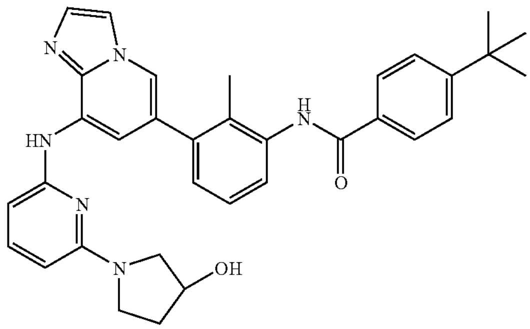 [SMILES: Cc1c(NC(=O)c2ccc(C(C)(C)C)cc2)cccc1-c1cc(Nc2cccc(N3CCC(O)C3)n2)c2nccn2c1] | 4-tert-Butyl-N-(3-{8-[6-(3-hydroxy-pyrrolidin-1-yl)-pyridin-2-ylamino]-imidazo[1,2-a]pyridin-6-yl}-2-methyl-phenyl)-benzamide | | |
| I-185 | 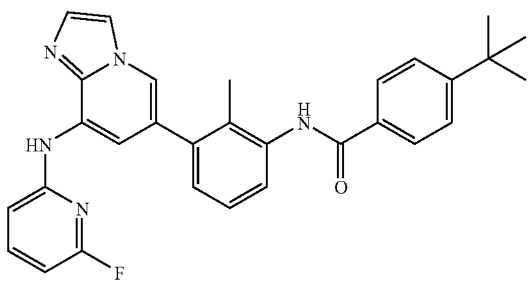 [SMILES: Cc1c(NC(=O)c2ccc(C(C)(C)C)cc2)cccc1-c1cc(Nc2cccc(F)n2)c2nccn2c1] | 4-tert-Butyl-N-{3-[8-(6-fluoro-pyridin-2-ylamino)-imidazo[1,2-a]pyridin-6-yl]-2-methyl-phenyl}-benzamide | | |
| I-186 | 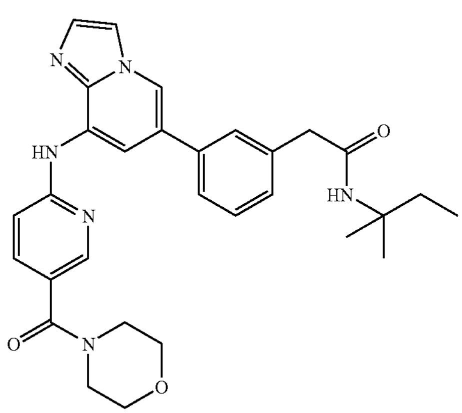 [SMILES: CCC(C)(C)NC(=O)Cc1cccc(-c2cc(Nc3ccc(C(=O)N4CCOCC4)cn3)c3nccn3c2)c1] | N-(1,1-Dimethyl-propyl)-2-(3-{8-[5-(morpholine-4-carbonyl)-pyridin-2-ylamino]-imidazo[1,2-a]pyridin-6-yl}-phenyl)-acetamide | | |

| # | Structure | MS | MP |
|---|-----------|----|----|
| I-187 | 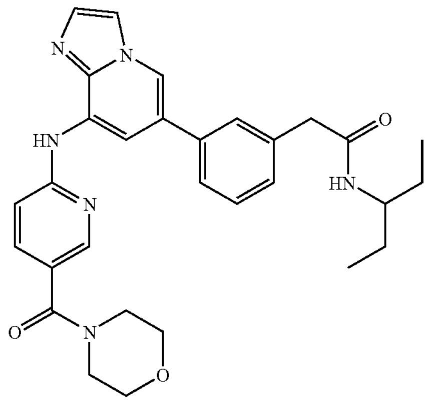 [SMILES: CCC(CC)NC(=O)Cc1cccc(-c2cc(Nc3ccc(C(=O)N4CCOCC4)cn3)c3nccn3c2)c1] | | N-(1-Ethyl-propyl)-2-(3-{8-[5-(morpholine-4-carbonyl)-pyridin-2-ylamino]-imidazo[1,2-a]pyridin-6-yl}-phenyl)-acetamide |
| I-188 | 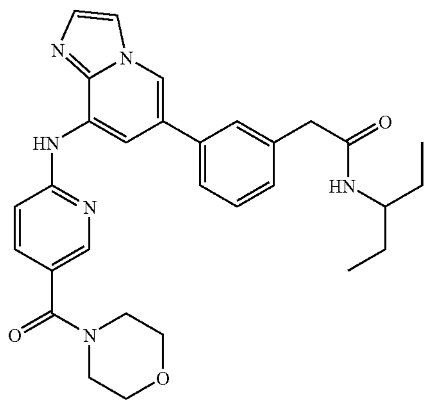 [SMILES: CCC(CC)NC(=O)Cc1cccc(-c2cc(Nc3ccc(C(=O)N4CCOCC4)cn3)c3nccn3c2)c1] | | N-(1-Ethyl-propyl)-2-(3-{8-[5-(morpholine-4-carbonyl)-pyridin-2-ylamino]-imidazo[1,2-a]pyridin-6-yl}-phenyl)-acetamide |
| I-189 | 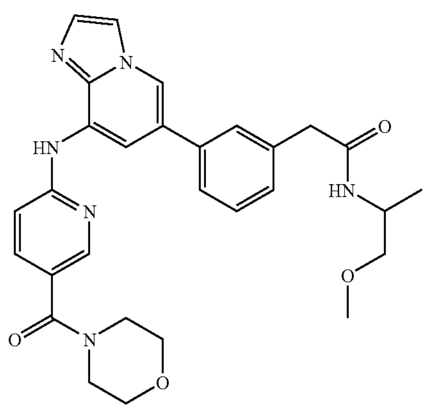 [SMILES: COCC(C)NC(=O)Cc1cccc(-c2cc(Nc3ccc(C(=O)N4CCOCC4)cn3)c3nccn3c2)c1] | | N-(2-Methoxy-1-methyl-ethyl)-2-(3-{8-[5-(morpholine-4-carbonyl)-pyridin-2-ylamino]-imidazo[1,2-a]pyridin-6-yl}-phenyl)-acetamide |
| I-190 | 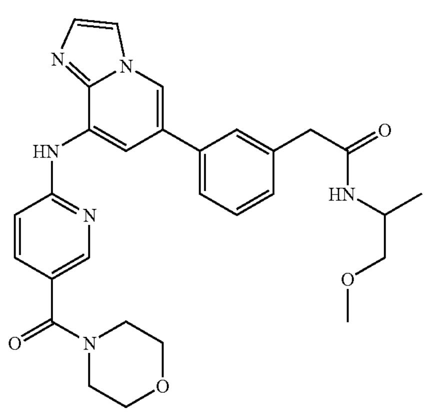 [SMILES: COCC(C)NC(=O)Cc1cccc(-c2cc(Nc3ccc(C(=O)N4CCOCC4)cn3)c3nccn3c2)c1] | | N-(2-Methoxy-1-methyl-ethyl)-2-(3-{8-[5-(morpholine-4-carbonyl)-pyridin-2-ylamino]-imidazo[1,2-a]pyridin-6-yl}-phenyl)-acetamide |

| # | Structure | MS | MP |
|---|---|---|---|
| I-191 | 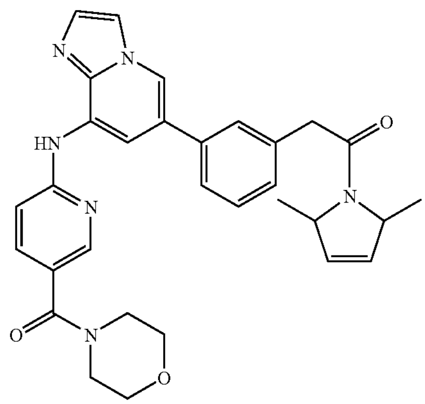 [SMILES: CC1C=CC(C)N1C(=O)Cc1cccc(-c2cc(Nc3ccc(C(=O)N4CCOCC4)cn3)c3nccn3c2)c1] | | 1-(2,5-Dimethyl-2,5-dihydro-pyrrol-1-yl)-2-(3-{8-[5-(morpholine-4-carbonyl)-pyridin-2-ylamino]-imidazo[1,2-a]pyridin-6-yl}-phenyl)-ethanone |
| I-192 | 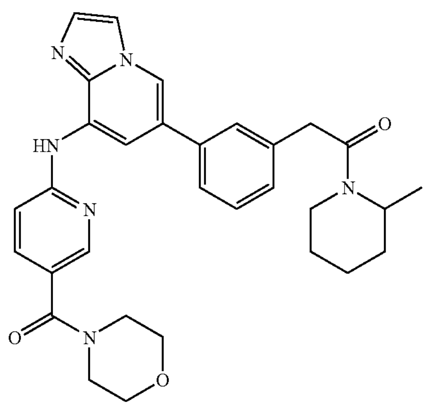 [SMILES: CC1CCCCN1C(=O)Cc1cccc(-c2cc(Nc3ccc(C(=O)N4CCOCC4)cn3)c3nccn3c2)c1] | | 1-(2-Methyl-piperidin-1-yl)-2-(3-{8-[5-(morpholine-4-carbonyl)-pyridin-2-ylamino]-imidazo[1,2-a]pyridin-6-yl}-phenyl)-ethanone |
| I-193 | 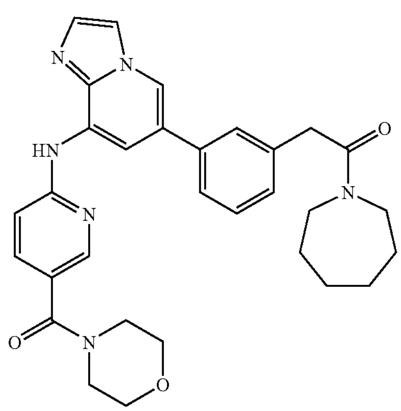 [SMILES: O=C(Cc1cccc(-c2cc(Nc3ccc(C(=O)N4CCOCC4)cn3)c3nccn3c2)c1)N1CCCCCC1] | | 1-Azepan-1-yl-2-(3-{8-[5-(morpholine-4-carbonyl)-pyridin-2-ylamino]-imidazo[1,2-a]pyridin-6-yl}-phenyl)-ethanone |

TABLE Y-continued

| # | Structure | MS | MP |
|---|-----------|----|----|
| I-194 | 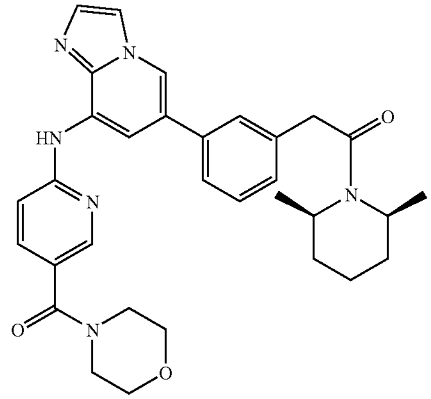 [SMILES: C[C@@H]1CCC[C@H](C)N1C(=O)Cc1cccc(-c2cc(Nc3ccc(C(=O)N4CCOCC4)cn3)c3nccn3c2)c1] | | 1-((2S,6R)-2,6-Dimethyl-piperidin-1-yl)-2-(3-{8-[5-(morpholine-4-carbonyl)-pyridin-2-ylamino]-imidazo[1,2-a]pyridin-6-yl}-phenyl)-ethanone |
| I-195 | 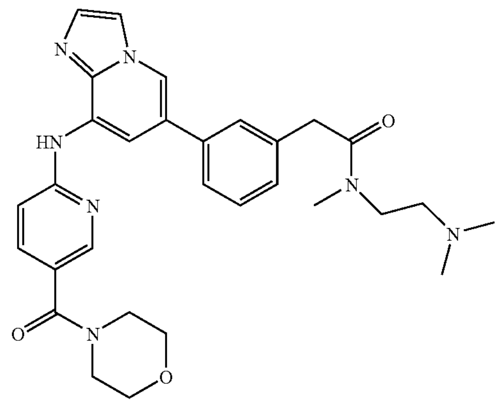 [SMILES: CN(C)CCN(C)C(=O)Cc1cccc(-c2cc(Nc3ccc(C(=O)N4CCOCC4)cn3)c3nccn3c2)c1] | | N-(2-Dimethylamino-ethyl)-N-methyl-2-(3-{8-[5-(morpholine-4-carbonyl)-pyridin-2-ylamino]-imidazo[1,2-a]pyridin-6-yl}-phenyl)-acetamide |
| I-196 | 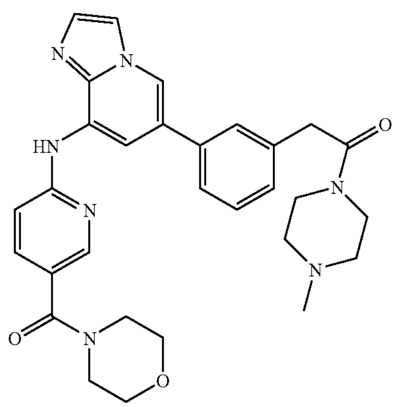 [SMILES: CN1CCN(C(=O)Cc2cccc(-c3cc(Nc4ccc(C(=O)N5CCOCC5)cn4)c4nccn4c3)c2)CC1] | | 1-(4-Methyl-piperazin-1-yl)-2-(3-{8-[5-(morpholine-4-carbonyl)-pyridin-2-ylamino]-imidazo[1,2-a]pyridin-6-yl}-phenyl)-ethanone |
| I-197 | 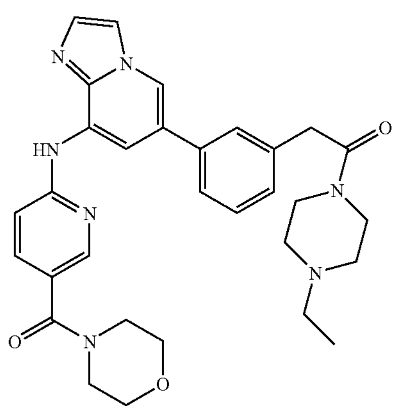 [SMILES: CCN1CCN(C(=O)Cc2cccc(-c3cc(Nc4ccc(C(=O)N5CCOCC5)cn4)c4nccn4c3)c2)CC1] | | 1-(4-Ethyl-piperazin-1-yl)-2-(3-{8-[5-(morpholine-4-carbonyl)-pyridin-2-ylamino]-imidazo[1,2-a]pyridin-6-yl}-phenyl)-ethanone |

TABLE Y-continued

| # | Structure | | MS | MP |
|---|---|---|---|---|
| I-198 | 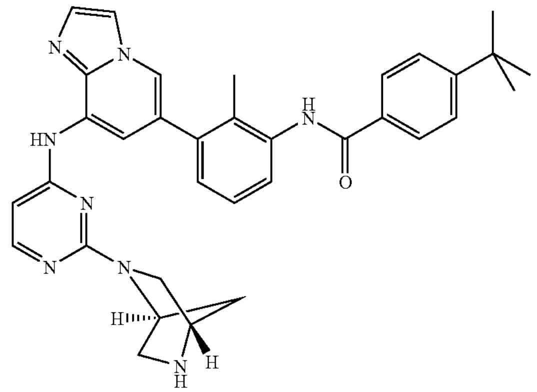 [SMILES: Cc1c(NC(=O)c2ccc(C(C)(C)C)cc2)cccc1-c1cc(Nc2ccnc(N3C[C@@H]4C[C@H]3CN4)n2)c2nccn2c1] | 4-tert-Butyl-N-(3-{8-[(1S,4S)-2-(2,5-diaza-bicyclo[2.2.1]hept-2-yl)-pyrimidin-4-ylamino]-imidazo[1,2-a]pyridin-6-yl}-2-methyl-phenyl)-benzamide | | |
| I-199 | 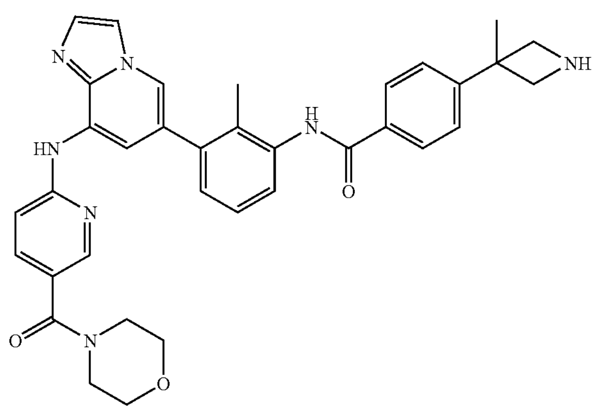 [SMILES: Cc1c(NC(=O)c2ccc(C3(C)CNC3)cc2)cccc1-c1cc(Nc2ccc(C(=O)N3CCOCC3)cn2)c2nccn2c1] | 4-(3-Methyl-azetidin-3-yl)-N-(2-methyl-3-{8-[5-(morpholine-4-carbonyl)-pyridin-2-ylamino]-imidazo[1,2-a]pyridin-6-yl}-phenyl)-benzamid | | |
| I-200 | 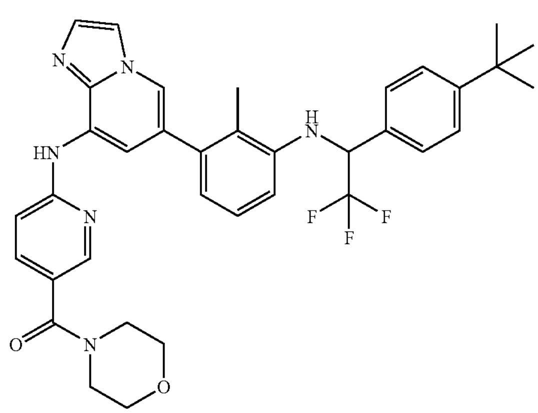 [SMILES: Cc1c(NC(c2ccc(C(C)(C)C)cc2)C(F)(F)F)cccc1-c1cc(Nc2ccc(C(=O)N3CCOCC3)cn2)c2nccn2c1] | [6-(6-{3-[1-(4-tert-Butyl-phenyl)-2,2,2-trifluoro-ethylamino]-2-methyl-phenyl}-imidazo[1,2-a]pyridin-8-ylamino)-pyridin-3-yl]-morpholin-4-yl-methanone | | |

TABLE Y-continued

| # | Structure | | MS | MP |
|---|---|---|---|---|
| I-201 | 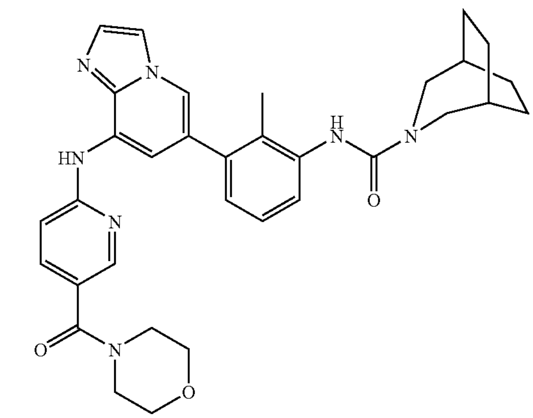 [SMILES: Cc1c(NC(=O)N2CC3CCC(CC3)C2)cccc1-c1cc(Nc2ccc(C(=O)N3CCOCC3)cn2)c2nccn2c1] | 3-Aza-bicyclo[3.2.2]nonane-3-carboxylic acid (2-methyl-3-{8-[5-(morpholine-4-carbonyl)-pyridin-2-ylamino]-imidazo[1,2-a]pyridin-6-yl}-phenyl)-amide | | |
| I-202 | 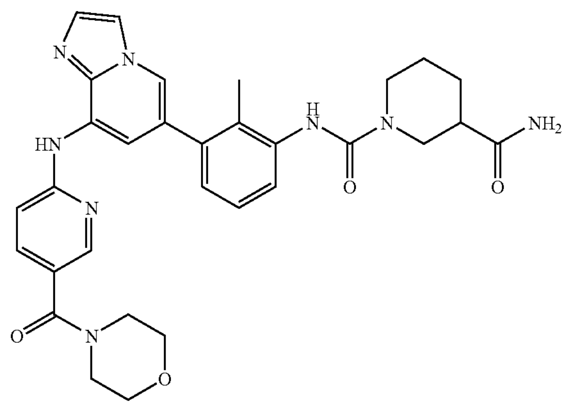 [SMILES: Cc1c(NC(=O)N2CCCC(C(N)=O)C2)cccc1-c1cc(Nc2ccc(C(=O)N3CCOCC3)cn2)c2nccn2c1] | Piperidine-1,3-dicarboxylic acid 3-amide 1-[(2-methyl-3-{8-[5-(morpholine-4-carbonyl)-pyridin-2-ylamino]-imidazo[1,2-a]pyridin-6-yl}-phenyl)-amide] | | |
| I-203 | 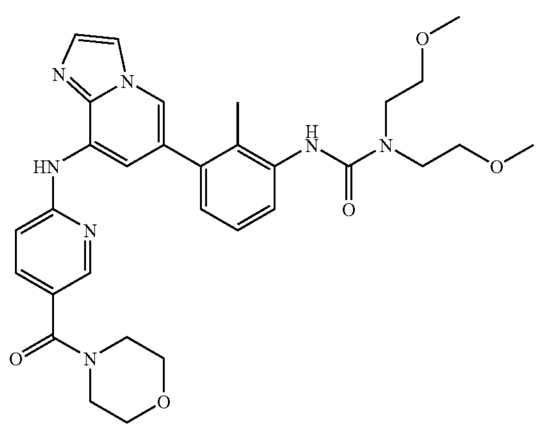 [SMILES: COCCN(CCOC)C(=O)Nc1cccc(-c2cc(Nc3ccc(C(=O)N4CCOCC4)cn3)c3nccn3c2)c1C] | 1,1-Bis-(2-methoxy-ethyl)-3-(2-methyl-3-{8-[5-(morpholine-4-carbonyl)-pyridin-2-ylamino]-imidazo[1,2-a]pyridin-6-yl}-phenyl)-urea | | |

TABLE Y-continued

| # | Structure | | MS | MP |
|---|---|---|---|---|
| I-204 | 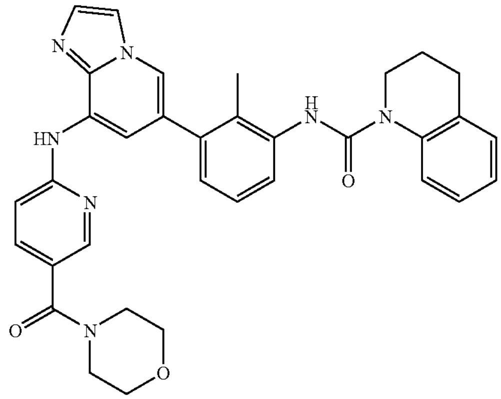 [SMILES: Cc1c(NC(=O)N2CCCc3ccccc32)cccc1-c1cc(Nc2ccc(C(=O)N3CCOCC3)cn2)c2nccn2c1] | 3,4-Dihydro-2H-quinoline-1-carboxylic acid (2-methyl-3-{8-[5-(morpholine-4-carbonyl)-pyridin-2-ylamino]-imidazo[1,2-a]pyridin-6-yl}-phenyl)-amide | | |
| I-205 | 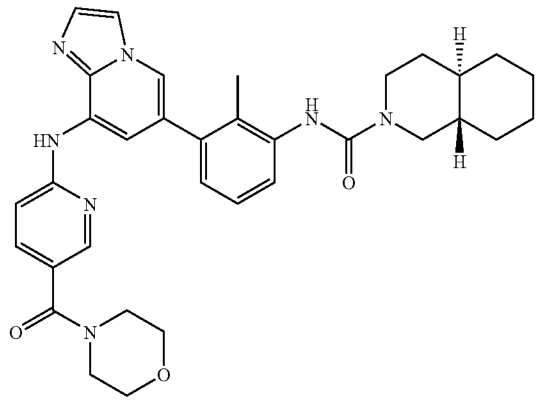 [SMILES: Cc1c(NC(=O)N2CC[C@H]3CCCC[C@@H]3C2)cccc1-c1cc(Nc2ccc(C(=O)N3CCOCC3)cn2)c2nccn2c1] | (4aR,8aS)-Octahydro-isoquinoline-2-carboxylic acid (2-methyl-3-{8-[5-(morpholine-4-carbonyl)-pyridin-2-ylamino]-imidazo[1,2-a]pyridin-6-yl}-phenyl)-amide | | |
| I-206 | 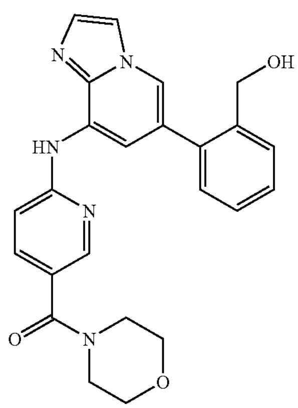 [SMILES: O=C(c1ccc(Nc2cc(-c3ccccc3CO)cn3ccnc23)nc1)N1CCOCC1] | {6-[6-(2-Hydroxymethyl-phenyl)-imidazo[1,2-a]pyridin-8-ylamino]-pyridin-3-yl}-morpholin-4-yl-methanone | | |
| I-207 | 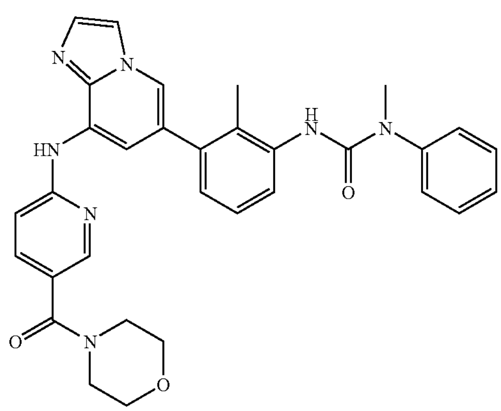 [SMILES: Cc1c(NC(=O)N(C)c2ccccc2)cccc1-c1cc(Nc2ccc(C(=O)N3CCOCC3)cn2)c2nccn2c1] | 1-Methyl-3-(2-methyl-3-{8-[5-(morpholine-4-carbonyl)-pyridin-2-ylamino]-imidazo[1,2-a]pyridin-6-yl}-phenyl)-1-phenyl-urea | | |

TABLE Y-continued
| # | Structure | | MS | MP |
|---|-----------|---|----|----|
| I-208 | 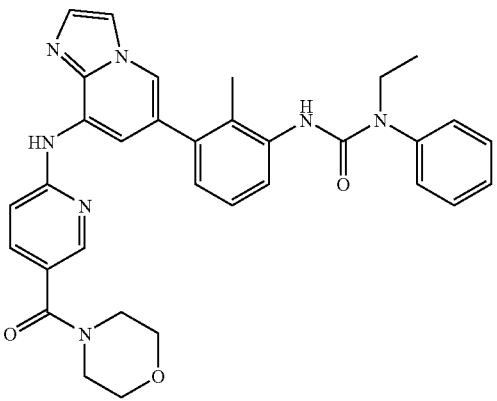 [SMILES: CCN(C(=O)Nc1cccc(-c2cc(Nc3ccc(C(=O)N4CCOCC4)cn3)c3nccn3c2)c1C)c1ccccc1] | 1-Ethyl-3-(2-methyl-3-{8-[5-(morpholine-4-carbonyl)-pyridin-2-ylamino]-imidazo[1,2-a]pyridin-6-yl}-phenyl)-1-phenyl-urea | | |
| I-209 | 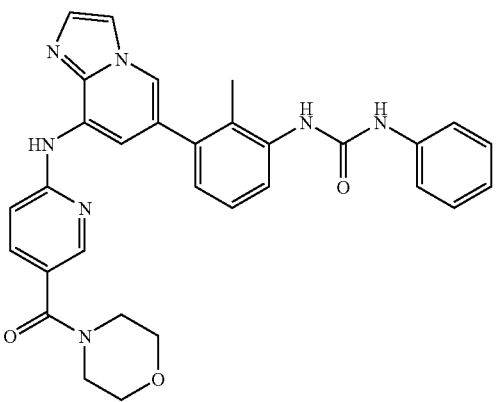 | 1-(2-Methyl-3-{8-[5-(morpholine-4-carbonyl)-pyridin-2-ylamino]-imidazo[1,2-a]pyridin-6-yl}-phenyl)-3-phenyl-urea | | |
| I-210 | 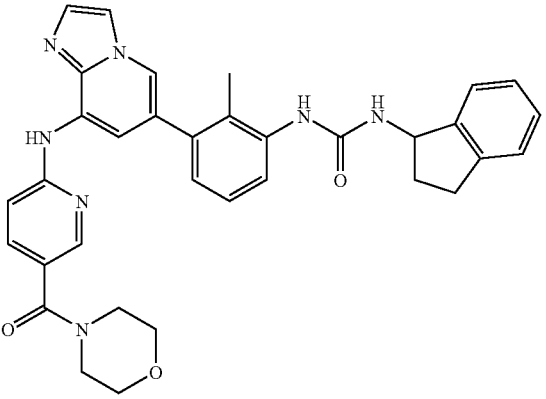 [SMILES: Cc1c(NC(=O)NC2CCc3ccccc32)cccc1-c1cc(Nc2ccc(C(=O)N3CCOCC3)cn2)c2nccn2c1] | 1-Indan-1-yl-3-(2-methyl-3-{8-[5-(morpholine-4-carbonyl)-pyridin-2-ylamino]-imidazo[1,2-a]pyridin-6-yl}-phenyl)-urea | | |

TABLE Y-continued

| # | Structure | MS | MP |
|---|---|---|---|
| I-211 | 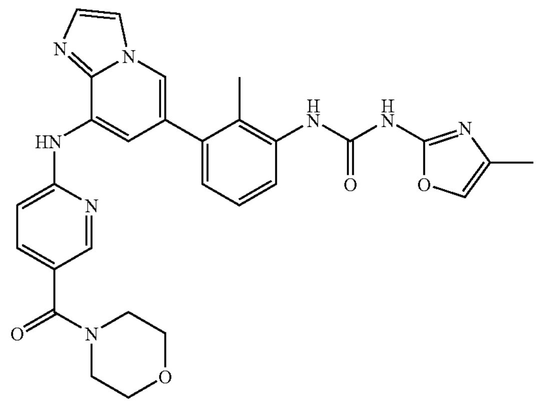 [SMILES: Cc1coc(NC(=O)Nc2cccc(-c3cc(Nc4ccc(C(=O)N5CCOCC5)cn4)c4nccn4c3)c2C)n1] | | |

1-(2-Methyl-3-{8-[5-(morpholine-4-carbonyl)-pyridin-2-ylamino]-imidazo[1,2-a]pyridin-6-yl}-phenyl)-3-(4-methyl-oxazol-2-yl)-urea

| I-212 | | | |

1-(3-Chloro-phenyl)-3-(2-methyl-3-{8-[5-(morpholine-4-carbonyl)-pyridin-2-ylamino]-imidazo[1,2-a]pyridin-6-yl}-phenyl)-urea

| I-213 | | | |

1-(2-Methyl-3-{8-[5-(morpholine-4-carbonyl)-pyridin-2-ylamino]-imidazo[1,2-a]pyridin-6-yl}-phenyl)-3-(2-trifluoromethyl-phenyl)-urea

| I-214 | | | |

1-(4-tert-Butyl-phenyl)-3-(2-methyl-3-{8-[5-(morpholine-4-carbonyl)-pyridin-2-ylamino]-imidazo[1,2-a]pyridin-6-yl}-phenyl)-urea TABLE Y-continued

| # | Structure | MS | MP |
|---|-----------|----|----|
| I-215 | 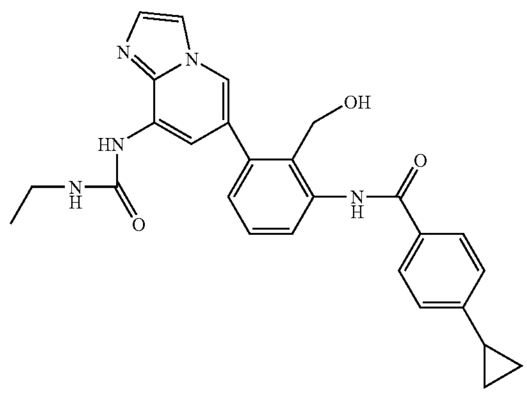 [SMILES: CCNC(=O)Nc1cc(-c2cccc(NC(=O)c3ccc(C4CC4)cc3)c2CO)cn2ccnc12] | | 4-Cyclopropyl-N-{3-[8-(3-ethyl-ureido)-imidazo[1,2-a]pyridin-6-yl]-2-hydroxymethyl-phenyl}-benzamide |
| I-216 | 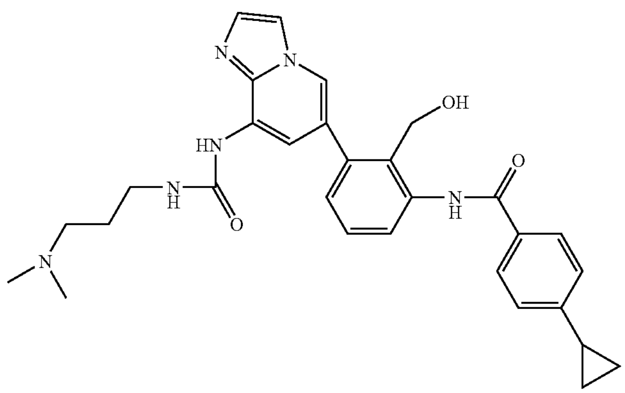 [SMILES: CN(C)CCCNC(=O)Nc1cc(-c2cccc(NC(=O)c3ccc(C4CC4)cc3)c2CO)cn2ccnc12] | | 4-Cyclopropyl-N-(3-{8-[3-(3-dimethylamino-propyl)-ureido]-imidazo[1,2-a]pyridin-6-yl}-2-hydroxymethyl-phenyl)-benzamide |
| I-217 | 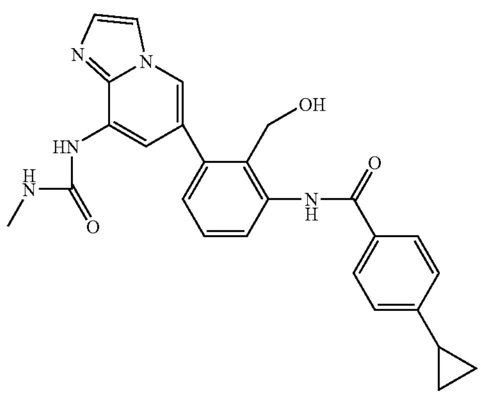 [SMILES: CNC(=O)Nc1cc(-c2cccc(NC(=O)c3ccc(C4CC4)cc3)c2CO)cn2ccnc12] | | 4-Cyclopropyl-N-{2-hydroxymethyl-3-[8-(3-methyl-ureido)-imidazo[1,2-a]pyridin-6-yl]-phenyl}-benzamide |
| I-218 | 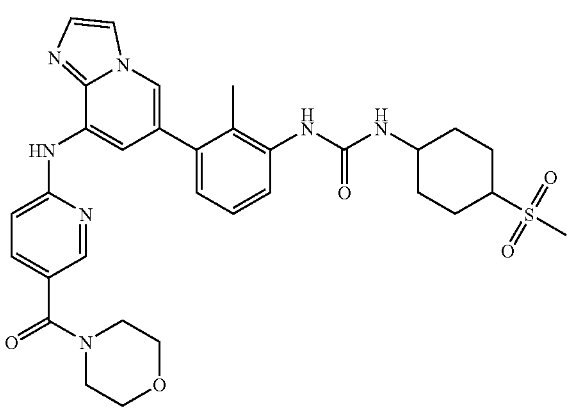 [SMILES: Cc1c(NC(=O)NC2CCC(S(C)(=O)=O)CC2)cccc1-c1cc(Nc2ccc(C(=O)N3CCOCC3)cn2)c2nccn2c1] | | 1-(4-Methanesulfonyl-cyclohexyl)-3-(2-methyl-3-{8-[5-(morpholine-4-carbonyl)-pyridin-2-ylamino]-imidazo[1,2-a]pyridin-6-yl}-phenyl)-urea |

Representative Scheme 1
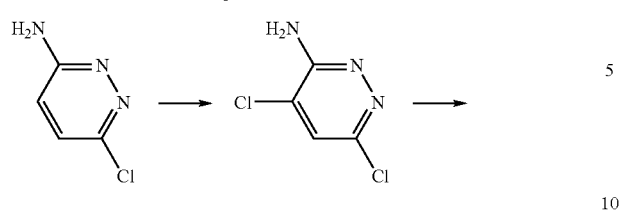
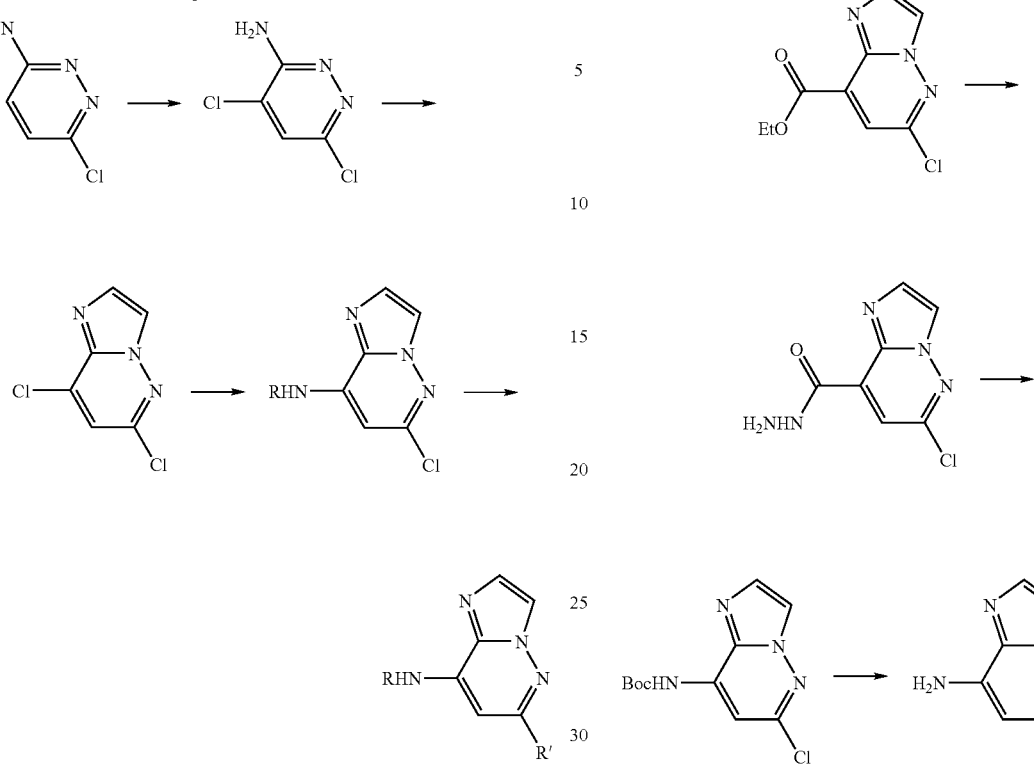
Representative Scheme 2
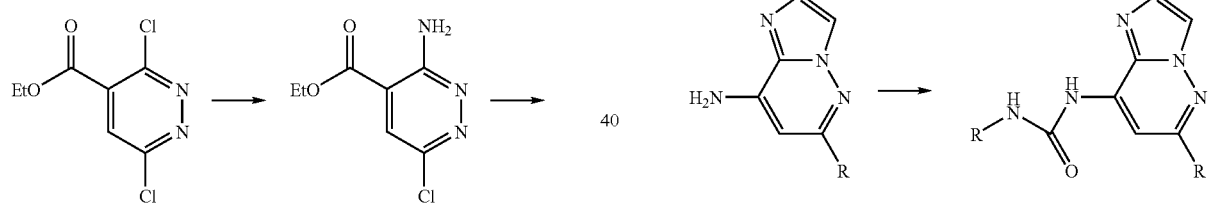
Representative Scheme 3
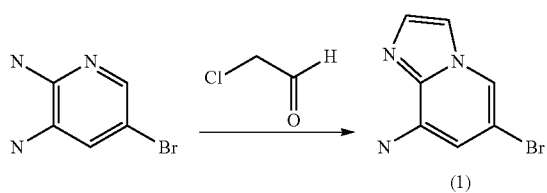
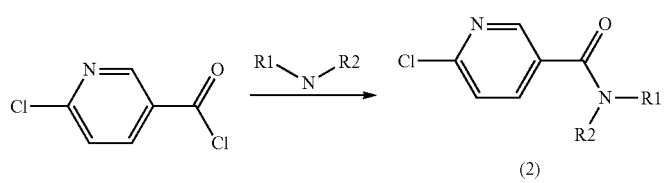

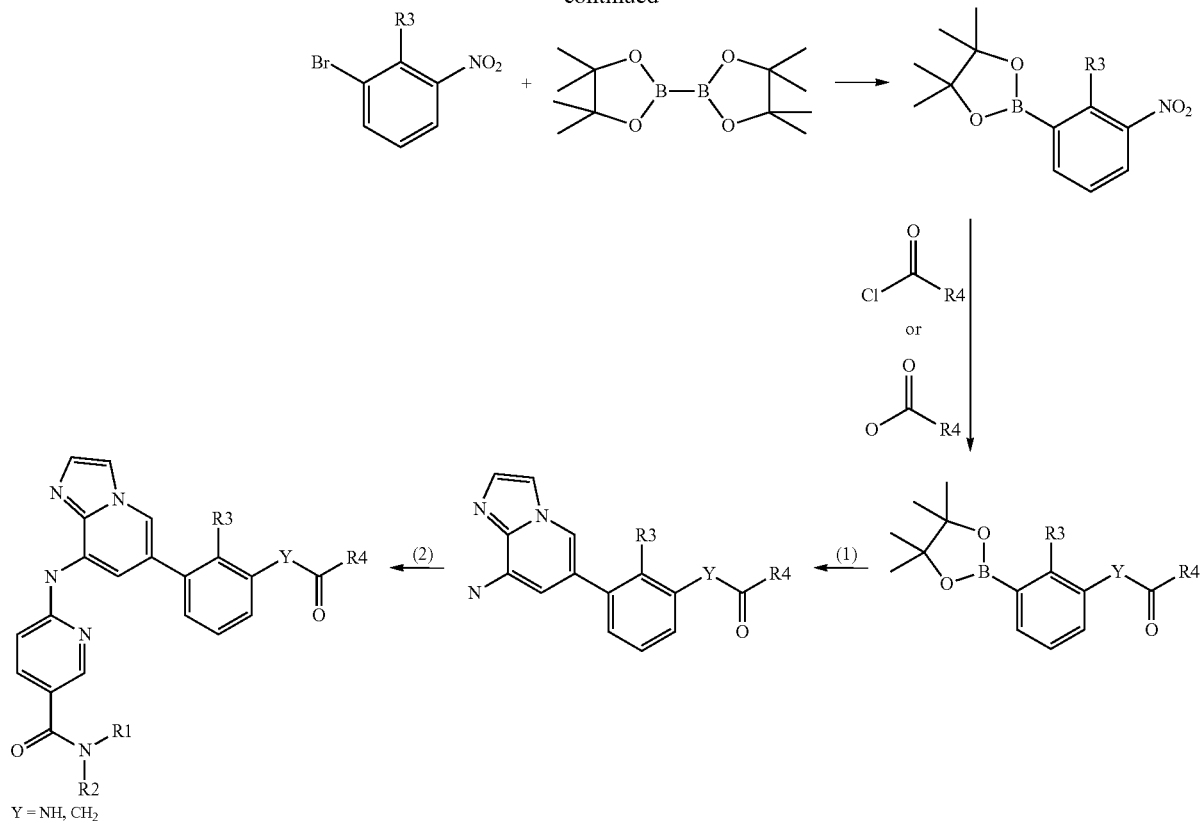
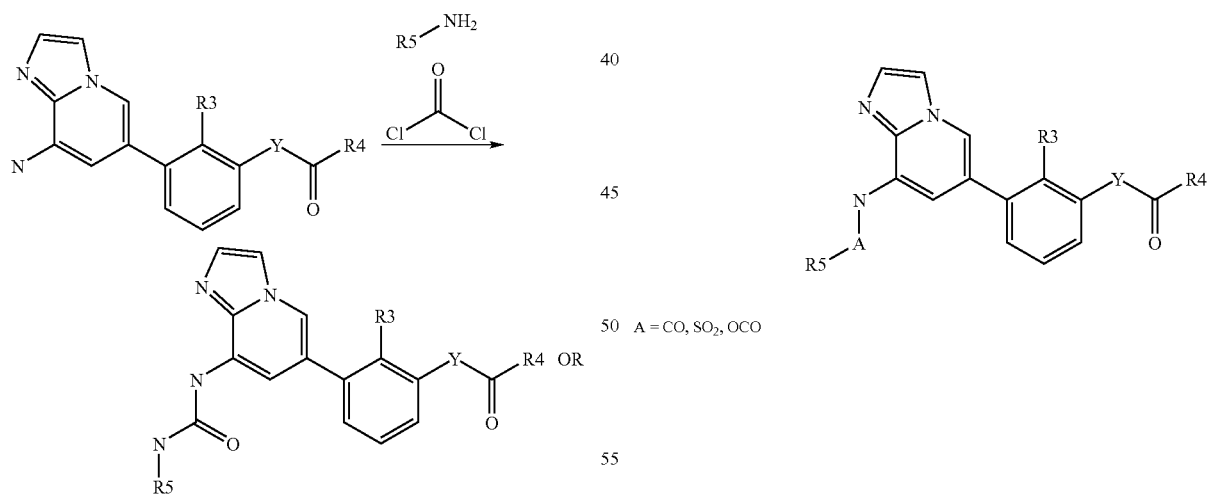
Representative Scheme 4
A = CO, SO$_2$, OCO
Representative Scheme 5
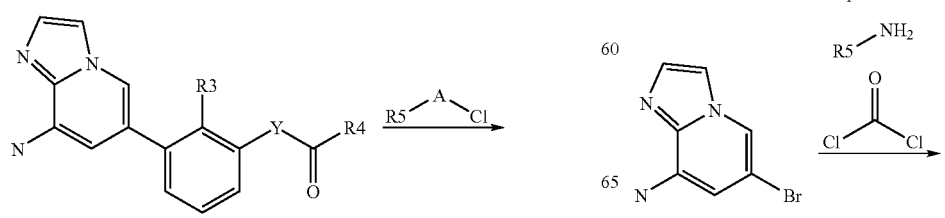

143
-continued
144
Representative Scheme 7
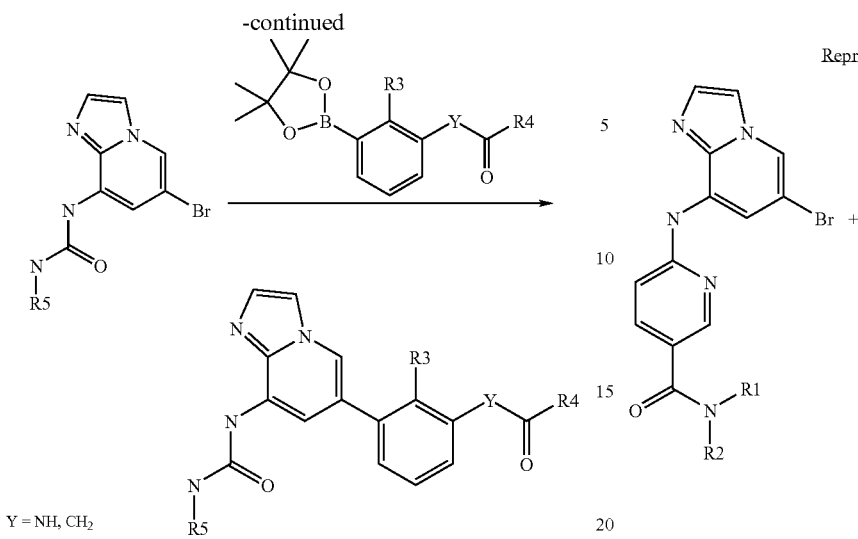
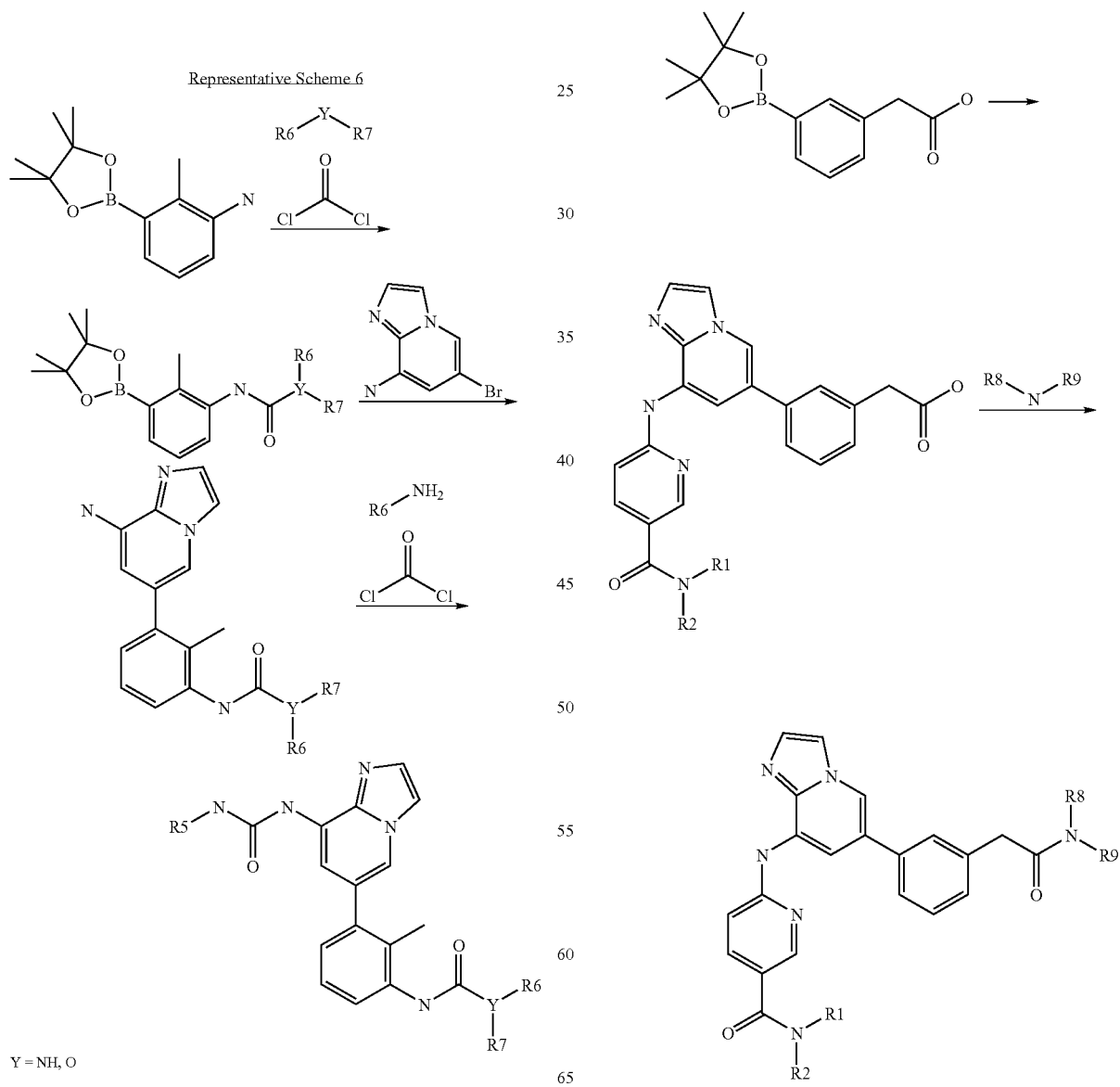

Representative Scheme 8

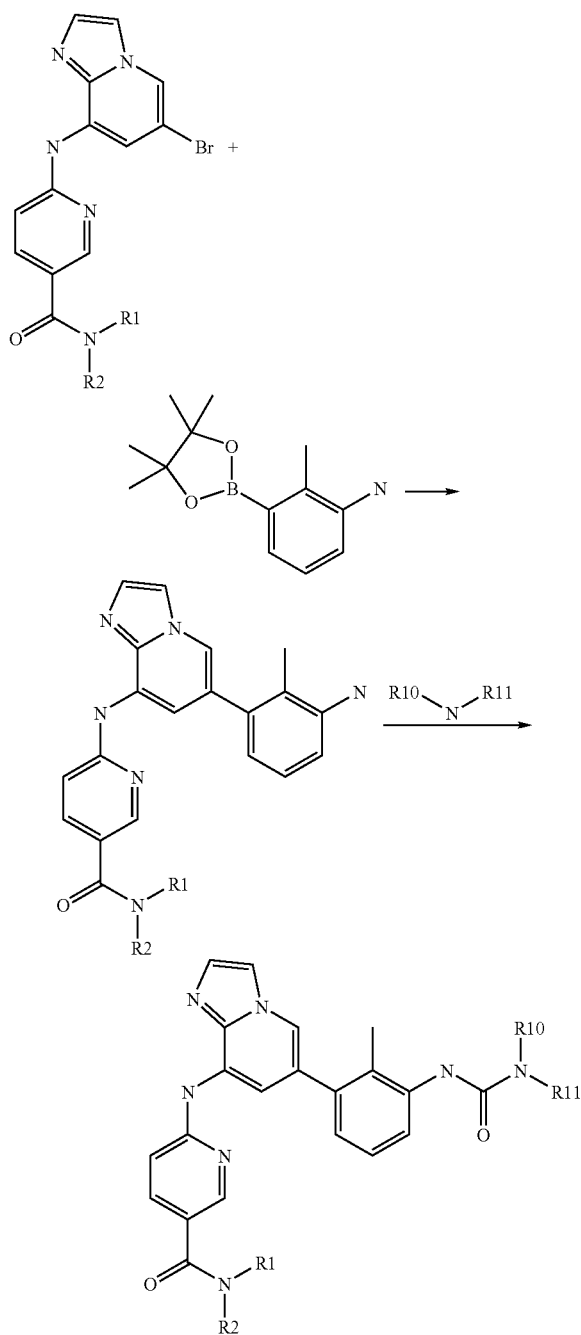

Pharmacological Activity

The pyrimidine and pyridine derivatives described herein are kinase inhibitors, in particular Btk inhibitors. These inhibitors can be useful for treating one or more diseases responsive to kinase inhibition, including diseases responsive to Btk inhibition and/or inhibition of B-cell proliferation, in mammals. Without wishing to be bound to any particular theory, it is believed that the interaction of the compounds of the invention with Btk results in the inhibition of Btk activity and thus in the pharmaceutical utility of these compounds. Accordingly, the invention includes a method of treating a mammal, for instance a human, having a disease responsive to inhibition of Btk activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to Btk include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of Btk activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis, Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., *J. Biol. Chem.* 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also be associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. *J. Exp. Med.* 2005 201(11):1837-1852)

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLES

Example 1

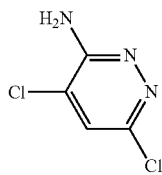

A mixture of 3-amino-6-chloro pyridazine (2.10 g, 16.2 mmol) and 16 mL of thionyl chloride was stirred at 125° C. in a sealed tube for 1 h, allowed to cool, transferred to a flask and concentrated to an orange oil. The flask was chilled to 0-5° C. Methanol (80 mL) was added, then 20 mL of triethylamine, then 40 g of silica gel. The mixture was concentrated to a tan solid. Column chromatography (0->33% EtOAc/hexanes, which afforded still-impure material; then a second column, also 0->33% EtOAc/hexanes) afforded 0.308 g (12%) of 3-amino-4,6-dichloro pyridazine as an orange solid.

Example 2

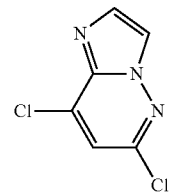

A mixture of 3-amino-4,6-dichloropyridazine (0.315 g, 1.92 mmol), 3 mL of isopropanol and 0.5 mL of a 50% chloroacetaldehyde in water solution was stirred at 80° C. for 20 h, then concentrated to remove isopropanol. The resulting yellow mixture was treated with 10 mL of a saturated aq. NaHCO$_3$ solution and extracted with two 10 mL portions of dichloromethane. The combined organic layers were dried over MgSO$_4$, filtered and concentrated to a yellow oil. Column chromatography (0->33% EtOAc/hexanes) afforded 0.313 g (87%) of 6,8-dichloro-imidazo[1,2-b]pyridazine as a light yellow solid.

Example 3

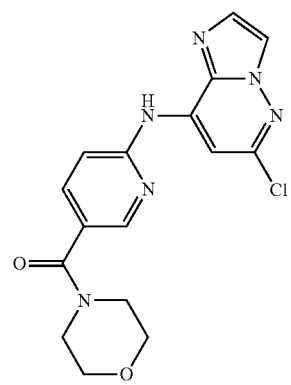 [SMILES: O=C(c1ccc(Nc2cc(Cl)nn3ccnc23)nc1)N1CCOCC1]

A mixture of 6,8-dichloro-imidazo[1,2-b]pyridazine (0.048 g, 0.26 mmol) and (6-amino-pyridin-3-yl)-morpholin-4-yl-methanone (0.059 g, 0.28 mmol) in 1 mL of N,N-dimethylformamide at 0-5° C. was treated with 60% sodium hydride/mineral oil (0.037 g, 0.92 mmol). The bubbling yellow mixture was stirred at 0-5° C. for 5 min., then at RT for 20 h. A saturated aq. NaHCO$_3$ solution (1 mL) was added, then 5 mL of water and 10 mL of ethyl acetate. Insoluble solid was removed by filtration, and the layers of the filtrate were separated. The organic layer was sequentially washed with two 5 mL portions of water and 5 mL of a sat. aq. NaCl solution, dried over MgSO$_4$, filtered and concentrated to 0.048 g (52% crude) of [6-(6-chloro-imidazo[1,2-b]pyridazin-8-ylamino)-pyridin-3-yl]-morpholin-4-yl-methanone as a white solid that was used without further purification.

Example 4

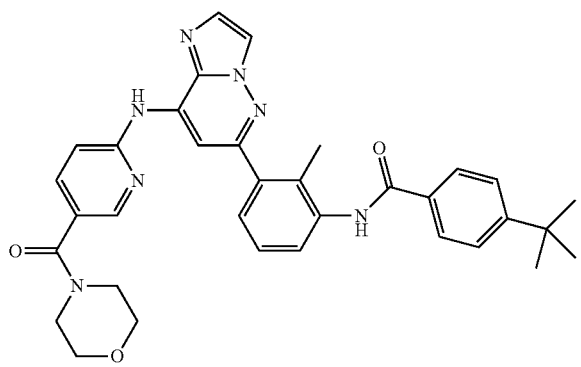 [SMILES: Cc1c(NC(=O)c2ccc(C(C)(C)C)cc2)cccc1-c1cc(Nc2ccc(C(=O)N3CCOCC3)cn2)c2nccn2n1]

A mixture of crude [6-(6-chloro-imidazo[1,2-b]pyridazin-8-ylamino)-pyridin-3-yl]-morpholin-4-yl-methanone (0.048 g, "0.133 mmol"), 4-tert-butyl-N-[2-methyl-3-(4,4,5,5-tetramethyl-[1,3,2]dioxaborolan-2-yl)-phenyl]-benzamide (0.087 g, 0.23 mmol), potassium carbonate (0.056 g, 0.41 mmol), Pd(PPh$_3$)$_4$ (0.016 g, 0.014 mmol), 1 mL of toluene, 0.25 mL of ethanol and 0.25 mL of water under N$_2$ was stirred at 170° C. in a microwave for 3 h. More Pd(PPh$_3$)$_4$ was added (0.025 g, 0.021 mmol) and the mixture was stirred for an additional 1 h at 170° C. in a microwave. The mixture was partitioned between 5 mL of water and 5 mL of ethyl acetate, and the aqueous layer was extracted with 5 mL of ethyl acetate. The combined organic layers were dried over MgSO$_4$, filtered and concentrated to 0.126 g of a yellow oil. Column chromatography (1$^{st}$ column: 0->10% MeOH/CH$_2$Cl$_2$; 2$^{nd}$ column: 0->5% MeOH/EtOAc) afforded 0.008 g (10%) of 4-tert-butyl-N-(2-methyl-3-{8-[5-(morpholine-4-carbonyl)-pyridin-2-ylamino]-imidazo[1,2-b]pyridazin-6-yl}-phenyl)-benzamide as an off-white solid.

4-tert-butyl-N-{2-methyl-3-[8-(thiazol-2-ylamino)-imidazo[1,2-b]pyridazin-6-yl]-phenyl}-benzamide was made in a similar fashion as 4-tert-butyl-N-(2-methyl-3-{8-[5-(morpholine-4-carbonyl)-pyridin-2-ylamino]-imidazo[1,2-b]pyridazin-6-yl}-phenyl)-benzamide.

Example 5

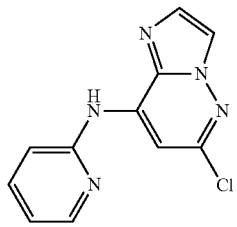 [SMILES: Clc1cc(Nc2ccccn2)c2nccn2n1]

A solution of 2-aminopyridine (0.388 g, 4.12 mmol) in 8 mL of N,N-dimethylformamide was treated with 60% sodium hydride/mineral oil (0.167 g, 4.18 mmol) and the lightly bubbling, pale yellow solution was stirred for 30 min., in which time it became a dark yellow cloudy solution. The solution was added via Pasteur pipette to a flask containing 6,8-dichloro-imidazo[1,2-b]pyridazine (0.310 g, 1.65 mmol), and the cloudy orange solution was stirred for 16 h then partitioned between 80 mL of a saturated aq. NH$_4$Cl solution and 80 mL of ether. The organic layer was sequentially washed with two 40 mL portions of water and 40 mL of a saturated aq. NaCl solution; dried over MgSO$_4$, filtered and concentrated to a pale yellow solid. Column chromatography (0->33% EtOAc/hexanes) afforded 0.141 g (35%) of (6-chloro-imidazo[1,2-b]pyridazin-8-yl)-pyridin-2-yl-amine as a white solid.

Example 6

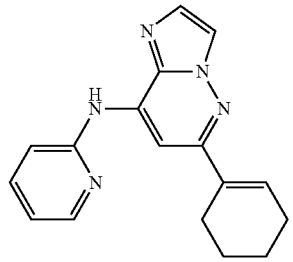 [SMILES: C1=C(c2cc(Nc3ccccn3)c3nccn3n2)CCCC1]

A mixture of (6-chloro-imidazo[1,2-b]pyridazin-8-yl)-pyridin-2-yl-amine (0.063 g, 0.26 mmol), 2 mL of toluene, 0.5 mL of ethanol, cyclohexen-1-yl boronic acid (0.065 g, 0.51 mmol), Pd(PPh$_3$)$_4$ (0.032 g, 0.027 mmol), and 0.36 mL of a 2 M aq. potassium carbonate solution under N$_2$ was stirred at 170° C. in a microwave for 3 h. The mixture was partitioned between 10 mL of a 10% NaOH solution and 10 mL of dichloromethane. The aqueous layer was further extracted with 10 mL of dichloromethane. The combined organic layers were dried over MgSO$_4$, filtered and concentrated to 0.093 g of a pale yellow oil. Column chromatography (0->33% EtOAc/hexanes) afforded 0.050 g (66%) of (6-cyclohex-1-enyl-imidazo[1,2-b]pyridazin-8-yl)-pyridin-2-yl-amine as a white solid.

(6-phenyl-imidazo[1,2-b]pyridazin-8-yl)-pyridin-2-yl-amine and [6-(1-methyl-1H-pyrrol-2-yl)-imidazo[1,2-b]pyridazin-8-yl]-pyridin-2-ylaminename were made in a similar fashion as (6-cyclohex-1-enyl-imidazo[1,2-b]pyridazin-8-yl)-pyridin-2-yl-amine.

Example 7

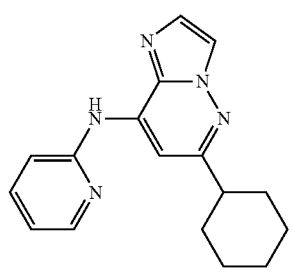 [SMILES: c1ccc(Nc2cc(C3CCCCC3)nn3ccnc23)nc1]

A two-necked flask with stirbar, vacuum/N$_2$ inlet and a ballon filled with hydrogen was charged with (6-cyclohex-1-enyl-imidazo[1,2-b]pyridazin-8-yl)-pyridin-2-yl-amine (0.016 g, 0.056 mmol), 1 mL of methanol, and 0.019 g of 10% palladium on carbon (Aldrich). The flask was evacuated and filled with hydrogen, and the black mixture was stirred for 2 d, filtered through Celite 521, and concentrated, chasing with hexanes, to 0.013 g of (6-cyclohexyl-imidazo[1,2-b]pyridazin-8-yl)-pyridin-2-yl-amine as a tan solid contaminated with ca. 8% starting material.

Example 8

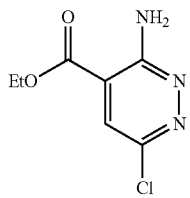

A sealed tube was charged with 3,6-dichloro-pyridazine-4-carboxylic acid ethyl ester (4.37 g, 19.8 mmol), 80 mL of dioxane and triethylamine (5.6 mL, 40 mmol). Ammonia was rapidly bubbled in via a dipersion tube for 2 minutes. The tube was capped and the yellow solution was stirred at 100° C. for 2 d, then allowed to cool. The mixture was transferred to a flask, using diethyl ether in rinsings, and concentrated to a yellow solid. The solid was partitioned between 100 mL of water and 100 mL of ethyl acetate. The aqueous layer was extracted with two 100 mL portions of ethyl acetate. There initially is undissolved solid in the aqueous layer that eventually disappears with the ethyl acetate extractions. The combined organic layers were concentrated to 3.93 g (99% crude) of 3-amino-6-chloro-pyridazine-4-carboxylic acid ethyl ester as a yellow solid that was used without further purification.

Example 9

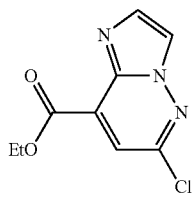 [SMILES: CCOC(=O)c1cc(Cl)nn2ccnc12]

A mixture of crude 3-amino-6-chloro-pyridazine-4-carboxylic acid ethyl ester (3.93 g, "19.5 mmol"), 90 mL of isopropanol, and 20 mL of a 50% chloroacetaldehyde solution was stirred at 80° C. for 4 h, then concentrated to remove isopropanol. The resulting orange liquid was partitioned between 100 mL of ether and 100 mL of a saturated aq. NaHCO₃ solution. The organic layer was sequentially washed with 100 mL of water and 100 mL of a saturated aq. NaCl solution, dried over MgSO₄, filtered and concentrated to 5.00 g (113% crude) of 6-chloro-imidazo[1,2-b]pyridazine-8-carboxylic acid ethyl ester as an orange liquid that was used without further purification.

Example 10

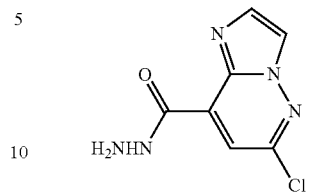

To a solution of crude 6-chloro-imidazo[1,2-b]pyridazine-8-carboxylic acid ethyl ester (5.00 g, "22 mmol") in 40 mL of ethanol at 0-5° C. was added 10 mL of hydrazine hydrate. Yellow solid immediately precipitated. After 15 min. at 0-5° C., the solid was isolated by Buchner filtration, rinsing well with ice-cold ethanol (250 mL total) and dried by sucking air through then in vacuo. A small amount of additional solid precipated from the filtrate and was isolated and dried similarly to the first crop. A total of 2.38 g (57% over three steps) of 6-chloro-imidazo[1,2-b]pyridazine-8-carboxylic acid hydrazide was isolated as a yellow solid.

Example 11

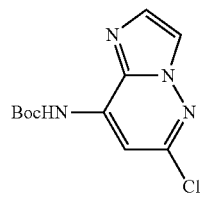 [SMILES: CC(C)(C)OC(=O)Nc1cc(Cl)nn2ccnc12]

A mixture of 6-chloro-imidazo[1,2-b]pyridazine-8-carboxylic acid hydrazide (2.09 g, 9.88 mmol), 50 mL of tert-butanol, and 2.5 mL of tert-butyl nitrite under N2 in a sealed tube was stirred at 100° C. for 3 h then allowed to cool. The cloudy orange mixture was transferred to a flask, using dichloromethane in rinsings, and concentrated to an oily orange residue. Column chromatography (20->40% EtOAc/hexanes) afforded 1.59 g (60%) of (6-chloro-imidazo[1,2-b]pyridazin-8-yl)-carbamic acid tert-butyl ester as a foamy yellow solid.

Example 12

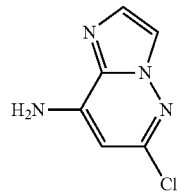 [SMILES: Nc1cc(Cl)nn2ccnc12]

A solution of (6-chloro-imidazo[1,2-b]pyridazin-8-yl)-carbamic acid tert-butyl ester (1.59 g, 5.91 mmol) in 30 mL of dichloromethane and 15 mL of trifluoroacetic acid was stirred for 5 h then concentrated to a yellow oil, which was treated (slowly) with 50 mL of a saturated aq. NaHCO₃ solution. Undissolved solid was isolated by Buchner filtration, rinsing well with water and dried by sucking air through then in vacuo to afford 1.10 g (102% crude) of 6-chloro-imidazo[1,2-b]pyridazin-8-ylamine as a yellow solid that was used without further purification.

Example 13

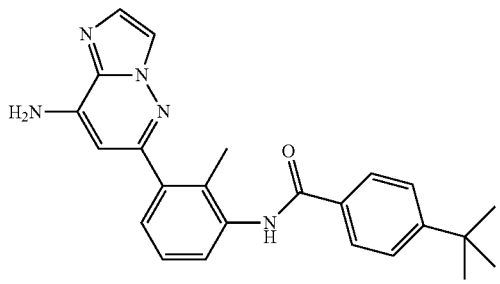 [SMILES: Cc1c(NC(=O)c2ccc(C(C)(C)C)cc2)cccc1-c1cc(N)c2nccn2n1]

Reference for Suzuki conditions: Billingsley and Buchwald, J. Am. Chem. Soc. 2007, 129, 3358-3366.

A mixture of 6-chloro-imidazo[1,2-b]pyridazin-8-ylamine (0.048 g, 0.29 mmol), 4-tert-butyl-N-[2-methyl-3-(4,4,5,5-tetramethyl-[1,3,2]dioxaborolan-2-yl)-phenyl]-benzamide (0.169 g, 0.444 mmol), potassium phosphate (0.120 g, 0.567 mmol), 2-dicyclohexylphosphino-2',6'-dimethoxybiphenyl (0.024 g, 0.058 mmol), palladium acetate (0.007 g, 0.03 mmol), 0.5 mL of n-butanol and 0.2 mL of water in a sealed tube was stirred at 100° C. for 2 d. The resulting cloudy orange mixture was partitioned between 5 mL of ethyl acetate and 5 mL of water, and the aqueous layer was extracted with 5 mL of ethyl acetate. The combined organic layers were dried over MgSO₄, filtered and concentrated to an orange oil. Column chromatography (60->100% EtOAc/hexanes) afforded 0.026 g (23%) of N-[3-(8-amino-imidazo[1,2-b]pyridazin-6-yl)-2-methyl-phenyl]-4-tert-butyl-benzamide as a yellow solid.

Example 14

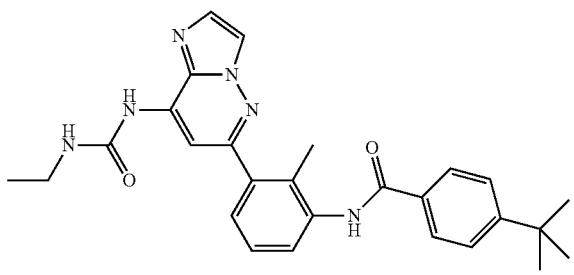 [SMILES: CCNC(=O)Nc1cc(-c2cccc(NC(=O)c3ccc(C(C)(C)C)cc3)c2C)nn2ccnc12]

To a solution of N-[3-(8-amino-imidazo[1,2-b]pyridazin-6-yl)-2-methyl-phenyl]-4-tert-butyl-benzamide (0.019 g, 0.047 mmol) and diisopropylethylamine (0.021 mL, 0.12 mmol) in 1 mL of dichloromethane at 0-5° C. was added a 20% phosgene in toluene solution (0.030 mL, 0.057 mmol) all at once. The cloudy yellow solution was stirred for 10 min., then ethylamine gas was bubbled in via a Pasteur pipette for 2 min. Silica gel (3 g) was added, and the mixture was concentrated to a pale yellow powder. Column chromatography (66%->100% EtOAc/hexanes) afforded 0.013 g (58%) of 4-tert-butyl-N-{3-[8-(3-ethyl-ureido)-imidazo[1,2-b]pyridazin-6-yl]-2-methyl-phenyl}-benzamide as a white solid.

4-tert-Butyl-N-{3-[8-(3-isopropyl-ureido)-imidazo[1,2-b]pyridazin-6-yl]-2-methyl-phenyl}-benzamide, 4-tert-butyl-N-{2-methyl-3-[8-(3-methyl-ureido)-imidazo[1,2-b]pyridazin-6-yl]-phenyl}-benzamide, 4-tert-butyl-N-{3-[8-(3-tert-butyl-ureido)-imidazo[1,2-b]pyridazin-6-yl]-2-methyl-phenyl}-benzamide, 4-tert-butyl-N-(3-{8-[3-(2-hydroxy-ethyl)-ureido]-imidazo[1,2-b]pyridazin-6-yl}-2-methyl-phenyl)-benzamide, 1-methyl-3-(6-phenyl-imidazo[1,2-b]pyridazin-8-yl)-urea, 1-(6-{3-[2-(1,3-dihydro-isoindol-2-yl)-2-oxo-ethyl]-phenyl}-imidazo[1,2-b]pyridazin-8-yl)-3-methyl-urea, and 1-methyl-3-[6-(1-methyl-1H-pyrrol-2-yl)-imidazo[1,2-b]pyridazin-8-yl]-urea were made in a similar fashion to 4-tert-butyl-N-{3-[8-(3-ethyl-ureido)-imidazo[1,2-b]pyridazin-6-yl]-2-methyl-phenyl}-benzamide.

4-tert-Butyl-N-(2-methyl-3-{8-[5-(morpholine-4-carbonyl)-pyridin-2-ylamino]-imidazo[1,2-a]pyridin-6-yl}-phenyl)-benzamide

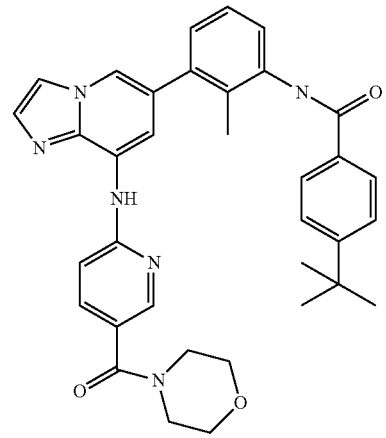 [SMILES: Cc1c(NC(=O)c2ccc(C(C)(C)C)cc2)cccc1-c1cc(Nc2ccc(C(=O)N3CCOCC3)cn2)c2nccn2c1]

Example 15

6-Bromo-imidazo[1,2-a]pyridin-8-ylamine 2,3-diamino-5-bromopyridine (10.0 g, 45.86 mmol) was dissolved in 80 ml of IPA and then 50% wt chloroacetaldehyde/H2O (6.51 ml, 50.45 mmol) was added. The resulting mixture was heated at reflux for 24 hrs. The mixture was cooled down and then filtered. The cake was dried to afford 9.10 g of product.

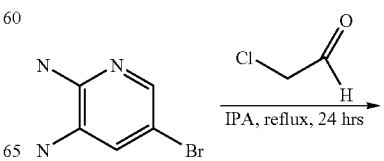

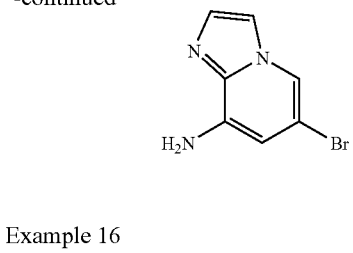

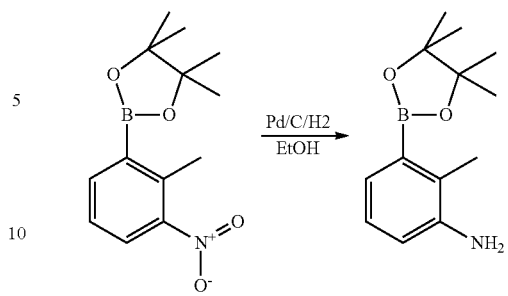

Example 16

4,4,5,5-tetramethyl-2-(2-methyl-3-nitro-phenyl-[1,3,2]dioxaborolane

To a solution of 2-bromo-6-nitrotoluene (12.08 g, 55.91 mmol) and Bis(pinacolato)diboron (15.61 g, 61.50 mmol) in 120 ml of dioxane was added potassium acetate (16.46 g, 167.74 mmol) and 1,1'-bis(diphenyl-phosphino)-ferrocene (3.09 g, 5.59 mmol) and [1,1'-bis(diphenylphosphino)-ferrocene]dichloropalladium(II) (4.56 g, 559 mmol). The reaction mixture was refluxing for 5 hours.

The mixture was filtered through celite and then partitioned between water and ethyl acetate. The aqueous layer was further extracted with 150 mL of ethyl acetate. The combined organic layers were washed with three 150 mL portions of water, dried over MgSO$_4$, filtered and concentrated. Column chromatography (0-12% EtOAc/Hexane) afforded 4.0 g of product.

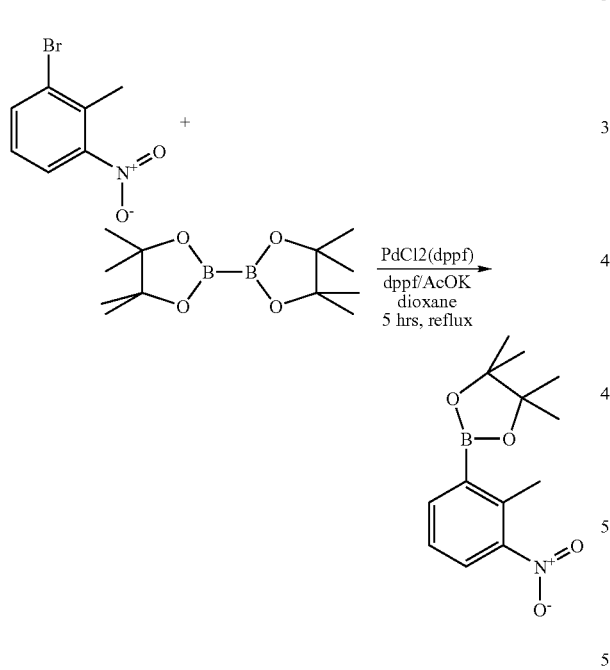

Example 17

2-Methyl-3-(4,4,5,5-tetramethyl-[1,3,2]dioxaborolane-2-yl)-phenylamine

To a solution of 4,4,5,5-tetramethyl-2-(2-methyl-3-nitrophenyl-[1,3,2]dioxaborolane (3.58 g, 12.91 mmol) in ethanol was added 350 mg of Pd/C. The reaction mixture was stirred at room temperature under hydrogen (balloon) for 6 hours. The reaction mixture was filtered through celite and then concentrated to afford 3.12 g of product.

Example 18

4-tert-Butyl-N-[2-methyl-3-(4,4,5,5-tetramethyl-[1,3,2]dioxaborolane-2-yl)-phenyl]-benzamide A solution of 4-tert-butylbenzoyl chloride (2.68 g, 13.63 mmol) in 40 ml CH$_2$Cl$_2$ was added portionwise to a solution of 4-tert-Butyl-N-[2-methyl-3-(4,4,5,5-tetramethyl-[1,3,2]dioxaborolane-2-yl)-phenyl]-benzamide (3.37 g, 13.63 mmol) and triethylamine (2.85 ml, 20.45 mmol). The resulting mixture was stirred at room temperature for 40 hours. Water was added, the mixture was extracted with CH$_2$Cl$_2$, dried over MgSO4 and concentrated to afford 5.15 g of product.

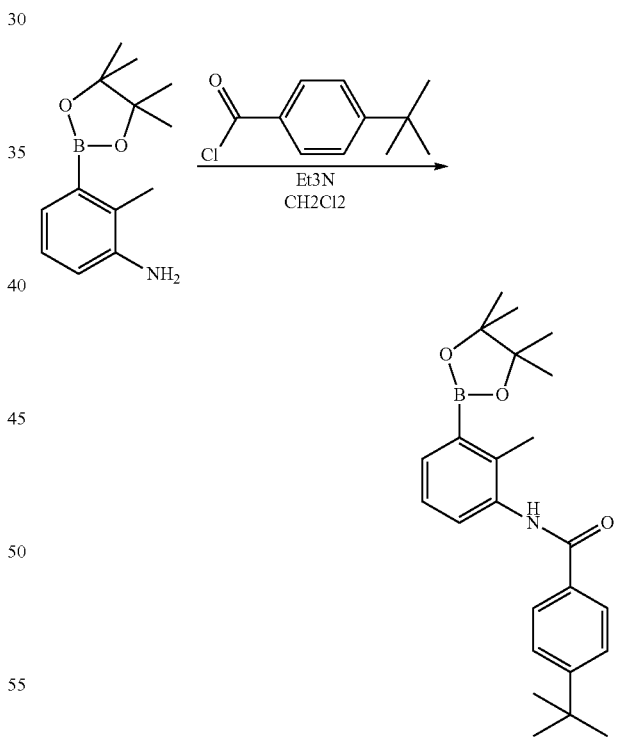

Example 19

N-[3-(8-Amino-imidazo[1,2-a]pyridin-6-yl)-2-methyl-phenyl]-4-tert-butyl-benzamide A mixture of 6-Bromo-imidazo[1,2-a]pyridin-8-ylamine (0.72 g, 3.43 mmol), 4-tert-Butyl-N-[2-methyl-3-(4,4,5,5-tetramethyl-[1,3,2]dioxaborolane-2-yl)-phenyl]-benzamide (1.0 g, 2.54 mmol), Pd(PPh₃)₄ (0.29 g, 0.25 mmol) in 5 ml 1M Na₂CO₃ and 10 mL of ethylene glycol dimethyl ether was stirred at 170° C. in a microwave for 20 min. The resulting suspension was filtered through celite and then partitioned between 100 mL of water and 100 mL of ethyl acetate, and the aqueous layer was further extracted with 50 mL of ethyl acetate. The combined organic layers were dried over MgSO₄, filtered, and concentrated to a residue. Column chromatography (0-6% MeOH/CH2Cl2) afforded 0.685 g of product.

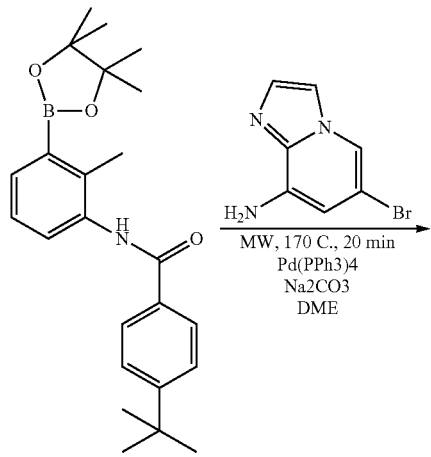

Example 20

(6-Chloro-pyridin-3-yl)-morpholin-4-yl-methanone

To a solution of 6-chloro nicotinic acid (1.11 g, 7.04 mmol) in CH₂Cl₂ at 0 C was added EDCI (2.70 g, 14.08 mmol) and HOBt and then the resulting mixture was stirred for 30 minutes at 0 C. After that, morpholine (2.46 ml, 28.17 mmol) was added, the ice-bath removed and the reaction was done in 15 minutes. Water was added, the mixture was extracted with CH₂Cl₂, dried over MgSO4 and concentrated to afford 1.55 g of product.

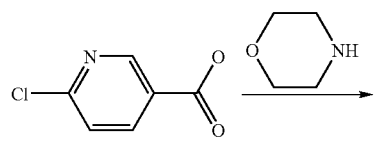

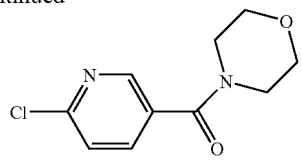

Example 21

4-tert-Butyl-N-(2-methyl-3-{8-[5-(morpholine-4-carbonyl)-pyridin-2-ylamino]-imidazo[1,2-a]pyridin-6-yl}-phenyl)-benzamide A mixture of N-[3-(8-Amino-imidazo[1,2-a]pyridin-6-yl)-2-methyl-phenyl]-4-tert-butyl-benzamide (0.69 g, 1.73 mmol), (6-Chloro-pyridin-3-yl)-morpholin-4-yl-methanone (1.17 g, 5.19 mmol), sodium t-butoxide (0.23 g, 2.42 mmol), Pd(II)acetate (19 mg, 0.08 mmol) and 2-(dicyclohexyl-phosphino)biphenyl was stirred at 200° C. in a microwave for 100 min.

The resulting suspension was partitioned between 50 mL of water and 50 mL of ethyl acetate, and the aqueous layer was further extracted with 25 mL of ethyl acetate. The combined organic layers were dried over MgSO₄, filtered, and concentrated to a residue. Column chromatography (0-5% MeOH/EtOAc) afforded 0.056 g of product.

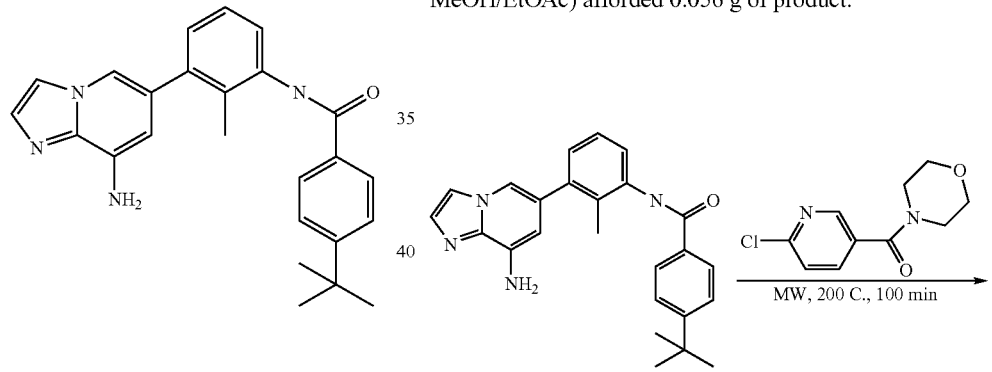

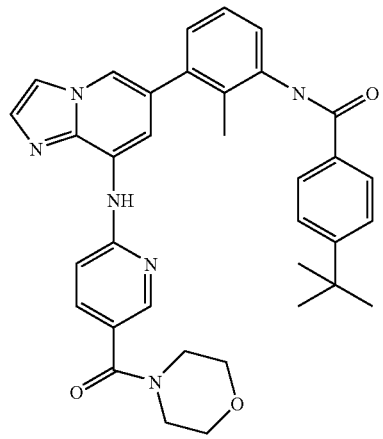

Example 22

Preparation of 4-tert-Butyl-N-{3-[8-(3-ethyl-ureido)-imidazo[1,2-a]pyridin-6-yl]-2-methyl-phenyl}-benzamide

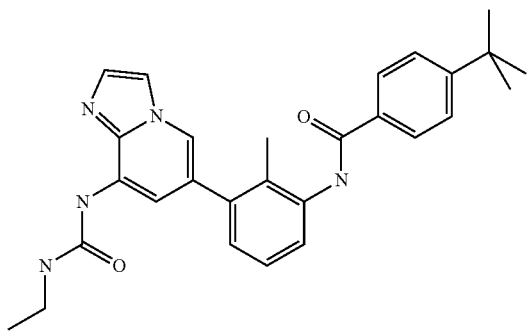 [SMILES: CCNC(=O)Nc1cc(-c2cccc(NC(=O)c3ccc(C(C)(C)C)cc3)c2C)cn2ccnc12]

To N-[3-(8-Amino-imidazo[1,2-a]pyridin-6-yl)-2-methyl-phenyl]-4-tert-butyl-benzamide (53 mg, 0.133 mmol) in dichloromethane (5 mL) at 0° C. was added diisopropylethylamine (60 μL, 2.5 eq) and the resulting mixture was stirred for 5 minutes. Then at 0° C. with stirring was added a 20% phosgene solution in toluene (84 μL, 1.2 eq) all at once, and the resulting solution was stirred at 0° C. for 5 minutes. Next, ethylamine$_{(g)}$ was bubbled through the solution for about 2 minutes. Additional phosgene solution (0.25 mL) was added at 0° C. and stirred an additional 5 minutes. Finally, ethylamine$_{(g)}$ was bubbled through the solution again for about 2 minutes. The reaction was quenched by adding ethyl acetate (35 mL) and water (25 mL). The layers were partitioned and then separated and the organic layer was further washed with brine (1×25 mL) and finally dried over magnesium sulfate, filtered and concentrated. This crude product was purified by Preparative Thin Layer Chromatography, eluting with 5% methanol in dichloromethane to give the title compound as a foamy solid (17 mg) ((M+H)$^+$=470).

Example 23

Preparation of 4-tert-Butyl-N-{2-methyl-3-[8-(3-methyl-ureido)-imidazo[1,2-a]pyridin-6-yl]-phenyl}-benzamide

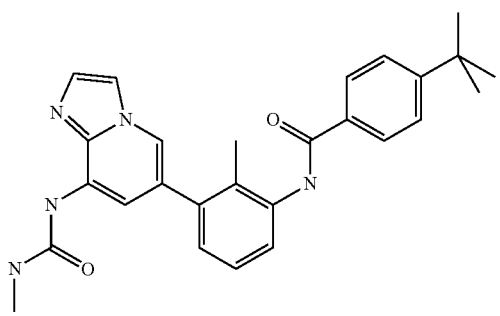 [SMILES: CNC(=O)Nc1cc(-c2cccc(NC(=O)c3ccc(C(C)(C)C)cc3)c2C)cn2ccnc12]

To N-[3-(8-Amino-imidazo[1,2-a]pyridin-6-yl)-2-methyl-phenyl]-4-tert-butyl-benzamide (120 mg, 0.3 mmol) in dichloromethane (10 mL) was added diisopropylethylamine (0.13 mL, 2.5 eq). The resulting mixture was cooled to 0° C. and with stirring was added a solution of 20% phosgene in toluene (0.94 mL, 6 eq), and this solution was stirred at 0° C. for 30 minutes. Next, a 2.0M solution of methylamine in THF (3 mL, 20 eq) was added and the resulting mixture was stirred from 0° C. to room temperature overnight. The next day the solvent was removed under reduced pressure at 55° C. and then added ethyl acetate (35 mL) and water (25 mL). The layers were partitioned and then separated and the organic layer was dried over magnesium sulfate, filtered, and concentrated. The crude material was purified by Preparative Thin Layer Chromatography eluting with 50% acetone in hexanes to give the title compound as an off-white powder (47 mg), ((M+H)$^+$=456).

Example 24

Preparation of N-[3-(8-Acetylamino-imidazo[1,2-a]pyridin-6-yl)-2-methyl-phenyl]-4-tert-butyl-benzamide

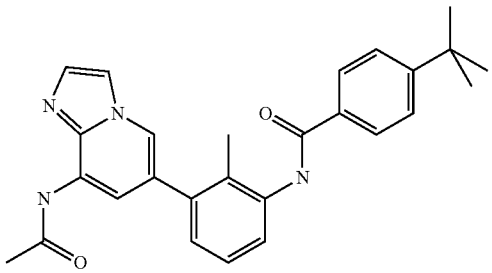 [SMILES: CC(=O)Nc1cc(-c2cccc(NC(=O)c3ccc(C(C)(C)C)cc3)c2C)cn2ccnc12]

To N-[3-(8-Amino-imidazo[1,2-a]pyridin-6-yl)-2-methyl-phenyl]-4-tert-butyl-benzamide (185 mg, 0.414 mmol) in dichloromethane (10 mL) was added diisopropylethylamine (0.24 mL, 3 eq). The resulting mixture was cooled to 0° C. and with stirring was added acetyl chloride (31 μL, 0.95 eq) and the resulting mixture was stirred from 0° C. to room temperature overnight. The next day the solvent was removed under reduced pressure at 55° C. and ethyl acetate (35 mL) and water (25 mL) were added to the residue. The organic layer was concentrated. Then added THF (5 mL) and 1N NaOH (5 mL) and stirred vigorously at room temperature overnight to hydrolize significant bis-amide. The next day added ethyl acetate (150 mL) and water (50 mL) and added 1N HCl to pH=2 and stirred vigorously for 10 minutes. The layers were separated, and the organic layer was washed with brine (1×50 mL), and then dried over magnesium sulfated, filtered and concentrated. The crude product was purified by Thin Layer Chromatography, eluting with 5% methanol in dichloromethane to give the title compound as an off-white powder (31 mg), ((M+H)$^+$=441).

6-[3-(4-tert-Butyl-benzoylamino)-2-methyl-phenyl]-imidazo[1,2-a]pyridin-8-yl}-carbamic acid methyl ester, and 4-tert-Butyl-N-[3-(8-methanesulfonylamino-imidazo[1,2-a]pyridin-6-yl)-2-methyl-phenyl]-benzamide were prepared in an analogous manner substituting methyl chloroformate and methane sulfonyl chloride respectively for acetyl chloride.

Example 25

Preparation of 4-(1-Hydroxy-1-methyl-ethyl)-N-{2-methyl-3-[8-(3-methyl-ureido)-imidazo[1,2-a]pyridin-6-yl]-phenyl}-benzamide

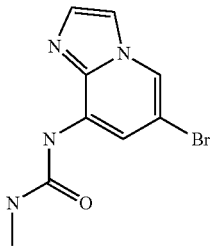

To 6-Bromo-imidazo[1,2-a]pyridin-8-ylamine (1.045 g, 4.93 mmol) in THF (100 mL) was added diisopropylethylamine (1.7 mL, 2.5 eq), and the resulting mixture was cooled to 0° C. With stirring, a solution of 20% phosgene in toluene (3.11 mL, 1.2 eq) was added and the resulting mixture was stirred at 0° C. for 20 minutes. Next, a 2.0M solution of methylamine in THF (24.6 mL, 10 eq) was added and the resulting mixture was stirred from 0° C. to room temperature overnight. Then next day, the solvent was removed under reduced pressure at 55° C., and ethyl acetate (175 mL) and water (50 mL) were added. The resulting mixture was stirred vigorously for 10 minutes and then the layers were separated. The organic layer was dried over magnesium sulfate, filtered and concentrated to give 1-(6-Bromo-imidazo[1,2-a]pyridin-8-yl)-3-methyl-urea as an off-white foamy powder (1.074 g).

Example 26

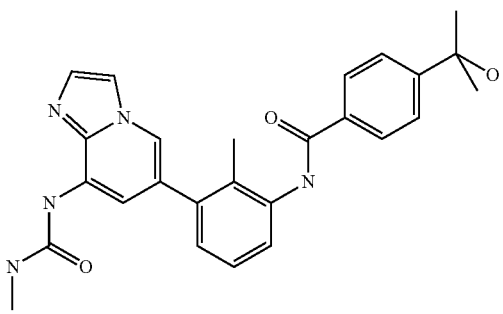 [SMILES: CNC(=O)Nc1cc(-c2cccc(NC(=O)c3ccc(C(C)(C)O)cc3)c2C)cn2ccnc12]

A 5 mL Microwave Reactor Vessel was charged with 1-(6-Bromo-imidazo[1,2-a]pyridin-8-yl)-3-methyl-urea (85 mg, 0.317 mmol), 4-(1-Hydroxy-1-methyl-ethyl)-N-[2-methyl-3-(4,4,5,5-tetramethyl-[1,3,2]dioxaborolan-2-yl)-phenyl]-benzamide (125 mg, 1 eq), tetrakis(triphenylphosphine)palladium (37 mg, 0.1 eq), 1M sodium carbonate (1 mL) and dimethoxyethane (2 mL). The reaction mixture was irradiated for 10 minutes at 150° C. on the Microwave Reactor. The reaction mixture was then partitioned between ethyl acetate (150 mL) and water (50 ml). Separated the layers and washed the organic layer with water (4×50 mL), then finally washed with brine (1×50 mL). The ethyl acetate layer was dried over magnesium sulfate, filtered and concentrated. The crude product was purified by Preparative Thin Layer Chromatography, eluting with 50% acetone in hexanes to give 4-(1-Hydroxy-1-methyl-ethyl)-N-{2-methyl-3-[8-(3-methyl-ureido)-imidazo[1,2-a]pyridin-6-yl]-phenyl}-benzamide as an off-white powder (20 mg), ((M+H)$^+$=458).

Example 27

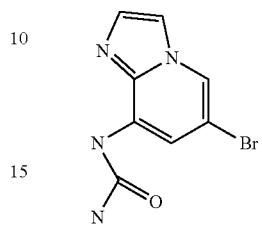

6-Bromo-imidazo[imidazo1,2-a]pyridine-8-ylamine (0.75 G, 0.0035 moles) and DIEA (1.35 G, 0.0104 moles) were placed in 50 ml dichloromethane. After cooling the mixture to 0° C., a 20% phosgene solution in toluene was added (2.5 ml, 0.0051 moles). The reaction mixture was stirred 1 hour at 0° C. and then ammonia 0.5M in dioxane (70 ml, 0.035 moles) was added. After stirring 4 hours at room temperature the mixture was concentrated in vacuo and the residue extracted with ethylacetate –200 ml. This solution was washed with brine, dried over sodium sulfate, concentrated in vacuo, then further dried in h.v. to give 0.5 G of (6-Bromo-imidazo[1,2-a]pyridin-8-yl)-urea (yield 56%) used in the next step without further purification.

Example 28

Preparation of N-[2-Methyl-3-(4,4,5,5-tetramethyl-[1,3,2]dioxaborolan-2-yl)-phenyl]-4-trimethylsilanyl-benzamide

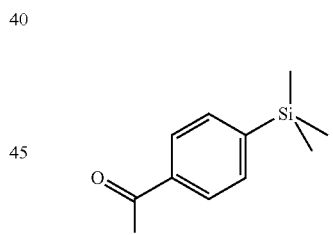

To 1-bromo-4-(trimethylsilyl)-benzene (Aldrich) (6.42 g, 28.04 mmol) in a clean, dry 250 mL round-bottom flask was added THF (100 mL) and the mixture was cooled to –78° C. with stirring for 10 minutes under nitrogen. Then, a 2.5M solution of n-butyllithium in hexanes (13.46 mL, 1.2 eq) was added slowly over about seven minutes. The resulting mixture was stirred at –78° C. for 1.5 hours (solution turned light yellow). Then, at –78° C. an excess of dry ice (4 large pieces) were added to the reaction mixture (solution turned color, then became clear) and the dry ice bath was removed and stirred for 15 minutes. TLC confirmed that the reaction was complete, and after stirring an additional 10 minutes at –78° C., the reaction was quenched with water (100 mL). Ethyl acetate (500 mL) was then added and with stirring 4N HCl was added to pH=2. The layers were separated and then washed the ethyl acetate layer with brine (1×250 mL) and finally the organic layer was dried over magnesium sulfate, filtered, concentrated and pumped to give 4-Trimethylsilanyl-benzoic acid as a white solid (5.49 g).

Example 29

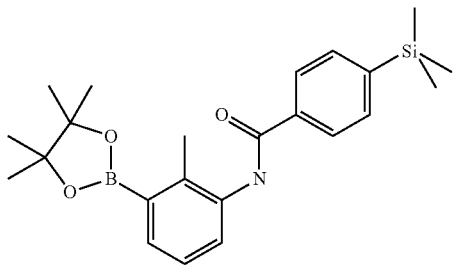

To 2-Methyl-3-(4,4,5,5-tetramethyl-[1,3,2]dioxaborolan-2-yl)-phenylamine (500 mg, 2.15 mmol) and 4-Trimethylsilanyl-benzoic acid (417 mg, 1 eq) in DMF (5 mL) was added disopropylethylamine (0.87 ml, 3 eq) followed by O-(7-Azabenzotriazol-1-yl)-N,N,N',N'-tetramethyluronium hexafluorophosphate (Aldrich) (897 mg, 1.1 eq), and the resulting mixture was stirred at room temperature overnight. The next day, ethyl acetate (170 mL) and water (50 mL) were added. The resulting mixture was stirred vigorously for 10 minutes, and then the layers were separated. The organic layer was washed with water (2×50 mL), saturated sodium bicarbonate (4×50 mL) and finally with brine (1×50 mL). The ethyl acetate layer was dried over magnesium sulfate, filtered, concentrated and pumped to give a white solid (1.03 g), (((M+H)$^+$=410)

Example 30

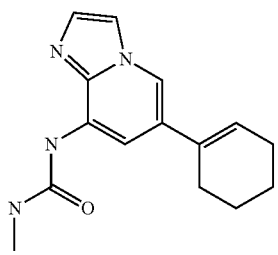 [SMILES: CNC(=O)Nc1cc(C2=CCCCC2)cn2ccnc12]

1) Procedures for Connection of Core to Cyclohexene 110.0 mg (0.472 mmol) 6-Bromo-imidazo[1,2-a]pyridin-8-ylamine, 73.6 ul (0.566 mmol; 1.2 eq.), cyclohexenel-yl boronic acid, 54.54 mg (0.0472 mmo; 0.1 eq.) Pd(PPH3)4 and 150.0 mg (1.416 mmol; 3.0 eq.) Na2CO3 in 2.5 ml DME and 1.2 ml H2O were stirred in the microwave at 170 C for 30 min.

The black suspension was extracted with 2×30.0 ml AcOEt and 1×30.0 ml H2O. Organical layers were combined, dried over MgSO4, filtered and evaporated. The crude product was chromatographed over a 12 g RediSep column with Hexane: AcOEt 0-100% in 15 min, to give: 82.4 mg yellow oil. Yield=82%

Example 31

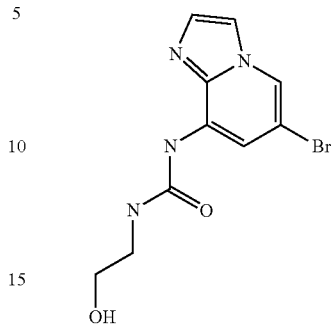

1) Procedure for Ethanolamine Urea Formation

To 50.0 mg (0.236 mmol)) 6-Bromo-imidazo[1,2-a]pyridin-8-ylamine and 82.2 ul (0.59 mmol; 2.5 eq.) Net3 in 3.0 ml dichloromethane was added 148.0 ul (0.285 mmol; 1.2 eq.) 20% phosgene in toluene solution at 0 C. The orange solution was stirred at 0 C for 10 min., then 71.2 ul (1.18 mmol; 5.0 eq.) ethanolamine was added at once at the resulting reaction mixture was continued stirring at 0 C for 10 min. ~5 g silica gel was added and the slurry was evaporated. Residue was chromatographed over a 12 g RediSep column, Hexane:AcOEt 0-100% in 15 min. To give: 45.8 mg off-white solid. Yield=68%

Example 32

1) Procedure for Formation of

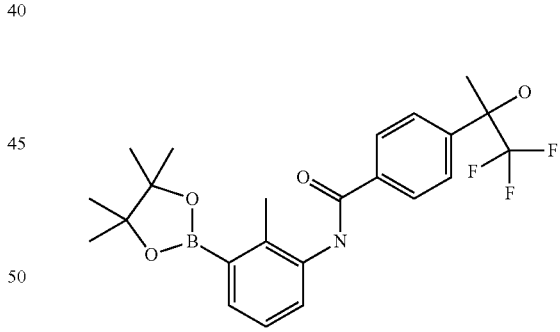

To 2.0 g (11.2 mmol) methyl-4-acetylbenzoate and 5.0 ml (33.6 mmol; 3.0 eq.) (trifluoromethyl)trimethylsilane in 60.0 ml THF was added 32.0 ml (31.36 mmol; 2.8 eq.) 1.0 M tetrabutylammonium fluoride solution in THF at 0 C. The dark-red solution was allowed to warm to RT and stirred at that temperature over night. The reaction mixture was washed with 2×80.0 ml saturated NaHCO3-solution and 50.0 ml brine. Organic layer was dried over MgSO4, filtered and evaporated. To give: 4.05 g orange oil=used crude. 4.05 g (16.3 mmol) crude product and 1.8 g (32.6 mmol; 2.0 eq.) KOH in 30.0 ml dioxane and 15.0 ml H2O were refluxed for 2 h. Orange solution was cooled down and dioxane was evaporated. Residue was acidified with a 10% HCl-solution and the aqueous layer was then extracted with 2×50.0 ml dichloromethane. Organical layers were combined, dried over MgSO₄, filtered and evaporated. The yellow solid was taken up in CH₂Cl₂ and insoluable solid was filtered off and dried under high-vacuo to give 726.9 mg white solid as a product. The mother liquor was evaporated and purified over a 40 g RediSep column with Hexane:AcOEt 0-10% in 15 min. and 10-50% in 10 min. To give: 1.03 g white solid. In total: 1.76 g white solid of the acid. Yield=46%. Normal HATU coupling to get to the boronate-amide. Yield=69%

Example 33

1) Procedure for Formation of

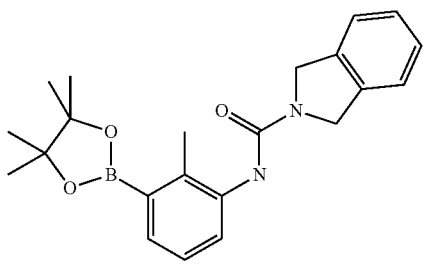 [SMILES: Cc1c(NC(=O)N2Cc3ccccc3C2)cccc1B1OC(C)(C)C(C)(C)O1]

To 150.0 mg (0.643 mmol) 3-(4,4,5,5-Tetramethyl-[1,3,2] dioxaborolan-2-yl)-phenylamine and 224.3 ul (1.61 mmol; 2.5 eq.) in 5.0 ml dichloromethane was added 402.4 ul (0.77 mmol; 1.2 eq.) 20% phosgene-solution in toluene at 0 C. The mixture was stirred at 0 C for 15 min., then 183.0 ul (1.61 mmol; 2.5 eq.) isoindoline was added. Reaction mixture was continued stirring at 0 C for 10 min, then 10 g silica gel was added. Slurry was evaporated and the residue was purified over a 12 g RediSep column with Hexane:AcOEt 0-20% in 15 min. To give: 124.7 mg white solid. Yield=51%

Example 34

Procedure for Formation of

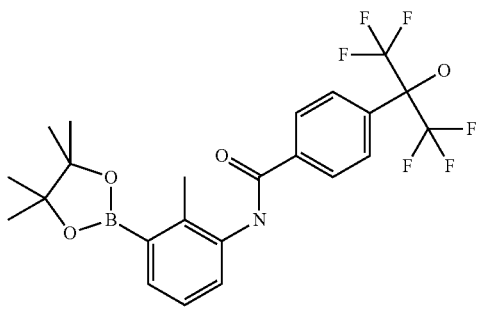 [SMILES: Cc1c(NC(=O)c2ccc(C(O)(C(F)(F)F)C(F)(F)F)cc2)cccc1B1OC(C)(C)C(C)(C)O1]

500.0 (1.74 mmol) 4-(2-hydroxyhexafluoroisopropyl)benzoic acid, 811.3 mg (3.48 mmol; 2.0 eq) 3-(4,4,5,5-Tetramethyl-[1,3,2]dioxaborolan-2-yl)-phenylamine, 722.4 mg (1.9 mmol; 1.1 eq.) HATU and 910.0 ul (5.22 mmol; 3.0 eq.) DIEA in 15 mmol DMF were stirred at RT over the weekend. Orange solution was extracted with 2×50.0 ml AcOEt/1×50.0 ml H2O. Organical layers were combined, washed 4× with 30.0 ml H2O, dried over MgSO4, filtered and evaporated. Purified over a 40 g RediSep column with Hexane:AcOEt 0-20% in 15 min. To give: 567.3 mg light-yellow solid. Yield=65%

Example 35

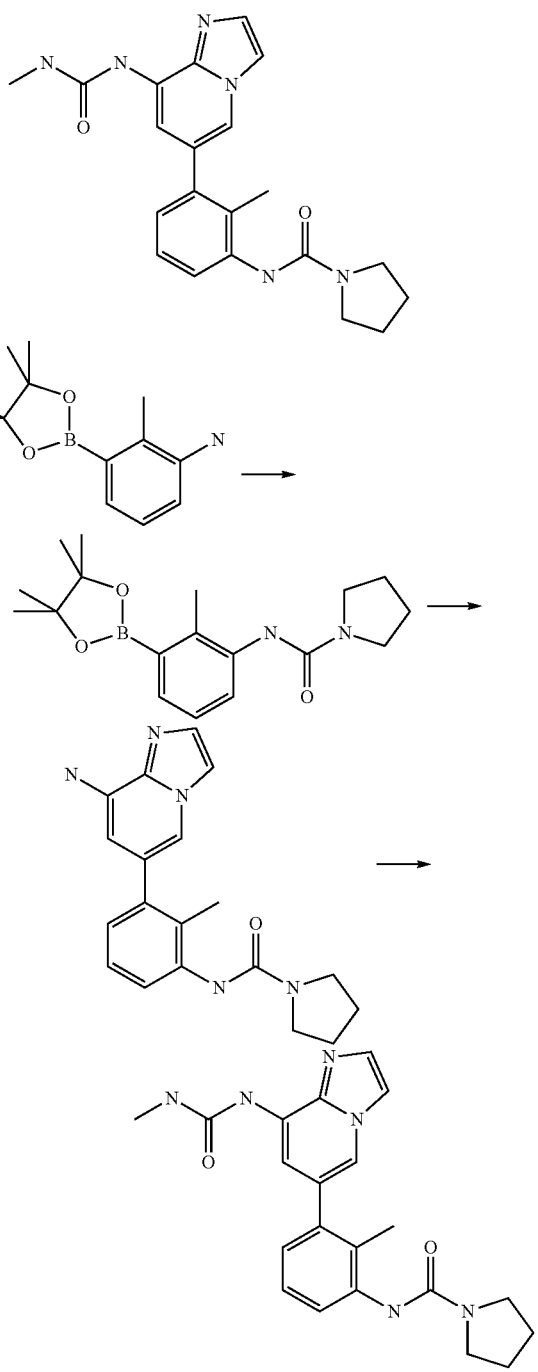

A. Pyrrolidine-1-carboxylic acid [2-methyl-3-(4,4,5, 5-tetramethyl-[1,3,2]dioxaborolan-2-yl)-phenyl]-amide To a cooled solution of 2-Methyl-3-(4,4,5,5-tetramethyl-[1,3,2]dioxaborolan-2-yl)-phenylamine (233 mg, 1.00 mmol) in 6 mL of dichloromethane were added 0.52 mL (3.00 mmol) of diisopropylethylamine and 0.55 mL of a 20% solution of phosgene in toluene at 0 C. The reaction mixture was stirred at 0 C for 10 minutes and pyrrolidine was added. The reaction mixture was stirred at 0 C for 1 hour then applied to column chromatography without workup. Chromatography (20->50% in hexanes/ethyl acetate in 20 minutes->100% in 30 minutes) gave 195 mg (0.591 mmol, 59%) of the title compound.

B. Pyrrolidine-1-carboxylic acid [3-(8-amino-imidazo[1,2-a]pyridin-6-yl)-2-methyl-phenyl]-amide The mixture of 105 mg (0.493 mmol) of 6-Bromo-imidazo[1,2-a]pyridin-8-ylamine, 195 mg (0.591 mmol) of Pyrrolidine-1-carboxylic acid [2-methyl-3-(4,4,5,5-tetramethyl-[1,3,2]dioxaborolan-2-yl)-phenyl]-amide, 157 mg (1.48 mmol) of sodium carbonate, and 57 mg (0.049 mmol) of tetrakis(triphenylphosphine)palladium in 5 mL of 1,2-dimethoxyethane and 2.5 mL of water was heated at 110 C for 30 minutes using microwave. The mixture was partitioned between 50 mL of ethyl acetate and 10 mL of water. The organic layer was dried (MgSO$_4$), and concentrated. Column chromatography (0->10% MeOH/CH$_2$Cl$_2$ in 20 minutes) gave 104 mg (0.310 mmol, 63%) of the title compound.

C.

To a cooled solution of Pyrrolidine-1-carboxylic acid [3-(8-amino-imidazo[1,2-a]pyridin-6-yl)-2-methyl-phenyl]-amide (54 mg, 0.161 mmol) in 2 ml of dichloromethane were added 84 uL (0.483 mmol) of diisopropylethylamine and 88 uL of a 20% solution of phosgene in toluene at 0 C. The reaction mixture was stirred at 0 C for 20 minutes and 0.11 mL of 2M solution of methylamine in THF was added. The reaction mixture was stirred at 0 C for 2 hour then applied to column chromatography without workup. Chromatography (0->5% MeOH/CH$_2$Cl$_2$ in 20 minutes) gave 15 mg (0.038 mmol, 24%) of product.

Example 36

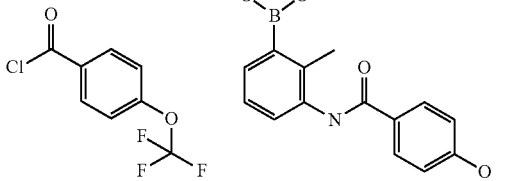

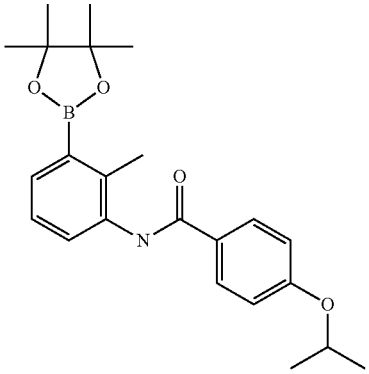

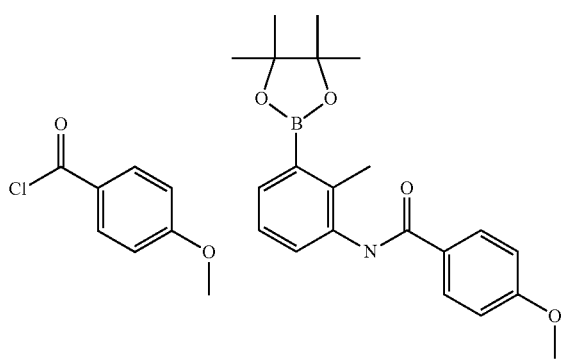

Method A.

4-Methoxy-N-[2-methyl-3-(4,4,5,5-tetramethyl-[1,3,2]dioxaborolan-2-yl)-phenyl]-benzamide To a solution of 117 mg (0.500 mmol) of 2-Methyl-3-(4,4,5,5-tetramethyl-[1,3,2]dioxaborolan-2-yl)-phenylamine and 0.11 mL (0.75 mmol) of triethylamine in 5 mL of dichloromethane was added 4-methoxybenzyl chloride at RT. The reaction mixture was stirred at RT for 5.5 hours then filtered, and washed with dichloromethane. The filtrate was concentrated. Column chromatography (0->50% ethyl acetate/hexanes in 30 minutes) gave 68 mg (0.185 mmol, 37%) of the title compound.

Method B.

4-Isopropoxy-N-[2-methyl-3-(4,4,5,5-tetramethyl-[1,3,2]dioxaborolan-2-yl)-phenyl]-benzamide To a solution of 117 mg (0.500 mmol) of 2-Methyl-3-(4,4,5,5-tetramethyl-[1,3,2]dioxaborolan-2-yl)-phenylamine, 0.26 mL (1.5 mmol) of triethylamine, and 4-isopropoxybenzoic acid in 2.5 mL of DMF was added HATU at RT. The reaction mixture was stirred at RT for 19 hours then partitioned between 50 mL of EtOAc and 50 mL of water. The organic layer was washed with 50 mL of saturated NaHCO3 solution, dried (MgSO4) and concentrated. Column chromatography (0->30% ethyl acetate/hexanes in 10 minutes) gave 175 mg (0.443 mmol, 88%) of the title compound.

Example 37

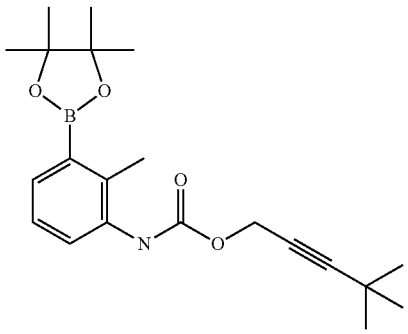 [SMILES: Cc1c(NC(=O)OCC#CC(C)(C)C)cccc1B1OC(C)(C)C(C)(C)O1]

A. 4,4-Dimethyl-pent-2-yn-1-ol

The solution of 0.50 mL (4.06 mmol) of 3,3-dimethyl-1-butyne in 10 mL of THF was treated with 0.81 mL of 2.5 M solution of n-BuLi in THF at 0 C. The reaction mixture was allowed to warm up to RT slowly, and stirred at RT for 5 minutes. To this mixture was added 122 mg (4.06 mmol) of paraformaldehyde at RT. The reaction mixture was stirred at 65 C for 17 hours then cooled to RT, and partitioned between 20 mL of ethyl ether and 20 mL of water. The aqueous layer was extracted with ethyl ether (20 mL×2). The combined organic layers were dried (MgSO4), and concentrated to give the title compound in quatitative yield.

B. (4,4-Dimethyl-pent-2-ynyl)-carbamic acid 2-methyl-3-(4,4,5,5-tetramethyl-[1,3,2]dioxaborolan-2-yl)-phenyl Ester To a cooled solution of 2-Methyl-3-(4,4,5,5-tetramethyl-[1,3,2]dioxaborolan-2-yl)-phenylamine (338 mg, 1.45 mmol) in 6 mL of dichloromethane were added 1.0 mL (5.8 mmol) of diisopropylethylamine and 0.92 mL of a 20% solution of phosgene in toluene at 0 C. The reaction mixture was stirred at 0 C for 20 minutes and a solution of 338 mg of 4,4-Dimethyl-pent-2-yn-1-ol in 6 mL of dichloromethane was added. The reaction mixture was heated to reflux for 64 hour then applied to column chromatography without workup. Chromatography (0->20% in hexanes/ethyl acetate in 20 minutes) gave 179 mg (0.482 mmol, 33%) of the title compound.

Example 38

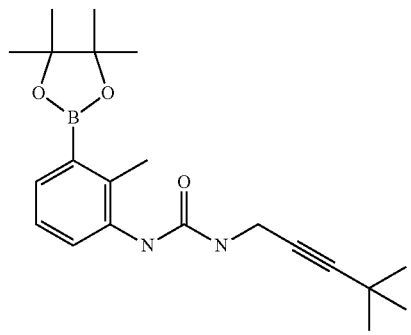 [SMILES: Cc1c(NC(=O)NCC#CC(C)(C)C)cccc1B1OC(C)(C)C(C)(C)O1]

A. 4,4-Dimethyl-pent-2-ynylamine

To a cooled solution of 0.31 mL (2.5 mmol) of 3,3-dimethyl-1-butyne in 5 mL of THF was treated with 1.0 mL of 2.5 M solution of n-BuLi in THF at 0 C. The reaction mixture was allowed to warm up to RT slowly, and stirred at RT for 5 minutes. To this mixture was added 819 mg (2.00 mmol) of N-(triphenylphosphoranylidene)-1H-benzotriazole-1-methaneamine at RT. The reaction mixture was stirred at RT for 18 hours, treated with 5 mL of NH4Cl solution and 6 mL of conc. NH4OH solution, stirred at RT for 1 hour, and extracted with 20 mL of ethyl ether three times. The combined organic layers were washed with 5 mL of 1M solution of NaOH, and dried (MgSO4), filtered and acidified with saturated solution of HCl in ether until there was no more solid formation. The solid was filtered and dried to give impure title compound (18% pure, impurity was triphenylphospine oxide) as a sticky solid.

B. 1-(4,4-Dimethyl-pent-2-ynyl)-3-[2-methyl-3-(4,4,5,5-tetramethyl-[1,3,2]dioxaborolan-2-yl)-phenyl]-urea To a cooled solution of 2-Methyl-3-(4,4,5,5-tetramethyl-[1,3,2]dioxaborolan-2-yl)-phenylamine (29 mg, 0.13 mmol) in 2.4 mL of dichloromethane were added 0.11 mL (0.66 mmol) of diisopropylethylamine and 78 uL of a 20% solution of phosgene in toluene at 0 C. The reaction mixture was stirred at 0 C for 20 minutes and transferred into a flask containing 140 mg (18% pure, 0.17 mmol) of dimethyl-pent-2-ynylamine. The reaction mixture was stirred at RT for 18 hour then applied to column chromatography without workup. Chromatography (0->50% in hexanes/ethyl acetate in 30 minutes) gave 27 mg (73 umol, 60%) of the title compound.

Example 39

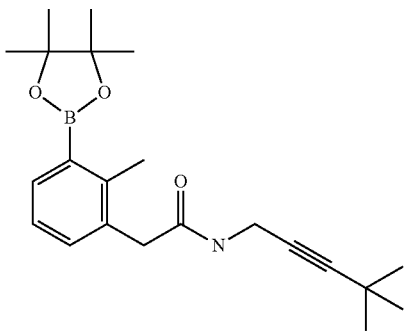 [SMILES: Cc1c(CC(=O)NCC#CC(C)(C)C)cccc1B1OC(C)(C)C(C)(C)O1]

N-(4,4-Dimethyl-pent-2-ynyl)-2-[2-methyl-3-(4,4,5,5-tetramethyl-[1,3,2]dioxaborolan-2-yl)-phenyl]-acetamide To a solution of 98 mg (0.374 mmol) of [2-Methyl-3-(4,4,5,5-tetramethyl-[1,3,2]dioxaborolan-2-yl)-phenyl]-acetic acid, 0.31 mL (2.2 mmol) of triethylamine, and mg (18% pure, 0.374 mmol) of dimethyl-pent-2-ynylamine in 4 mL of DMF was added BOP at RT. The reaction mixture was stirred at RT for 16 hours then concentrated. The residue was dissolved in 50 mL of EtOAc and washed with sat. aqueous solution of NaHCO3 (50 mL). The aqueous layer was extracted with 50 mL of EtOAc. The combined organic layers were washed with 50 mL of brine, dried (MgSO4) and concentrated. Column chromatography (0->50% ethyl acetate/hexanes in 30 minutes) gave 65 mg (0.18 mmol, 49%) of the title compound.

Example 40

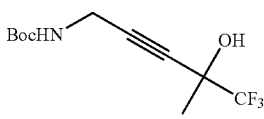 [SMILES: CC(C)(C)OC(=O)NCC#CC(C)(O)C(F)(F)F]

To a solution of prop-2-ynyl-carbamic acid tert-butyl ester (0.646 g, 4.16 mmol) in 15 mL of tetrahydrofuran at −78° C. was added lithium diisopropylamide (2.0 M solution in heptane/THF/EtPh, 4.6 mL, 9.2 mmol) all at once. The orange solution was stirred at −78° C. for 2 h, at which point it is a cloudy yellow mixture. 1,1,1-Trifluoroacetone (0.5 mL, 5 mmol) was added all at once, and the yellow mixture was stirred, allowing to slowly warm to RT, for 17.5 h. A sat. aq. NH4Cl solution (30 mL) was added, and the mixture was extracted with 30 mL of ether. The organic layer was sequentially washed with 30 mL of water and 30 mL of a sat. aq. NaCl solution, dried over MgSO4, filtered and concentrated to an orange cloudy oil. Column chromatography (20->40% EtOAc/hexanes) afforded 0.687 g (62%) of slightly impure (5,5,5-trifluoro-4-hydroxy-4-methyl-pent-2-ynyl)-carbamic acid tert-butyl ester as a yellow oil that was used without further purification.

Example 41

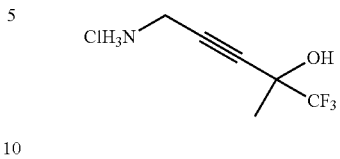

A solution of (5,5,5-trifluoro-4-hydroxy-4-methyl-pent-2-ynyl)-carbamic acid tert-butyl ester (0.687 g, 2.57 mmol) in 10 mL of methanol was treated with a premixed solution of 12 mL of methanol and 3 mL of acetyl chloride. The yellow solution was stirred for 5 h, then concentrated, chasing with ether, to 0.435 g (83%) of slightly impure 5-amino-1,1,1-trifluoro-2-methyl-pent-3-yn-2-ol hydrochloride as a light orange solid that was used without further purification.

Example 42

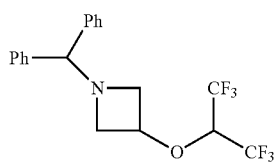

A solution of methanesulfonic acid 1-benzhydryl-azetidin-3-yl ester (0.194 g, 0.61 mmol) in 2 mL of hexafluoroisopropanol in a sealed tube was stirred at 100° C. for 14 h, then concentrated. The residue was partitioned between 5 mL of ethyl acetate and 5 mL of a 10% NaOH solution. The organic layer was sequentially washed with 5 mL of water and 5 mL of a sat. aq. NaCl solution; dried over MgSO$_4$, filtered and concentrated to an orange-yellow oil. Column chromatography (0-<20% EtOAc/hexanes) afforded 0.059 g (25%) of 1-benzhydryl-3-(2,2,2-trifluoro-1-trifluoromethyl-ethoxy)-azetidine as a colorless oil.

Example 43

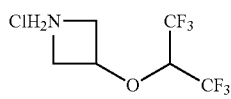

A mixture of 1-benzhydryl-3-(2,2,2-trifluoro-1-trifluoromethyl-ethoxy)-azetidine (0.358 g, 0.920 mmol), 10% palladium on carbon (0.351 g), ammonium formate (1.19 g, 18.9 mmol) and 7 mL of methanol under nitrogen in a sealed tube was stirred at 65° C. for 3.5 h, then allowed to cool. The mixture was filtered through celite 521, rinsing with 50 mL of ether. The filtrate was sequentially washed with three 50 mL portions of water and 50 mL of a sat. aq. NaCl solution. The combined aqueous layers were then extracted with three 50 mL portions of dichloromethane. The combined dichloromethane layers were dried over MgSO$_4$, filtered, treated with a premised solution of 8 mL of methanol and 2 mL of acetyl chloride, and concentrated, chasing with toluene, to 0.141 g (59%) of slightly impure 3-(2,2,2-trifluoro-1-trifluoromethyl-ethoxy)-azetidine hydrochloride that was used without further purification.

Example 44

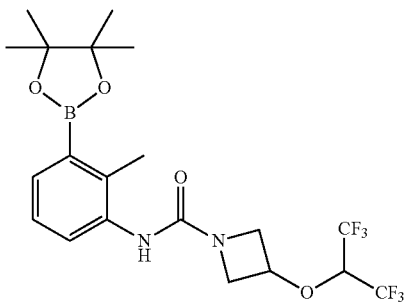 [SMILES: Cc1c(NC(=O)N2CC(OC(C(F)(F)F)C(F)(F)F)C2)cccc1B1OC(C)(C)C(C)(C)O1]

Phosgene (20% in toluene, 0.26 mL, 0.49 mmol) was added to a solution of 2-methyl-3-(4,4,5,5-tetramethyl-[1,3,2]dioxaborolan-2-yl)-phenylamine (0.096 g, 0.411 mmol) and diisopropylethylamine (0.29 mL, 1.7 mmol) in 4 mL of dichloromethane at 0-5° C. The reaction mixture was then stirred at RT for 30 min., then transferred via Pasteur pipette to a flask containing 3-(2,2,2-trifluoro-1-trifluoromethyl-ethoxy)-azetidine hydrochloride prepared as in the above example (0.41 mmol). A total of 6 mL of additional dichloromethane was used in rinsing. The very pale yellow solution was stirred for 18.5 h. 10 g of silica gel was added, and the mixture was concentrated to a white powder. Column chromatography (0->50% EtOAc/hexanes) afforded 0.117 g (59%) of 3-(2,2,2-trifluoro-1-trifluoromethyl-ethoxy)-azetidine-1-carboxylic acid [2-methyl-3-(4,4,5,5-tetramethyl-[1,3,2]dioxaborolan-2-yl)-phenyl]-amide as a colorless oil.

Example 45

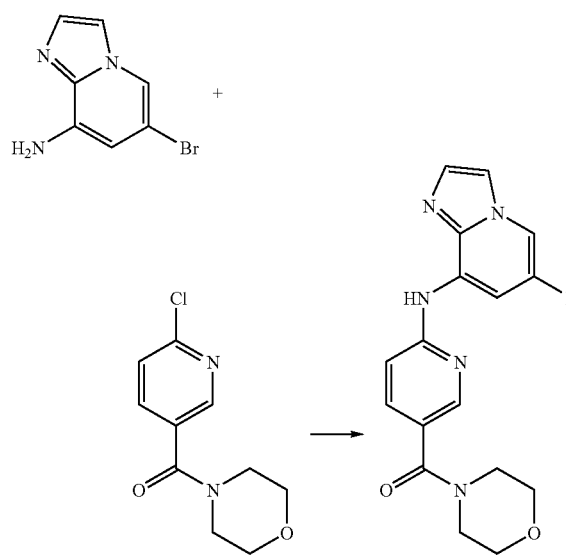

4.5 g (21 mmol) of 6-Bromo-imidazo[1,2-a]pyridine-8-yl-amine, 5.29 g (23 mmol) of (6-Chloropyridine-3-yl)morpholin-4-yl-methanone and 4.76 g (43 mmol) of potassium tert-butoxide were dissolved in 20 ml dioxane. This suspension was heated for 20 min at 150° C. in the microwave. The reaction mixture was concentrated. The residue was diluted with dichloromethane. Deionized water was added and the basic water phase was neutralized with an 1 N HCl solution. An excess of sodium sulfate was added and stirred for a while. The slimy mixture was filtered over a plug of celite. The filtrate was extracted with dichloromethane; org. phase was dried over sodium sulfate; filtered; concentrated. This residue was purified by a 200 g silica gel column with the solvent ethyl acetate for 15 min, then dichloromethane for 20 min, then 0-10% Methanol in dichloromethane during 40 min. 4.66 g of a light brown foam was obtained. LCMS: M(H+)= 402.

Example 46

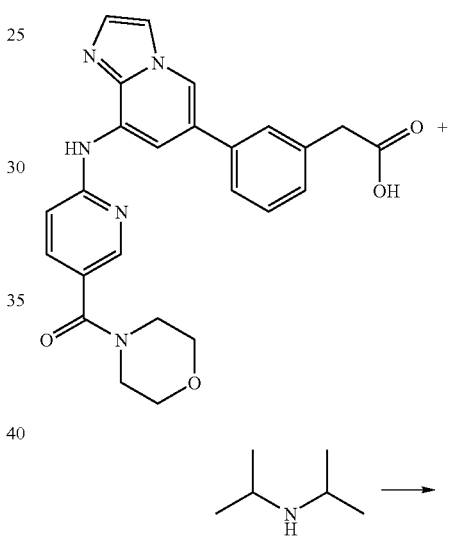

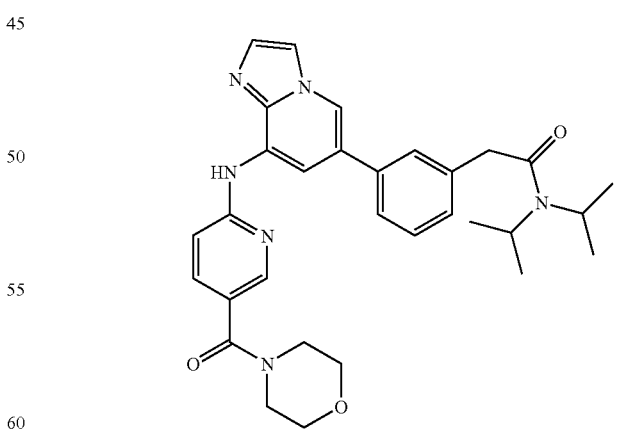

40 mg (0.09 mmol) of the acid and diisopropyl amine were dissolved in 1 ml dimethylformamide. HATU was added and stirred over night. The whole reaction mixture was purified by preparative HPLC to give 9 mg of the product (yield 20%). LCMS: M(H+)=541.2

Example 47

Isocyanate Formation

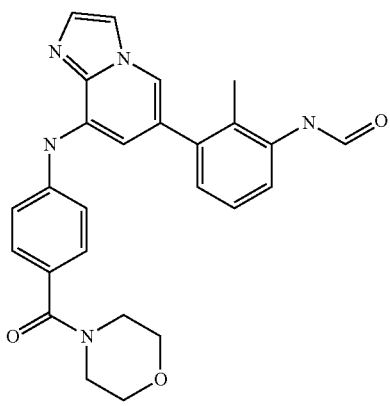 [SMILES: Cc1c(NC=O)cccc1-c1cc(Nc2ccc(C(=O)N3CCOCC3)cc2)c2nccn2c1]

A solution of 643 mg of {4-[6-(3-Amino-2-methyl-phenyl)-imidazo[1,2-a]pyridin-8-ylamino]-phenyl}-morpholin-4-yl-methanone and 290 µL of diisopropylethylamine in 4 mL dichloroethane was added dropwise over 30 min to 196 mg of triphosgene in 4 mL of dichloroethane with stirring at room temperature. After the addition was complete the reaction mixture was stirred at room temperature for 10 minutes. Added enough dichloroethane to give a total solution volume of 10 mL and used immediately as a 0.15 M stock solution for reaction with amines to form the desired ureas.

Example 48

Urea Formation

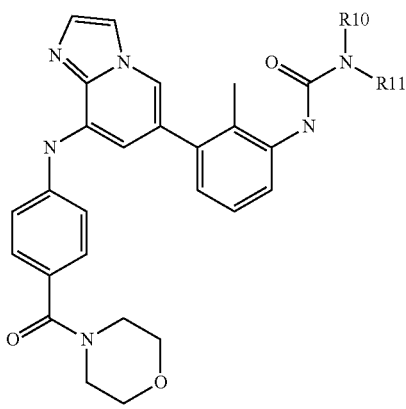

mL of a the stock solution above was added in one portion to a stirred solution of 86 µL of cyclohexylamine in 1.0 mL dichloroethane. Stirred the reaction at room temperature overnight. Diluted the reaction mixture with 2 mL dichloroethane, added 4 mL water and heated the mixture until all the solids dissolved. Separated phases, dried the organic phase over $Na_2SO_4$, and filtered hot. A white precipitate formed on cooling. Removed the solvent on a vacuum centrifuge. The residue was purified by HPLC to give 24 mg of product as an off-white solid.

Example 49

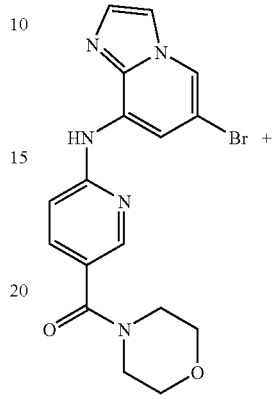

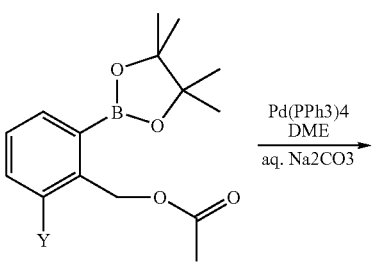

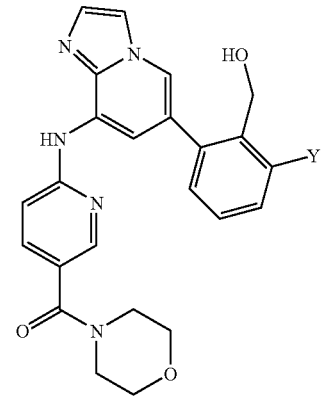

A mixture of the imidazopyridine bromide (0.14 mmol), the aryl boronic acid (0.14 mmol), $Pd(PPh_3)_4$ (0.014 mmol), ethylene glycol dimethyl ether (3 mL), and aqueous $Na_2CO_3$ (1 M, 1 mL) are maintained at 120° C. in a microwave for 30 min. The resulting suspension is partitioned between water and ethyl acetate, and the aqueous layer is further extracted with ethyl acetate. The combined organic layers ware dried over $MgSO_4$, filtered, and concentrated in vacuo. The crude product is treated with LiOH (0.28 mmol) in $THF:H_2O$ (1:1, 10 mL) and the resulting suspension is stirred vigorously overnight. The suspension is partitioned between water and ethyl acetate. The organic layers are dried over $MgSO_4$, filtered, and concentrated in vacuo. The product is purified by chromatography (5% MeOH/DCM).

Example 50

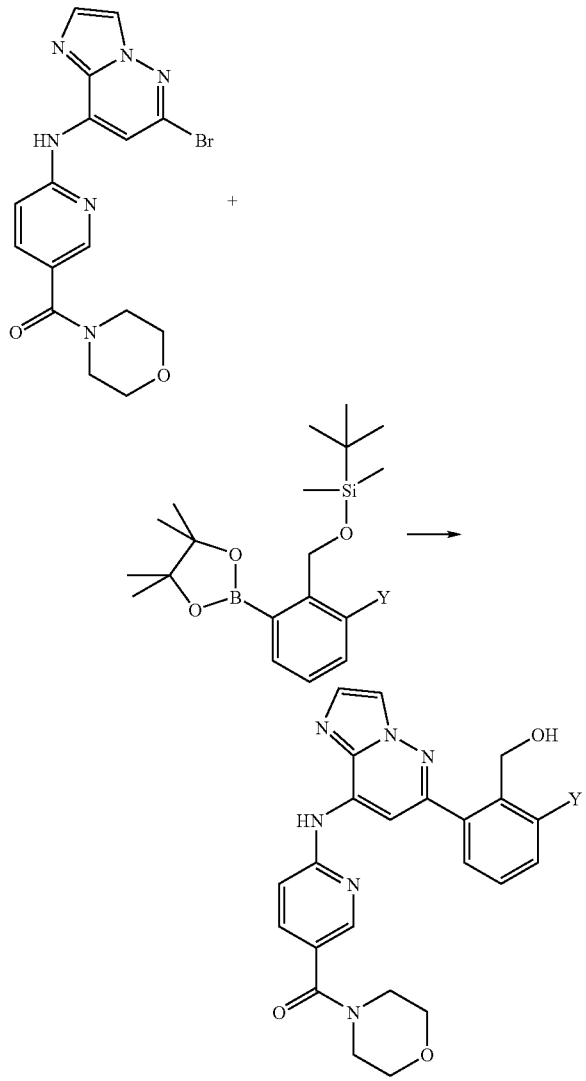

A mixture of the imidazopyridizine bromide (0.16 mmol), the aryl boronate (0.16 mmol), Pd(dba)$_2$ (0.005 mmol), Xphos ligand (0.01 mmol), and K$_3$PO$_4$ (0.32 mmol) in n-BuOH:H$_2$O (5:1, 3.6 mL) is stirred at 120° C. in a microwave for 0.5 hour. The reaction is concentrated in vacuo, is dissolved in 10 ml MeOH with 2 drops of conc H$_2$SO$_4$, and then is stirred for 30 min. The solution is neutralized with solid NaHCO$_3$, is extracted with dichloromethane (20 mL), and is dried over MgSO$_4$. Concentration of the reaction mixture in vacuo is followed by purification with flash chromatography (0-10% MeOH/DCM).

Assay Data

Example 51

Bruton's Tyrosine Kinase (Btk) Inhibition Assay

The assay is a capture of radioactive $^{33}$P phosphorylated product through filtration. The interactions of Btk, biotinylated SH$_2$ peptide substrate (Src homology), and ATP lead to phosphorylation of the peptide substrate. Biotinylated product is bound streptavidin sepharose beads. All bound, radiolabeled products are detected by scintillation counter.

Plates assayed are 96-well polypropylene (Greiner) and 96-well 1.2 μm hydrophilic PVDF filter plates (Millipore). Concentrations reported here are final assay concentrations: 10-100 μM compounds in DMSO (Burdick and Jackson), 5-10 nM Btk enzyme (His-tagged, full-length), 30 μM peptide substrate (Biotin-Aca-AAAEEIYGEI-NH$_2$), 100 μM ATP (Sigma), 8 mM imidazole (Sigma, pH 7.2), 8 mM glycerol-2-phosphate (Sigma), 200 μM EGTA (Roche Diagnostics), 1 mM MnCl$_2$ (Sigma), 20 mM MgCl$_2$ (Sigma), 0.1 mg/ml BSA (Sigma), 2 mM DTT (Sigma), 1 μCi $^{33}$P ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

IC$_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 μM and ending at 3 nM. The control compound was staurosporine. Background was counted in the absence of peptide substrate. Total activity was determined in the presence of peptide substrate. The following protocol was used to determine Btk inhibition.

1) Sample preparation: The test compounds were diluted at half-log increments in assay buffer (imidazole, glycerol-2-phosphate, EGTA, MnCl$_2$, MgCl$_2$, BSA).

2) Bead preparation
   a.) rinse beads by centrifuging at 500 g
   b.) reconstitute the beads with PBS and EDTA to produce a 20% bead slurry 3) Pre-incubate reaction mix without substrate (assay buffer, DTT, ATP, P ATP) and mix with substrate (assay buffer, DTT, ATP, $^{33}$P ATP, peptide substrate) 30° C. for 15 min.

4) To start assay, pre-incubate 10 μL Btk in enzyme buffer (imidazole, glycerol-2-phosphate, BSA) and 10 μL of test compounds for 10 min at RT.

5) Add 30 μL reaction mixture without or with substrate to Btk and compounds.

6) Incubate 50 μL total assay mix for 30 min at 30° C.

7) Transfer 40 μL of assay to 150 μL bead slurry in filter plate to stop reaction.

8) Wash filter plate after 30 min, with following steps
   a. 3×250 μL NaCl
   b. 3×250 μL NaCl containing 1% phosphoric acid
   c. 1×250 μL H$_2$O 9) Dry plate for 1 h at 65° C. or overnight at RT 10) Add 50 μL microscint-20 and count $^{33}$P cpm on scintillation counter.

Calculate percent activity from raw data in cpm $$\text{percent activity} = (\text{sample} - bkg)/(\text{total activity} - bkg) \times 100$$

Calculate IC$_{50}$ from percent activity, using one-site dose response sigmoidal model $$y = A + ((B-A)/(1+((x/C)^D)))$$

x=cmpd conc, y=% activity, A=min, B=max, C=IC$_{50}$, D=1 (hill slope)

Representative results are in Table Z.

TABLE Z

| Compound | Btk inhibition IC$_{50}$ (µM) |
|---|---|
| I-7 | 0.022 |
| I-8 | 0.01 |
| I-11 | 0.019 |
| I-43 | 0.013 |
| I-45 | 0.015 |
| I-53 | 0.013 |
| I-56 | 0.024 |
| I-77 | 0.018 |
| I-218 | 0.01 |

Example 52

Inhibition of B-Cell Activation—B Cell FLIPR Assay in Ramos Cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of 0.5×10$^6$/mL in tissue culture flasks. On day of assay, cells are counted and set at a concentration of 1×10$^6$/mL in growth media supplemented with 1 µM FLUO-3AM (TefLabs Cat-No. 0116, prepared in anhydrous DMSO and 10% Pluronic acid) in a tissue culture flask, and incubated at 37° C. (4% CO$_2$) for one h. To remove extracellular dye, cells were collected by centrifugation (5 min, 1000 rpm), resuspended in FLIPR buffer (described below) at 1×10$^6$ cells/mL and then dispensed into 96-well poly-D-lysine coated black/clear plates (BD Cat-No. 356692) at 1×10$^5$ cells per well. Test compounds were added at various concentrations ranging from 100 µM to 0.03 µM (7 concentrations, details below), and allowed to incubate with cells for 30 min at RT. Ramos cell Ca$^{2+}$ signaling was stimulated by the addition of 10 µg/mL anti-IgM (Southern Biotech, Cat-No. 2020-01) and measured on a FLIPR (Molecular Devices, captures images of 96 well plates using a CCD camera with an argon laser at 480 nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM CaCl$_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528)

Compound Dilution Details:

In order to achieve the highest final assay concentration of 100 µM, 24 µL of 10 mM compound stock solution (made in DMSO) is added directly to 576 µL of FLIPR buffer. The test compounds are diluted in FLIPR Buffer (using Biomek 2000 robotic pipettor) resulting in the following dilution scheme: vehicle, 1.00×10$^{-4}$ M, 1.00×10$^{-5}$, 3.16×10$^{-6}$, 1.00×10$^{-6}$, 3.16×10$^{-7}$, 1.00×10$^{-7}$, 3.16×10$^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The IC$_{50}$ was determined using a non-linear curve fit (GraphPad Prism software).

Example 53

Pharmaceutical compositions of the subject Compounds for administration via several routes were prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:
1. A compound of formula III:

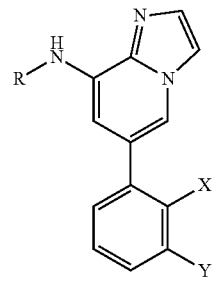

wherein:
R is —R$^1$, —R$^1$—R$^2$—R$^3$, —R$^1$—R$^3$, or —R$^2$—R$^3$;
  R$^1$ is aryl, heteroaryl, cycloalkyl, or heterocycloalkyl, and is optionally substituted with lower alkyl, hydroxy, lower alkoxy, halo, nitro, amino, cyano, or halo-lower alkyl;
  R$^2$ is —C(=O) or —C(=O)NH;
  R$^3$ is R$^4$;
  R$^4$ is lower alkoxy, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, lower alkyl sulfonyl, heterocycloalkyl, or halo-lower alkyl;
X is H, lower alkyl, hydroxy, hydroxy lower alkyl, or lower alkoxy;
Y is H, —R$^5$—R$^6$, —R$^6$ or —R$^5$—R$^6$—R$^7$;
  R$^5$ is —NHC(=O), —NHC(=O)NR$^{5'}$, —(CH$_2$)$_n$C(=O)NR$^{5'}$, —NH, or —(CH$_2$)$_n$C(=O);
  n is 0, 1, or 2; and
  R$^{5'}$ is H, lower alkyl, lower alkoxy, or hydroxy lower alkyl;
  R$^6$ is lower alkyl, lower alkenyl, lower alkynyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl and is optionally substituted with one or more substituents selected from the group consisting of lower alkyl, hydroxy, halo-lower alkyl, lower alkoxy, halo-lower alkoxy, halo, nitro, amino, cyano, or trialkylsilanyl; and
  R$^7$ is aryl, heteroaryl, cycloalkyl, or heterocycloalkyl, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl, or is optionally connected to an aryl, heteroaryl, cycloalkyl, or heterocycloalkyl ring, such that the two rings form a bicyclic fused or spirocyclic ring system, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl;
with the proviso that if R is C(=O)CH$_3$ and X is H, then Y is not CF$_3$ or H;
or a pharmaceutically acceptable salt thereof.

2. A compound of formula IV

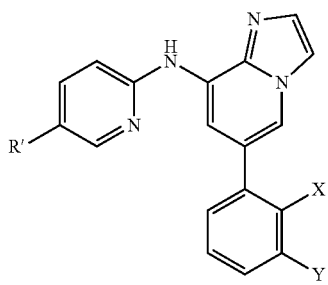

wherein:
R' is —R²—R³ or —R³;
R² is —C(=O), —C(=O)O, —C(=O)NH, —S(=O)₂, O, NR³, or lower alkyl;
R³ is H or R⁴;
  R⁴ is lower alkyl, lower alkoxy, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, lower alkyl sulfonyl, heterocycloalkyl, or halo-lower alkyl;
X is H, halo, lower alkyl, hydroxy, hydroxy lower alkyl, or lower alkoxy;
Y is H, —R⁵—R⁶, —R⁶ or —R⁵—R⁶—R⁷;
R⁵ is —NHC(=O), —NHC(=O)NR⁵', —(CH₂)ₙC(=O)NR⁵', —NH, or —(CH₂)ₙC(=O);
n is 0, 1, or 2;
R⁵' is H, lower alkyl, lower alkoxy, or hydroxy lower alkyl;
R⁶ is lower alkyl, lower alkenyl, lower alkynyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl and is optionally substituted with one or more substituents selected from the group consisting of lower alkyl, hydroxy, halo-lower alkyl, lower alkoxy, halo-lower alkoxy, halo, nitro, amino, amido, amido lower alkyl, cyano, lower alkyl sulfonyl, or trialkylsilanyl; and
R⁷ is aryl, heteroaryl, cycloalkyl, or heterocycloalkyl, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl, or is optionally connected to an aryl, heteroaryl, cycloalkyl, or heterocycloalkyl ring, such that the two rings form a bicyclic fused or spirocyclic ring system, optionally substituted with one or more substituents selected from the group consisting of lower alkyl, hydroxy, halo-lower alkyl, lower alkoxy, halo-lower alkoxy, halo, nitro, amino, oxo, cyano, or trialkylsilanyl;
or a pharmaceutically acceptable salt thereof.

3. The compound of claim 1 wherein R is —R¹—R²—R³ and R¹ is heteroaryl.

4. The compound of claim 3, wherein the heteroaryl is pyridinyl.

5. The compound of claim 4, wherein R² is —C(=O).

6. The compound of claim 5, wherein R³ is R⁴ and R⁴ is heterocycloalkyl.

7. The compound of claim 6, wherein the heterocycloalkyl is morpholinyl.

8. The compound of claim 2 wherein R' is —R²—R³ and R² is —C(=O).

9. The compound of claim 8, wherein R³ is R⁴ and R⁴ is heterocycloalkyl.

10. The compound of claim 2, wherein X is hydroxymethyl.

11. The compound of claim 7, wherein X is hydroxymethyl.

12. The compound of claim 1, wherein Y is —R⁵—R⁶ and R⁵ is —C(=O)NH.

13. The compound of claim 12, wherein R⁶ is phenyl.

14. The compound of claim 12, wherein R⁶ is 4-tert butyl-phenyl.

15. The compound of claim 2, wherein Y is —R⁵—R⁶ and R⁵ is —C(=O)NH.

16. The compound of claim 15, wherein R⁶ is phenyl and X is methyl.

17. The compound of claim 16, wherein R⁶ is 4-tert butyl-phenyl and X is methyl.

18. The compound of claim 15, wherein X is hydroxymethyl.

19. The compound of claim 1 selected from the group consisting of:
  N-[3-(8-Amino-imidazo[1,2-a]pyridin-6-yl)-2-methylphenyl]-4-tert-butyl-benzamide;
  4-tert-Butyl-N-[2-methyl-3-(8-propionylamino-imidazo[1,2-a]pyridin-6-yl)-phenyl]-benzamide;
  4-tert-Butyl-N-(3-{8-[2-((R)-3-hydroxy-pyrrolidin-1-yl)-pyrimidin-4-ylamino]-imidazo[1,2-a]pyridin-6-yl}-2-methyl-phenyl)-benzamide;
  N-(3-{8-[2-((R)-3-Amino-pyrrolidin-1-yl)-pyrimidin-4-ylamino]-imidazo[1,2-c]pyridin-6-yl}-2-methyl-phenyl)-4-tert-butyl-benzamide;
  4-tert-Butyl-N-{3-[8-(6-fluoro-pyridin-2-ylamino)-imidazo[1,2-c]pyridin-6-yl]-2-methyl-phenyl}-benzamide; and
  4-tert-Butyl-N-(3-{8-[(1S,4S)-2-(2,5-diaza-bicyclo[2.2.1]hept-2-yl)-pyrimidin-4-ylamino]-imidazo[1,2-c]pyridin-6-yl}-2-methyl-phenyl)-benzamide.

20. The compound of claim 2 selected from the group consisting of
  6-(6-Phenyl-imidazo[1,2-c]pyridin-8-ylamino)-nicotinic acid ethyl ester;
  (6-Phenyl-imidazo[1,2-c]pyridin-8-yl)-pyridin-2-yl-amine;
  Morpholin-4-yl-[6-(6-phenyl-imidazo[1,2-c]pyridin-8-ylamino)-pyridin-3-yl]-methanone;
  4-tert-Butyl-N-(2-methyl-3-{8-[5-(morpholine-4-carbonyl)-pyridin-2-ylamino]-imidazo[1,2-c]pyridin-6-yl}-phenyl)-benzamide;
  4-tert-Butyl-N-(2-methyl-3-{8-[5-(4-methyl-piperazine-1-carbonyl)-pyridin-2-ylamino]-imidazo[1,2-c]pyridin-6-yl}-phenyl)-benzamide;
  2-(3-{8-[5-(Morpholine-4-carbonyl)-pyridin-2-ylamino]-imidazo[1,2-c]pyridin-6-yl}-phenyl)-N-(5,5,5-trifluoro-4-hydroxy-4-methyl-pent-2-ynyl)-acetamide;
  N,N-Diisopropyl-2-(3-{8-[5-(morpholine-4-carbonyl)-pyridin-2-ylamino]-imidazo[1,2-c]pyridin-6-yl}-phenyl)-acetamide;
  1-(4-Methoxy-piperidin-1-yl)-2-(3-{8-[5-(morpholine-4-carbonyl)-pyridin-2-ylamino]-imidazo[1,2-c]pyridin-6-yl}-phenyl)-ethanone;

N-(4-Fluoro-phenyl)-2-(3-{8-[5-(morpholine-4-carbonyl)-pyridin-2-ylamino]-imidazo[1,2-c]pyridin-6-yl}-phenyl)-acetamide;

N-[2-(4-Methoxy-phenyl)-1-methyl-ethyl]-2-(3-{8-[5-(morpholine-4-carbonyl)-pyridin-2-ylamino]-imidazo[1,2-c]pyridin-6-yl}-phenyl)-acetamide;

1-(4-Fluoro-phenyl)-3-(2-methyl-3-{8-[5-(morpholine-4-carbonyl)-pyridin-2-ylamino]-imidazo[1,2-c]pyridin-6-yl}-phenyl)-urea;

2-(3-{8-[5-(Morpholine-4-carbonyl)-pyridin-2-ylamino]-imidazo[1,2-c]pyridin-6-yl}-phenyl)-1-[3-(2,2,2-trifluoro-1-trifluoromethyl-ethoxy)-azetidin-1-yl]-ethanone;

Pyrrolidine-1-carboxylic acid (2-methyl-3-{8-[5-(morpholine-4-carbonyl)-pyridin-2-ylamino]-imidazo[1,2-c]pyridin-6-yl}-phenyl)-amide;

4-Hydroxymethyl-piperidine-1-carboxylic acid (2-methyl-3-{8-[5-(morpholine-4-carbonyl)-pyridin-2-ylamino]-imidazo[1,2-c]pyridin-6-yl}-phenyl)-amide;

1-[2-(4-Methoxy-phenyl)-1-methyl-ethyl]-3-(2-methyl-3-{8-[5-(morpholine-4-carbonyl)-pyridin-2-ylamino]-imidazo[1,2-c]pyridin-6-yl}-phenyl)-urea;

Azetidine-1-carboxylic acid (2-methyl-3-{8-[5-(morpholine-4-carbonyl)-pyridin-2-ylamino]-imidazo[1,2-c]pyridin-6-yl}-phenyl)-amide;

1-Isopropyl-3-(2-methyl-3-{8-[5-(morpholine-4-carbonyl)-pyridin-2-ylamino]-imidazo[1,2-a]pyridin-6-yl}-phenyl)-urea;

1-Isobutyl-3-(2-methyl-3-{8-[5-(morpholine-4-carbonyl)-pyridin-2-ylamino]-imidazo[1,2-a]pyridin-6-yl}-phenyl)-urea;

1-sec-Butyl-3-(2-methyl-3-{8-[5-(morpholine-4-carbonyl)-pyridin-2-ylamino]-imidazo[1,2-a]pyridin-6-yl}-phenyl)-urea;

3,6-Dihydro-2H-pyridine-1-carboxylic acid (2-methyl-3-{8-[5-(morpholine-4-carbonyl)-pyridin-2-ylamino]-imidazo[1,2-c]pyridin-6-yl}-phenyl)-amide;

Morpholine-4-carboxylic acid (2-methyl-3-{8-[5-(morpholine-4-carbonyl)-pyridin-2-ylamino]-imidazo[1,2-c]pyridin-6-yl}-phenyl)-amide;

1-(1,1-Dimethyl-propyl)-3-(2-methyl-3-{8-[5-(morpholine-4-carbonyl)-pyridin-2-ylamino]-imidazo[1,2-c]pyridin-6-yl}-phenyl)-urea;

1-(1-Ethyl-propyl)-3-(2-methyl-3-{8-[5-(morpholine-4-carbonyl)-pyridin-2-ylamino]-imidazo[1,2-c]pyridin-6-yl}-phenyl)-urea;

1-(2-Methoxy-1-methyl-ethyl)-3-(2-methyl-3-{8-[5-(morpholine-4-carbonyl)-pyridin-2-ylamino]-imidazo[1,2-c]pyridin-6-yl}-phenyl)-urea;

N-Isobutyl-2-(3-{8-[5-(morpholine-4-carbonyl)-pyridin-2-ylamino]-imidazo[1,2-c]pyridin-6-yl}-phenyl)-acetamide;

1-Cyclopropyl-3-(2-methyl-3-{8-[5-(morpholine-4-carbonyl)-pyridin-2-ylamino]-imidazo[1,2-a]pyridin-6-yl}-phenyl)-urea;

1,1-Diethyl-3-(2-methyl-3-{8-[5-(morpholine-4-carbonyl)-pyridin-2-ylamino]-imidazo[1,2-a]pyridin-6-yl}-phenyl)-urea;

N-Furan-2-ylmethyl-2-(3-{8-[5-(morpholine-4-carbonyl)-pyridin-2-ylamino]-imidazo[1,2-a]pyridin-6-yl}-phenyl)-acetamide;

N-Cyclopropyl-2-(3-[8-[5-(morpholine-4-carbonyl)-pyridin-2-ylamino]-imidazo[1,2-c]pyridin-6-yl]-phenyl)-acetamide;

N-Isopropyl-2-(3-{8-[5-(morpholine-4-carbonyl)-pyridin-2-ylamino]-imidazo[1,2-c]pyridin-6-yl}-phenyl)-acetamide;

1-(4-Methyl-piperidin-1-yl)-2-(3-{8-[5-(morpholine-4-carbonyl)-pyridin-2-ylamino]-imidazo[1,2-c]pyridin-6-yl}-phenyl)-ethanone;

N,N-Diethyl-2-(4-{8-[5-(morpholine-4-carbonyl)-pyridin-2-ylamino]-imidazo[1,2-c]pyridin-6-yl}-phenyl)-acetamide;

N-sec-Butyl-2-(3-{8-[5-(morpholine-4-carbonyl)-pyridin-2-ylamino]-imidazo[1,2-c]pyridin-6-yl}-phenyl)-acetamide;

1-(3,6-Dihydro-2H-pyridin-1-yl)-2-(3-{8-[5-(morpholine-4-carbonyl)-pyridin-2-ylamino]-imidazo[1,2-c]pyridin-6-yl}-phenyl)-ethanone;

2-(3-{8-[5-(Morpholine-4-carbonyl)-pyridin-2-ylamino]-imidazo[1,2-c]pyridin-6-yl}-phenyl)-1-morpholin-4-yl-ethanone;

1-(2-Cyano-ethyl)-3-(2-methyl-3-{8-[5-(morpholine-4-carbonyl)-pyridin-2-ylamino]-imidazo[1,2-c]pyridin-6-yl}-phenyl)-urea;

1-(2-Cyano-ethyl)-1-ethyl-3-(2-methyl-3-{8-[5-(morpholine-4-carbonyl)-pyridin-2-ylamino]-imidazo[1,2-c]pyridin-6-yl}-phenyl)-urea;

1-Benzyl-1-(2-cyano-ethyl)-3-(2-methyl-3-{8-[5-(morpholine-4-carbonyl)-pyridin-2-ylamino]-imidazo[1,2-c]pyridin-6-yl}-phenyl)-urea;

2,5-Dimethyl-2,5-dihydro-pyrrole-1-carboxylic acid (2-methyl-3-{8-[5-(morpholine-4-carbonyl)-pyridin-2-ylamino]-imidazo[1,2-c]pyridin-6-yl}-phenyl)-amide;

1-Cyclohexyl-3-(2-methyl-3-{8-[5-(morpholine-4-carbonyl)-pyridin-2-ylamino]-imidazo[1,2-a]pyridin-6-yl}-phenyl)-urea;

4-Methyl-piperidine-1-carboxylic acid (2-methyl-3-{8-[5-(morpholine-4-carbonyl)-pyridin-2-ylamino]-imidazo[1,2-c]pyridin-6-yl}-phenyl)-amide;

Azepane-1-carboxylic acid (2-methyl-3-{8-[5-(morpholine-4-carbonyl)-pyridin-2-ylamino]-imidazo[1,2-c]pyridin-6-yl}-phenyl)-amide;

1-(2-Methyl-3-{8-[5-(morpholine-4-carbonyl)-pyridin-2-ylamino]-imidazo[1,2-a]pyridin-6-yl}-phenyl)-3-(tetrahydro-pyran-4-yl)-urea;

2-Ethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide;

3,5-Dimethyl-piperidine-1-carboxylic acid (2-methyl-3-{8-[5-(morpholine-4-carbonyl)-pyridin-2-ylamino]-imidazo[1,2-a]pyridin-6-yl}-phenyl)-amide;

2,6-Dimethyl-morpholine-4-carboxylic acid (2-methyl-3-{8-[5-(morpholine-4-carbonyl)-pyridin-2-ylamino]-imidazo[1,2-a]pyridin-6-yl}-phenyl)-amide;

N-(2-Methyl-3-{8-[5-(morpholine-4-carbonyl)-pyridin-2-ylamino]-imidazo[1,2-a]pyridin-6-yl}-phenyl)-4-(3-methyl-oxetan-3-yl)-benzamide;

N-(2-Methyl-3-{8-[5-(morpholine-4-carbonyl)-pyridin-2-ylamino]-imidazo[1,2-a]pyridin-6-yl}-phenyl)-4-(3-methyl-oxetan-3-yl)-benzamide;

4-Methyl-piperazine-1-carboxylic acid (2-methyl-3-{8-[5-(morpholine-4-carbonyl)-pyridin-2-ylamino]-imidazo[1,2-a]pyridin-6-yl}-phenyl)-amide;

1-(2-Dimethylamino-ethyl)-1-methyl-3-(2-methyl-3-{8-[5-(morpholine-4-carbonyl)-pyridin-2-ylamino]-imidazo[1,2-a]pyridin-6-yl}-phenyl)-urea; compound with formic acid;

1-[2-(3H-Imidazol-4-yl)-ethyl]-3-(2-methyl-3-{8-[5-(morpholine-4-carbonyl)-pyridin-2-ylamino]-imidazo[1,2-a]pyridin-6-yl}-phenyl)-urea;

4-Methyl-[1,4]diazepane-1-carboxylic acid (2-methyl-3-{8-[5-(morpholine-4-carbonyl)-pyridin-2-ylamino]-imidazo[1,2-a]pyridin-6-yl}-phenyl)-amide;

4-Ethyl-piperazine-1-carboxylic acid (2-methyl-3-{8-[5-(morpholine-4-carbonyl)-pyridin-2-ylamino]-imidazo[1,2-a]pyridin-6-yl}-phenyl)-amide;

4-Pyrrolidin-1-yl-piperidine-1-carboxylic acid (2-methyl-3-{8-[5-(morpholine-4-carbonyl)-pyridin-2-ylamino]-imidazo[1,2-a]pyridin-6-yl}-phenyl)-amide;

4-Dimethylcarbamoylmethyl-piperazine-1-carboxylic acid (2-methyl-3-{8-[5-(morpholine-4-carbonyl)-pyridin-2-ylamino]-imidazo[1,2-a]pyridin-6-yl}-phenyl)-amide;

4-(4-Chloro-benzyl)-piperazine-1-carboxylic acid (2-methyl-3-{8-[5-(morpholine-4-carbonyl)-pyridin-2-ylamino]-imidazo[1,2-a]pyridin-6-yl}-phenyl)-amide;

1-(2-Methyl-3-{8-[5-(morpholine-4-carbonyl)-pyridin-2-ylamino]-imidazo[1,2-a]pyridin-6-yl}-phenyl)-3-(1H-pyrazol-3-yl)-urea;

4-(2-Trifluoromethyl-benzyl)-piperazine-1-carboxylic acid (2-methyl-3-{8-[5-(morpholine-4-carbonyl)-pyridin-2-ylamino]-imidazo[1,2-c]pyridin-6-yl}-phenyl)-amide;

N—((S)-1-Hydroxymethyl-2-methyl-propyl)-2-(3-{8-[5-(morpholine-4-carbonyl)-pyridin-2-ylamino]-imidazo[1,2-c]pyridin-6-yl}-phenyl)-acetamide;

N—((S)-2-Hydroxy-1-methyl-ethyl)-2-(3-{8-[5-(morpholine-4-carbonyl)-pyridin-2-ylamino]-imidazo[1,2-c]pyridin-6-yl}-phenyl)-acetamide;

1-(1,4-Dioxa-8-aza-spiro[4.5]dec-8-yl)-2-(3-{8-[5-(morpholine-4-carbonyl)-pyridin-2-ylamino]-imidazo[1,2-c]pyridin-6-yl}-phenyl)-ethanone;

N—[(S)-2-Hydroxy-propyl)-2-(3-{8-[5-(morpholine-4-carbonyl)-pyridin-2-ylamino]-imidazo[1,2-a]pyridin-6-yl}-phenyl)-acetamide;

N-(2,3-Dihydroxy-propyl)-2-(3-{8-[5-(morpholine-4-carbonyl)-pyridin-2-ylamino]-imidazo[1,2-a]pyridin-6-yl}-phenyl)-acetamide;

N—((R)-2-Hydroxy-1-methyl-ethyl)-2-(3-{8-[5-(morpholine-4-carbonyl)-pyridin-2-ylamino]-imidazo[1,2-c]pyridin-6-yl}-phenyl)-acetamide;

1-(4-Hydroxy-piperidin-1-yl)-2-(3-{8-[5-(morpholine-4-carbonyl)-pyridin-2-ylamino]-imidazo[1,2-c]pyridin-6-yl}-phenyl)-ethanone;

N,N-Bis-(2-hydroxy-ethyl)-2-(3-{8-[5-(morpholine-4-carbonyl)-pyridin-2-ylamino]-imidazo[1,2-a]pyridin-6-yl}-phenyl)-acetamide;

1-(3-Hydroxy-piperidin-1-yl)-2-(3-{8-[5-(morpholine-4-carbonyl)-pyridin-2-ylamino]-imidazo[1,2-c]pyridin-6-yl}-phenyl)-ethanone;

N-(2-Hydroxy-1,1-dimethyl-ethyl)-2-(3-{8-[5-(morpholine-4-carbonyl)-pyridin-2-ylamino]-imidazo[1,2-c]pyridin-6-yl}-phenyl)-acetamide;

1-(3-Hydroxy-pyrrolidin-1-yl)-2-(3-{8-[5-(morpholine-4-carbonyl)-pyridin-2-ylamino]-imidazo[1,2-c]pyridin-6-yl}-phenyl)-ethanone;

N-(4,4-Dimethyl-pent-2-ynyl)-2-(3-{8-[5-(morpholine-4-carbonyl)-pyridin-2-ylamino]-imidazo[1,2-c]pyridin-6-yl}-phenyl)-acetamide;

1-((R)-2-Hydroxy-1-methyl-ethyl)-3-(2-methyl-3-{8-[5-(morpholine-4-carbonyl)-pyridin-2-ylamino]-imidazo[1,2-c]pyridin-6-yl}-phenyl)-urea;

1-((S)-2-Hydroxy-propyl)-3-(2-methyl-3-{8-[5-(morpholine-4-carbonyl)-pyridin-2-ylamino]-imidazo[1,2-c]pyridin-6-yl}-phenyl)-urea;

1-(2-Hydroxy-1,1-dimethyl-ethyl)-3-(2-methyl-3-{8-[5-(morpholine-4-carbonyl)-pyridin-2-ylamino]-imidazo[1,2-c]pyridin-6-yl}-phenyl)-urea;

1-((S)-1-Hydroxymethyl-2-methyl-propyl)-3-(2-methyl-3-{8-[5-(morpholine-4-carbonyl)-pyridin-2-ylamino]-imidazo[1,2-c]pyridin-6-yl}-phenyl)-urea;

1-(1-Hydroxymethyl-cyclopentyl)-3-(2-methyl-3-{8-[5-(morpholine-4-carbonyl)-pyridin-2-ylamino]-imidazo[1,2-c]pyridin-6-yl}-phenyl)-urea;

1-((1S,2S)-1-Hydroxymethyl-2-methyl-butyl)-3-(2-methyl-3-{8-[5-(morpholine-4-carbonyl)-pyridin-2-ylamino]-imidazo[1,2-c]pyridin-6-yl}-phenyl)-urea;

2,5-Dihydro-pyrrole-1-carboxylic acid (2-methyl-3-{8-[5-(morpholine-4-carbonyl)-pyridin-2-ylamino]-imidazo[1,2-c]pyridin-6-yl}-phenyl)-amide;

1-Cyclopropylmethyl-3-(2-methyl-3-{8-[5-(morpholine-4-carbonyl)-pyridin-2-ylamino]-imidazo[1,2-c]pyridin-6-yl}-phenyl)-1-propyl-urea;

1-(2-Methyl-3-{8-[5-(morpholine-4-carbonyl)-pyridin-2-ylamino]-imidazo[1,2-c]pyridin-6-yl}-phenyl)-3-(1-phenyl-propyl)-urea;

1-((S)-1-Hydroxymethyl-2,2-dimethyl-propyl)-3-(2-methyl-3-{8-[5-(morpholine-4-carbonyl)-pyridin-2-ylamino]-imidazo[1,2-c]pyridin-6-yl}-phenyl)-urea;

1-(2-Methyl-3-{8-[5-(morpholine-4-carbonyl)-pyridin-2-ylamino]-imidazo[1,2-c]pyridin-6-yl}-phenyl)-3-((S)-1-phenyl-ethyl)-urea;

1-((3S,4S)-4-Hydroxy-1,1-dioxo-tetrahydro-1$\lambda^6$-thiophen-3-yl)-3-(2-methyl-3-{8-[5-(morpholine-4-carbonyl)-pyridin-2-ylamino]-imidazo[1,2-c]pyridin-6-yl}-phenyl)-urea;

1-(2-Methyl-3-{8-[5-(morpholine-4-carbonyl)-pyridin-2-ylamino]-imidazo[1,2-c]pyridin-6-yl}-phenyl)-3-(2,2,2-trifluoro-ethyl)-urea;

1-((S)-2-Hydroxy-1-methyl-ethyl)-3-(2-methyl-3-{8-[5-(morpholine-4-carbonyl)-pyridin-2-ylamino]-imidazo[1,2-c]pyridin-6-yl}-phenyl)-urea;

3-Hydroxy-pyrrolidine-1-carboxylic acid (2-methyl-3-{8-[5-(morpholine-4-carbonyl)-pyridin-2-ylamino]-imidazo[1,2-c]pyridin-6-yl}-phenyl)-amide;

(S)-2-Hydroxymethyl-pyrrolidine-1-carboxylic acid (2-methyl-3-{8-[5-(morpholine-4-carbonyl)-pyridin-2-ylamino]-imidazo[1,2-c]pyridin-6-yl}-phenyl)-amide;

4-Hydroxy-piperidine-1-carboxylic acid (2-methyl-3-{8-[5-(morpholine-4-carbonyl)-pyridin-2-ylamino]-imidazo[1,2-c]pyridin-6-yl}-phenyl)-amide;

3-Hydroxy-piperidine-1-carboxylic acid (2-methyl-3-{8-[5-(morpholine-4-carbonyl)-pyridin-2-ylamino]-imidazo[1,2-c]pyridin-6-yl}-phenyl)-amide;

1,1-Bis-(2-hydroxy-ethyl)-3-(2-methyl-3-{8-[5-(morpholine-4-carbonyl)-pyridin-2-ylamino]-imidazo[1,2-c]pyridin-6-yl}-phenyl)-urea;

2-Hydroxymethyl-piperidine-1-carboxylic acid (2-methyl-3-{8-[5-(morpholine-4-carbonyl)-pyridin-2-ylamino]-imidazo[1,2-c]pyridin-6-yl}-phenyl)-amide;

3-Hydroxymethyl-piperidine-1-carboxylic acid (2-methyl-3-{8-[5-(morpholine-4-carbonyl)-pyridin-2-ylamino]-imidazo[1,2-c]pyridin-6-yl}-phenyl)-amide;

1-(4-Hydroxy-cyclohexyl)-3-(2-methyl-3-{8-[5-(morpholine-4-carbonyl)-pyridin-2-ylamino]-imidazo[1,2-c]pyridin-6-yl}-phenyl)-urea;

4-tert-Butyl-N-(3-{8-[6-(3-hydroxy-pyrrolidin-1-yl)-pyridin-2-ylamino]-imidazo[1,2-c]pyridin-6-yl}-2-methyl-phenyl)-benzamide;

N-(1,1-Dimethyl-propyl)-2-(3-{8-[5-(morpholine-4-carbonyl)-pyridin-2-ylamino]-imidazo[1,2-c]pyridin-6-yl}-phenyl)-acetamide;

N-(1-Ethyl-propyl)-2-(3-{8-[5-(morpholine-4-carbonyl)-pyridin-2-ylamino]-imidazo[1,2-c]pyridin-6-yl}-phenyl)-acetamide;

N-(1-Ethyl-propyl)-2-(3-{8-[5-(morpholine-4-carbonyl)-pyridin-2-ylamino]-imidazo[1,2-c]pyridin-6-yl}-phenyl)-acetamide;

N-(2-Methoxy-1-methyl-ethyl)-2-(3-{8-[5-(morpholine-4-carbonyl)-pyridin-2-ylamino]-imidazo[1,2-c]pyridin-6-yl}-phenyl)-acetamide;

N-(2-Methoxy-1-methyl-ethyl)-2-(3-{8-[5-(morpholine-4-carbonyl)-pyridin-2-ylamino]-imidazo[1,2-c]pyridin-6-yl}-phenyl)-acetamide;

1-(2,5-Dimethyl-2,5-dihydro-pyrrol-1-yl)-2-(3-{8-[5-(morpholine-4-carbonyl)-pyridin-2-ylamino]-imidazo[1,2-c]pyridin-6-yl}-phenyl)-ethanone;

1-(2-Methyl-piperidin-1-yl)-2-(3-{8-[5-(morpholine-4-carbonyl)-pyridin-2-ylamino]-imidazo[1,2-c]pyridin-6-yl}-phenyl)-ethanone;

1-Azepan-1-yl-2-(3-{8-[5-(morpholine-4-carbonyl)-pyridin-2-ylamino]-imidazo[1,2-c]pyridin-6-yl}-phenyl)-ethanone;

1-((2S,6R)-2,6-Dimethyl-piperidin-1-yl)-2-(3-{8-[5-(morpholine-4-carbonyl)-pyridin-2-ylamino]-imidazo[1,2-c]pyridin-6-yl}-phenyl)-ethanone;

N-(2-Dimethylamino-ethyl)-N-methyl-2-(3-{8-[5-(morpholine-4-carbonyl)-pyridin-2-ylamino]-imidazo[1,2-c]pyridin-6-yl}-phenyl)-acetamide;

1-(4-Methyl-piperazin-1-yl)-2-(3-{8-[5-(morpholine-4-carbonyl)-pyridin-2-ylamino]-imidazo[1,2-c]pyridin-6-yl}-phenyl)-ethanone;

1-(4-Ethyl-piperazin-1-yl)-2-(3-{8-[5-(morpholine-4-carbonyl)-pyridin-2-ylamino]-imidazo[1,2-a]pyridin-6-yl}-phenyl)-ethanone;

4-(3-Methyl-azetidin-3-yl)-N-(2-methyl-3-{8-[5-(morpholine-4-carbonyl)-pyridin-2-ylamino]-imidazo[1,2-c]pyridin-6-yl}-phenyl)-benzamide;

[6-(6-{3-[1-(4-tert-Butyl-phenyl)-2,2,2-trifluoro-ethylamino]-2-methyl-phenyl}-imidazo[1,2-c]pyridin-8-ylamino)-pyridin-3-yl]-morpholin-4-yl-methanone;

3-Aza-bicyclo[3.2.2]nonane-3-carboxylic acid (2-methyl-3-{8-[5-(morpholine-4-carbonyl)-pyridin-2-ylamino]-imidazo[1,2-c]pyridin-6-yl}-phenyl)-amide;

Piperidine-1,3-dicarboxylic acid 3-amide 1-[(2-methyl-3-{8-[5-(morpholine-4-carbonyl)-pyridin-2-ylamino]-imidazo[1,2-c]pyridin-6-yl}-phenyl)-amide];

1,1-Bis-(2-methoxy-ethyl)-3-(2-methyl-3-{8-[5-(morpholine-4-carbonyl)-pyridin-2-ylamino]-imidazo[1,2-c]pyridin-6-yl}-phenyl)-urea;

3,4-Dihydro-2H-quinoline-1-carboxylic acid (2-methyl-3-{8-[5-(morpholine-4-carbonyl)-pyridin-2-ylamino]-imidazo[1,2-c]pyridin-6-yl}-phenyl)-amide;

(4aR,8aS)-Octahydro-isoquinoline-2-carboxylic acid (2-methyl-3-{8-[5-(morpholine-4-carbonyl)-pyridin-2-ylamino]-imidazo[1,2-c]pyridin-6-yl}-phenyl)-amide;

{6-[6-(2-Hydroxymethyl-phenyl)-imidazo[1,2-c]pyridin-8-ylamino]-pyridin-3-yl}-morpholin-4-yl-methanone;

1-Methyl-3-(2-methyl-3-{8-[5-(morpholine-4-carbonyl)-pyridin-2-ylamino]-imidazo[1,2-a]pyridin-6-yl}-phenyl)-1-phenyl-urea;

1-Ethyl-3-(2-methyl-3-{8-[5-(morpholine-4-carbonyl)-pyridin-2-ylamino]-imidazo[1,2-a]pyridin-6-yl}-phenyl)-1-phenyl-urea;

1-(2-Methyl-3-{8-[5-(morpholine-4-carbonyl)-pyridin-2-ylamino]-imidazo[1,2-c]pyridin-6-yl}-phenyl)-3-phenyl-urea;

1-Indan-1-yl-3-(2-methyl-3-{8-[5-(morpholine-4-carbonyl)-pyridin-2-ylamino]-imidazo[1,2-a]pyridin-6-yl}-phenyl)-urea;

1-(2-Methyl-3-{8-[5-(morpholine-4-carbonyl)-pyridin-2-ylamino]-imidazo[1,2-c]pyridin-6-yl}-phenyl)-3-(4-methyl-oxazol-2-yl)-urea;

1-(3-Chloro-phenyl)-3-(2-methyl-3-{8-[5-(morpholine-4-carbonyl)-pyridin-2-ylamino]-imidazo[1,2-c]pyridin-6-yl}-phenyl)-urea;

1-(2-Methyl-3-{8-[5-(morpholine-4-carbonyl)-pyridin-2-ylamino]-imidazo[1,2-c]pyridin-6-yl}-phenyl)-3-(2-trifluoromethyl-phenyl)-urea;

1-(4-tert-Butyl-phenyl)-3-(2-methyl-3-{8-[5-(morpholine-4-carbonyl)-pyridin-2-ylamino]-imidazo[1,2-c]pyridin-6-yl}-phenyl)-urea; and 1-(4-Methanesulfonyl-cyclohexyl)-3-(2-methyl-3-{8-[5-(morpholine-4-carbonyl)-pyridin-2-ylamino]-imidazo[1,2-c]pyridin-6-yl}-phenyl)-urea.

21. A pharmaceutical composition comprising the compound of claim 1, admixed with at least one pharmaceutically acceptable carrier, excipient or diluent.

* * * * *